(12) United States Patent
Pell et al.

(10) Patent No.: US 8,915,845 B2
(45) Date of Patent: Dec. 23, 2014

(54) METHODS AND DEVICES TO DECREASE TISSUE TRAUMA DURING SURGERY

(75) Inventors: Charles Anthony Pell, Durham, NC (US); Hugh Charles Crenshaw, Durham, NC (US)

(73) Assignee: Physcient, Inc., Durham, NC (US)

( * ) Notice: Subject to any disclaimer, the term of this patent is extended or adjusted under 35 U.S.C. 154(b) by 0 days.

(21) Appl. No.: 12/465,978

(22) Filed: May 14, 2009

(65) Prior Publication Data

US 2009/0287060 A1 Nov. 19, 2009

Related U.S. Application Data

(60) Provisional application No. 61/127,520, filed on May 14, 2008, provisional application No. 61/054,866, filed on May 21, 2008, provisional application No. 61/127,598, filed on May 14, 2008, provisional application No. 61/133,669, filed on Jul. 1, 2008, provisional application No. 61/134,278, filed on Jul. 8, 2008.

(51) Int. Cl.
*A61B 1/32* (2006.01)
*A61B 17/02* (2006.01)
*A61B 18/02* (2006.01)

(52) U.S. Cl.
CPC ........ *A61B 17/02* (2013.01); *A61B 18/02* (2013.01)
USPC .......................................... 600/210; 600/201

(58) Field of Classification Search
CPC ............... A61F 2013/1543; A61F 2013/15439
USPC ................................................. 600/200–248
See application file for complete search history.

(56) References Cited

U.S. PATENT DOCUMENTS

| | | | |
|---|---|---|---|
| 2,013,892 A | 9/1935 | Lucas | |
| 2,313,164 A | 3/1943 | Nelson | |
| 3,008,239 A | 11/1961 | Lange | |
| 3,572,326 A | 3/1971 | Jensen | |
| 3,665,925 A | 5/1972 | Dersookian | |
| 3,766,909 A | 10/1973 | Ozbey | |
| 3,785,381 A | 1/1974 | Lower et al. | |
| 3,789,849 A | 2/1974 | Laufe et al. | |
| 3,888,117 A | 6/1975 | Lewis | |
| 3,965,890 A | 6/1976 | Gauthier | |
| 4,041,937 A * | 8/1977 | Diaz | 600/240 |
| 4,066,082 A | 1/1978 | Arcan et al. | |
| 4,155,355 A | 5/1979 | Yamamoto | |

(Continued)

OTHER PUBLICATIONS

Albin, M.D. et al., "Brain Retraction Pressure During Intracranial Procedures," Surg. Forum., 1975, pp. 499-500, vol. 26.

(Continued)

*Primary Examiner* — David Bates
*Assistant Examiner* — Samuel Hanna
(74) *Attorney, Agent, or Firm* — Withrow & Terranova, PLLC

(57) ABSTRACT

Methods and devices are disclosed to reduce the tissue trauma that occurs when a physician retracts or otherwise deforms a patient's tissues for surgery or other medical procedures. In one part, methods and devices are disclosed for cooling the tissue around the incision. In another part, methods and devices are disclosed that elute drugs into the tissues of the tissue margin. In another part, methods and devices are disclosed to engage tissues during retraction to cushion, to sense tissue state, and to modulate tissue state.

19 Claims, 107 Drawing Sheets

(56) References Cited

U.S. PATENT DOCUMENTS

| | | | |
|---|---|---|---|
| 4,254,763 A | 3/1981 | McCready et al. | |
| 4,297,884 A | 11/1981 | Leveque et al. | |
| 4,424,724 A | 1/1984 | Bookwalter et al. | |
| 4,432,376 A | 2/1984 | Huszar | |
| 4,622,955 A | 11/1986 | Fakhrai | |
| 4,777,943 A * | 10/1988 | Chvapil | 128/850 |
| 4,784,150 A | 11/1988 | Voorhies et al. | |
| 4,899,761 A | 2/1990 | Brown et al. | |
| 4,945,896 A | 8/1990 | Gade | |
| 4,989,587 A | 2/1991 | Farley | |
| 5,020,933 A | 6/1991 | Salvestro et al. | |
| 5,184,601 A | 2/1993 | Putman | |
| 5,201,325 A | 4/1993 | McEwen et al. | |
| 5,213,112 A | 5/1993 | Niwa et al. | |
| 5,359,995 A | 11/1994 | Sewell, Jr. | |
| 5,578,043 A | 11/1996 | Galstian | |
| 5,679,245 A | 10/1997 | Manica | |
| 5,735,791 A * | 4/1998 | Alexander et al. | 600/37 |
| 5,769,781 A | 6/1998 | Chappuis | |
| 5,782,746 A * | 7/1998 | Wright | 600/37 |
| 5,957,950 A | 9/1999 | Mockros et al. | |
| 6,007,552 A * | 12/1999 | Fogarty et al. | 606/157 |
| 6,139,493 A | 10/2000 | Koros et al. | |
| 6,241,706 B1 | 6/2001 | Leschinsky et al. | |
| 6,251,093 B1 | 6/2001 | Valley et al. | |
| 6,312,377 B1 * | 11/2001 | Segermark et al. | 600/232 |
| 6,517,563 B1 * | 2/2003 | Paolitto et al. | 606/205 |
| 6,730,021 B2 | 5/2004 | Vassiliades, Jr. et al. | |
| 6,767,324 B2 | 7/2004 | D'Alessandro et al. | |
| 6,837,851 B1 * | 1/2005 | Valentini et al. | 600/210 |
| 7,059,182 B1 | 6/2006 | Ragner | |
| 2002/0022770 A1 | 2/2002 | Borsody | |
| 2003/0060685 A1 | 3/2003 | Houser et al. | |
| 2003/0083648 A1 | 5/2003 | Wang et al. | |
| 2003/0181800 A1 | 9/2003 | Bonutti | |
| 2003/0216619 A1 | 11/2003 | Scirica et al. | |
| 2003/0236472 A1 | 12/2003 | Van Hoeck et al. | |
| 2004/0073301 A1 | 4/2004 | Donlon et al. | |
| 2004/0077931 A1 | 4/2004 | Larnard | |
| 2004/0102806 A1 | 5/2004 | Broome et al. | |
| 2004/0143166 A1 * | 7/2004 | Larnard | 600/210 |
| 2004/0206365 A1 | 10/2004 | Knowlton | |
| 2004/0225197 A1 | 11/2004 | Roux et al. | |
| 2004/0230101 A1 | 11/2004 | Martin et al. | |
| 2004/0260229 A1 | 12/2004 | Meir | |
| 2005/0043592 A1 | 2/2005 | Boyd et al. | |
| 2005/0119568 A1 | 6/2005 | Salcudean et al. | |
| 2005/0175872 A1 | 8/2005 | Trabold et al. | |
| 2005/0215866 A1 | 9/2005 | Kim | |
| 2006/0025656 A1 | 2/2006 | Buckner et al. | |
| 2006/0084843 A1 * | 4/2006 | Sommerich et al. | 600/210 |
| 2006/0273135 A1 | 12/2006 | Beetel | |
| 2007/0225558 A1 | 9/2007 | Hauck et al. | |
| 2007/0250172 A1 | 10/2007 | Moskowitz et al. | |
| 2009/0192360 A1 | 7/2009 | Riess et al. | |
| 2009/0259107 A1 | 10/2009 | Crenshaw et al. | |
| 2009/0259109 A1 | 10/2009 | Bucefari et al. | |

OTHER PUBLICATIONS

Albin, MS et al., "Clinical and Experimental Brain Retraction Pressure Monitoring," Acta Neurol Scand Suppl 1977; 64:522-3.

Andrews RJ et al., "Retraction Brain Ischaemia: Cerebral Blood Flow, Evoked Potentials, Hypotension and Hyperventilation in a New Animal Model," Neurol Res Mar. 1992; 14(1):12-8.

Andrews, RJ et al., "Retraction Brain Ischaemia: Mannitol Plus Nimodipine Preserves Both Cerebral Blood Flow and Evoked Potentials During Normoventilation and Hyperventilation," Neurol Res Mar. 1992; 14(1):19-25.

Andrews, RJ, et al. "A Review of Brain Retraction and Recommendations for Minimizing Intraoperative Brain Injury," Neurosurgery 1993; 33(6):1052-64.

Bennett, M et al., "Evoked potential changes during brain retraction in dogs," Stroke Jul.-Aug. 1977; 8(4):487-92.

Davidson, Ri et al., "Compression-Expansion Forceps for Intracranial Dissection and Retraction," Technical note. J Neurosurg Oct. 1986; 65(4):563.

Harada, S., et al., "Retraction induced brain edema," Acta. Neurochir. Suppl. (Wien), 1994; 60: 449-51.

Hongo, K., et al., "Monitoring Retraction Pressure on the Brain. An Experimental and Clinical Study," J. Neurosurg., Feb. 1987; 66(2): 270-5.

Kawaguchi, M.D. et al., "Back Muscle Injury After Posterior Lumbar Spine Surgery," Spine, 1996, pp. 2683-2688, vol. 21, No. 22.

Moss, E., "Effect of propofol on brain retraction pressure and cerebral perfusion pressure," Br J Anaesth, Dec. 1, 1990; 65(6): 823-5.

Rosenorn, J., et al., "Reduction of regional cerebral blood flow during brain retraction pressure in the rat." J Neurosurg, Jun. 1982; 56(6): 826-9.

Rosenorn, J., et al., "The risk of cerebral damage during graded brain retractor pressure in the rat," J Neurosurg, Oct. 1985;63(4): 608-11.

Sandler, A.N., "Post-thoracotomy analgesia and perioperative outcome," Minerva Anestesiol, May 1999; 65(5): 267-272, abstract only.

Styf, M.D. et al., "The Effects of External Compression by Three Different Retractors on Pressure in the Erector Spine Muscles During and After Posterior Lumbar Spine Surgery in Humans," Spine, 1998, pp. 354-358, vol. 23, No. 3.

Thiex, R., et al., "Technical pitfalls in a porcine brain retraction model. The impact of brain spatula on the retracted brain tissue in a porcine model: A feasibility study and its technical pitfalls," Neuroradiology, Oct. 2005; 47(10): 765-73.

Wang, et al., "A Compound Sensor for Biomechanical Analyses of Buttock Soft Tissue in vivo," Journal of Rehabilitation Research and Development, vol. 37, No. 4, Aug. 2000, pp. 433-443.

Yokoh, A., et al., "Intermittent versus continuous brain retraction. An experimental study," J Neurosurg, Jun. 1983; 58(6): 918-23.

Baisden, CE et al., "Occult Rib Fractures and Brachial Plexus Injury Following Median Sternotomy for Open-Heart Operations," Ann Thorac Surg, Sep. 1984; 38(3):192-4.

Benedetti et al., "Postoperative Pain and Superficial Abdominal Reflexes after Posterolateral Thoracotomy," Ann. Thorac. Surg., Jul. 1997, 64(1): 207-210.

Bolotin et al., "A Novel Instrumented Retractor to Monitor Tissue-Disruptive Forces during Lateral Thoracotomy", J. Thorac. Cardiovasc. Surg., Apr. 2007, 133(4):949-954.

Bonfils-Roberts, EA. "The Rib Spreader: A Chapter in the History of Thoracic Surgery," Chest, May 1, 1972; 61(5):469-74.

Bromage, P.R., "The Control of Post-Thoracotomy Pain," Anesthesia, May 1989, 44(5):445-446.

Candaele et al., "Chest Pain After Partial Upper Versus Complete Sternotomy for Aortic Value Surgery," Acta Cardiol, Feb. 2003, 58(1): 17-21.

Cerfolio et al., "Intercostal Muscle Flap Reduces the Pain of Thoracotomy: A Prospective Randomized Trial," J. Thorac. Cardiovasc. Surg., Oct. 2005, 130(4): 987-993.

Chaudhuri, O et al., "Reversible Stress Softening of Actin Networks," Nature, 2007; 445(7125):295-8.

Clark, JD et al., "Blockade of the Complement C5A Receptor Reduces Incisional Allodynia, Edema, and Cytokine Expression," Anesthesiology, Jun. 2006; 104(6):1274-82.

Clark, JD et al., "Morphine Reduces Local Cytokine Expression and Neutrophil Infiltration After Incision," Mol Pain, 2007; 3:28.

Dajczman, E., et al. "Long-Term Postthoracotomy Pain," Chest, Feb. 1991, 99(2): 270-274.

Datta et al., "Back Pain and Disability after Lumbar Laminectomy: Is There a Relationship to Muscle Retraction?" Neurosurgery, Jun. 2004, 54(6): 1413-1420, discussion 20.

De Silva, RJ, et al., "Apt070 Inhibits Complement Activation During in Vitro Cardiopulmonary Bypass," Eur J Cardiothorac Surg, Jul. 2006; 30(1):72-6.

Defalque et al., "Long-Term Postthoracotomy Pain," Chest, Mar. 1992, 101(3): 884.

Dorfmann, A, et al. "A Constitutive Model for Muscle Properties in a Soft-Bodied Arthropod," Journal of the Royal Society Interface, 2007; 4(13):257-69.

(56) References Cited

OTHER PUBLICATIONS

Dowling et al., "Improved Pain Control After Cardiac Surgery: Results of a Randomized, Double-Blind, Clinical Trial," J. Thorac. Cardiovasc. Surg., Nov. 2003, 126(5): 1271-1278.
Eisenberg, E, et al., "Prevalence and Characteristics of Post Coronary Artery Bypass Graft Surgery Pain (PCP)," Pain, May 2001; 92(1-2):11-7.
Eng, J. et al., "Post-Thoracotomy Analgesia," J R Coll Surg Edinb, Apr. 1993; 38(2):62-8.
Erdek, MA et al., "Chronic Pain and Thoracic Surgery," Thorac Surg Clin, Feb. 2005; 15(1):123-30.
Erdogan, M. et al., "Prospective, Randomized, Placebo-Controlled Study of the Effect of Tens on Postthoracotomy Pain and Pulmonary Function," World J Surg, Dec. 2005; 29(12):1563-70.
Evans, Krista, "The Hole-N-Ator: An Analysis of the Relation Between the Forces Applied to the Retracted Tissue and the Reactions Applied at the Crank Mechanism," 1999, http://em-ntserver.unl.edu:80/Mechanics-Pages/KristaEvans/holenator%20revised.htm.
Fanning, NF et al., "Inhibition of Neutrophil Apoptosis After Elective Surgery," Surgery, Sep. 1999; 126(3):527-34.
Flatters, SJ., "Characterization of a Model of Persistent Postoperative Pain Evoked by Skin/Muscle Incision and Retraction (smir)," Pain, Jun. 20, 2007.
Fleck, C., et al., "Deformation Behaviour and Damage Accumulation of Cortical Bone Specimens form the Equine Tibia Under Cyclic Loading," J Biomech, Feb. 2003; 36(2):179-89.
Fonseca, P., "Postthoracotomy Pain," J. Thorac. Cardiovasc. Surg., Dec. 1998; 116(6): 1081-2.
Greenwald, L.V., et al., "Rib Fractures in Coronary Bypass Patients: Radionuclide Detection," Radiology, Aug. 1993; 148(2): 553-4.
Hazelrigg, S.R., et al., "Acute and Chronic Pain Syndromes After Thoracic Surgery," Surg. Clin. North. Am., Aug. 2002; 82(4): 849-65.
Ho, S.C., et al., "Persistent Pain After Cardiac Surgery: An Audit of High Thoracic Epidural and Primary Opioid Analgesia Therapies," Anesth. Analg., Oct. 2002; 95(4): 820-3, table of contents.
Horgan, C.O., et al., "A Theory of Stress Softening of Elastomers Based on Finite Chain Extensibility," Proceedings of the Royal Society A: Mathematical, Physical and Engineering Sciences, 2004; 460(2046): 1737-54.
Kalso, E., et al., "Chronic Post-Sternotomy Pain," Acta Anaesthesiol Scand, Sep. 2001; 45(8): 935-9.
Karmakar, M.K., et al., "Postthoracotomy Pain Syndrome," Thorac Surg Clin, Aug. 2004; 14(3): 345-52.
Katz, J., et al., "Acute Pain After Thoracic Surgery Predicts Long-term Post-Thoracotomy Pain," Clin J Pain, Mar. 2006; 12(1): 50-5.
Kavanagh, B.P., et al., "Pain control after thoracic surgery. A review of current techniques," Anesthesiology, Sep. 1994; 81(3): 737-59.
Kawaguchi, Y, et al., "Back muscle injury after posterior lumbar spine surgery. Part 1: Histologic and histochemical analyses in rats," Spine, Nov. 15, 1994; 19(22):2590-7.
Kawaguchi, M.D. et al., "Back Muscle Injury After Posterior Lumbar Spine Surgery," Spine, 1996, pp. 941-944, vol. 21, No. 8.
Kawaguchi, M.D. et al., "Preventative Measures of Back Muscle Injury After Posterior Lumbar Spine Sugery in Rats," Spine, 1998, 2282-2287, vol. 23, No. 21.
Kirton, R.S., et al., "Strain softening behaviour in nonviable rat right-ventricular trabeculae, in the presence and the absence of butanedione monoxime," Exp Physiol, Sep. 1, 2004; 89(5): 593-604.
Kirton, R.S., et al., "Strain softening is not present during axial extensions of rat intact right ventricular trabeculae in the presence or absence of 2,3-butanedione monoxime," Am J Physiol Heart Circ Physiol, Feb. 1, 2004; 286(2): H708-15.
Koehler, R.P., et al., "Management of postthoracotomy pain: Acute and chronic." Thorac Surg Clin, Aug. 2006; 16(3): 287-97.
Kruger, M., et al., "Pain management in cardiothoracic practice," Surg Clin North Am., Apr. 1999; 79(2): 387-400.
Lewis, R.J., "The advent of vats. In My Opinion," CTSNet, Jun. 19, 2007, http://www.ctsnet.org/sections/newsandviews/inmyopinion/articles/article-62.html.
Long, J.H., Jr., "Stiffness and damping forces in the intevertebral joints of blue marlin (*Makaira nigricans*)," J exp Biol, 1992; 162: 131-55.
Long, J.H., Jr., et al., "Locomotor design of dolphin vertebral columns: Bending mechanics and morphology of *Delphinus delphis*," J Exp Biol, Jan. 1997; 200(Pt 1): 65-81.
Magnano, D., et al., "Ineffectiveness of local wound anesthesia to reduce postoperative pain after median sternotomy," J Card Surg, Jul.-Aug. 2005; 20(4): 314-8.
Minor, A.A., "Alternative management for post-thoracotomy pain syndrome," Can J Surg, Oct. 1996; 39(5): 430-1.
Murphy, G.S., et al., "The effects of morphine and fentanyl on the inflammatory response to cardiopulmonary bypass in patients undergoing elective coronary artery bypass graft surgery," Anesth Analg, Jun. 2007; 104(6): 1334-42, table of contents.
Ochroch, E.A., et al., "Women suffer more short and long-term pain than men after major thoracotomy," Clin J Pain, Jun. 2006; 22(5): 491-8.
Peeters-Asdourian, C., et al., "Choices in pain management following thoracotomy," Chest, May 1999; 115(5 Suppl): 122S-4S.
Perkins, F.M., et al., "Chronic pain as an outcome of surgery. A review of predictive factors, " Anesthesiology, Oct. 2000; 93(4): 1123-33.
Perttunen, K., et al., "Chronic pain after thoracic surgery: A follow-up study," Acta Anaesthesiol Scand, May 1999; 43(5): 563-7.
Pluijms, W.A., et al., "Chronic post-thoracotomy pain: A retrospective study," Acta Anaesthesiol Scand, Aug. 2006; 50(7): 804-8.
Provenzano, P., et al., "Nonlinear ligament viscoelasticity," Ann Biomed Eng, Oct. 2001; 29(10): 908-14.
Richardson, J., et al., "Postthoracotomy pain," Ann Thorac Surg, Jan. 1998; 65(1): 300-2.
Rogers, M.L., et al., "Preliminary findings in the neurophysiological assessment of intercostal nerve injury during thoracotomy," Eur J Cardiothorac Surg, Feb. 1, 2002; 21(2): 298-301.
Sabanathan, S., et al., "Management of pain in thoracic surgery," Br J Hosp Med, Jul. 14-Aug. 17, 1993; 50(2-3): 114-20.
Savage, C., et al., "Postthoracotomy pain management," Chest Surg Clin N Am, May 2002; 12(2): 251-63.
Sihoe, A.D., et al. "The use of gabapentin for post-operative and post-traumatic pain in thoracic surgery patients," Eur J Cardiothorac Surg, May 2006; 29(5): 795-9.
Speich, J.E., et al., "Rok-induced cross-link formation stiffens passive muscle: Reversible strain-induced stress softening in rabbit detrusor," Am J Physiol Cell Physiol, Jul. 1, 2005; 289(1): C12-21.
Strebel, B.M., et al., "Chronic post-thoracic pain syndrome," CMAJ, 2007; 177(9): 1029.
Takamori, S., et al., "Intraoperative intercostal nerve blockade for postthoracotomy pain," Ann Thorac Surg, Aug. 2002; 74(2): 338-41.
Taylor, H., et al., "The impact of self-retaining retractors on the paraspinal muscles during posterior spinal surgery," Spine, Dec. 15, 2001; 27(24): 2758-62.
Tiippana, E., et al., "Post-thoracotomy pain after thoracic epidural analgesia: A prospective follow-up study," Acta Anaesthesiol Scand, Apr. 2003; 47(4): 433-8.
Vander Salm, T.J., et al., "Brachial plexus injury following median sternotomy. Part II," J Thorac Cardiovasc Surg, Jun. 1982; 83(6): 914-7.
Vanderby, R., et al., "Collagen in connective tissue: From tendon to bone," J Biomech, Oct. 2003; 36(10): 1523-7.
Vincent, J.F.V., "Locust oviposition: Stress softening of the extensible intersegmental membranes," Proceedings of the Royal Society of London Series B, Biological Sciences (1934-1990), 1975; 188(1091): 189-201.
Wainwright, et al., 1976, Mechanical Design in Organisms, John Wiley & Sons.
Weisman, G., et al., "Cyclic loading in knee ligament injuries," Am J Sports Med, Jan.-Feb. 1980; 8(1): 24-30.
White et al., "Use of a continuous local anesthetic infusion for pain management after median sternotomy", Anesthesiology, Oct. 2003, 99(4): 918-923.
Woo et al., 1999, Animal Models in Orthopaedic Research, CRC Press. pp. 175-196.

(56) References Cited

OTHER PUBLICATIONS

Woodring, J.H., et al., "Upper rib fractures following median sternotomy," Ann Thorac Surg, Apr. 1985; 39(4): 355-7.

Yin, L., et al., "A biphasic and transversely isotropic mechanical model for tendon: Application to mouse tail fascicles in uniaxial tension," J Biomech, Jun. 2004; 37(6): 907-16.

International Search Report for PCT/US2011/037191 mailed Aug. 29, 2011, 2 pages.

Foering, K. et al., "Percutaneous Transluminal Angioplasty Balloon Inflation with Syringes: Who Needs an Inflator?" Journal of Vascular and Interventional Radiology, vol. 20, pp. 629-633.

Honye, J. et al., "Morphological Effects of Coronary Balloon Angioplasty in Vivo Assessed by Intravascular Ultrasound Imaging," Circulation, vol. 85, pp. 1012-1025.

Ochroch, E.A., et al., "Impact of acute pain and its management for thoracic surgical patients," Thorac Surg Clin, Feb. 2005; 15(1): 105-21.

Non-final Office Action for U.S. Appl. No. 13/832,378 mailed Mar. 30, 2012, 11 pages.

Non-final Office Action for U.S. Appl. No. 12/422,584 mailed Apr. 24, 2012, 13 pages.

Advisory Action for U.S. Appl. No. 12/422,584 mailed Mar. 15, 2012, 2 pages.

Final Office Action for U.S. Appl. No. 12/422,584 mailed Dec. 21, 2011, 14 pages.

Non-final Office Action for U.S. Appl. No. 12/422,584 mailed Apr. 27, 2011, 12 pages.

Notice of Allowance for U.S. Appl. No. 11/187,207 mailed Apr. 12, 2010, 6 pages.

Final Office Action for U.S. Appl. No. 11/187,207 mailed Dec. 8, 2009, 7 pages.

Final Office Action for U.S. Appl. No. 11/187,207 mailed Jun. 13, 2008, 11 pages.

Non-final Office Action for U.S. Appl. No. 11/187,207 mailed Feb. 2, 2009, 9 pages.

Final Office Action for U.S. Appl. No. 11/187,207 mailed Oct. 9, 2007, 5 pages.

International Search Report for PCT/US09/40348 mailed Oct. 4, 2010, 9 pages.

International Search Report for PCT/US2011/037191 mailed Aug. 29, 2011, 12 pages.

International Search Report for PCT/US09/43954 mailed Nov. 8, 2011, 13 pages.

Final Office Action for U.S. Appl. No. 12/823,378 mailed Oct. 17, 2012, 18 pages.

International Search Report and Written Opinion for PCT/US2012/054442 mailed Nov. 26, 2012, 9 pages.

International Preliminary Report on Patentability for PCT/US2011/037191 mailed Nov. 29, 2012, 10 pages.

Notice of Allowance for U.S. Appl. No. 12/832,378 mailed Aug. 28, 2013, 12 pages.

Final Office Action for U.S. Appl. No. 12/422,584 mailed Sep. 9, 2013, 11 pages.

Extended European Search Report for European patent application 09747577.6 mailed Sep. 3, 2013, 12 pages.

Non-final Office Action for U.S. Appl. No. 13/111,762 mailed Aug. 8, 2013, 8 pages.

Advisory Action for U.S. Appl. No. 12/832,378 mailed Feb. 26, 2013, 3 pages.

Non-final Office Action for U.S. Appl. No. 12/422,584 mailed Mar. 7, 2013, 13 pages.

Advisory Action for U.S. Appl. No. 12/422,584, mailed Jan. 27, 2014, 7 pages.

Non-final Office Action for U.S. Appl. No. 13/111,577 mailed Oct. 23, 2013, 22 pages.

International Preliminary Report on Patentability for PCT/US2012/054442 mailed Mar. 20, 2014, 8 pages.

Advisory Action for U.S. Appl. No. 12/422,584 mailed Mar. 24, 2014, 3 pages.

Final Office Action for U.S. Appl. No. 13/111,762 mailed Mar. 26, 2014, 8 pages.

* cited by examiner

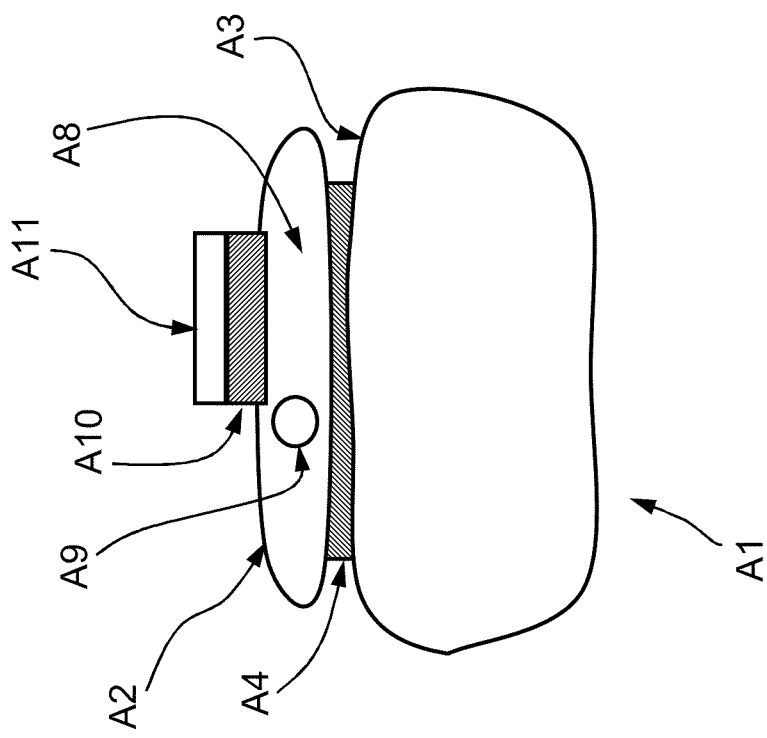
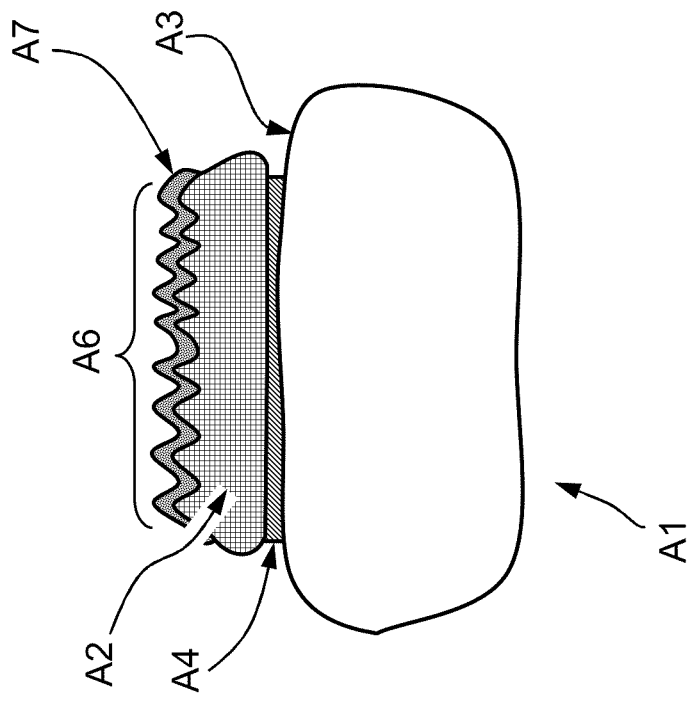
FIG. 2B
FIG. 2A

Arrows show directions of fluid flow

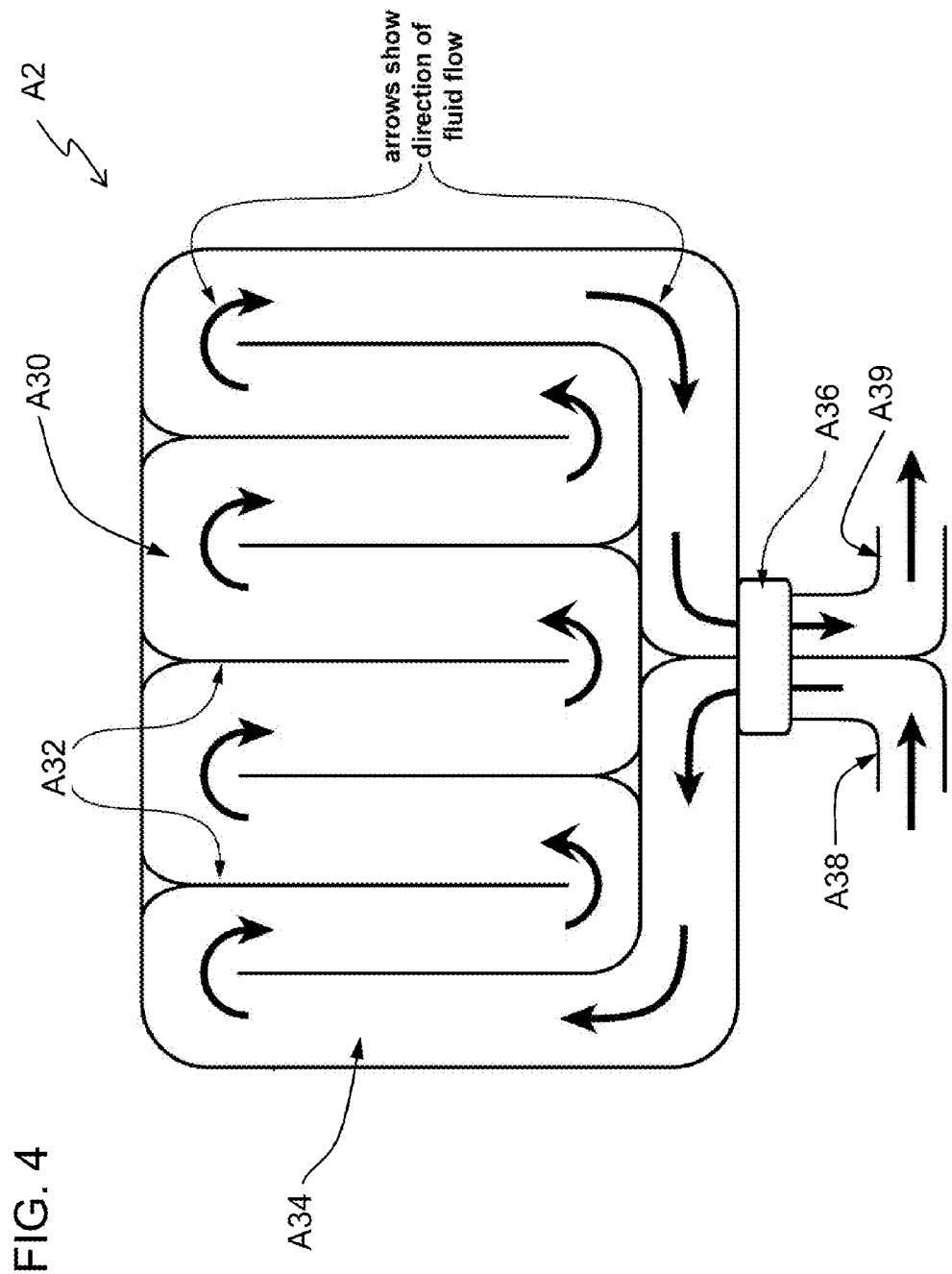

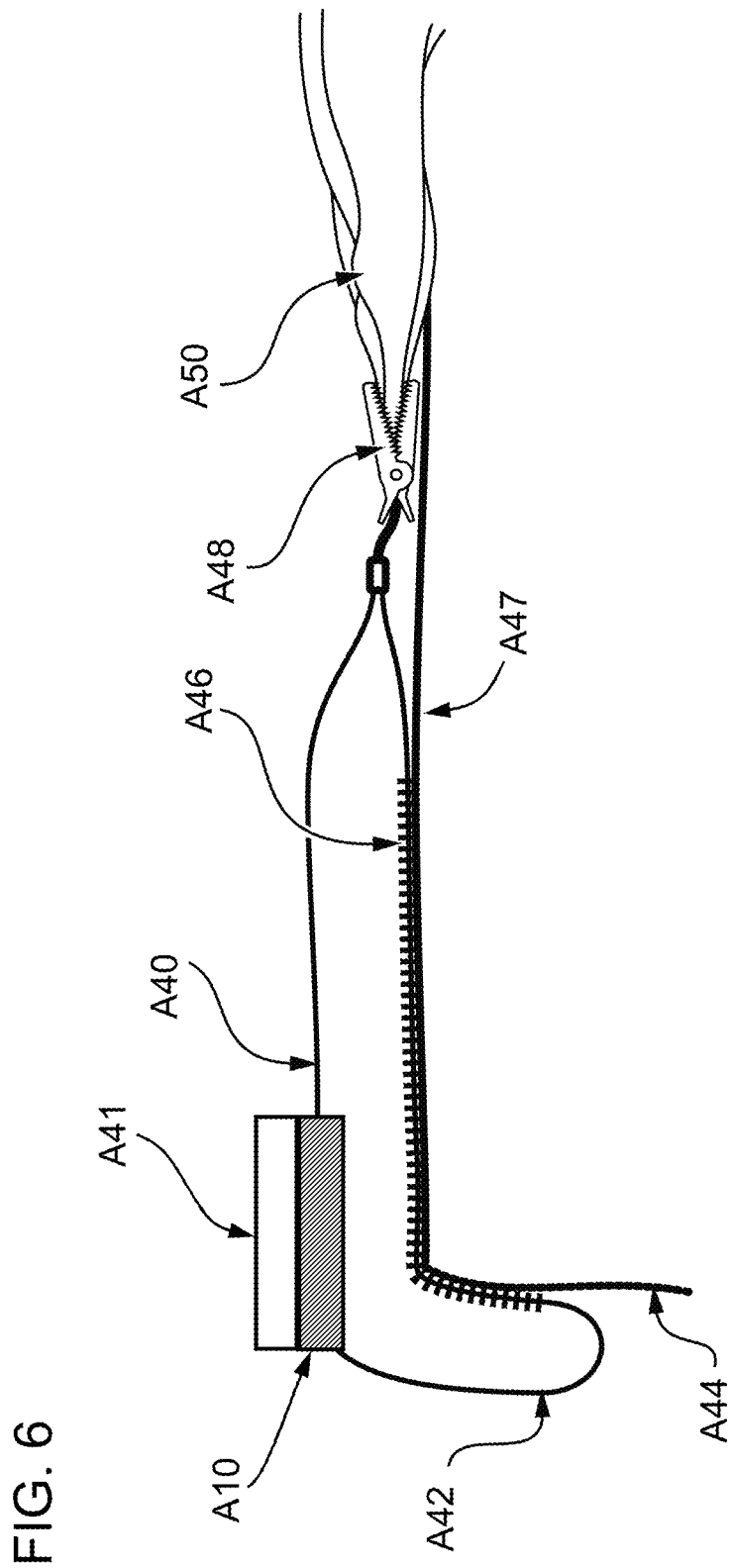

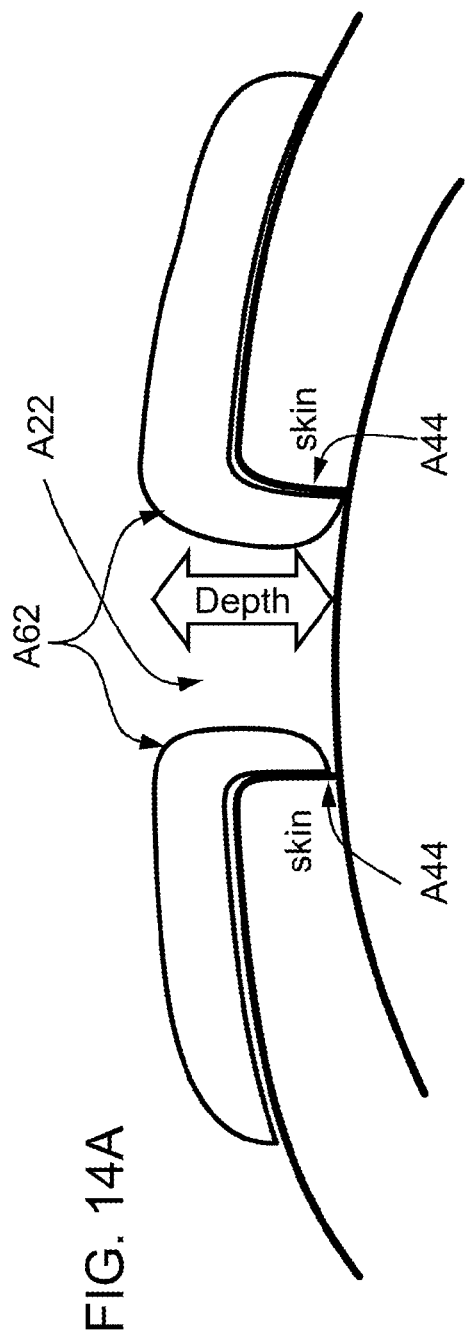
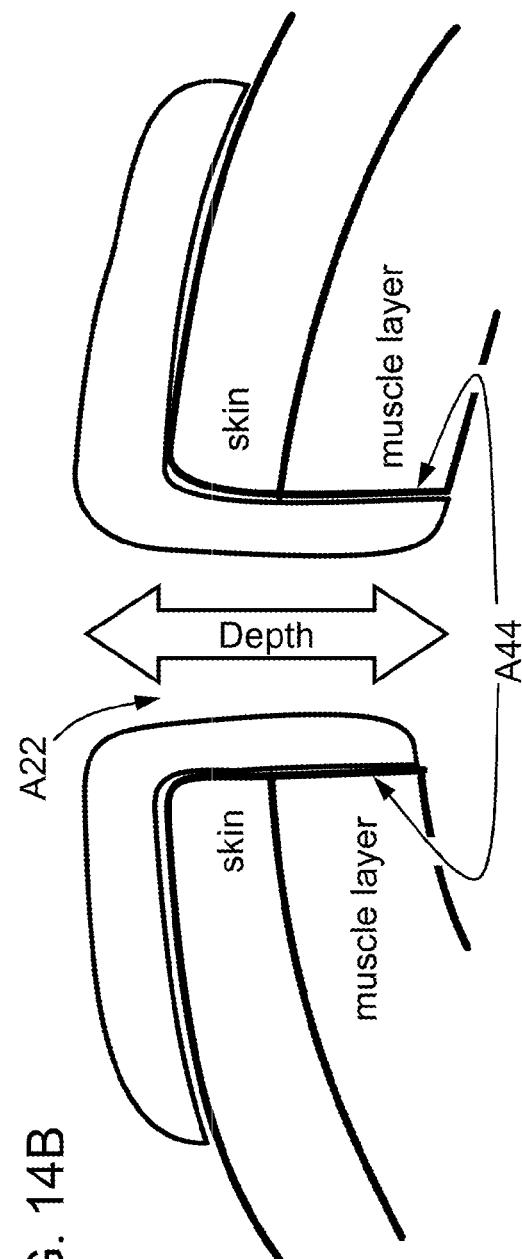
FIG. 14A
FIG. 14B

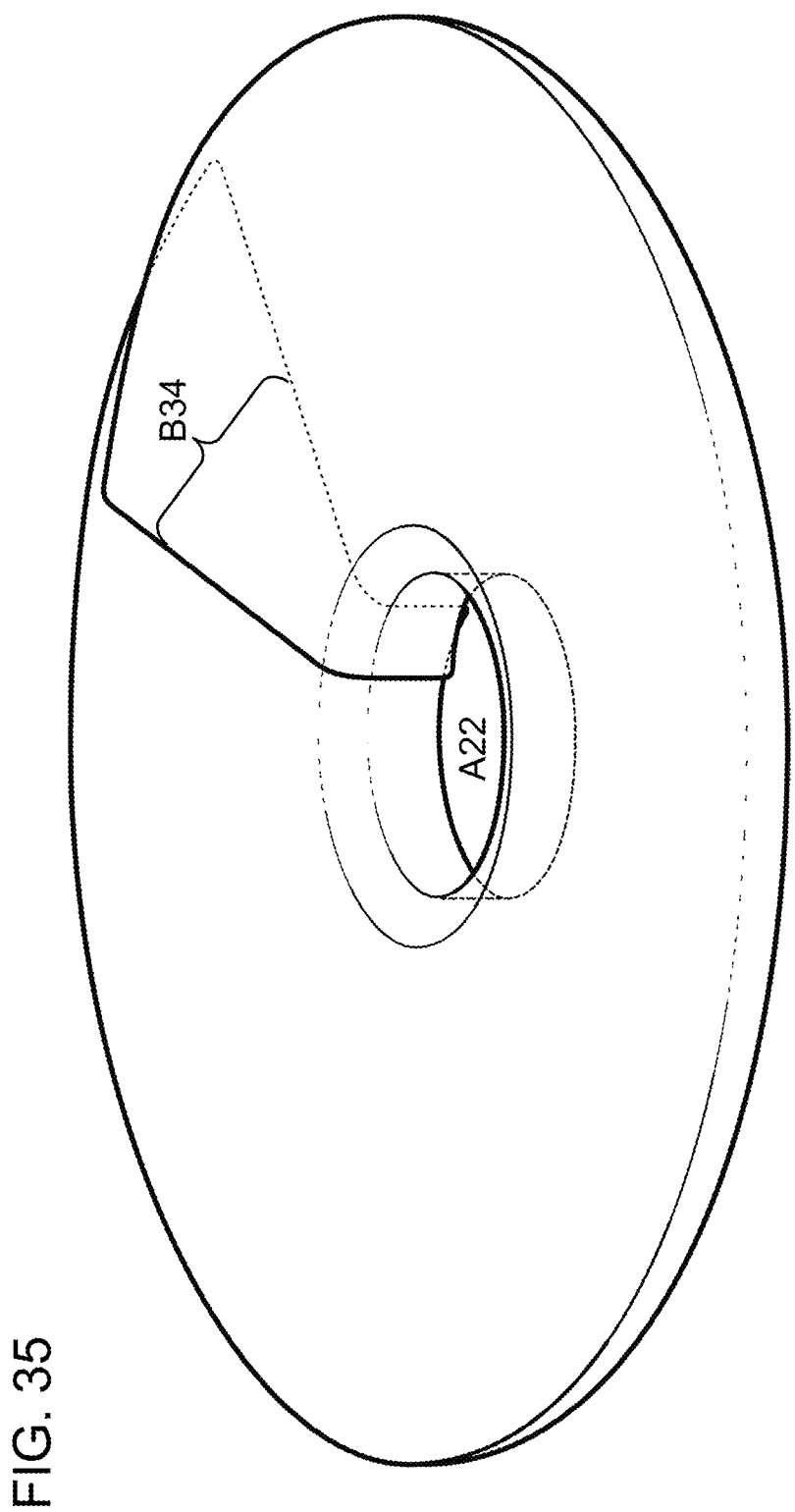

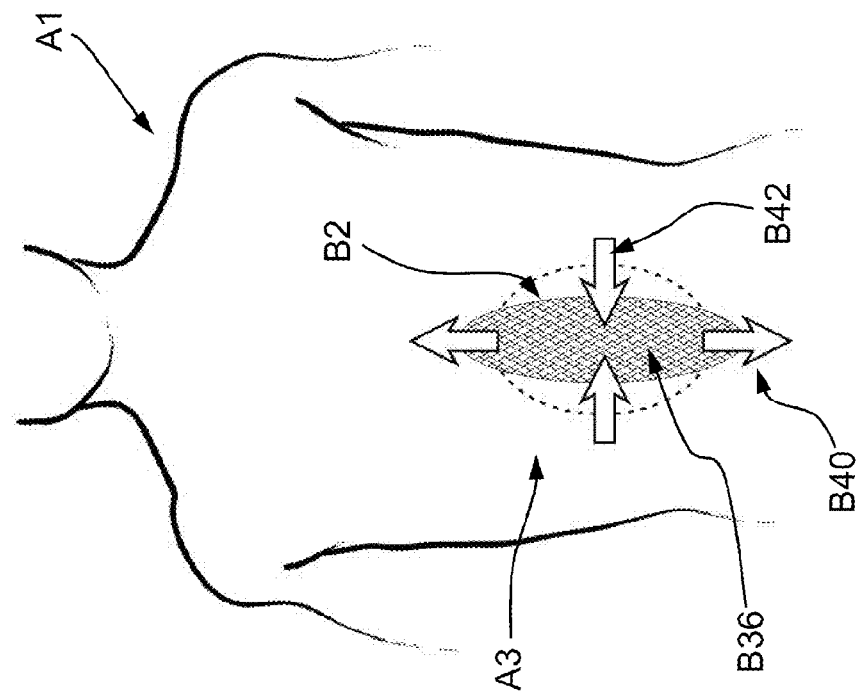
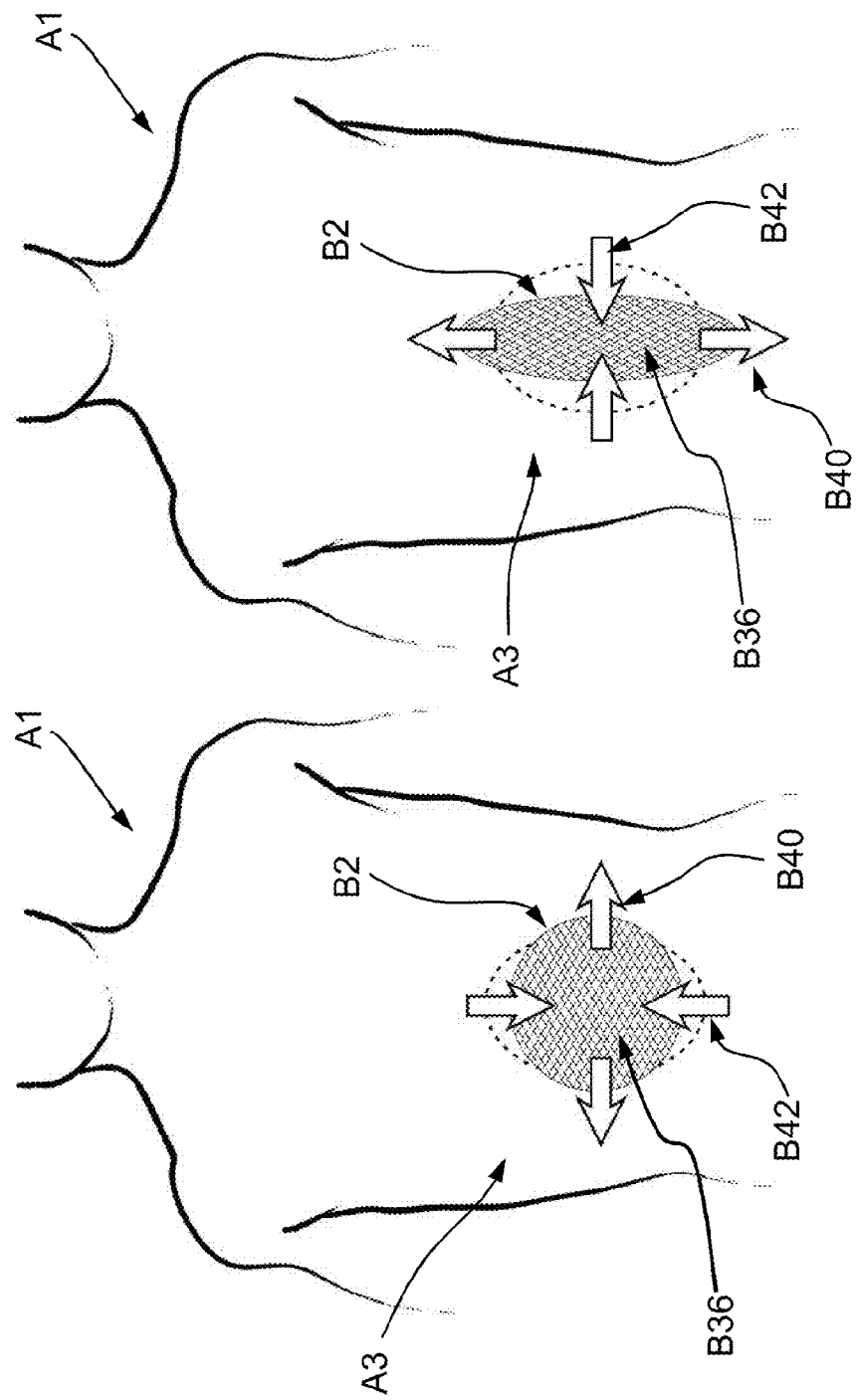

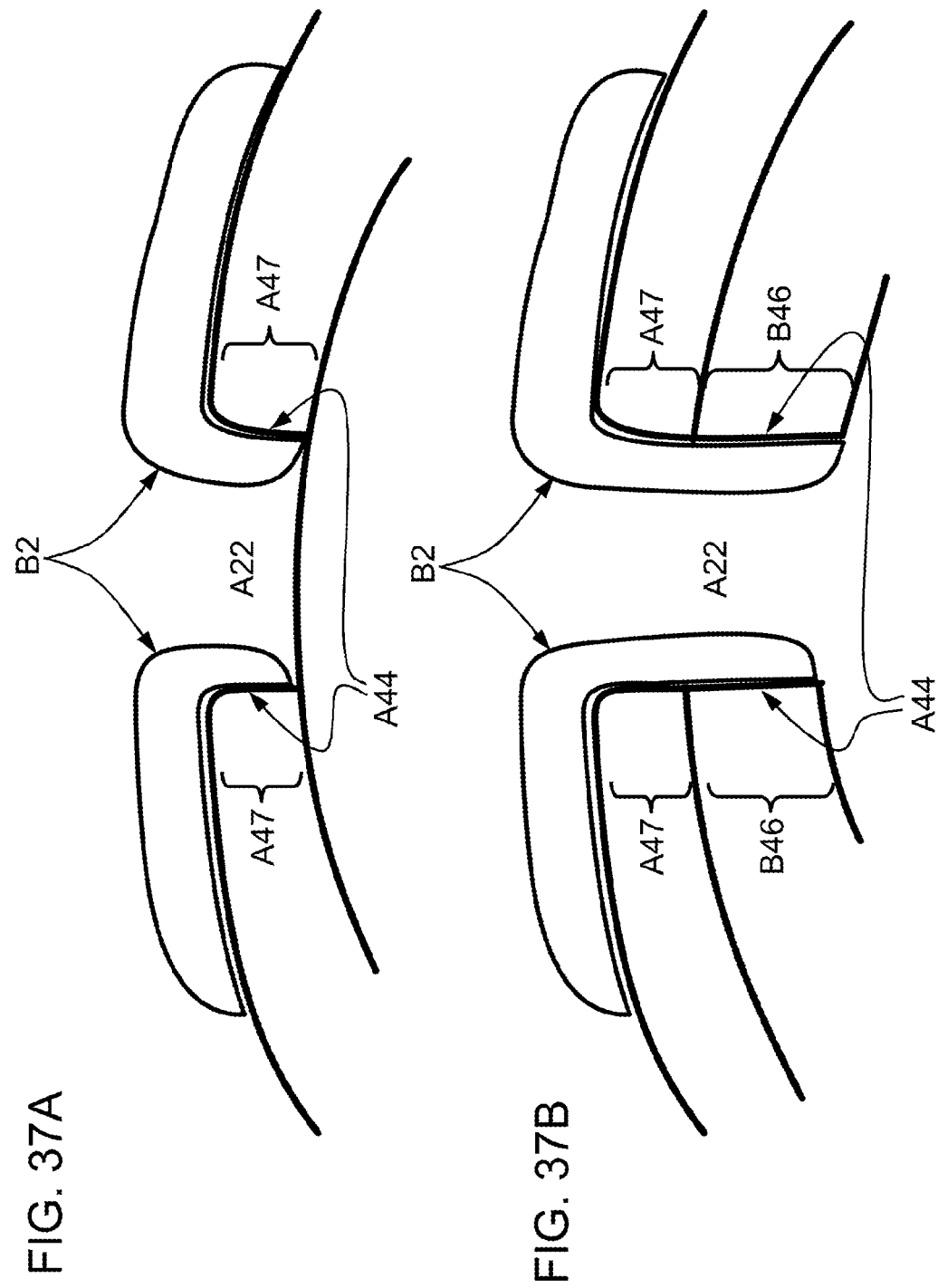

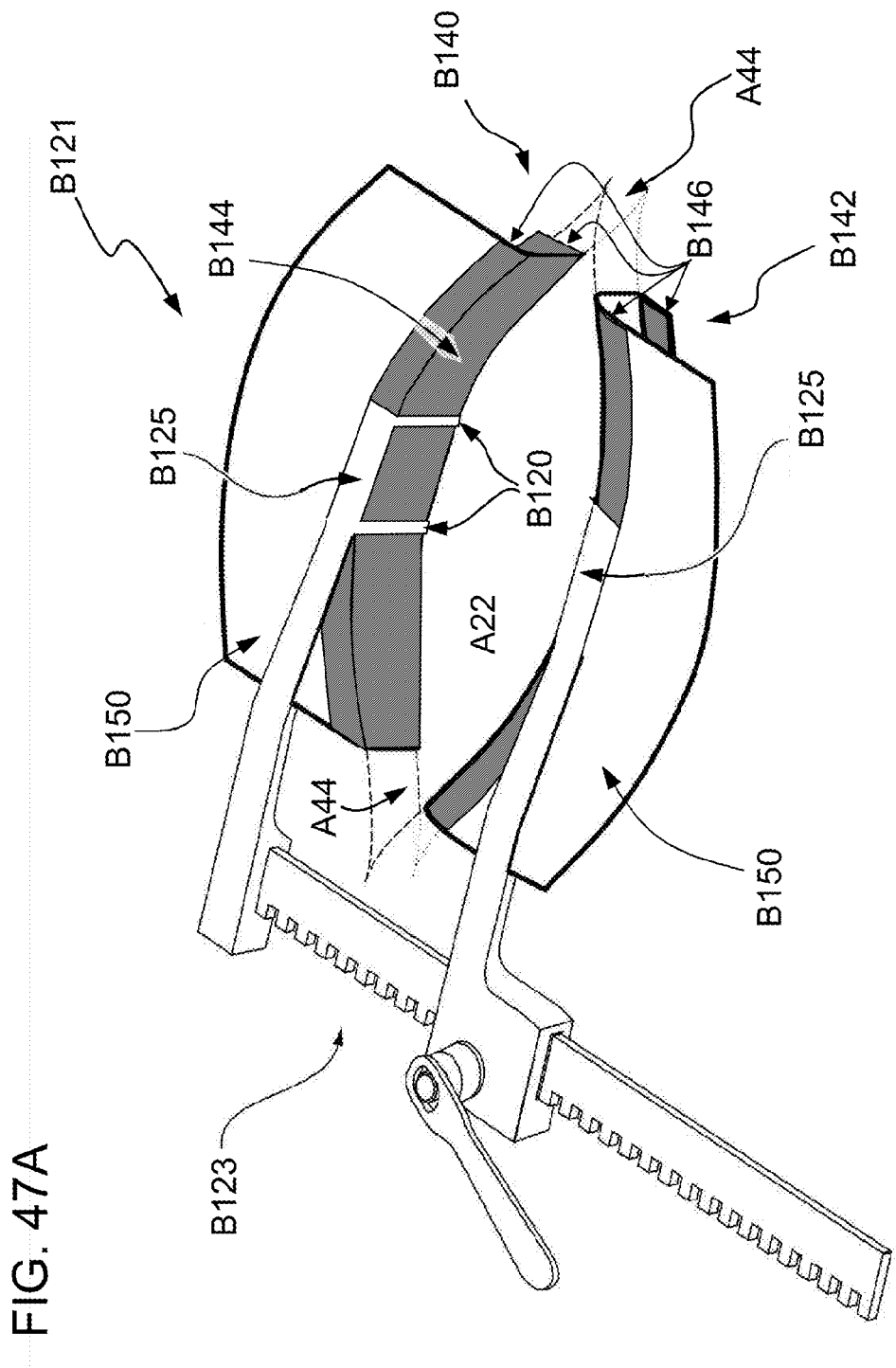

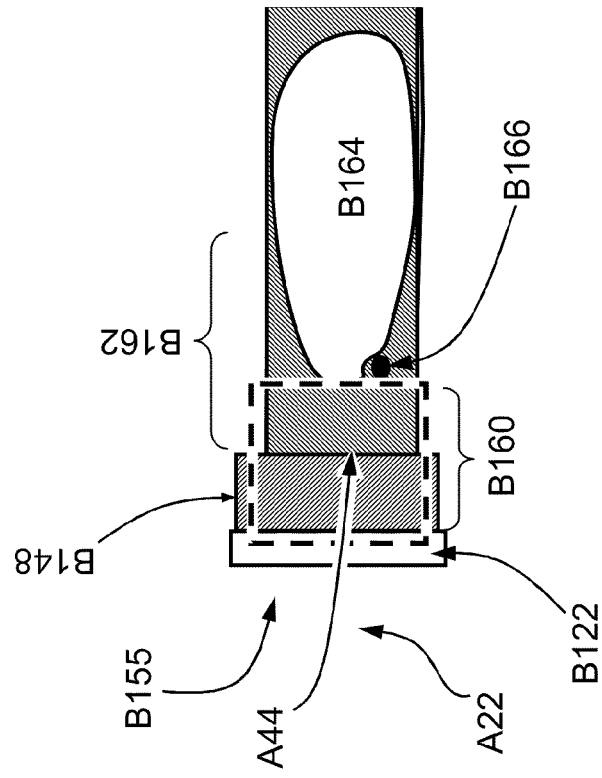
FIG. 48B Side View
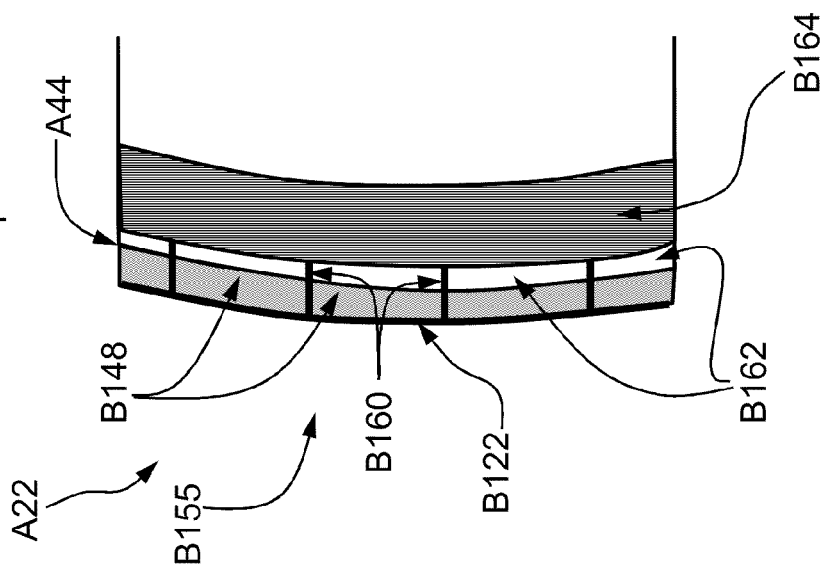
FIG. 48A Top View

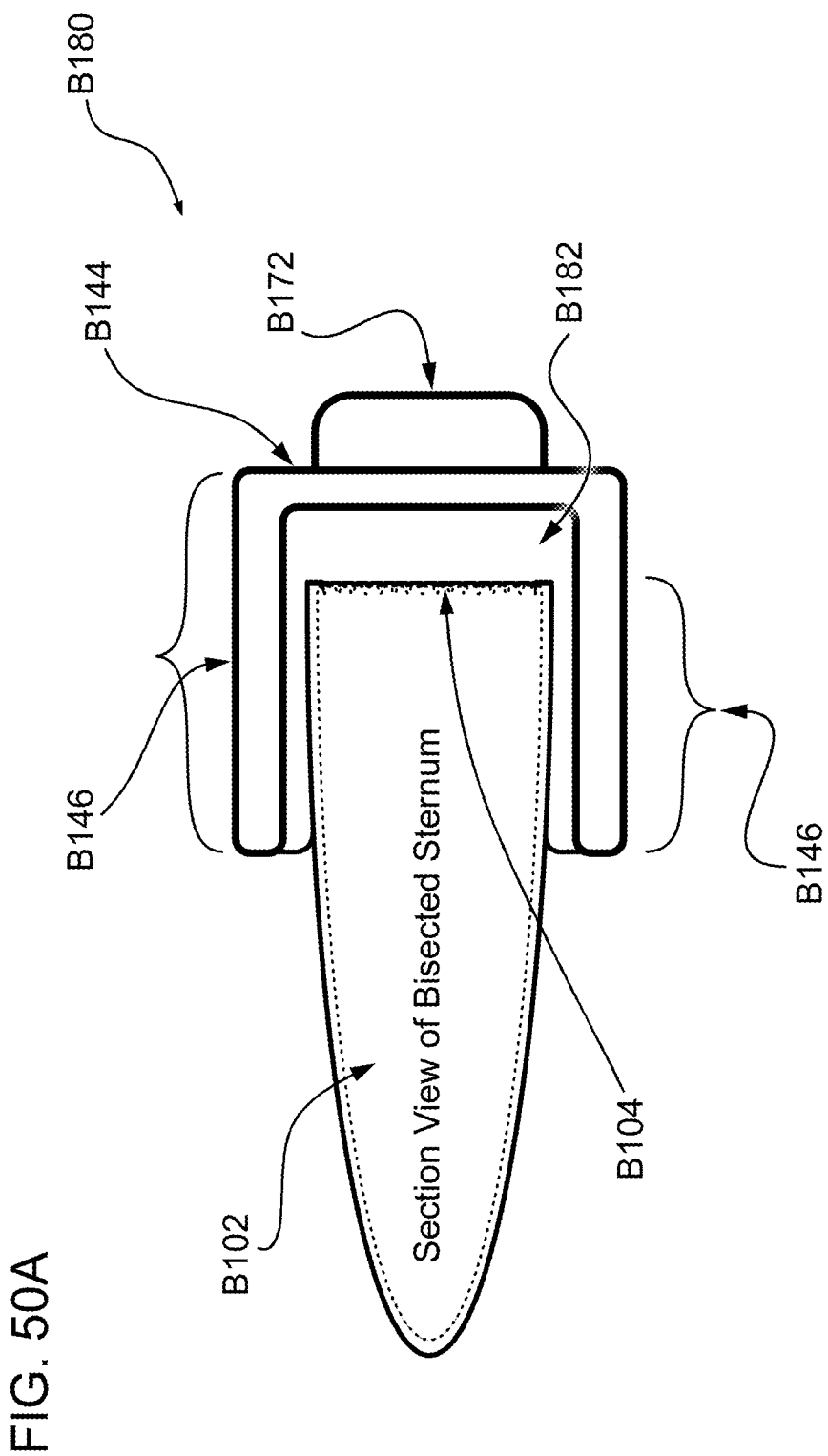

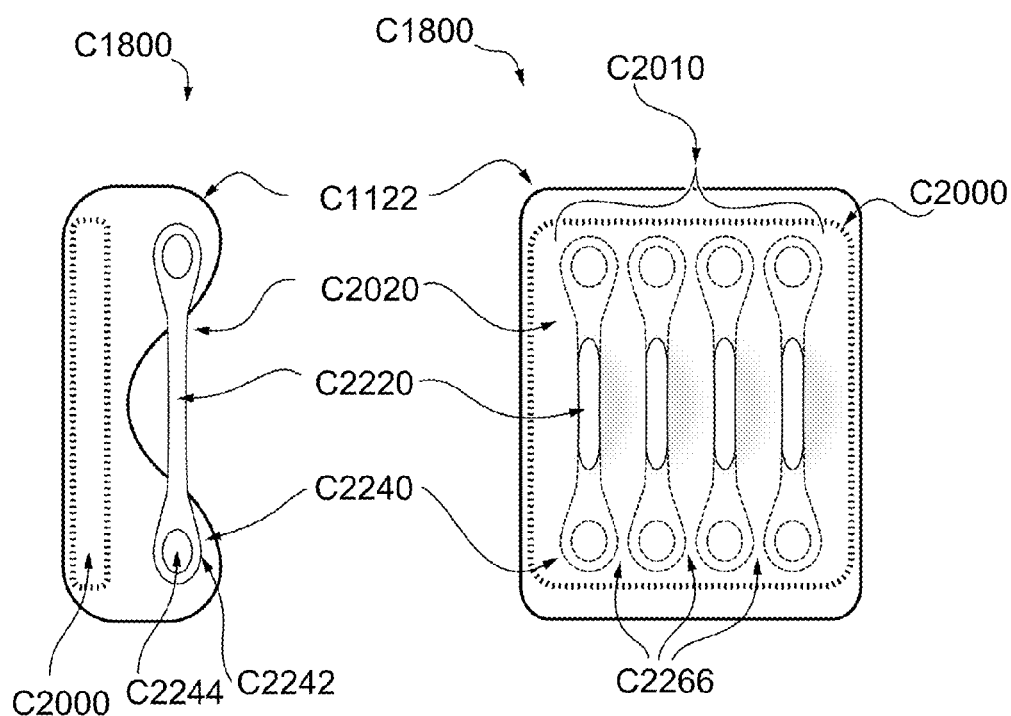

C5334: Alternating Push-and-Relax with Constant Force

C5336: Push 2, Relax 1, with Constant Force

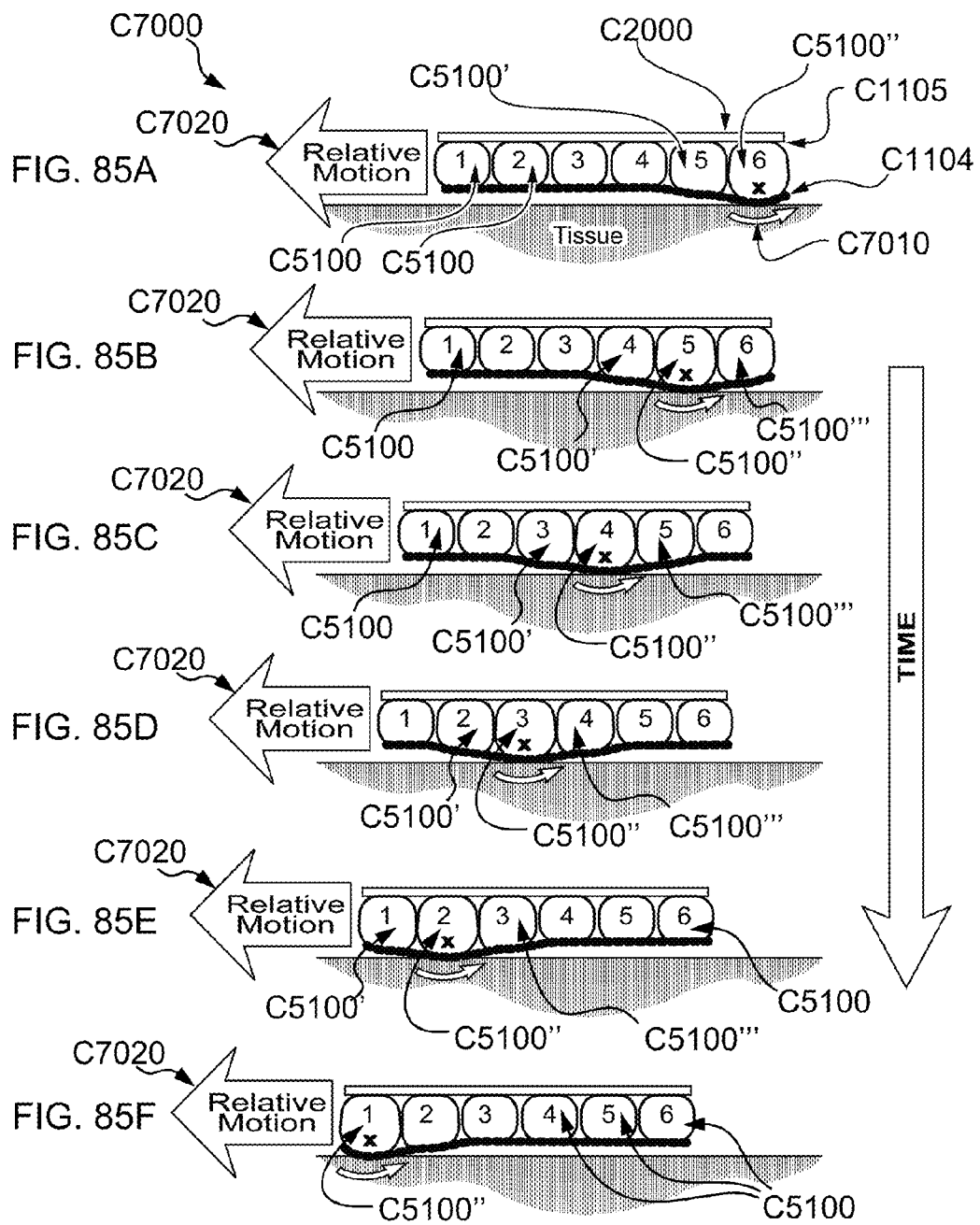

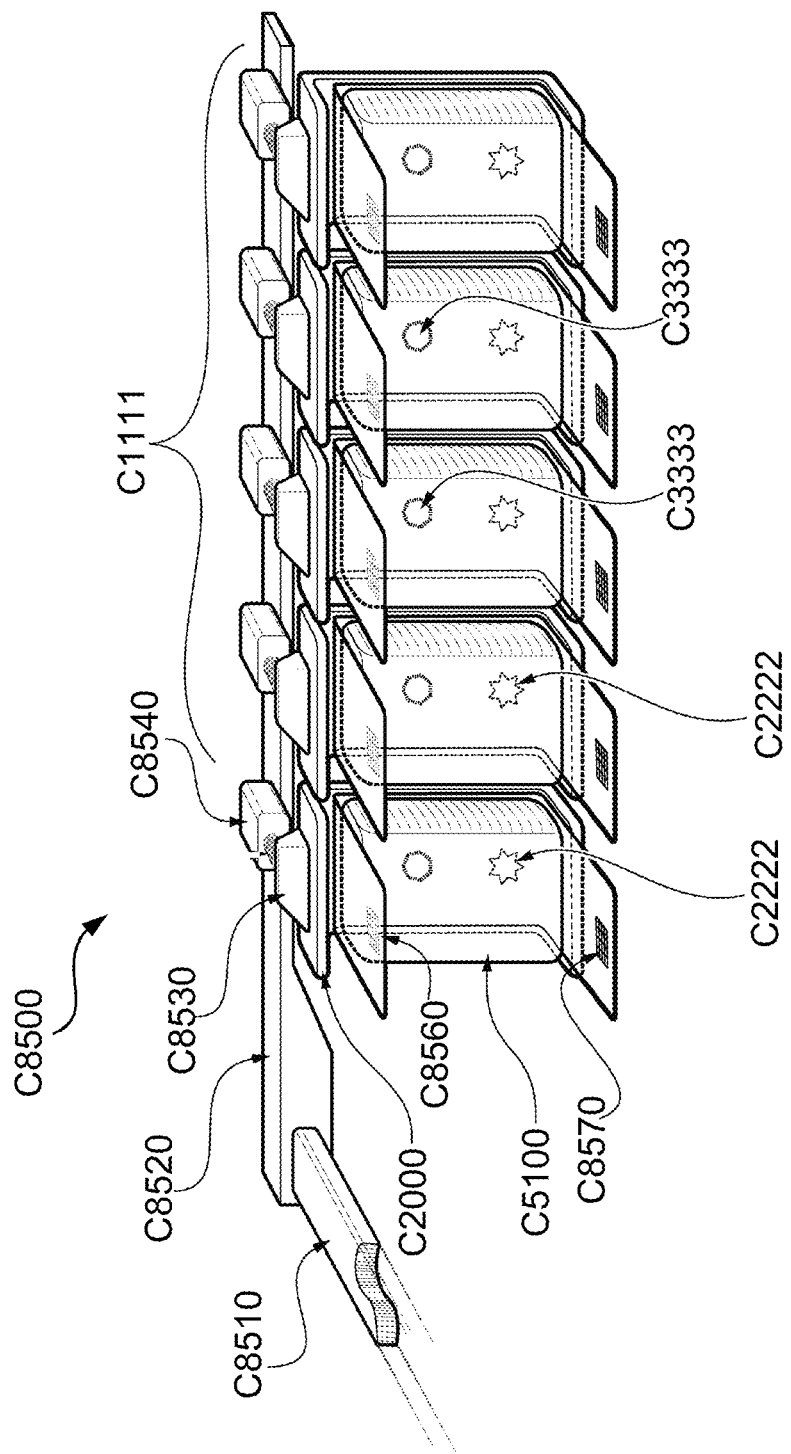

METHODS AND DEVICES TO DECREASE TISSUE TRAUMA DURING SURGERY

RELATED APPLICATIONS

The present application claims priority to U.S. Provisional Patent Application No. 61/127,520, entitled "COOLING PADS TO REDUCE PAIN AND INFLAMMATION AT SURGICAL INCISIONS," filed on May 14, 2008, which is incorporated herein by reference in its entirety.

The present application also claims priority to U.S. Provisional Patent Application No. 61/054,866, entitled "COOLING PADS TO REDUCE PAIN AND INFLAMMATION AT SURGICAL INCISIONS," filed on May 21, 2008, which is incorporated herein by reference in its entirety.

The present application also claims priority to U.S. Provisional Patent Application No. 61/127,598, entitled "DRUG ELUTING PADS TO REDUCE PAIN AND INFLAMMATION AT SURGICAL INCISIONS," filed on May 14, 2008, which is incorporated herein by reference in its entirety.

The present application also claims priority to U.S. Provisional Patent Application No. 61/133,669, entitled "PADS FOR PROTECTING TISSUES, SENSING TISSUE STATE, AND ACTIVE TISSUE MODULATION DURING MEDICAL PROCEDURES," filed on Jul. 1, 2008, which is incorporated herein by reference in its entirety.

The present application also claims priority to U.S. Provisional Patent Application No. 61/134,278, entitled "DRUG ELUTING PADS TO REDUCE PAIN AND INFLAMMATION AT SURGICAL INCISIONS," filed on Jul. 8, 2008, which is incorporated herein by reference in its entirety.

FIELD OF THE DISCLOSURE

The field of the disclosure relates to spreaders, retractors, and retraction devices used to deform tissue during surgery or other medical procedures.

BACKGROUND

Deformation of tissues is commonly performed during surgery or other medical procedures either to achieve surgical access or to specifically alter the dimensions of one part of the anatomy. Examples of deformations of tissue for surgical access include spreading ribs during a thoracotomy, spreading a bisected sternum during sternotomy, and separating the vertebrae of the spine for surgery on the intervertebral disk. Examples of deformation of tissues to alter the dimensions of the tissue include distraction to adjust the position of vertebrae. Such deformations will collectively be referred to as "retraction" here.

Spreaders, retractors, distractors, and even trocars (collectively called "retractors") can impose significant forces on surrounding tissues during retraction. The resulting strain on these tissues, and on associated tissues, such as the ligaments attaching ribs to vertebrae for example, can be large, leading to damage of these tissues, including the fracture of ribs and the rupture or irreversible deformation of ligaments and other fibrous tissues.

Retraction occurs in two different phases—deforming the tissue in a first retraction phase and holding the tissue at that deformation in a second retraction phase. Both are usually done with the same instrument. For example, a rib spreader is used both to force the ribs apart during a thoracotomy (first phase of retraction) and to hold the ribs apart during the surgical procedure (second phase of retraction). In the medical literature, both phases are frequently referred to as retraction.

Both phases of retraction traumatize tissue. Trauma from the first phase of retraction can include the rending and tearing of tissues; bones bend and break; muscles stretch beyond normal limits; ligaments and other connective tissues stretch and tear; nerves are stretched. Trauma from the second phase of retraction can include trauma arising from the force of the retraction device holding the tissue open and can include ischemia of the tissue due to elevated tissue pressure, blockage of nerves, and blockage of blood vessels causing ischemia in tissues distant from retraction.

Tissue trauma and ensuing complications resulting from both phases of retraction can be greater than the trauma resulting from the medical procedure that required the retraction. For example, thoracotomies are extremely traumatic, and can result in post-surgical pain and respiratory complications that exceed that of the thoracic procedure, such as a lung segmentectomy.

There is, therefore, need for improved devices, systems, and methods to perform one or both phases of retraction.

SUMMARY OF THE DETAILED DESCRIPTION

The above and other needs are met by several embodiments disclosed herein. In one embodiment, tissue is cooled around an incision. A pad with cooling means is placed onto the margin of an incision and cools the tissues at and near the margin of the incision during both the first and second phases of retraction.

In another embodiment, a retraction device adapted to retract tissue comprises at least one retraction member, with the at least one retraction member being able to operably engage the tissue to be retracted. A pad with cooling means is integrated with the retractor such that the tissues being retracted are cooled throughout the first and second phases of retraction.

In another embodiment, a trocar is fitted with a cooling device such that tissues cut and deformed on insertion of the trocar are cooled throughout a medical procedure.

In another embodiment, a retraction device includes at least one pad in contact with the margins of an incision. The pad is adapted to elute pharmacologically active compounds into the tissues at the margin of the incision to achieve beneficial outcomes, such as hemostasis or reduced inflammation, as examples.

In another embodiment, a thoracic retractor is fitted with pads that underlie the retractor blades of the retractor. The pads are adapted to both cool the tissue and to elute pharmacologically active compounds into the tissues at the margin of the incision.

In another embodiment, a retraction device is fitted with a pad having a gradient of stiffness modulus with the least stiff material apposed to the tissue to be retracted and the most stiff material apposed to the retraction device.

In another embodiment, a retraction device is fitted with a pad having fluid-filled columns embedded in an elastomeric material, with the columns being adapted to conform to the shape of a tissue when pressed against the tissue during the first and second phases of retraction.

In another embodiment, a retraction device includes an array of elastomeric bladders, each in communication with a hydraulic actuator controlled by a controller. Actuation of the hydraulic actuators permits inflation and deflation of the elastomeric bladders.

BRIEF DESCRIPTION OF THE DRAWINGS

FIGS. 2A and 2B show exemplary cooling pads for convective air cooling and for cooling with a thermoelectric device;

FIG. 4 shows an exemplary cooling pad having internal channels for circulation of a cooling fluid;

FIG. 6 shows a side view of an exemplary pad having a stiffened rolled edge for placement at the margin of an incision, a friction coating to prevent sliding along a patient's skin, and a clip for anchoring the pad to a surgical drape;

FIGS. 14A and 14B show an exemplary cooling pad that can be adjusted to different depths of incision;

FIG. 35 shows an exemplary drug-eluting pad with an overlapping margin that permits adjustment to incisions having different circumferences;

FIGS. 36A and 36B show an exemplary drug-eluting pad with fiber windings that permit adjustment of the length and width of the pad;

FIGS. 37A and 37B show an exemplary drug-eluting pad that can be adjusted to different depths of incision;

FIGS. 47A and 47B show exemplary drug-eluting pads fitted to the retractor blades of a thoracic retractor, where the drug-eluting pads have a rigid component, a hydrogel drug-eluting portion apposed to the cut tissues, and a cooling portion covering the skin overlaying the edge of the incision;

FIGS. 48A and 48B show an exemplary drug-eluting pad fitted to a retractor blade of a thoracic retractor, where the drug-eluting pad has a rigid component and blades adapted to penetrate the soft tissues overlaying the rib and to push against the rib;

FIGS. 50A and 50B show cross-sectional and oblique views of an exemplary drug-eluting pad fitted to the retractor blades of a thoracic retractor for sternotomy, where the drug-eluting pads have a rigid component and the drug-eluting pad is a hydrogel;

FIGS. 68A and 68B show another embodiment of an exemplary TED comprising steel rods mounted into an elastomeric pad;

FIGS. 85A through 85F show exemplary means by which a retractor blade can be made to move sideways by controlled activation of the elastomer bladders of the retractor blade shown in FIG. 77;

FIG. 90 shows an exemplary TED comprising a row of pressure bladders, each individually engaged with a motorized drive attached to a retractor arm, and each individually fitted with a variety of sensors.

DETAILED DESCRIPTION

A. Cooling Pads

Figure 1B:
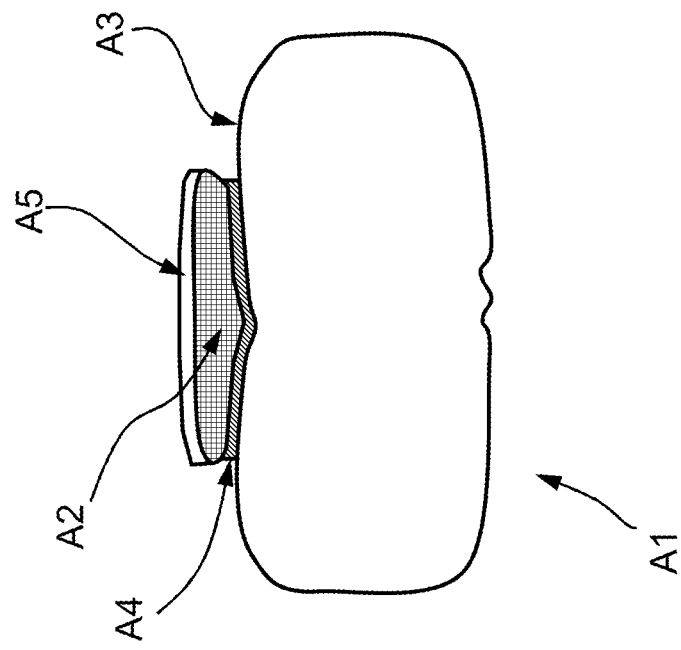
FIGS. 1A and 1B show an exemplary cooling pad that can be placed over the site of a planned incision to cool tissues before incision.

Surgery typically proceeds through an incision in the body wall that provides surgical access to the interior of the body where the bulk of the surgical procedure is performed. For example, for direct coronary artery bypass grafting, surgical access is provided by a sternotomy—the skin is cut, the sternum is bisected, and the two halves of the sternum are pried apart by a thoracic retractor called a sternal spreader. For an appendectomy, the abdominal skin and muscle layer is cut open and pulled back by a retractor to provide access to the appendix.

There is frequently post-surgical pain at the site of incision, known as "incisional pain". Incisional pain can be severe, requiring the administration of analgesics after surgery. Even for minimally invasive approaches (e.g., "keyhole" surgery and laparoscopy), port site pain (where the trocars and other instruments are inserted) is common. For some procedures, incisional pain can last long after surgery, leading to the definition of various pain syndromes, such as post-thoracotomy pain syndrome and chronic regional pain syndrome. Subsequently, post-surgical pain management places a large burden on health care and detracts from post-surgical quality of life for many patients.

The cause of incisional pain is not known. It is believed to be caused by a complex series of physiological processes arising from the trauma of incision and retraction. These include nerve damage, tissue damage from lack of perfusion due to the pressure of retraction (which is believed to lead to tissue anoxia, tissue reperfusion damage, etc.), and localized inflammation. Most of the proposed mechanisms of pain are initiated at the time of incision; however, ameliorative procedures are usually not initiated until hours after the incision. For example, during a thoracotomy, an incision is made between the ribs and a rib spreader is then used to pry apart the ribs. During retraction, considerable tissue trauma occurs, including stretching and breaking of ligaments and bending and sometimes breaking of ribs. Considerable force is required to pry apart the ribs and to hold them apart. Thus, tissue pressures in the tissues underlying the retractor blades are sufficiently high to block tissue perfusion. Intrathoracic procedures can last hours, and retraction is maintained throughout. After the procedure, retraction is relieved, the ribs are re-apposed and sewn back into position, and the muscles and skin over the incision are sutured back together.

Analgesia typically only begins at the conclusion of surgery, which is frequently hours after the incision is made. There has been growing use of techniques such as nerve block with anesthetics (e.g., epidural) immediately before surgery and of catheter delivery of opioid analgesics commencing immediately after surgery, but results have been mixed.

Embodiments disclosed herein include an improved means of reducing incisional inflammation and pain. In one embodiment, a cooling pad is optionally placed preoperatively over the site of an incision to locally cool the tissues affected by the incision. This pad is removed just before the incision is made. After the incision, a second cooling pad is immediately placed over the edges of the incision, or surrounding a trocar entry, and is kept on the edges of the incision throughout surgery. Surface and subcutaneous temperatures can be measured to regulate the cooling pad. The temperature of the pad can be controlled to avoid cold damage of tissues. At the surgeon's discretion, either or both cooling pads can be used.

A.1 Pre-Surgical Cooling Pad

Figure 1A:
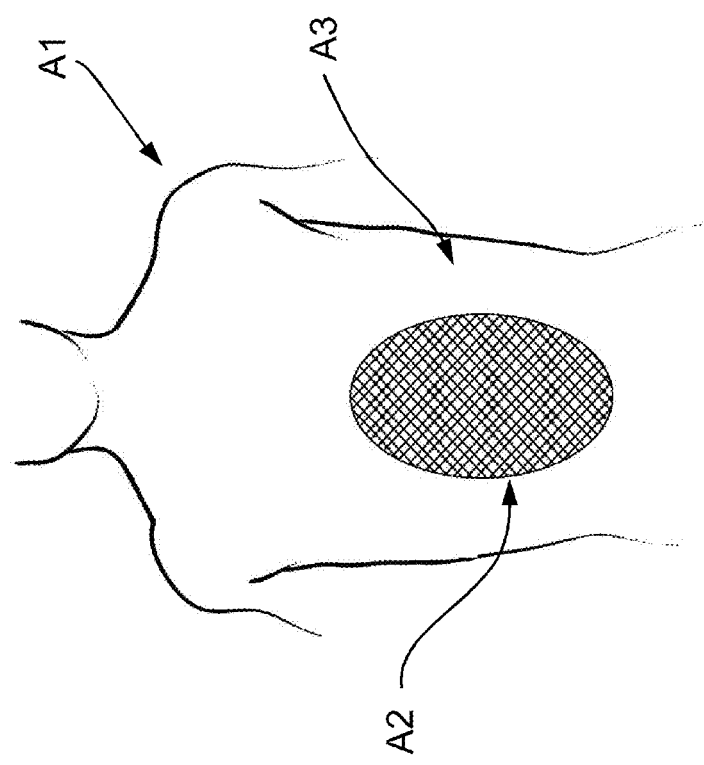

FIGS. 1A and 1B show top and side cross sections of an example of a Pre-Incision Cooling Pad (pre-ICP) A2. Pre-ICP A2 is capable of removing heat from the underlying skin A3 and subdermal tissues. As such, pre-ICP A2 is designed for efficient thermal transfer from skin A3 to pre-ICP A2, including conforming to the surface of the body A1 to maximize the area of contact and being constructed of materials having good thermal conductivity. Pre-ICP A2 may also optionally include a conducting medium A4, such as a fluid or gel (e.g., sterile saline, hydrogel, thermally conductive gel, etc.), placed between the surface of the pre-ICP A2 and the skin A3 to improve thermal conduction between the skin A3 and pre-ICP A2. Pre-ICP A2 may also have an insulating layer A5 over the top surface (i.e., the surface not in contact with the patient) both to reduce thermal transfer with the surrounding air, thereby improving thermal efficiency, and to prevent cooling of objects coming into contact with pre-ICP A2, such as tubing, surgical instruments, or the surgeon's hands.

As shown in FIG. 2A, pre-ICP A2 may also employ evaporative cooling, potentially enhanced by greatly increasing the evaporative surface area A6 (i.e., by sporting a convoluted or sculptured surface), by continuously supplying evaporating fluid from a reservoir, and by increasing convection of air over the surface of the pre-ICP A2. Pre-ICP A2 may also be covered with a tough, penetration resistant material A7 to prevent accidental puncture or cutting of the pre-ICP A2 or of the patient's skin A3.

As shown in FIG. 2B, means of cooling the interior of pre-ICP A2 include filling the interior of the pre-ICP A2 with a cooling medium A8, such as cool water or ice or with gels or solids having high thermal capacity (e.g., the polymer resin filling found in PolarPaks offered by sale from Adagen Medical International, Atlanta, Ga.) or with gels undergoing phase transitions at appropriate, cool temperatures. Cooling can also be achieved by endothermic chemical reactions of reactants comprising or contained within cooling medium A8 and initiated by rupture of an internal compartment A9 (such as the Nexcare Instant Cold Pack from 3M, Inc.). Cooling can also be achieved by circulating chilled water through pre-ICP A2 from an external recirculating cooling unit connected to pre-ICP A2 by tubing. Cooling can also be achieved by a Peltier thermoelectric unit A10 placed into pre-ICP A2, with heat removed from the warm side of the thermoelectric unit A10 by a heat sink A11 that is air-cooled or by a heat sink that is cooled by circulating water from an external cooling unit connected to the heat exchanger by tubing. Cooling can be to reduce the temperature of the tissues to be retracted by any appropriate temperature, e.g. 5° Celsius. below normal body temperature. Larger or smaller differences from body temperature can be established, such as 2° Celsius. below normal body temperature, 15° Celsius. below normal body temperature, or others.

Figure 3A:
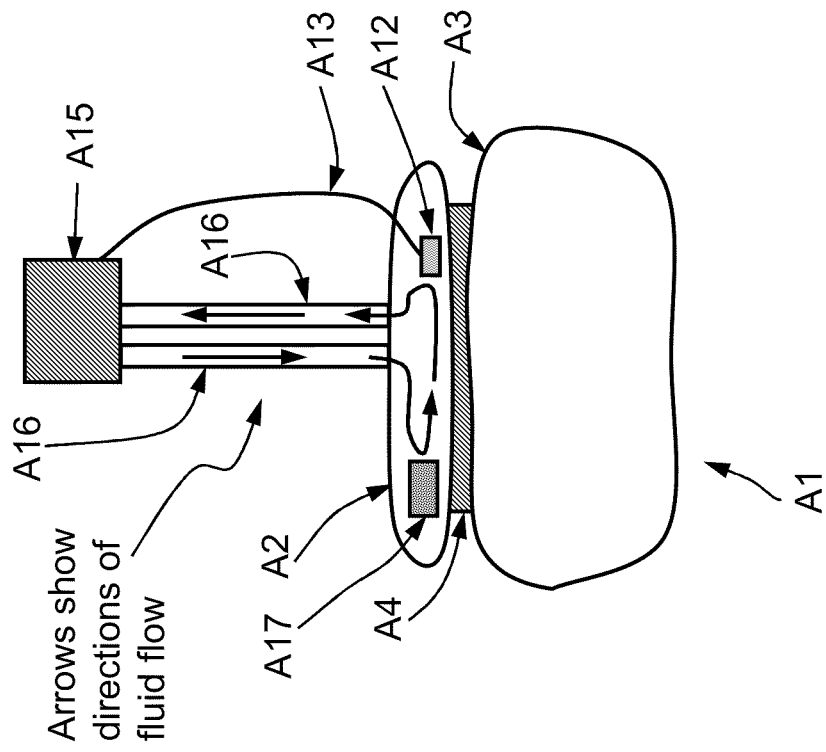
FIGS. 3A and 3B show exemplary cooling devices having thermoelectric cooling devices, recirculating cooling fluids, and temperature sensors.
Figure 3B:
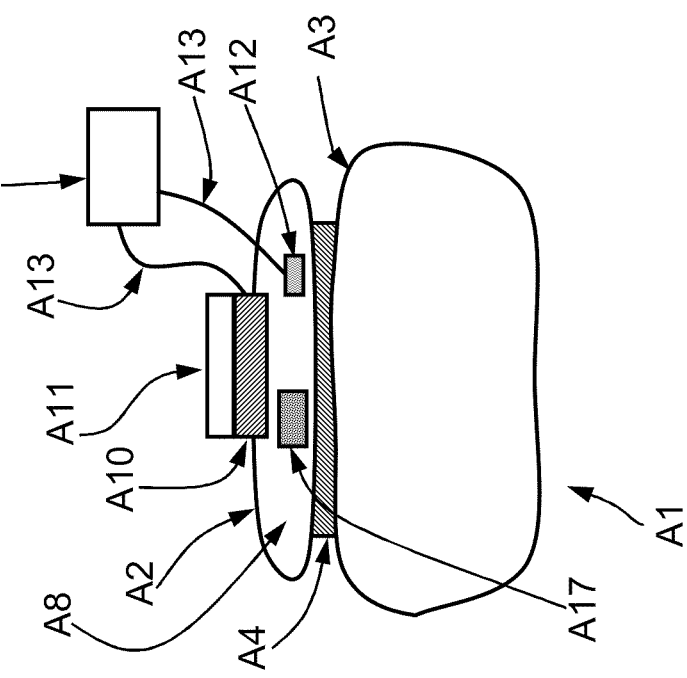

Also, as shown in FIGS. 3A and 3B, the temperature can also be regulated actively, by means of a temperature measuring sensor A12 connected by electrical connections A13 to a feedback circuit as part of the temperature regulation system A14 connected by electrical connections A13 and controlling the output of a cooling source, such as a thermoelectric unit A10, as shown in FIG. 3A, or of a recirculating cooling unit A15 connected by tubes A16, as shown in FIG. 3B. There can, optionally, be one or more heating elements A17 inside pre-ICP A2 and connected to temperature regulation system A14 (connections not shown) such that heating elements A17 are used to rapidly elevate the temperature inside pre-ICP A2, or to heat one portion of pre-ICP A2 (and thus the underlying tissue), or to counter a cooling unit (e.g., thermoelectric unit A10 or recirculating cooling unit A15) to control temperature. The temperature of the contents of pre-ICP A2 is measured by temperature measuring sensor A12 (e.g., a thermocouple, thermopile, microprocessor-based sensor, or other suitable sensor) placed inside pre-ICP A2 or an array of temperature measuring sensors A12 distributed over pre-ICP A2 for local measurement and control of temperature. The temperature of the skin can be measured by placing a temperature measuring sensor A12 inside pre-ICP A2, between the skin A3 and pre-ICP A2, including a temperature measuring sensor A12 placed on the surface of pre-ICP A2, or in direct contact with the skin A3, or beneath the surface of the skin A3, or within a conducting medium A4 between pre-ICP A2 and the skin A3.

Pre-ICP A2 can be constructed with a surface that contacts the skin, or a material overlaying the skin (such as an adhesive surgical drape, including Steri-Drape from 3M, Inc.), and is designed not to slide on that surface, including adhesive, frictional coatings, coatings or surfaces relying on van der Waal's interactions or hydrophobic/hydrophilic interactions, suction cups, Velcro, etc. Attachment devices, such as Velcro strips or suction cups or clips that attach to the skin or to surgical drapes, can also be placed around the periphery of pre-ICP A2.

FIG. 4 shows pre-ICP A2 containing a circulating cooling fluid A30, and the pre-ICP A2 is molded with internal walls A32 creating a serpentine channel A34 (or other shapes), permitting flow of the circulating cooling fluid A30 through the pre-ICP A2. This flow may be uni-directional, bidirectional, radial, dendritic, countercurrent, steady-state, cyclic, or any other pattern permitting the control and distribution of heat along the surface of pre-ICP A2, or through the volume of pre-ICP A2, the better to manage the distribution of heat on the surfaces of the body A1 of the patient (i.e., to act as a heat sink to remove heat, so as to cool the patient's tissues). To provide cooled circulating fluid A30, pre-ICP A2 is attached by a union A36 that permits attachment of an inlet tube A38 carrying the cooled circulating cooling fluid A30 into pre-ICP A2 and an outlet tube A39 carrying the warmed circulating cooling fluid A30 away from pre-ICP A2 to an external cooling unit A15 (not shown).

When thermoelectric units A10 are used to cool pre-ICP A2, then the thermoelectric units A10 can be oriented with a "cool side" directed to one surface of pre-ICP A2 and the "warm side" directed to the opposite surface of pre-ICP A2. The surface of pre-ICP A2 having the cool side is then placed against the patient's tissues, and the surface of pre-ICP A2 having the warm side can be configured to optimize heat transfer from the warm side of the thermoelectric unit A10. As described above, the warm side of pre-ICP A2 can be configured with components and structures to remove heat from the warm side of the thermoelectric unit A10 (e.g., a heat sink A11 that is air cooled or a heat sink A11 that is cooled by circulating fluid). Optionally, the warm side of pre-ICP A2 can also include structures and components to provide heat to other objects in the operating room, including fluids, surgical instruments, and the surgeon's hands. These structures can include pockets, bags, flaps, or projections for holding these objects to be warmed.

The pre-ICP A2 is removed just before the incision is made. Then the incision is made (or the trocar is inserted) and a second, cooling post-incision pad (post-ICP) is then placed on the edges of the incision to keep the edges of the incision, and the tissues immediately surrounding the incision, cool.

A.2 Post-Incision Cooling Pad, Post-ICP

Once an incision is made, treatment of the tissues, especially those at the margin of the incision, can slow or block inflammation responses initiated by the incision, by retraction that is performed after the incision, or by any other injurious action of gaining surgical access. Whether or not a tissue is cooled before incision, cooling and other treatments immediately after incision and throughout the procedure will best slow or block inflammation or other injurious responses by the tissue. Section A.2 describes new devices and means for cooling tissues after incision and throughout a procedure.

Figure 5B:
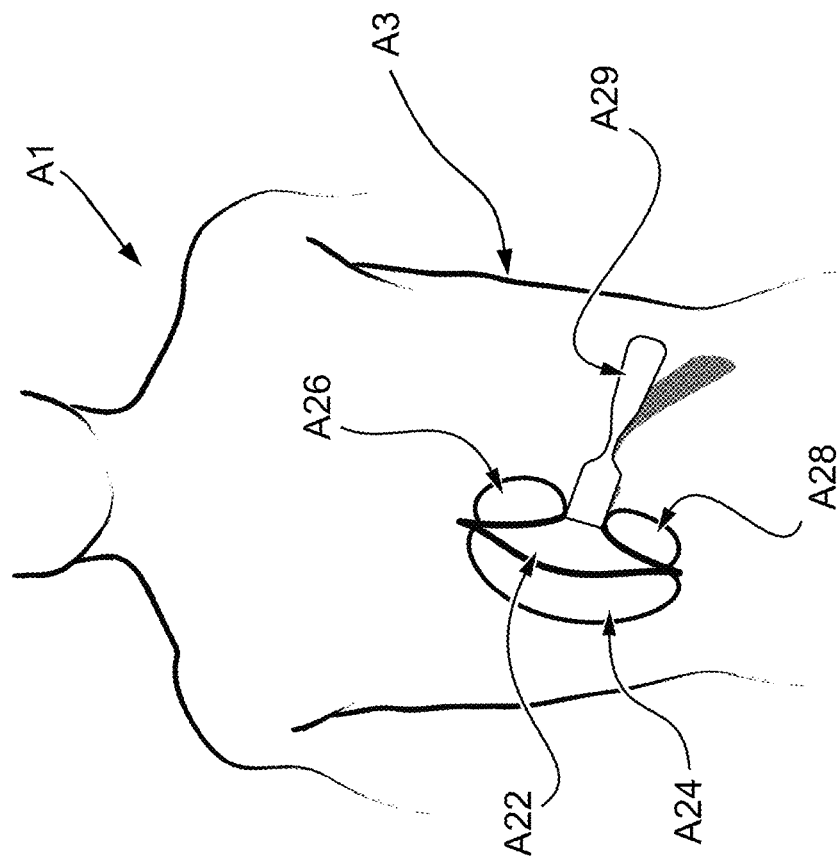
FIGS. 5A and 5B shows exemplary cooling pads that can be placed into an incision to cool the tissues at and surrounding the margin of the incision.
Figure 5A:
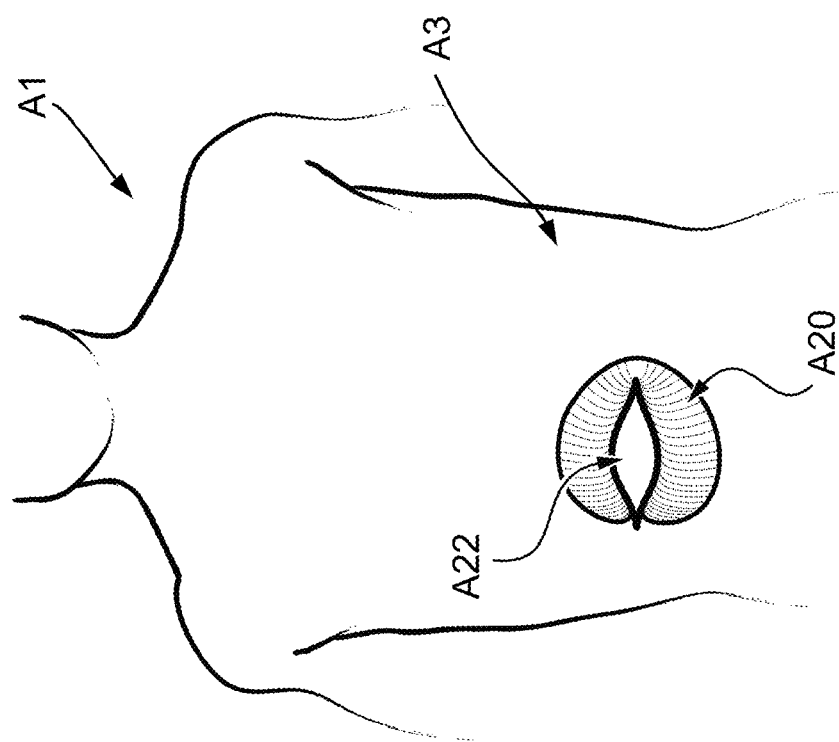

FIG. 5A shows a post-ICP A20 that is one piece that completely wraps the margins of an incision A22. Alternatively, as shown in FIG. 5B, a post-ICP A20 can be made of multiple pieces A24, A26, A28 (three pieces are shown, but more or less can be used), permitting positioning of the post-ICP A20 around the edges of the incision and including positioning around surgical instruments, such as a hand-held retractor A29.

All of the embodiments described for the pre-ICP A2 can be incorporated into the post-ICP A20.

Additionally, the post-ICP A20 can include means to facilitate placement of the post-ICP A20 on the edges of the incision A22 and for maintaining the position of the post-ICP A20, including means to prevent the post-ICP A20 from being knocked into, slipping into, or otherwise moving into the incision A22. These can include a combination of hooks or a stiffer, rolled edge to engage the edge of the incision A22 surfaces composed such as not to slide (including textured surfaces, adhesive coatings, frictional coatings, coatings relying on van der Waal's interactions or on hydrophobic/hydrophilic interactions), suction cups, Velcro, weighted saddles, etc. These means can also include attachment devices, such as Velcro strips, suction cups, or clips that attach to the skin or to surgical drapes, that can also be placed onto the post-ICP A20, for example around the periphery of the post-ICP A20.

FIG. 6 shows one embodiment of a post-ICP A40 having a stiffened, rolled edge A42 that engages the edge (i.e., margin) of an incision A44, a frictional coating A46 or surface preparation that engages a patient's skin A47 and/or the edge of the incision A44, and an anchoring means, such as a clip A48, that engages a surgical drape A50. Additionally, post-ICP A40 can be cooled by a thermoelectric unit A10 with a "cool side" directed into the post-ICP A40 (toward the skin A47) and the "warm side" directed to the opposite surface of post-ICP A40 (e.g., toward the top of the post-ICP A40). Thus the surface of post-ICP A40 nearest the cool side of thermoelectric unit A10 is then placed against the patient's tissues, and the surface of pre-ICP A2 having the warm side can be configured to optimize heat transfer from the warm side of the thermoelectric unit A10. As described above, the warm side of thermoelectric unit A10 can be configured with components and structures to remove heat from the warm side of the thermoelectric unit A10 (e.g., a heat sink A11 that is air cooled or a heat sink A11 that is cooled by circulating fluid). Optionally, the warm side of thermoelectric unit A10 can also include structures A41 and components to provide heat to other objects in the operating room, including fluids, surgical instruments, and the surgeon's hands. Structures A41 can include pockets, bags, flaps, or projections for holding these objects to be warmed.

The post-ICP A40 can include malleable components to facilitate conformation of the post-ICP A40 to the incision A22 and to the skin A47, thereby facilitating both heat transfer to the margins of the incision A44 and skin A47 and maintaining position on the contours of the skin A47. The malleable components can be metal, polymer, or any other material that holds a resting shape to which it is forcefully deformed. The malleable components can be formed into foils, wires, ribs, coils, or stays.

Figure 7:
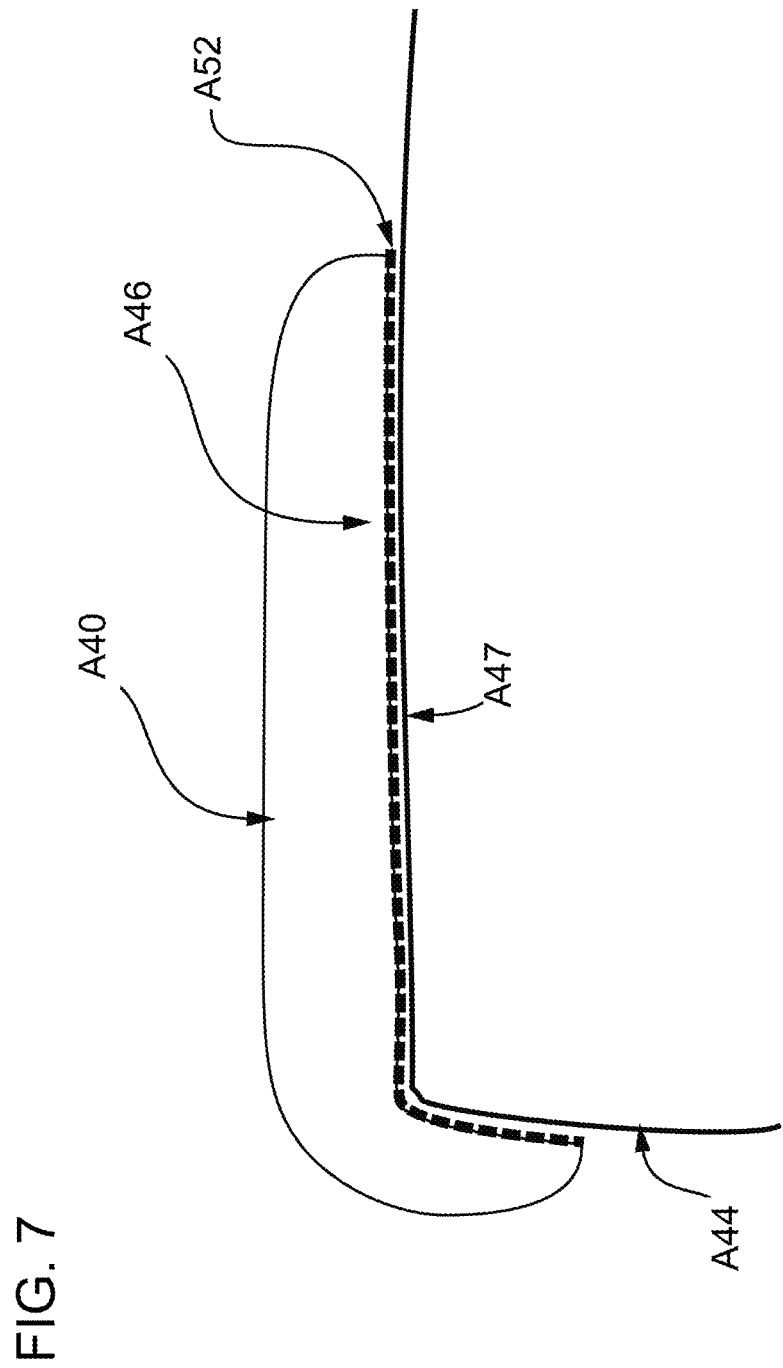
FIG. 7 shows a side view of an exemplary pad having both a metal foil and a friction coating on the surface apposed to the patient's skin.

FIG. 7 shows one embodiment of a post-ICP A40 having a malleable component, here shown as a malleable metal foil A52, on the bottom surface of the post-ICP A40 (the surface contacting the skin A47 and the edge of the incision A44). The metal foil A52 has high thermal conductivity, facilitating heat transfer, and it retains the shape of the post-ICP A40 when it is bent by the surgeon. The metal foil A52 can be "prepuckered," having small folds, creases, indentions, or other such structures (spaced periodically or aperiodically) to facilitate forming or conforming to three-dimensional, compound curved surfaces.

Figure 8A:
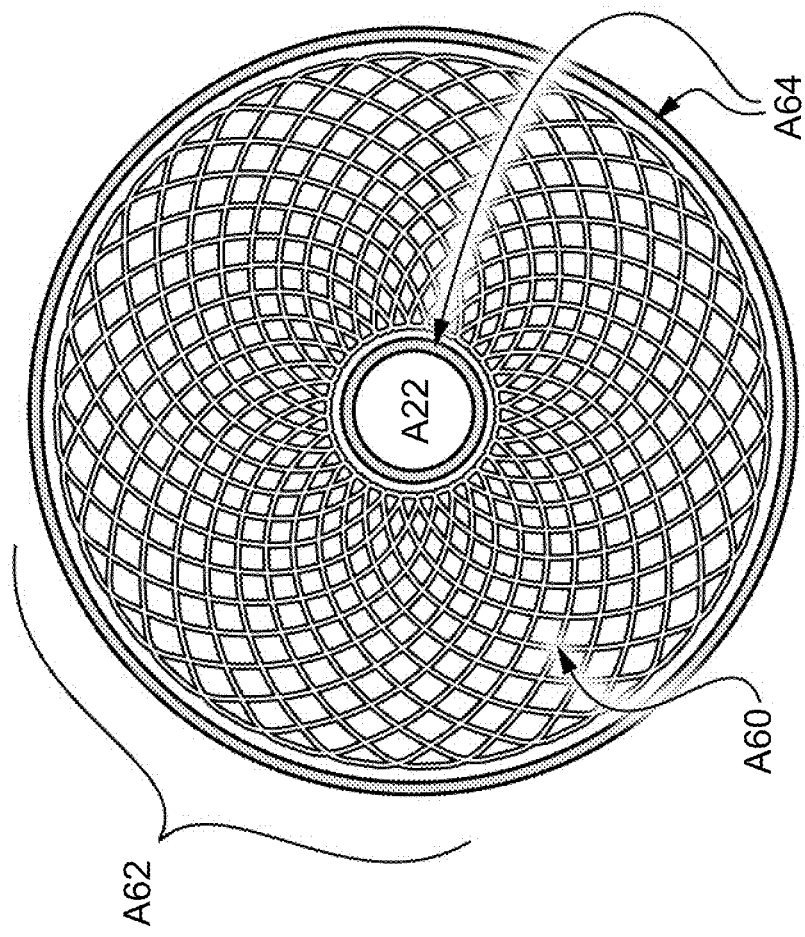
FIGS. 8A through 8D show top and cross-sectional views of exemplary cooling pads having a malleable wire mesh inside the pad to permit shaping of the pad or having a mesh of interspersed fluid-filled channels and malleable wires also to permit shaping of the pad.

FIG. 8A shows a top view of another embodiment of a post-ICP A62 having a wire mesh A60 inside the post-ICP A62. The surgeon can deform the wire mesh A60 to shape the post-ICP A62 to the incision A22. The wire mesh A60 can be free inside a membrane A64 of the post-ICP A62, or wire mesh A60 can adhere to one surface of the post-ICP A62 (as shown in side view in FIG. 8B). Conversely, as shown in top view in FIG. 8C, the post-ICP A62 can be an interwoven set of malleable wires forming a wire mesh A66 and flexible, fluid-filled tubes A68, with no membrane covering the wire mesh A66. The malleable wires of the wire mesh A66 permit the post-ICP A62 to be bent to shape to conform to the surface of the skin A47 and to the edges of the incision A22, and cooling fluid flows through the interspersed net of flexible, fluid-filled tubes A68 to remove heat from the area around the incision A22. The wire mesh A66 may also serve as a universal surface for attaching sutures or other means of attaining and sustaining retraction.

Figure 8B:
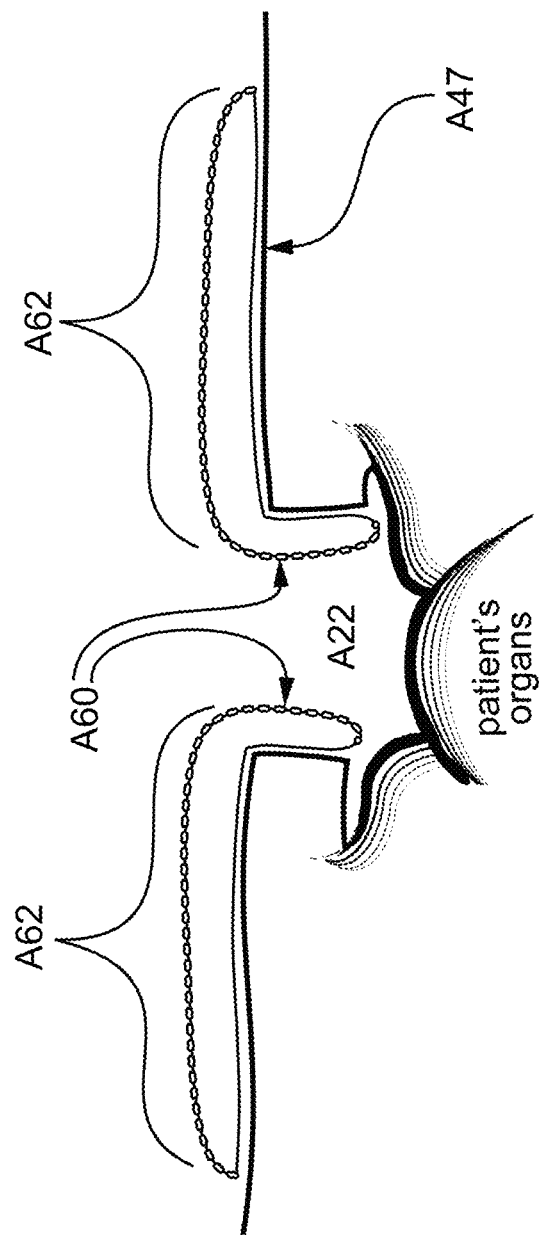

The shape of the wire mesh A60 or A66 can be substantially two-dimensional, as shown in FIG. 8B. Alternatively, as shown in side view in FIG. 8D, the shape of wire mesh (here numbered A69) can be substantially three-dimensional (i.e., volume-filling), having a membrane A64 filled with wire mesh A69, or alternatively a metal felt (not shown) having a composition similar to a low density steel or bronze wool, with the wire mesh A69 filling the lumen of the post-ICP A62 such that it can be pressed to shape but fluids can still circulate through the wire mesh A69. For high pressures, the membrane A64 of the post-ICP A62 can be bonded to the surface of the wire mesh A69, which then resists inflation of the membrane A64 under pressure.

Figure 9A:
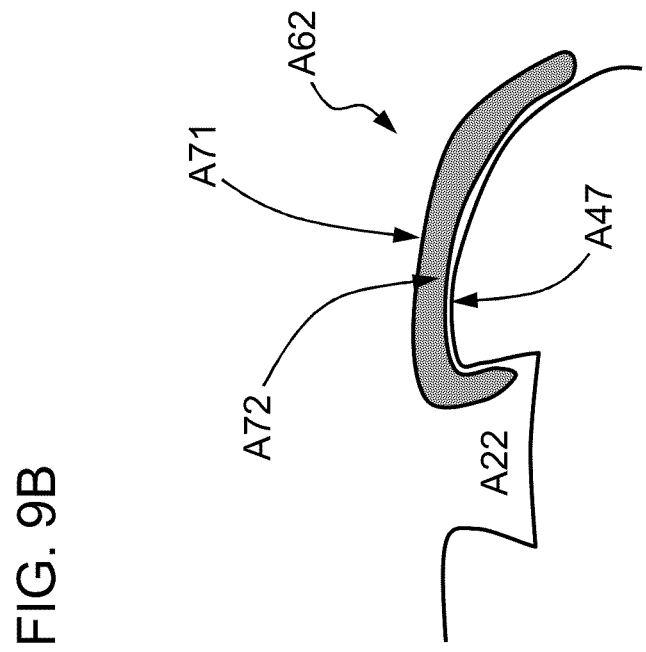
FIGS. 9A through 9C show exemplary cooling pads made of pliable and deformable materials.
Figure 9B:
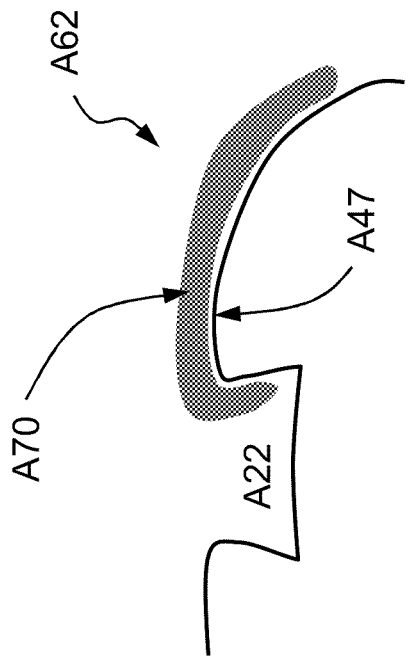
Figure 9C:
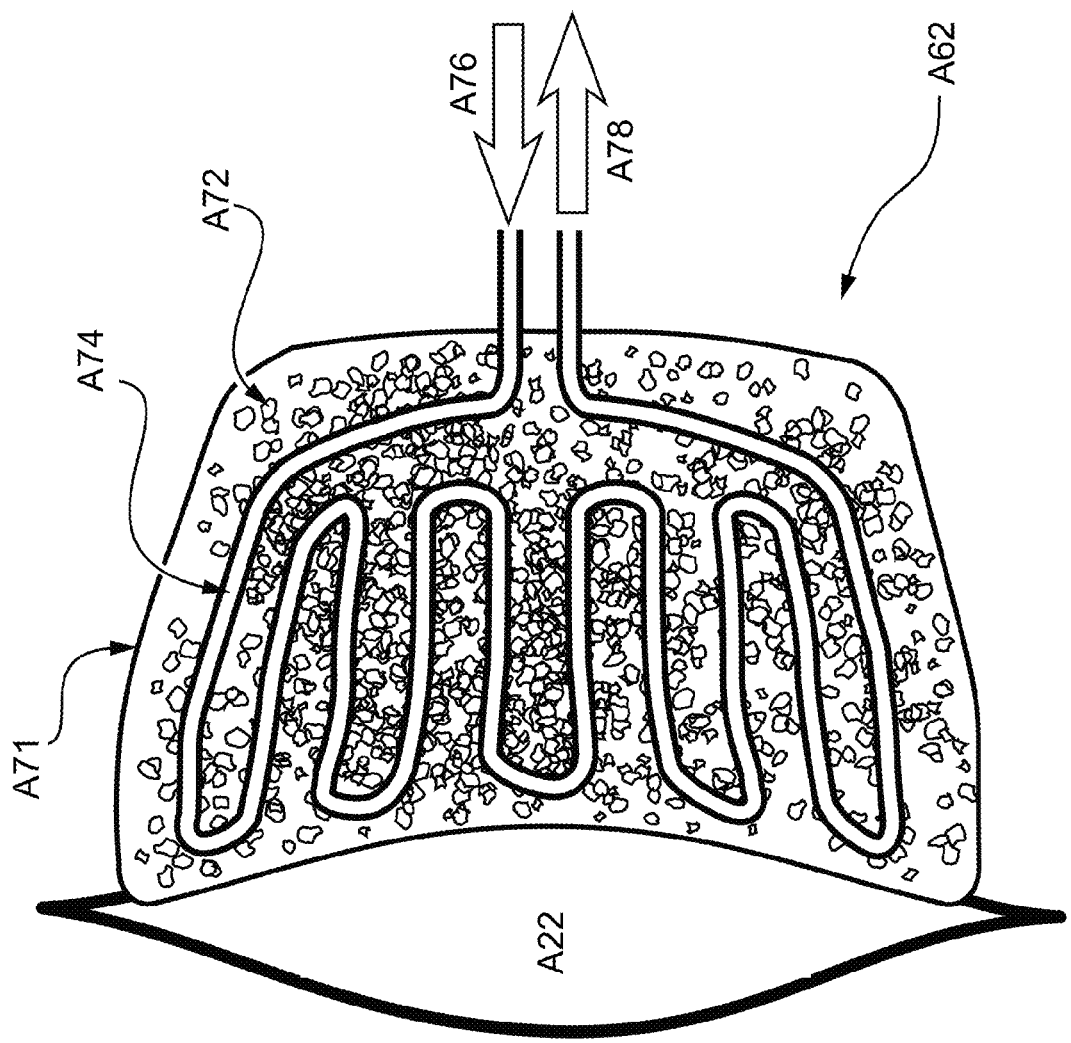

Another means of making a post-ICP A62 pliable to permit shaping by a surgeon is shown in FIG. 9A. Post-ICP A62 can be composed of a pliable material A70, such as putty, or to have the post-ICP A62 be a membrane A71 filled with a pliable material A70 or with granules A72. Thus post-ICP A62 can be shaped by the surgeon to the shape of the incision A22. Preferably pliable material A70 or granules A72 have high thermal conductivity. Such pliable material A70 or granules A72 can include tubing A74 coursing through pliable material A70 or granules A72 to carry circulating fluid to and from a recirculating cooling unit A15. For example, as shown in FIG. 9B, the post-ICP A62 can have a membrane A71 filled with polymeric granules A72, like the polymer resin filling found in PolarPaks offered by sale from Adagen Medical International (Atlanta, Ga.), in which the polymeric granules A72 move past one another to permit easy deformation of the post-ICP A62. Optionally, as shown in FIG. 9C, flexible tubing A74 coursing through the polymeric granules A72 inside the post-ICP A62 can carry cooling fluid A30 to (A78, outflow from the post-ICP A62) and from (A76, inflow to the post-ICP A62) a recirculating cooling unit A15 (such as in FIG. 3B).

Figure 8C:
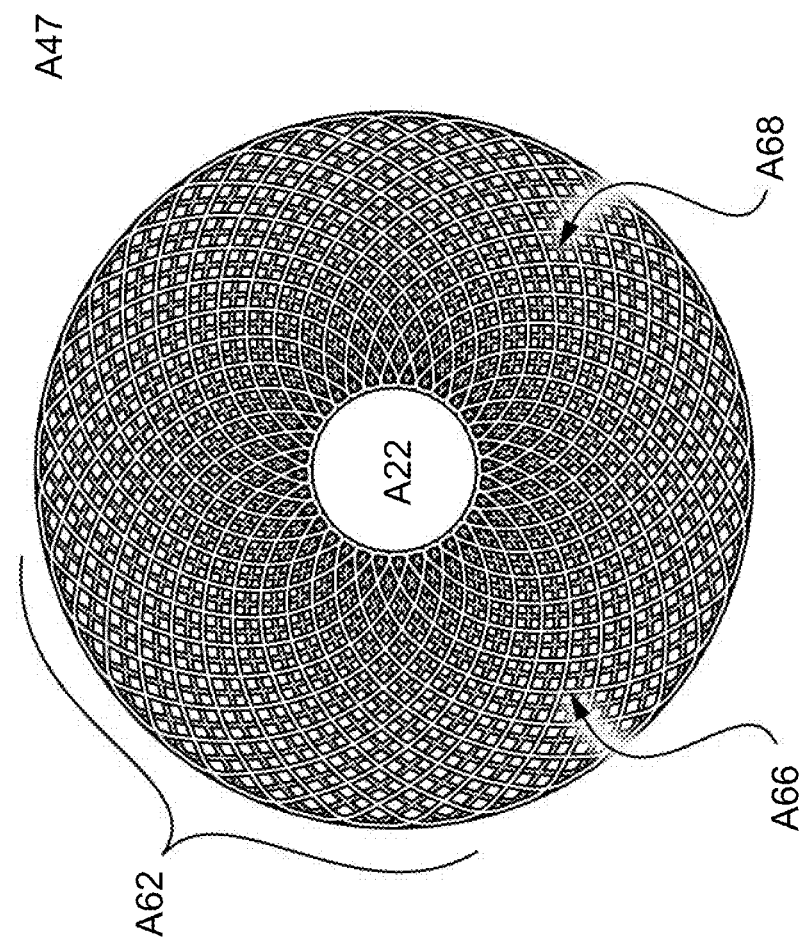
Figure 8D:
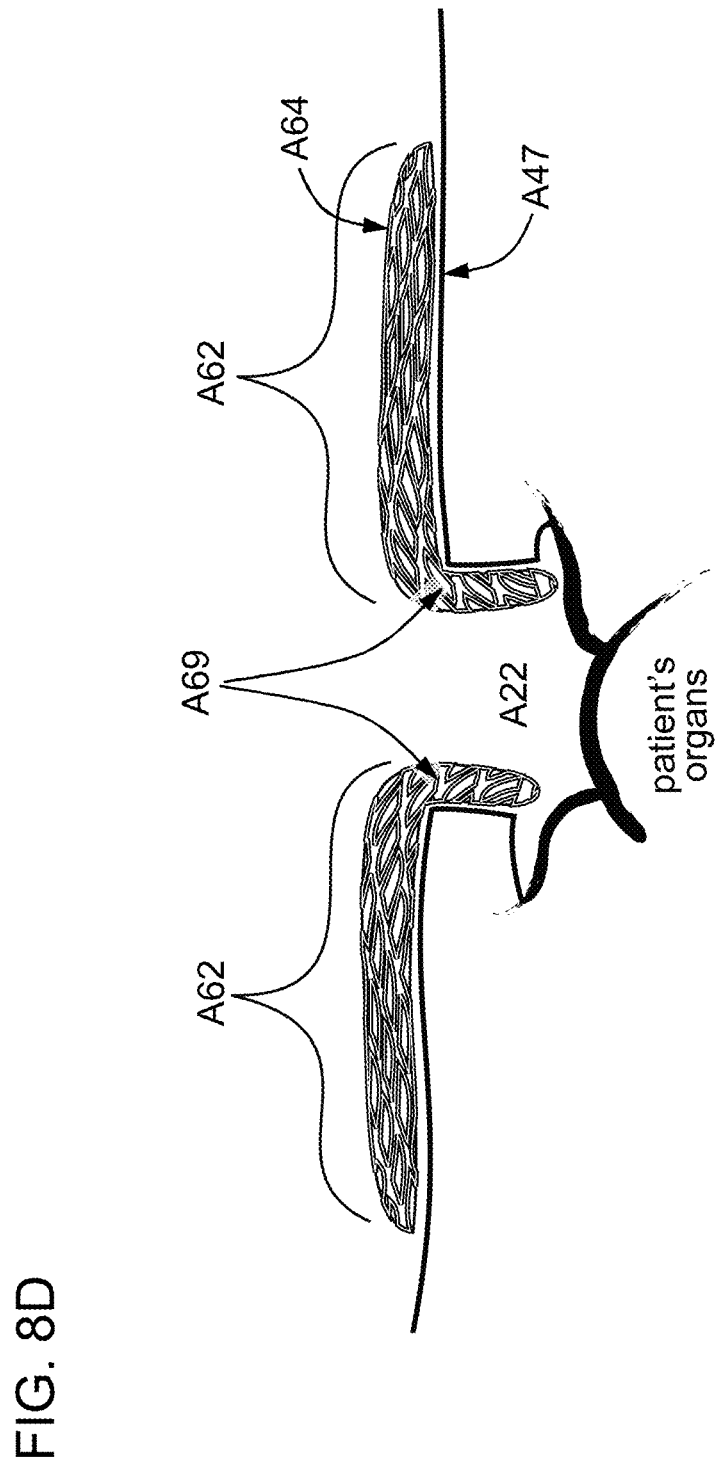
Figure 10A:
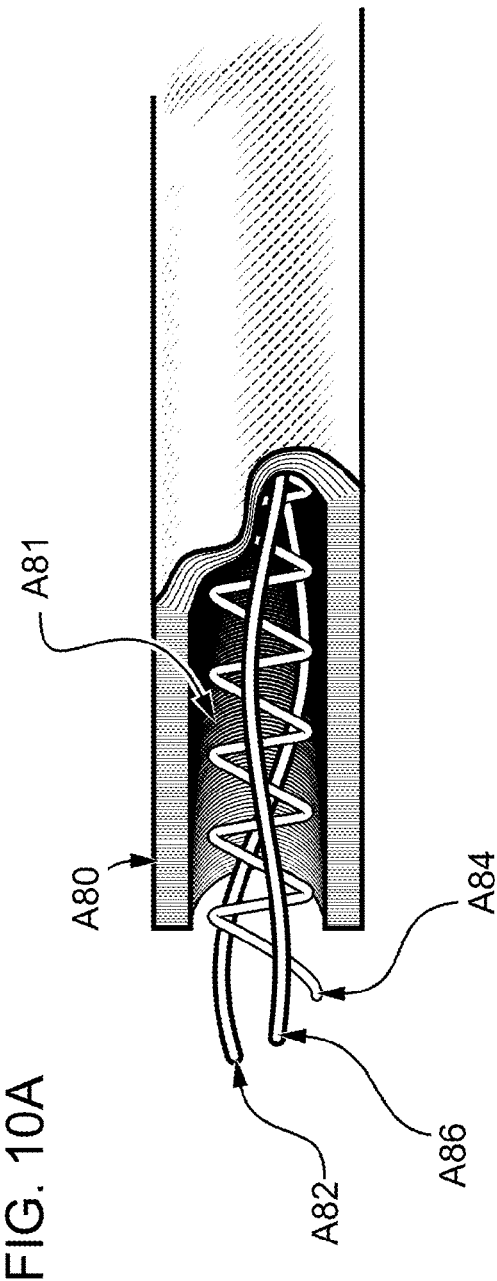
FIGS. 10A through 10C show exemplary tubing in which the tubing carries cooling fluid but also contains filamentous components with separate functions, such as heating or sensing.
Figure 10B:
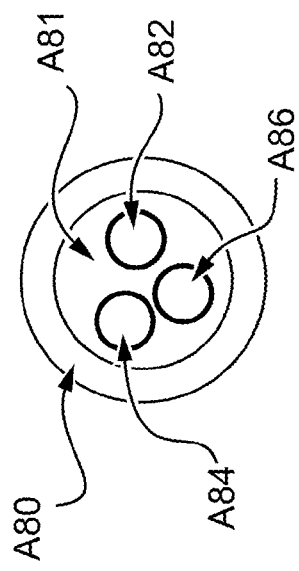
Figure 10C:
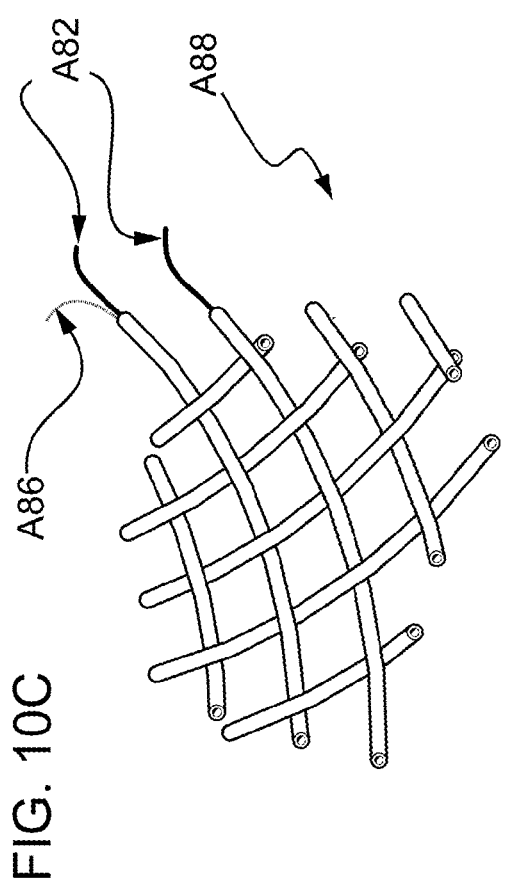

A post-ICP A62 containing fluid-filled tubes, whether the tubes are part of a mesh (as shown in FIG. 8C) or are distributed through some medium filling a membrane A71 (such as in FIG. 9C), can have components placed inside the tube to provide other advantageous features. For example, as shown in FIGS. 10A and 10B, a tube A80, such as an elastomer tube, can have various filamentous components coursing inside a fluid-filled lumen A81 of the tube A80. These filamentous components can include a malleable wire A82 to retain a bend in the tube A80, a heat management cable A84 (such as a heating wire), and a sensing wire A86. Such tubes A80 containing multiple filamentous components can then be woven into more complex arrays, such as a crossed array A88 as shown in FIG. 10C. Alternatively, these same filamentous components might be helically woven around the tubes A80.

Figure 11:
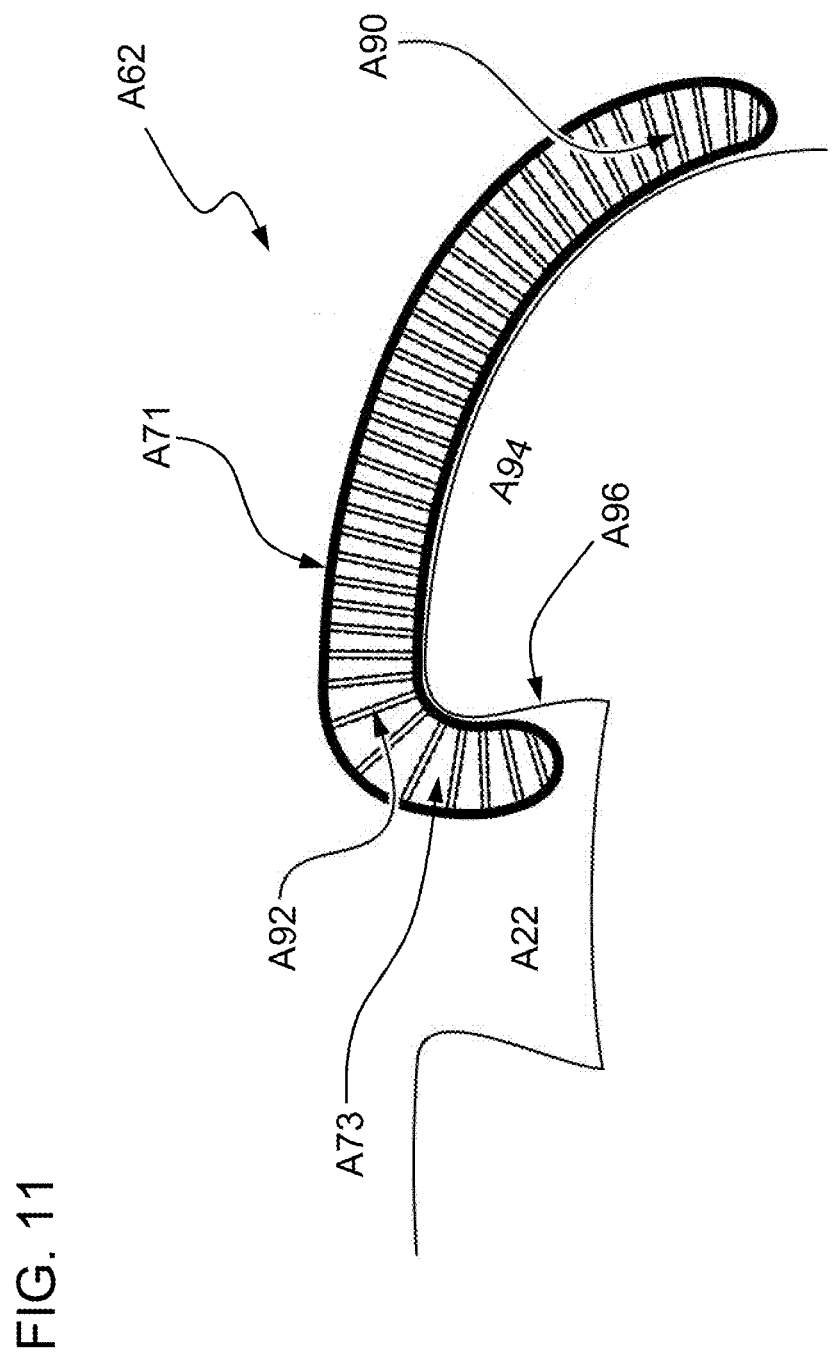
FIG. 11 shows an exemplary liquid-filled cooling pad in which internal struts prevent pooling of the liquid.

As shown in FIG. 11, when a post-ICP A62 is a membrane A71 filled with fluid A73 and placed on the patient's body wall A94 such that one part of post-ICP A62 is higher than the other, then fluid A73 would tend to pool in one portion of the post-ICP A62, causing another portion of the post-ICP A62 to empty. To resist such pooling, the post-ICP A62 can include internal struts, fibers, or other reinforcements that act as internal tension-resisting elements A90 that resist swelling of the post-ICP A62 and also as internal compression-resisting elements A92 that resist emptying of the post-ICP A62. Further, one may arrange these internal tension A90 and/or compression-resisting A92 elements to provide, permit, or prevent specific shapes that the post-ICP A62 may take, for example the internal tension-resisting elements A90 or internal compression-resisting elements A92 can be serially and obliquely arranged to encourage the curl of the post-ICP's A62 edge around the margin of an incision A96.

Figure 12:
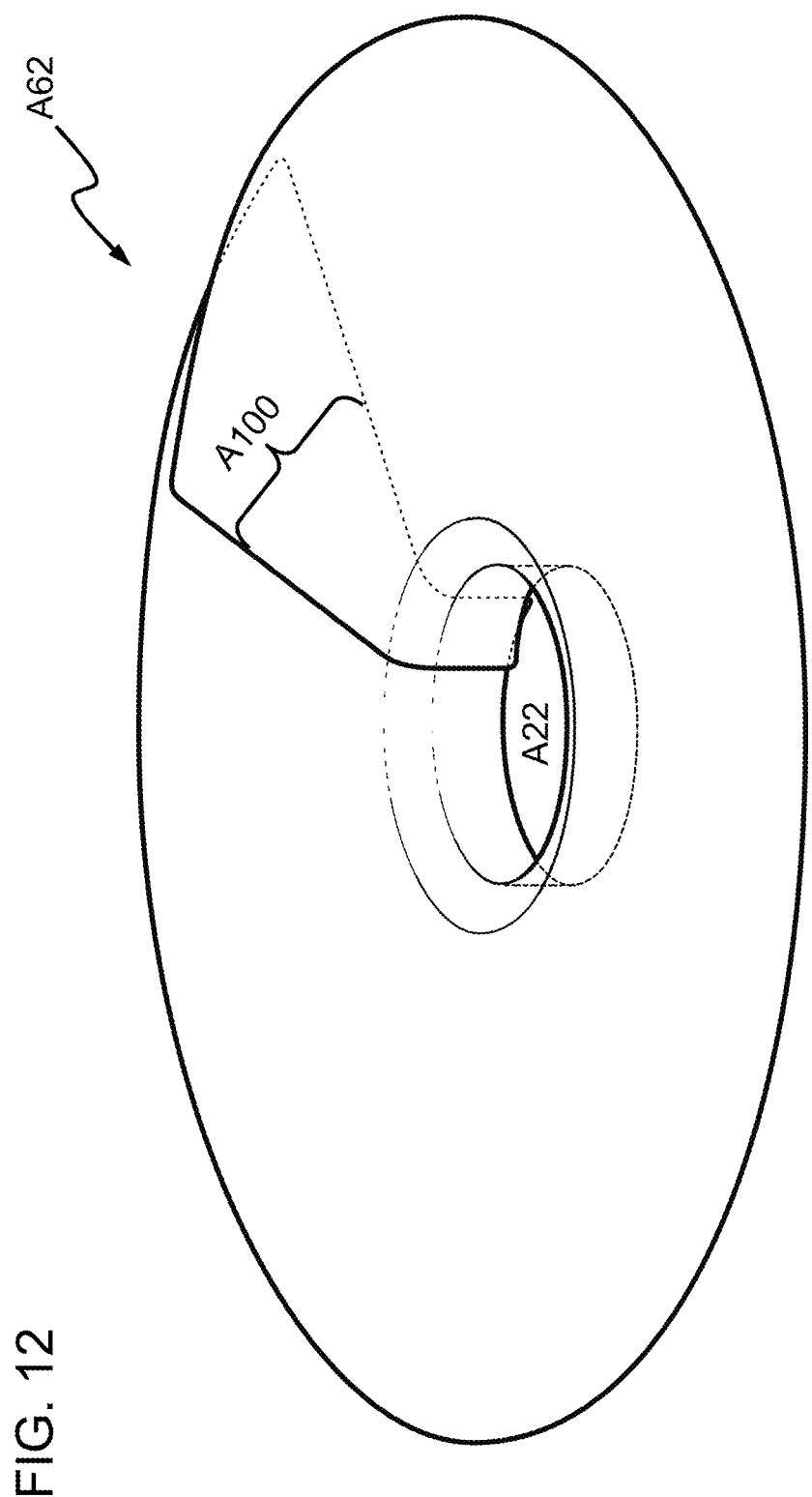
FIG. 12 shows an exemplary cooling pad with an overlapping margin that permits adjustment to incisions having different circumferences.
Figure 13A:
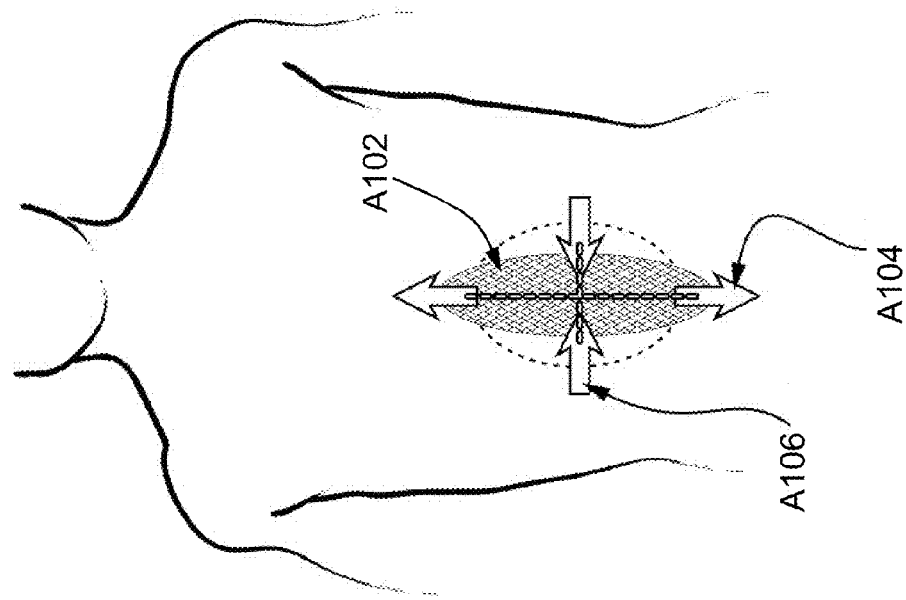
FIGS. 13A and 13B show an exemplary cooling pad with fiber windings that facilitate adjustment of the length and width of the pad.
Figure 13B:
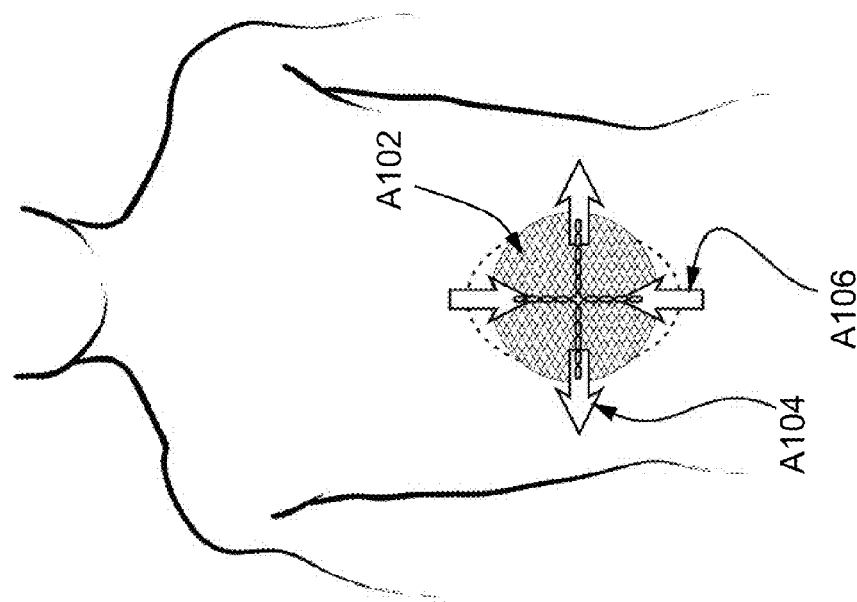

A post-ICP A62 can be adjusted to match the circumference of an incision A22 by overlapping itself, as shown in FIG. 12. Such a post-ICP A62 has an overlapping region A100 such that post-ICP A62 can automatically adjust to the changing circumference of an incision A22 as it is retracted to provide surgical access. Alternately, as shown in FIGS. 13A and 13B, the post-ICP A62 can have a helically wound fiber surface A102, or the post-ICP A62 can possess a surface made of a bias-cut, warp and weft woven fabric, permitting adjustment of length, whereby pulling the post-ICP A62 to elongate it on one axis A104 causes the post-ICP to shorten on the perpendicular axis A106 (and vice versa, as shown in FIG. 13B). More complex geometries are possible. Alternately, the post-ICP A62 can be like a piece of tube, flattened tube tape, or rope (not shown) that is cut to length, with the cut end being closed by mechanical means, such as a clip.

The portion of the post-ICP A62 that wraps the edge of the incision A44 can be configured for surgeries requiring incisions to different depths and penetrating through different tissues. As shown in FIG. 14A, when the incision is through only skin A47 or some other thin tissue, then the portion of the post-ICP A62 that wraps the edge A44 of the incision A22 extends only a short distance into the incision A22. When the incision A22 is through skin and an underlying muscle layer or thick adipose layer or other thick tissue, the portions of the post-ICP A62 wrapping the edge A44 of the incision A22 can extend down far enough to cover the deeper edge A44 of the incision A22 through both the skin and the muscle, as shown in FIG. 14B.

Figure 15:
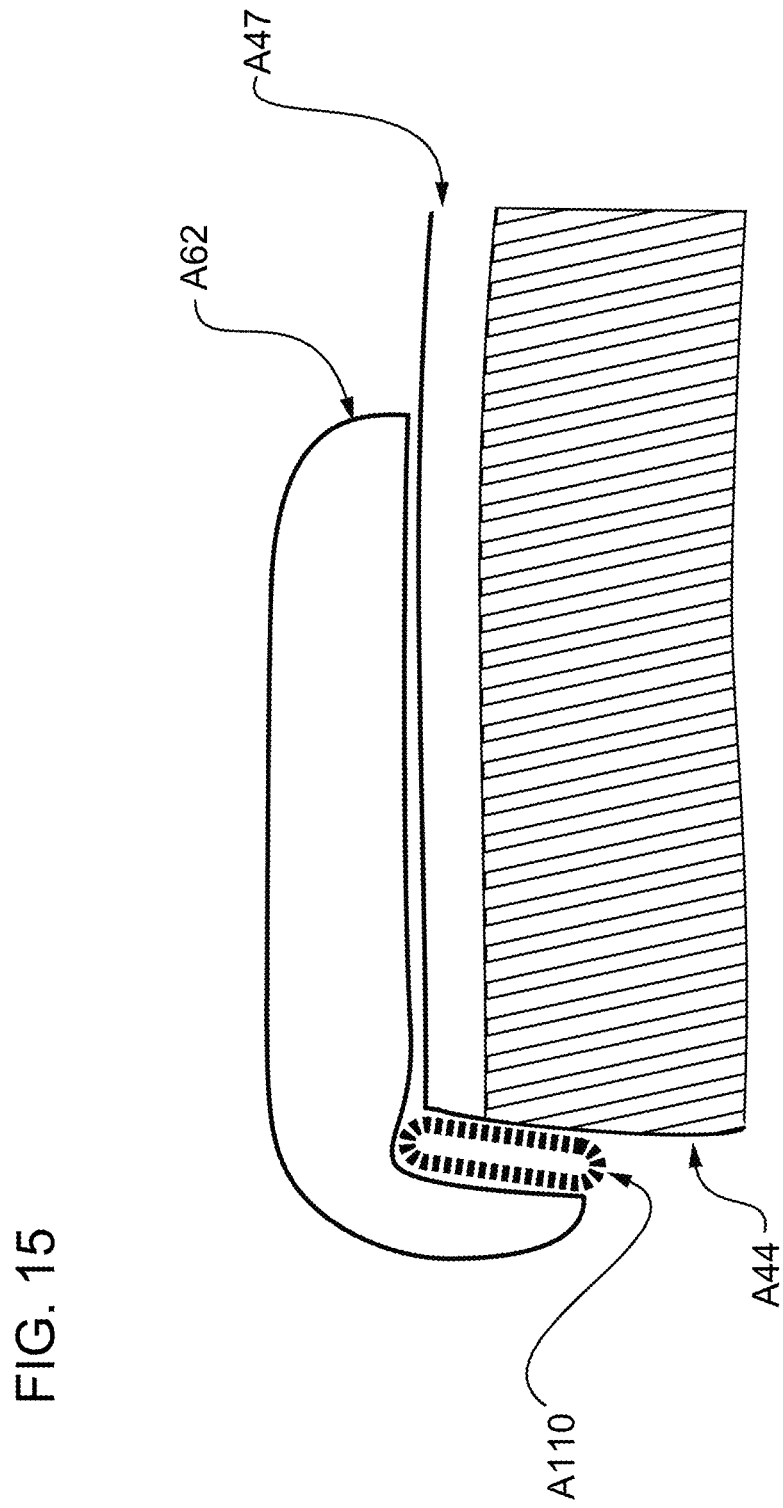
FIG. 15 shows an exemplary cooling pad having a fluid-saturated sponge to prevent dehydration of tissues at the wound margin.

FIG. 15 shows a post-ICP A62 that includes means to prevent dehydration of tissues facing the edge A44 of the incision A22, including having the post-ICP A62 constructed of vapor impermeable materials. The post-ICP A62 can also have a felted or sponge-like layer A110 to retain fluids, such as sterile saline, that acts both as a hydrating fluid and as a thermally conducting fluid.

Cooling post-ICPs A62 can be transparent, or can have transparent windows, and be filled with transparent fluids, allowing the surgeon clear view of the tissues under the cooling post-ICP A62.

Figure 16:
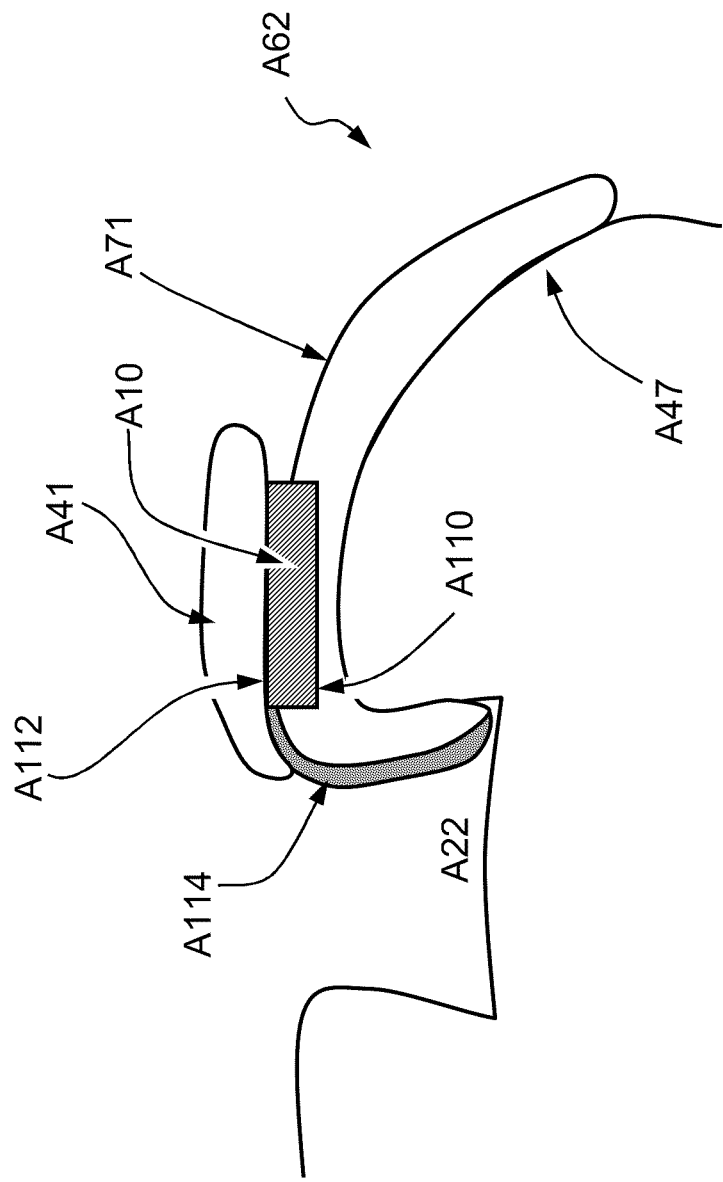
FIG. 16 shows an exemplary cooling pad having a thermoelectric cooling device and a surface adapted for warming a surgeon's hands.

A post-ICP A62, like the pre-ICP A2 (such as in FIG. 3A), can be cooled by a thermoelectric unit A10. As shown in FIG. 16, the thermoelectric unit is placed such that its cold side A110 faces the patient's tissues and its warm side A112 is attached, for example, to a structure A41 that is to warm something in the surgery. In this example, the structure A41 is shown as being a warming plate, made of a thermally conductive material, that a surgeon places his/her hands against to warm the hands throughout an operation. Optionally, the warming plate shown as structure A41 can be a conformable foil or other conformable materials permitting the pre-ICP A62 to better conform to the incision A22. Thus, the thermoelectric unit A10 can serve the functions of both a cooler of the patient's tissues and a hand warmer for the surgeon. Configurations can include multiple thermoelectric units A10 arrayed for optimal cooling of the tissues. Optionally, an insulating layer A114 can cover the top of the membrane A71, separating the cold post-ICP A62 from the warm structure A41 and the surgeon's hands when placed into the incision A22.

A.3 Post-Incision Cooling Pad Integral with Retractor

Retraction is used in surgery to move or otherwise deform tissues to gain surgical access. For example, to gain access to the heart or lungs, a sternotomy is commonly performed. Retraction is then maintained throughout the procedure. Retraction is performed with a device variably known as a retractor, spreader, distractor, and other names. For all methods and instruments of retraction, it is desirable to cool the tissue before and during retraction, possibly including the entire duration of the procedure.

In this Section A.3, new devices and means of integrating cooling pads with retractors to cool tissues before and during retraction, optionally spanning the entire duration of the surgical procedure are described.

Figure 17:
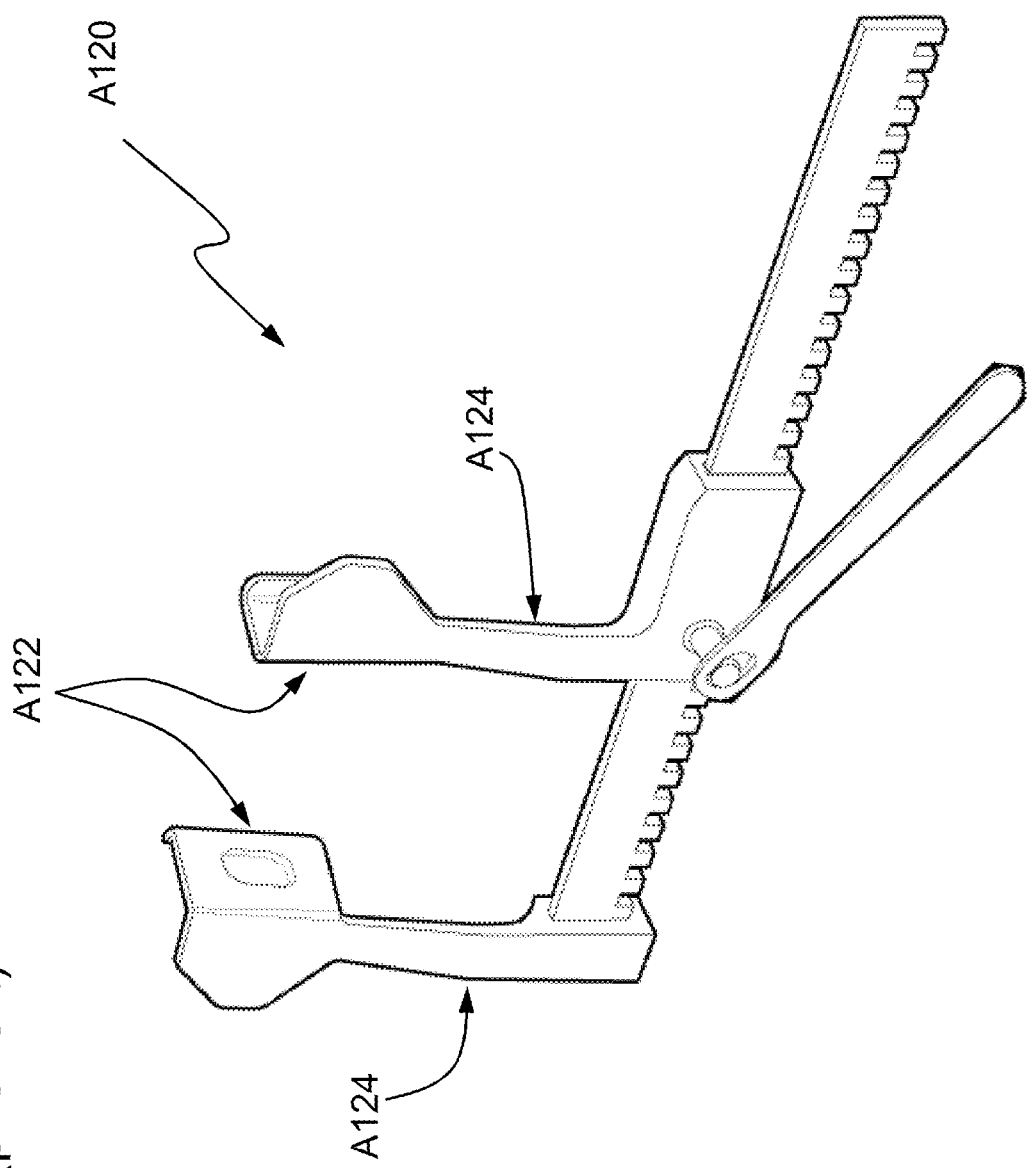
FIG. 17 shows an example of a Finochietto thoracic retractor in the prior art.
Figure 18:
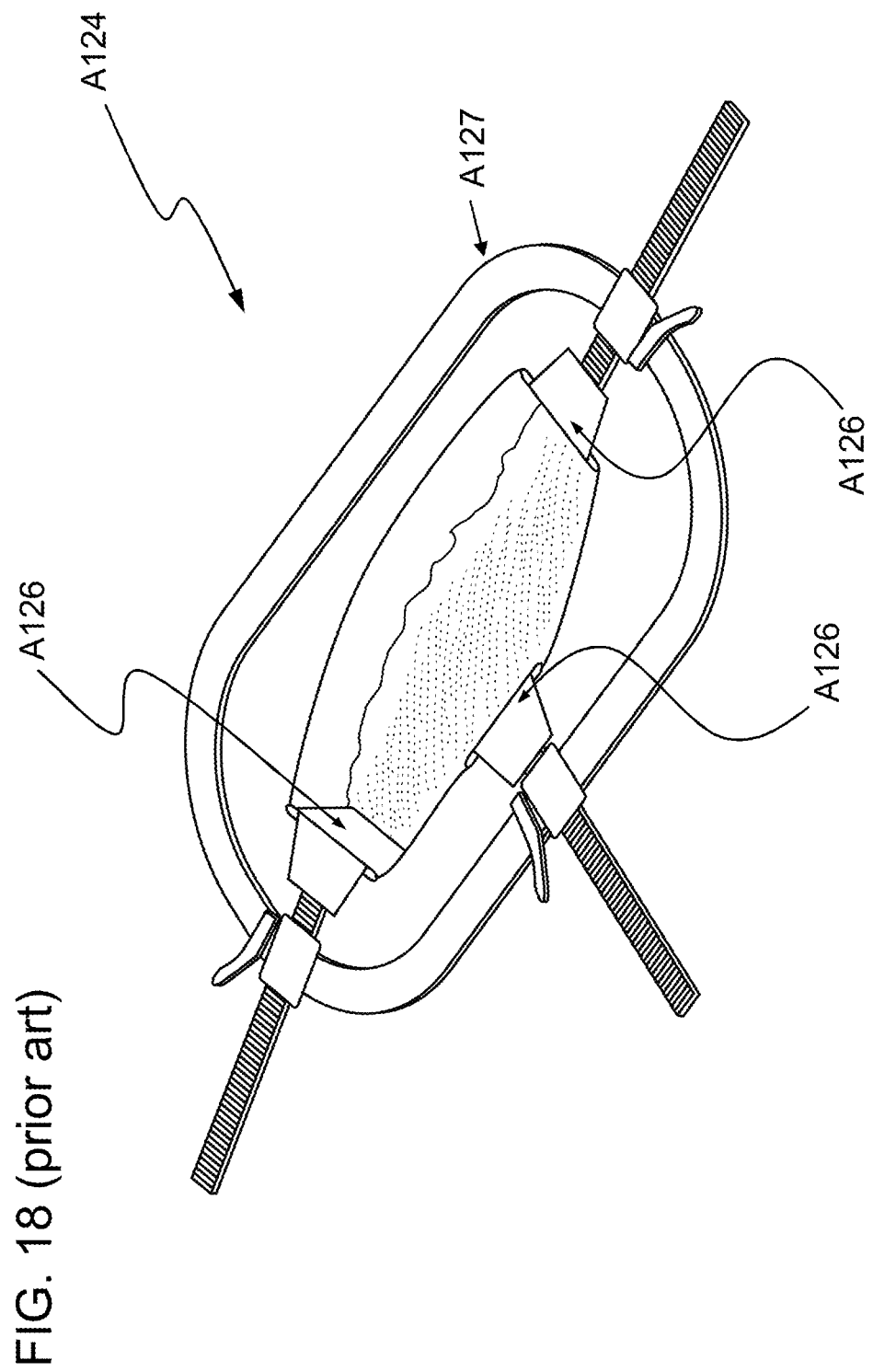
FIG. 18 shows an example a ring retractor for abdominal surgery in the prior art.
Figure 19:
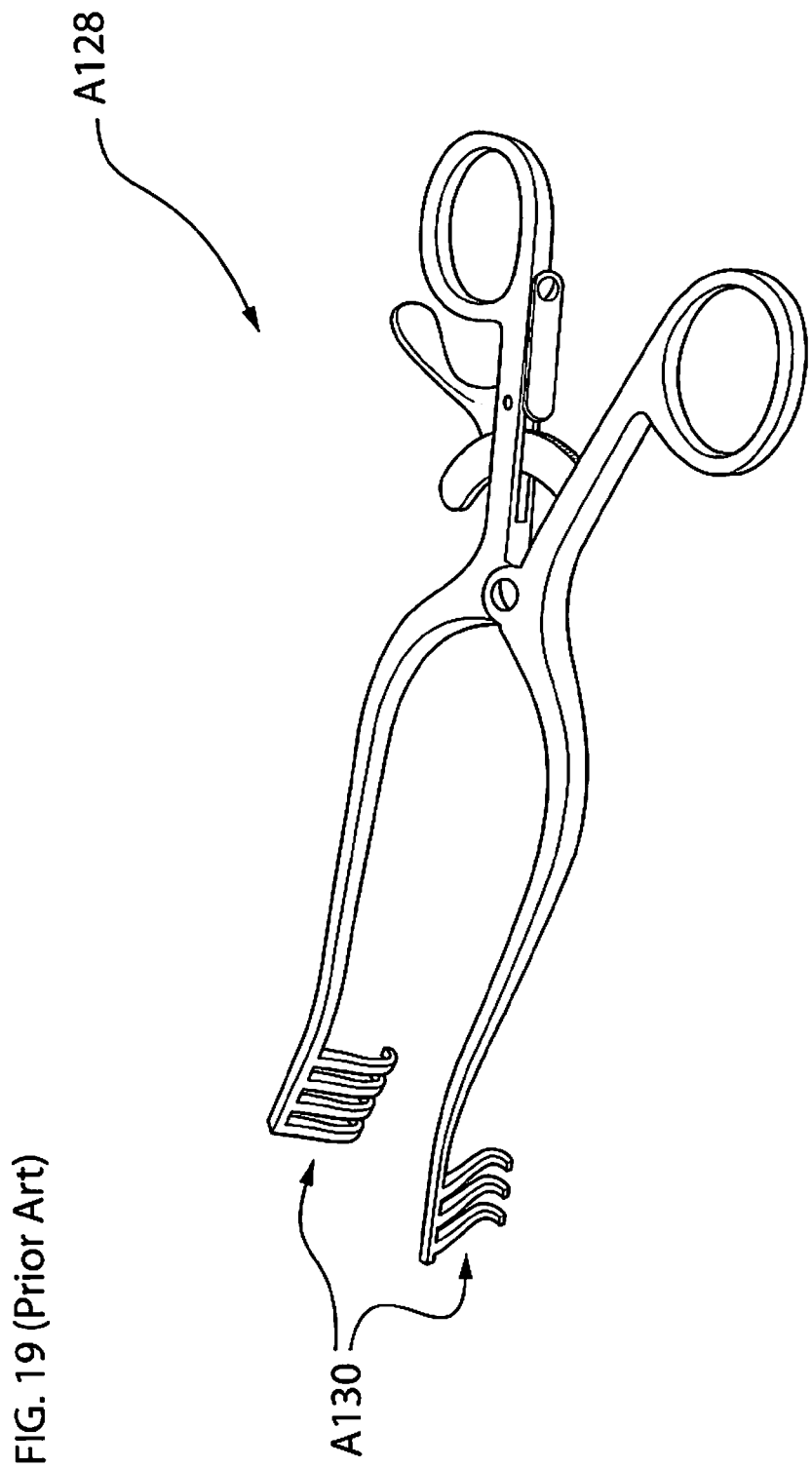
FIG. 19 shows an example of a Weitlander retractor in the prior art for retracting skin.

Frequently, the edges of an incision must be pulled apart with a surgical device called a retractor (also sometimes called a spreader). Retractors can be of several shapes and configurations, each having one or more tissue engaging elements. For example, as shown in FIG. 17, a Finochietto rib spreader A120 for thoracotomies has two opposing arms A124 each bearing a retractor blade A122 that serve as the tissue engaging elements. As shown in FIG. 18, a ring retractor A124 for abdominal surgeries has multiple retractor blades A126 (three (3) shown here) that serve as the tissue engaging elements and these retractor blades A126 are mounted to a ring frame A127 to support them. The ring frame A127 is typically attached to the operating bed by a mounting arm. As shown in FIG. 19, a Weitlander retractor A128 for retracting skin has two opposing retractor forks A130 as the tissue engaging elements.

Figure 20:
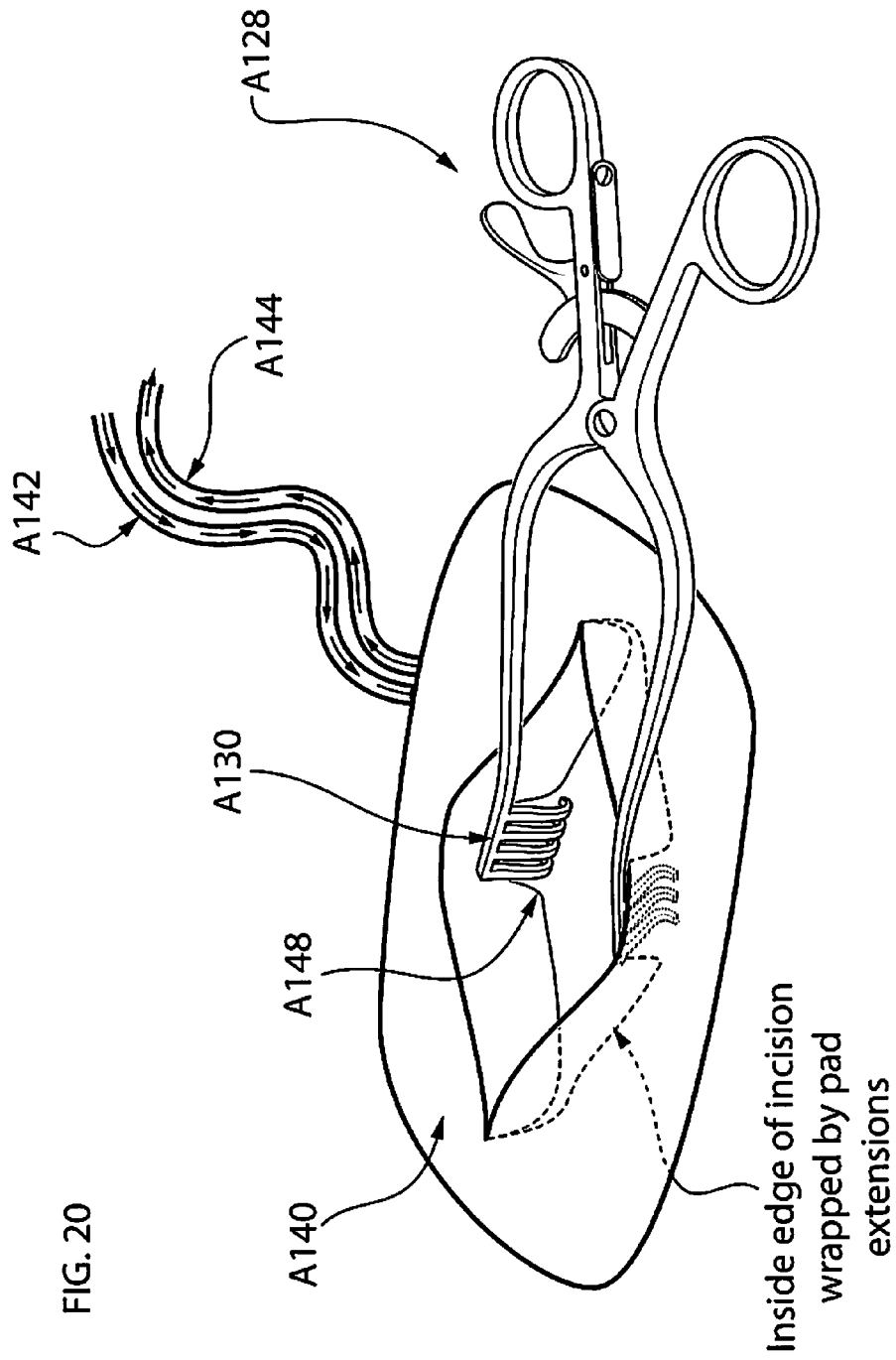
FIG. 20 shows an exemplary cooling pad fitted to the Weitlander retractor of FIG. 19.

Cooling post-ICPs can be made to fit around the tissue engaging elements (e.g., retractor blades or forks) of such retractors. FIG. 20 shows a cooling post-ICP A140, cooled with recirculating fluid supplied by a fluid inlet tube A142 and a fluid outlet tube A144, which fits around the forks A130 of a Weitlander retractor A128 by means of a cut-out A148 where the retractor forks A130 engage the tissue. Such a post-ICP A140 can be placed after retraction has advanced to the point that the post-ICP A140 can be easily positioned.

Figure 21:
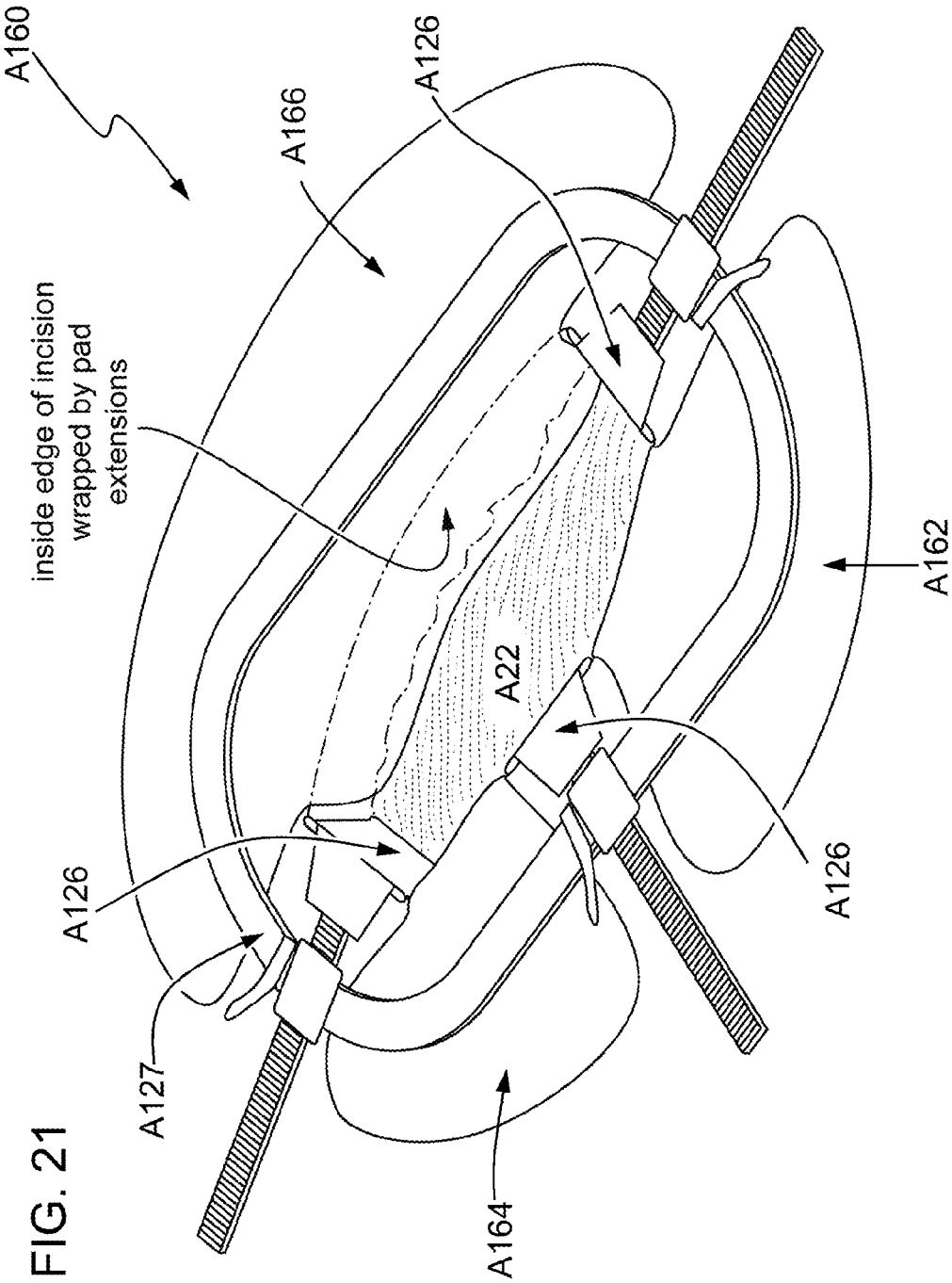
FIG. 21 shows an exemplary pad having multiple segments for variable placement around the margins of an incision.

FIG. 21 shows a multi-segment post-ICP A160 composed of three (3) segments A162, A164, A166 (more or fewer segments can be used) that permits adjustment to retractor blades A126 that can be variably placed around the margin of an incision. The segments A162, A164, A166 of the post-ICP A160 can, themselves, be independently adjusted. Conversely, the segments A162, A164, A166 of the post-ICP A160 can be connected, for example, by tubing to permit flow of cooling fluid between segments A162, A164, A166.

Figure 22:
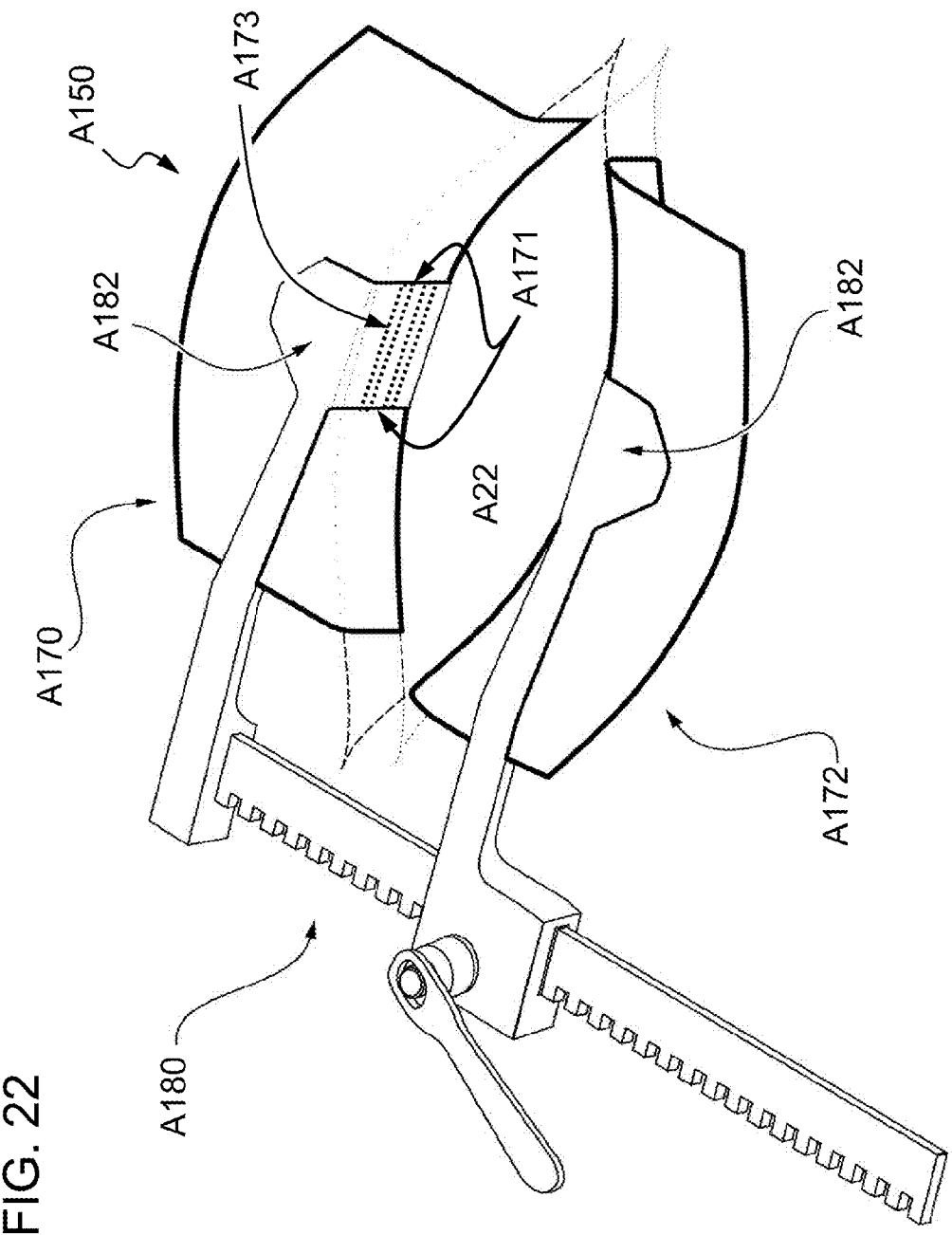
FIG. 22 shows an exemplary cooling pad attached to the Finochietto thoracic retractor of FIG. 17.

Cooling post-ICPs A140, A160 can be integral to the retractor, permitting coordinated placement of the post-ICP A140, A160 with the retractor. Additionally, the post-ICP A140, A160 can cool parts of the retractor, such as the tissue engaging elements (e.g., retractor blades or retractor hooks) such that these components of the retractor also serve to cool the tissue underlying the tissue engaging elements. FIG. 22 shows a thoracic retractor A180 with a cooling post-ICP A150 having two halves A170, A172, each attached to the Finochietto rib spreader A120 such that the dense, metal retractor blade A182 also acts (as a heat sink) to cool the tissues under the retractor blade A182. The two halves A170, A172 of the post-ICP A150 are attached to each of the two retractor blades A182. The halves A170, A172 are physically attached to the sides A171 of the retractor blades A182, with both halves A170, A172 cooling the blades A182 and allowing the post-ICP A150 to be inserted into the incision A22, during a thoracotomy for example. Retractor blades A182 and halves A170, 172 of post-ICP A150 can be inserted before retraction starts, allowing the margins A44 of the incision to be cooled immediately, before retraction, and throughout the duration of the surgical procedure. Cooling of the tissue engaging element for any retractor can be by one of several means, such as by conduction from the post-ICP A150. Alternatively, the tissue engaging element, such as retractor blade A182, can have internal channels A173 connected to a cooling fluid in the post-ICP A150 to permit the flow of cooling fluid from the cooling post-ICP A150 into and out of the retractor blade A182. Cooling fluid can also be run directly into the base of the arms of the thermally conductive retractor, out a hollow arm, and through the tissue engaging element, such as the retractor blade A182. The cooling fluid might run inside the retractor arm alongside the post-ICP A150, or into the retractor blade A182 and then out into the post-ICP A150, or in some combination.

Figure 23:
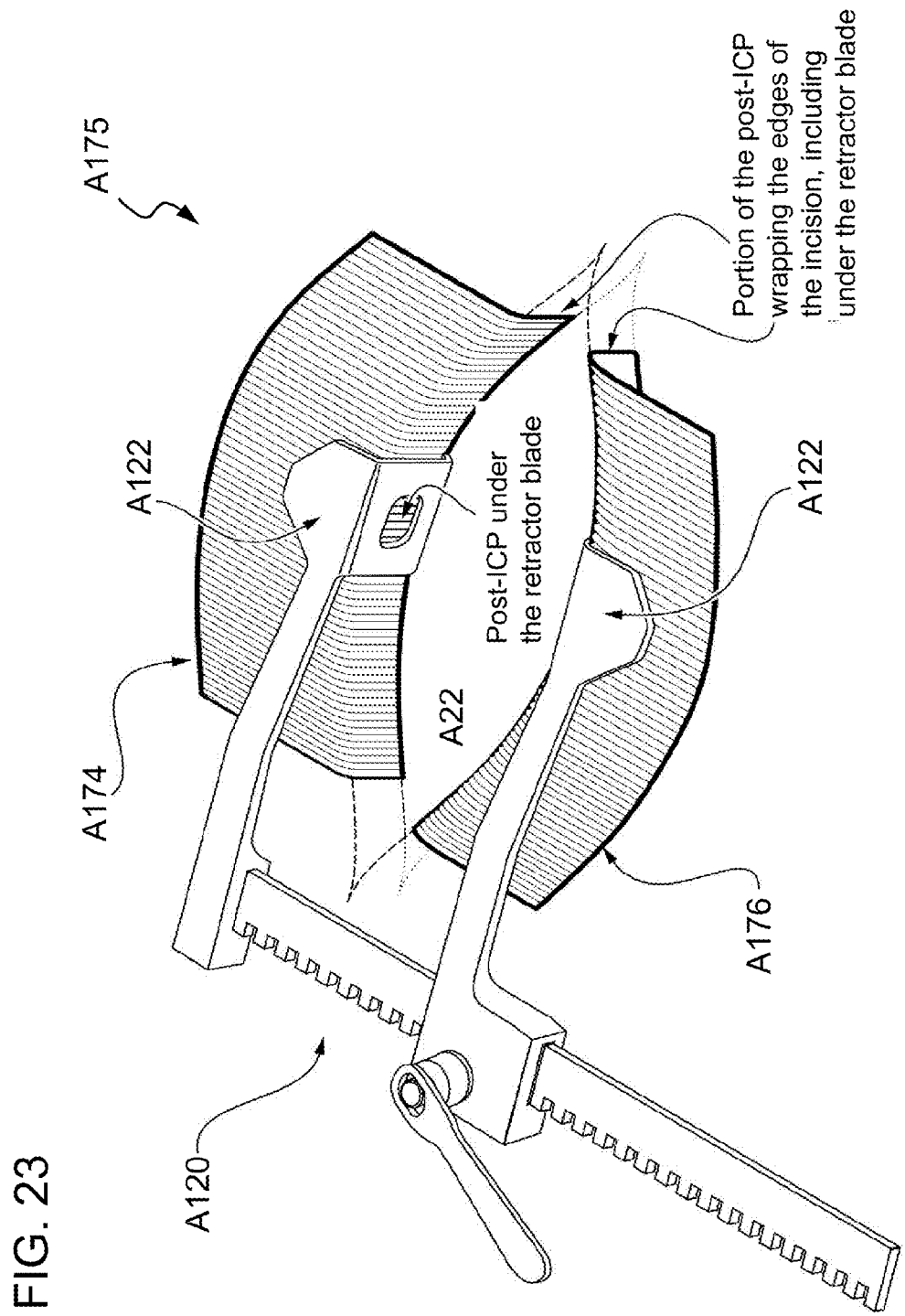
FIG. 23 shows an exemplary cooling pad having two halves for use with the Finochietto thoracic retractor of FIG. 17.

Cooling post-ICPs can also underlie the tissue engaging element of a retractor. FIG. 23 shows a cooling post-ICP A175 having two halves A174, A176 placed into an incision A22 such that the retractor blades A122 of a Finochietto rib spreader A120 overlay the halves A174, A176, thereby each half A174, A176 is interposed between the tissue and the retractor blade A122. The material or the internal structure of the halves A174, A176 would need to be able to perform cooling while also withstanding the retraction pressure under the retractor blades A122. Thus, the halves A174, A176 can be composed of a stiff gel, or the halves A174, A176 can be filled with a fluid and with a reticular material (like a stiff sponge or a series of tubes) that is able to withstand the retraction forces while still permitting fluid to flow through.

Note that such a post-ICP as shown in FIG. 23 can also be separate from the retractor, with the post-ICP placed after the incision and the retractor placed next, overlaying the post-ICP. Cooling post-ICPs A40, A162 can be placed under the tissue engaging elements of any retractor, such as a single-bladed hand-held retractor (e.g., FIG. 5B showing a hand-held retractor A30 without a post-ICP under the blade), the retractor blades A126 of a ring retractor A124 (e.g., FIG. 18), or the forks A130 of a Weitlander retractor A128 (e.g., FIG. 19).

Integration of the post-ICP and the retractor permits integration of other functions as well. For example, the large metallic structure of the retractor can be used as a heat sink for a thermoelectric cooling device. This would offer the advantage of cooling the tissues at the incision while warming the retractor to keep the surgeon's hands warm.

A post-incisional cooling post-ICP A150, A175 can work with a sternal spreader in ways similar to those shown for the Finochietto rib spreader A120 in FIGS. 22 and 23. This permits cooling of the margins of the bisected sternum throughout lengthy procedures, such as multiple coronary artery bypass grafting.

A.4 Post-ICPs Integral with Trocars and Other Inserted Devices

Figure 24:
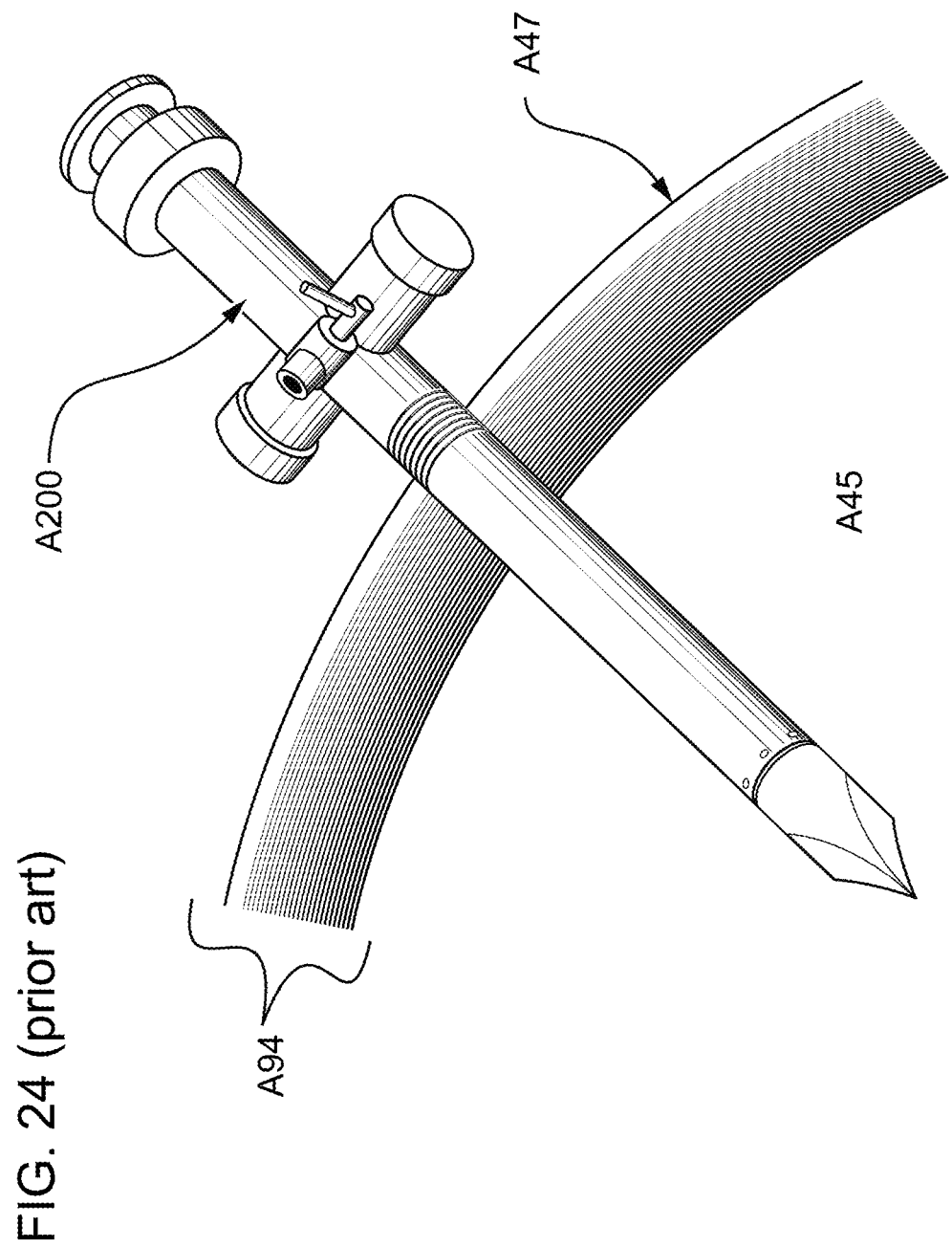
FIG. 24 shows an example trocar in side view penetrating a patient's body wall in the prior art.

Trocars A200 are surgical devices that are used to make openings through the body wall A94 for endoscopic procedures (e.g., laparoscopy) within the patient's body cavity A45 (see FIG. 24). Once inserted, trocars A200 provide a hollow tube for the insertion of other surgical implements, such as a borescope, forceps, or scissors. Thus, like a retractor, a trocar A200 is used to deform tissue (here, strained circumferentially, around the shaft) to achieve surgical access. As with retractors described in Section A.3, Section A.4 describes new devices and means for cooling tissues commencing on insertion of the trocar A200 and, optionally, spanning the duration of the surgical procedure.

Figure 25:
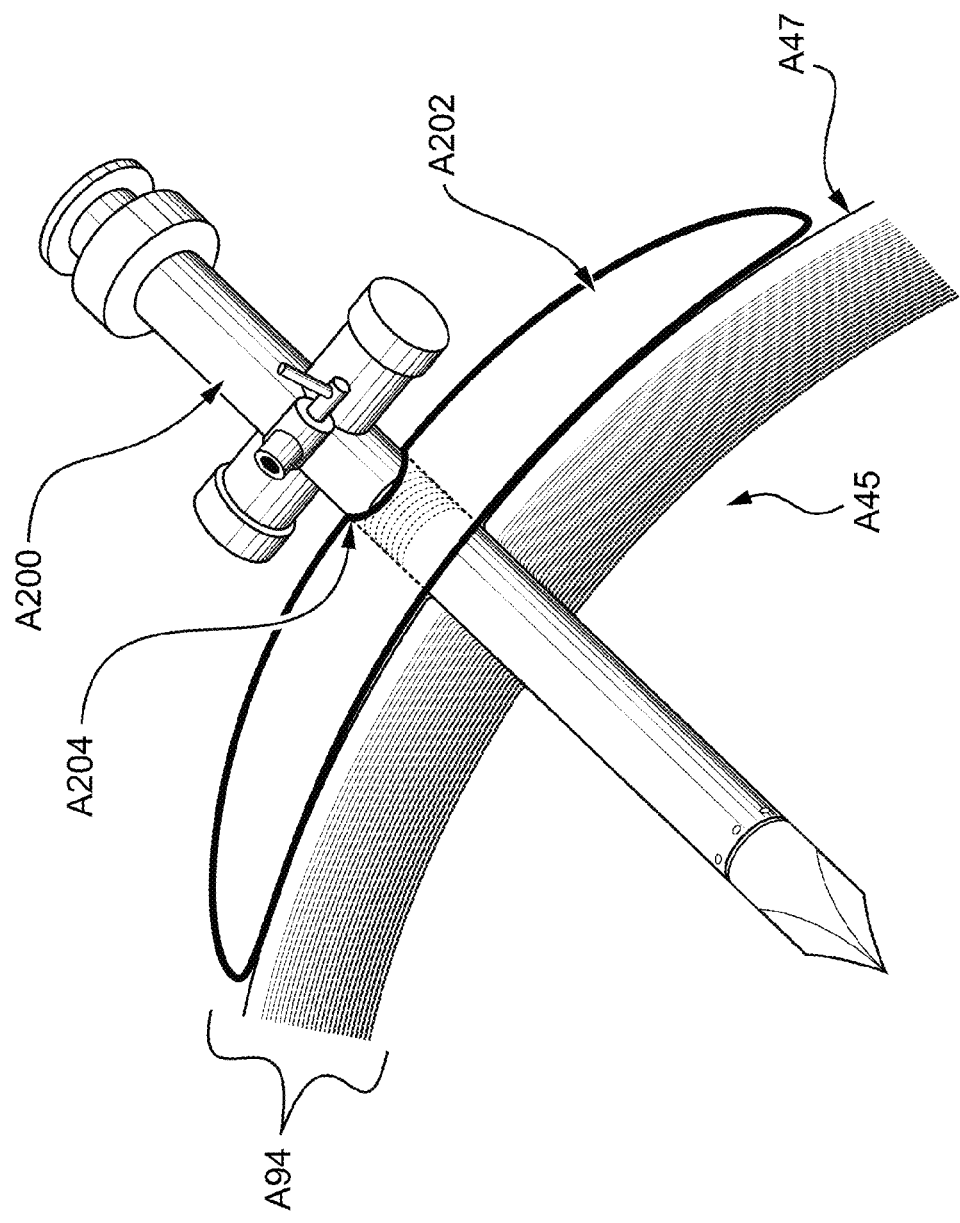
FIG. 25 shows a trocar in side view fitted with an exemplary cooling pad.

As shown in FIG. 25, a post-ICP A202 shaped like a donut, pierced lens, or other substantially toroidal form can be placed around the shaft of a trocar A200, or the shaft of a trocar A200 can be inserted through a hole A204 in a cooling post-ICP A202 and into the skin A47, such that the trocar A200 passes through the post-ICP A202, and the post-ICP A202 covers and cools all tissue A45 surrounding the trocar A200.

Figure 26:
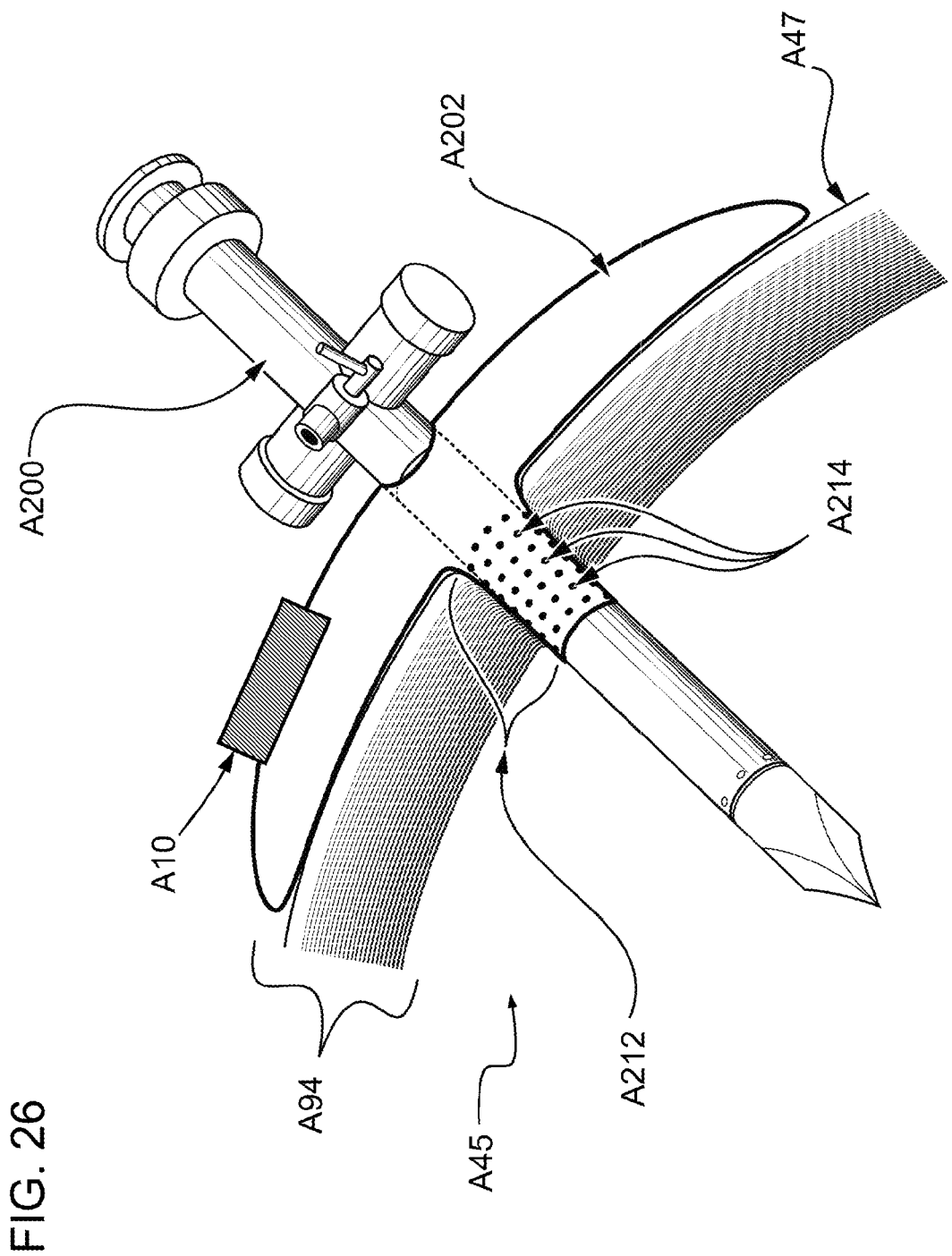
FIG. 26 shows a trocar in side view fitted with an exemplary cooling pad adapted to cool the margins of the incision created by the trocar.

Alternatively, as depicted in FIG. 26, a post-ICP (here numbered as A210) can be integral with the trocar A200 such that the shaft of the trocar A200, or a section A212 of the shaft of the trocar A200, is kept cool and acts as a cooling element, cooling the tissues of the patient's body wall A94 apposed to the trocar A200. The section A212 of the shaft of the trocar A200 can be made of materials having high thermal conductivity to efficiently convey heat from the margin of the incision to the cooling medium in the post-ICP A210; additionally, section A212 can have other features to facilitate transport of heat from the margins of the incision to the cooling medium of the post-ICP A210, such as channels A214 in the wall of the trocar A200 for circulating cooling fluids, or the post-IPC A210 can be equipped with one or more Peltier thermoelectric cooling devices A10 to cool the cooling medium in the post-ICP A210. Alternatively, one or more Peltier thermoelectric cooling devices A10 can be mounted to the wall of the trocar A200, and the wall of trocar A200 designed such that heat is conducted from the tissues A45 around trocar A200 to the Peltier thermoelectric cooling devices A10.

Figure 27:
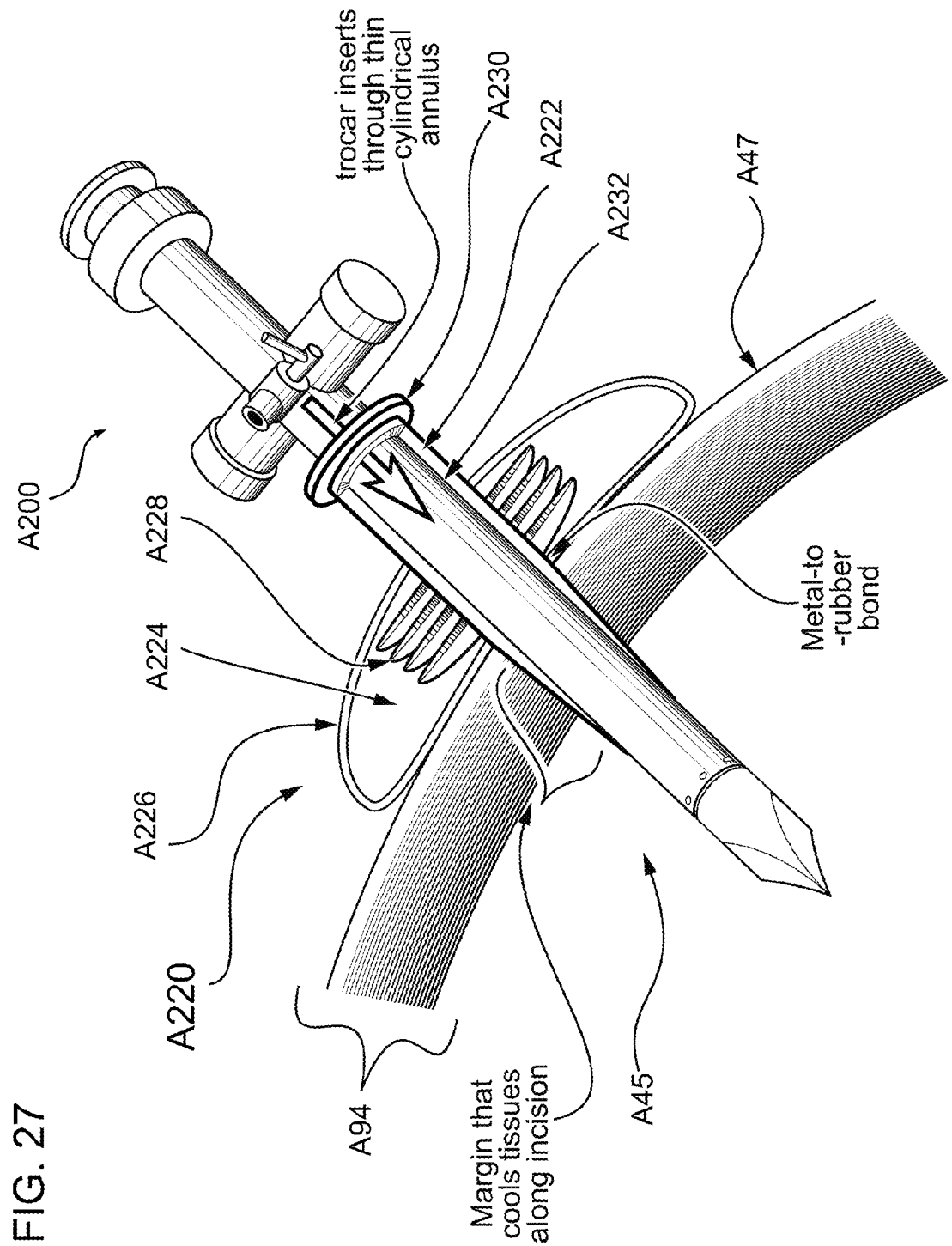
FIG. 27 shows a trocar in side view with an exemplary cooling pad that has an annulus to slide onto the trocar and to cool the margins of the incision created by the trocar.

Alternatively, as shown in FIG. 27, a cooling post-ICP (here numbered A220) can possess a cylindrical inner annulus A222 to permit trocar A200 to easily insert through the body wall (here, the abdominal wall A94) with post-ICP A220 attached. Such a post-ICP A220 with a cylindrical inner annulus A222 permits fitting of all trocars A200 with a cooling post-ICP that also cools the patient's tissue A45 along the depth of the trocar's A200 incision. The cylindrical inner annulus A222 has a thin wall A232 that closely fits the shaft of the trocar A200 and extends into the incision made by the trocar A200. The cylindrical inner annulus A222 should be made of material having high thermal conductivity to conduct heat from the patient's tissue A45 to the cooling devices of the post-ICP A220 (e.g., to a cooling fluid A224 if the post-ICP A220 is cooled by chilled liquid). Similarly, the cylindrical inner annulus A222 should be thermally coupled to the cooling devices of the post-ICP A220. In the example shown in FIG. 27, the post-ICP A220 is filled with a cooling liquid A224. A bladder A226 material of the post-ICP A220 can be composed of an elastomer, such as rubber, and could be bonded to the cylindrical inner annulus A222 with a metal/rubber bond such that the material of the cylindrical inner annulus A222 is in direct contact with the cooling liquid A224. The cylindrical inner annulus A222 can have cooling fins A228 that project into the cooling liquid A224 inside the cooling post-ICP A220 such that heat passes readily from the cylindrical inner annulus A222 to the cooling liquid A224 and can thus cool the cylindrical inner annulus A222. The cylindrical inner annulus A222 could extend away from the cooling post-ICP A220 forming a margin to contact the tissue A45 along the incision made by the trocar A200, and the trocar A200 might insert into the cylindrical inner annulus A222. The cylindrical inner annulus A222 can fit the trocar A200 snugly and can have a low profile such that it easily enters the incision made by the trocar A200. The cooling post-ICP A220 can include a rim A230 attached to the cylindrical inner annulus A222 that permits the surgeon to push with her fingers to ensure the cylindrical inner annulus A222 positions properly in the incision. Thus, when the trocar A200 is inserted into the patient's abdominal wall A94, the margin of the cylindrical inner annulus A222 conducts heat from the tissue A45 along the depth of the incision into the cooling liquid A224 inside the post-ICP A220, thereby cooling the tissue A45 along the incision.

B. Drug Eluting Pads

There is frequently post-surgical pain at the site of incision, known as "incisional pain." Incisional pain can be severe, requiring the administration of analgesics after surgery. Even for minimally invasive approaches (e.g., "keyhole" surgery), port site pain (where the trocars and other instruments are inserted) is common. For some procedures, incisional pain can last long after surgery, leading to the definition of various pain syndromes, such as post-thoracotomy pain syndrome and chronic regional pain syndrome. Subsequently, post-surgical pain management places a large burden on health care and detracts from post-surgical quality of life for many patients.

The cause of incisional pain is not known. It is believed to be caused by a complex series of physiological processes arising from the trauma of incision and retraction. These include nerve damage, tissue damage from lack of perfusion due to the pressure of retraction (e.g., tissue anoxia, tissue reperfusion damage), and localized inflammation. Most of the proposed mechanisms of pain are initiated at the time of incision; however, ameliorative procedures are usually not initiated until hours after the incision. For example, during a thoracotomy, an incision is made between the ribs and a rib spreader is then used to pry apart the ribs. During retraction, considerable tissue trauma occurs, including stretching and breaking of ligaments and bending and sometimes breaking of ribs. Considerable force is required to pry apart the ribs and to hold them apart. Thus, tissue pressure in the tissues underlying the retractor blades is sufficiently high to block tissue perfusion. Intrathoracic procedures can last hours, and retraction is maintained throughout. After the procedure, retraction is relieved, the ribs are re-apposed and sewn back into position, and the muscles and skin over the incision are sutured back together. Tissue reperfusion occurs on relief of retraction and, while its sequelae are not well-studied, reperfusion injury is possible.

Typically, anesthesia is used during surgery, and analgesia begins at the conclusion of surgery, which is frequently hours after the incision is made. There has been growing use of delivery of analgesics and of anesthetics via catheters that are placed into the incision immediately before closing the incision, e.g., after sternotomy (12, 30, 49).

One underlying cause of post-surgical pain is inflammation of tissues after incision and retraction. Trauma to the tissues from cutting, from the deformations (and rending) of retraction, and from physiological response to absence of perfusion all initiate pro-inflammatory and inflammatory signals leading to inflammation responses at the site of the incision and retraction.

It is also desirable to achieve other important goals at the edge of an incision, either to improve surgical outcome or to enhance healing. These include the following:
1. It is desirable to minimize bleeding at the edges of the incision. Electrocautery is commonly used to minimize bleeding of freshly cut soft tissues. For bones, the most common approach is to apply a material to the cut surface of the bone to stop bleeding. Commonly used materials are bone wax (a mixture of bees wax, paraffin, and, optionally, a wax softening agent) and thrombin. Less commonly used materials are Ostene™ (from Ceremed, Inc. of Los Angeles, Calif.) and Surgicel (from Pfizer, Inc. of New York City, N.Y.).
2. It is desirable to block inflammation at the incision and at tissues neighboring the incision that are damaged during retraction. It is also desirable to accomplish this block of inflammation as soon as possible after immunological challenge, typically the surgical incision, before pro-inflammatory and inflammatory signals are initiated.
3. It is desirable to encourage wound healing. Failure of an incision to heal is itself problematic and can lead to other significant post-surgical complications.
4. It is desirable to eliminate post-surgical infection.

In this Section B, new devices and means of reducing incisional inflammation and post-surgical pain and of enhancing healing of incisions by pharmacological treatment of the tissues cut during the incision or deformed during surgical retraction are described. In general, a pad is placed over the site of an incision to locally release pharmacological agents to the tissues affected by the incision. This pad is placed after the incision, over the edges of the incision, or surrounding a trocar entry, and is kept on the edges of the incision throughout surgery to block or otherwise reduce post-surgical inflammation, bleeding, pain, or other undesirable consequence of the incision or of surgical retraction.

B.1 Drug-Eluting Pads (DEPs) at the Margins of an Incision

In this section B.1, new devices and means to release a drug or other pharmacological agent directly to the edges of an incision are described. After the surgeon makes the incision, such as with a scalpel or other means, a device configured as a pad is placed such that it overlaps the edges of the incision and releases drug directly to the freshly cut tissues throughout the duration of the surgery. In this Section B, a pad configured to release drug to the tissues is referred to as a drug-eluting pad DEP.

The drug or other pharmacological agent can include (singly or as combinations):
Agents to prevent infection, such as antibiotics and antimicrobials.
Agents to reduce blood flow during surgery, such as thrombin, gelatin (denatured collagen), solubilized or microfibrillar collagen, cellulose powder, or clotting factors.
Agents to reduce inflammation, such as opioid analgesics (7, 32), inhibitors of complement response (e.g., C5a receptor agonists, APT070, TP10 from AVANT Pharmaceutical) (6, 10), anti-inflammatory cytokines IL-10 (16), inhibitors of inflammatory cytokines (e.g., infliximab, adalimumab, etanercept, pentoxifylline), inhibitors of nuclear factor-kappa B activation (e.g., curcumin).
Agents to encourage healing of the sternum, including agents to promote revascularization of the wound (examples include fibroblast growth factor 1 FGF-1, vascular endothelial growth factor VEGF, transforming growth factor beta TGF-$\beta$, platelet derived growth factor PDGF) and agents that promote osteogenesis (examples include the bone morphogenetic proteins, BMP, transforming growth factor beta, TGF-$\beta$).

Release of drug from the DEP to the tissues can be by any of several means. The DEP can be made of a hydrogel or another material into which the drug is dissolved, and release of drug from the DEP to the tissues is by diffusion (aided by convection driven by DEP and tissue deformations) out of the DEP and into the tissues. Examples of non-hydrogel materials into which drug is dissolved include hydrophobic gels composed of cross-linked polymers (which can be used to carry hydrophobic drugs), polydimethylsiloxane, PDMS, and fluoro-elastomers, such as Fluorocur from Liquidia Technologies, Inc. (Durham, N.C.). The DEP can be a fluid-filled membrane, with the membrane being permeable to the drug thereby allowing diffusion of drug out of the DEP and into the tissue. The DEP can be a fluid filled membrane, with the membrane being porous such that fluid slowly flows out of the DEP and into the tissues. The DEP can include means for flowing physiological saline or other fluid (into which drug is dissolved) onto the tissue, such means including (a) tubes for delivery either from the ends or from the sides of the tubes; (b) orifices; or (c) channels.

Flow-based drug delivery means require an elevated pressure (e.g., to drive a fluid flow). The pressure can be supplied by an external pressure source (e.g., a pump attached to the DEP, an elastomeric pump or pressure chamber, or a pressure reservoir) or by a pressure source integrated into the DEP (e.g., an elastomeric pump or pressure chamber, a pressure reservoir, a gas-generating reaction, osmotic pressure, or pressure generated by surgical retraction).

Note that a DEP can also reduce tissue drying during surgery both by acting as a barrier to evaporation or absorption (for example, by surgical gauze) and as a fluid delivery system that directly perfuses the tissues with an appropriate fluid, such as a physiological saline.

A DEP can also prevent accidental injury of the tissue, for example, by stabbing with a surgical implement, by cutting with a scalpel, or by other means.

Figure 28:
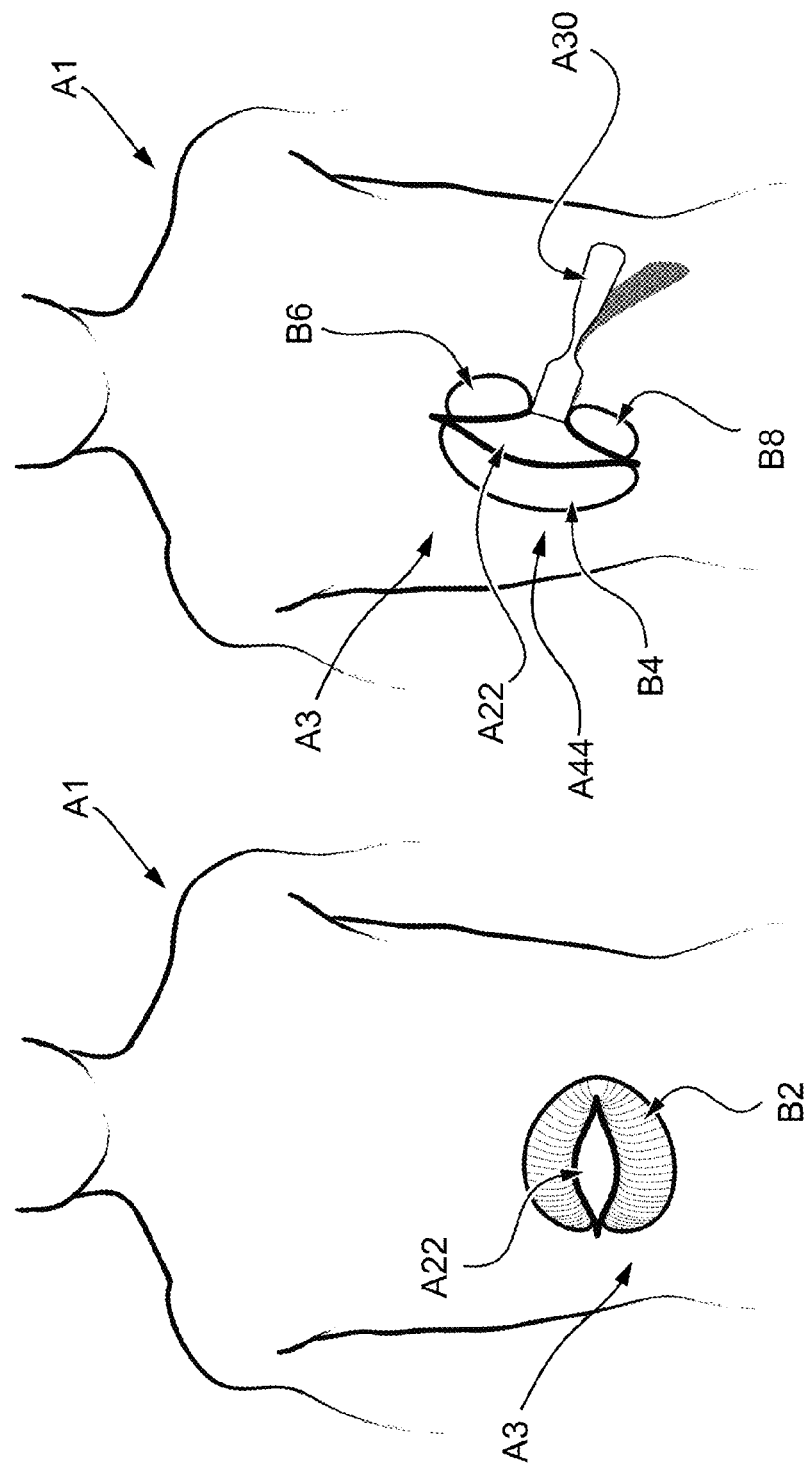
FIGS. 28A and 28B show exemplary drug-eluting pads that completely wrap the margins of an incision.

As shown in FIG. 28A, a drug-eluting pad (DEP) B2 can be in one piece that completely wraps the incision A22, or it can be in a plurality of pieces B4, B6, B8 (as shown in FIG. 28B), permitting positioning of the DEP B2 around the edge of the incision A22 and including positioning around other surgical instruments, such as retractors (shown in FIG. 28B as a hand-held retractor A30) and other pads.

Figure 29:
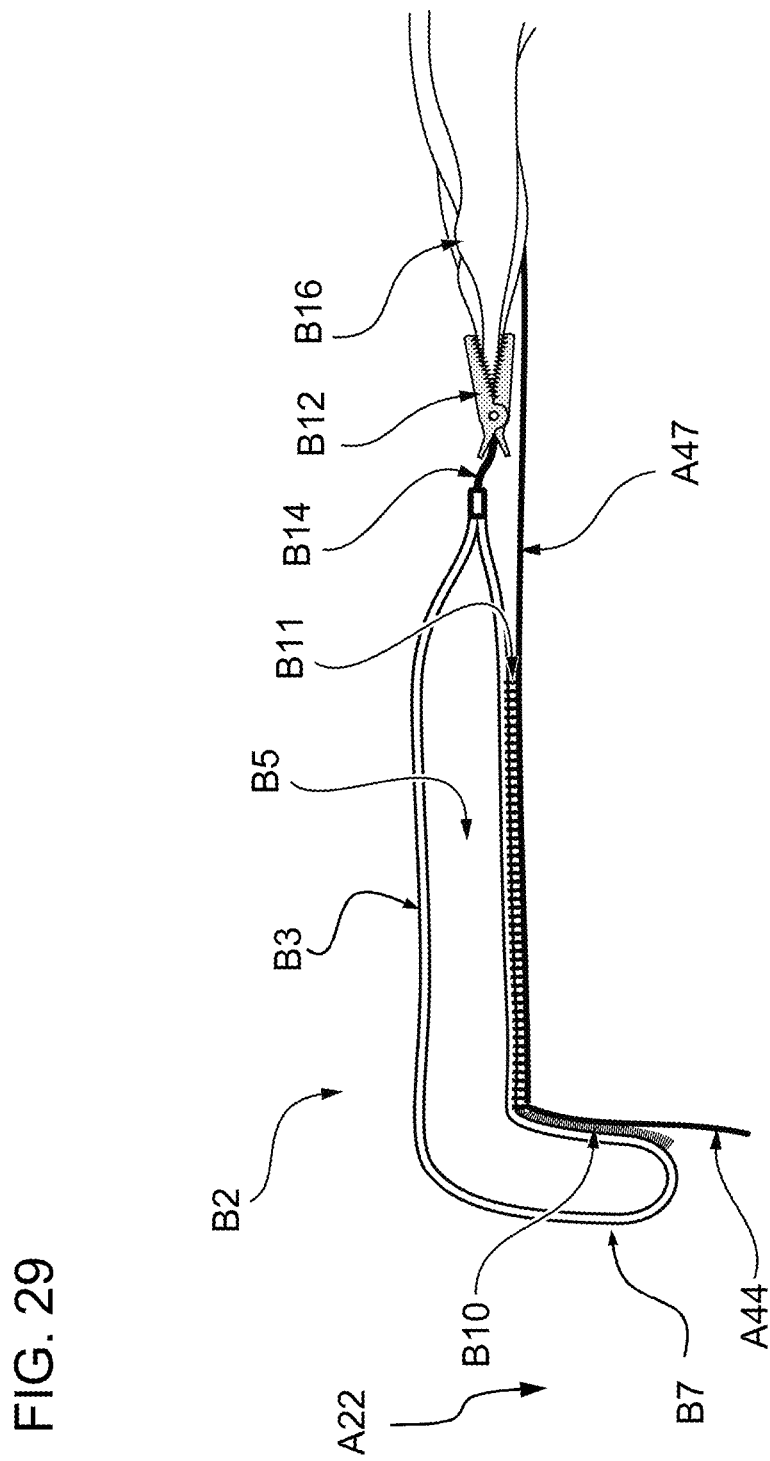
FIG. 29 shows the side view of an exemplary pad having a stiffened rolled edge for placement at the margin of an incision, a drug-eluting surface apposed to the cut tissues at the margin of the incision, a friction coating to prevent sliding along the patient's skin, and a clip for anchoring the pad to a surgical drape.

A DEP B2 can include specialized regions of the DEP B2, including multiple components that enhance or augment the functions of the DEP B2. The DEP B2 (also including pieces B4, B6, B8) can include means to facilitate placement of the DEP B2 on the edges A44 of an incision A22 and for maintaining the position of the DEP B2, including means to prevent the DEP B2 from being knocked into, slipping into, or otherwise moving into the incision A22. These can include a combination of hooks or a stiffer rolled edge to engage the edge A44 of the incision A22; surfaces composed such as not to slide (including textured surfaces, angled bristles to provide biased traction, adhesive coatings, frictional coatings, surfaces relying on van der Waal's interactions or on hydrophobic/hydrophilic interactions), suction cups, Velcro, weighted saddles, etc. These means can also include attachment devices, such as Velcro strips, suction cups, or clips that attach to the skin, to surgical drapes, or to other structures surrounding the incision A22. FIG. 29 shows one embodiment having a DEP B2 formed from an elastomeric membrane B5, filled with a drug-bearing fluid B7, a stiffened, rolled edge B8 that engages the edge A44 of an incision A22, a drug-eluting surface B10 apposed to the edge A44 of the incision A22, a frictional coating B11 that engages the patient's skin A47, and a clip B12, attached by a cord B14, that engages a surgical drape B16.

Figure 30:
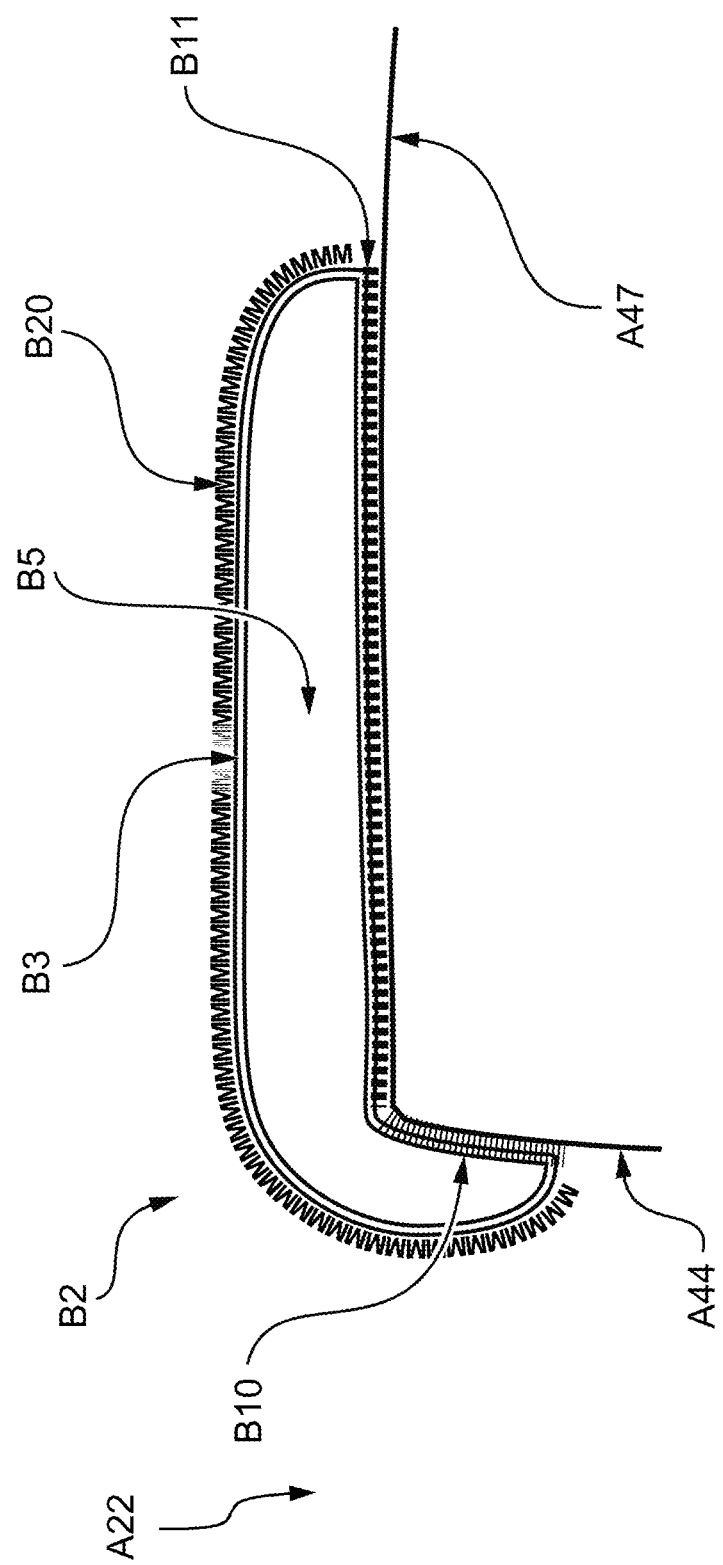
FIG. 30 shows the side view of an exemplary pad having a drug eluting surface apposed to the cut tissues at the margin of the incision, a frictional coating apposed to the skin surrounding the incision, and a metal foil surface to facilitate shaping of the pad.
Figure 31A:
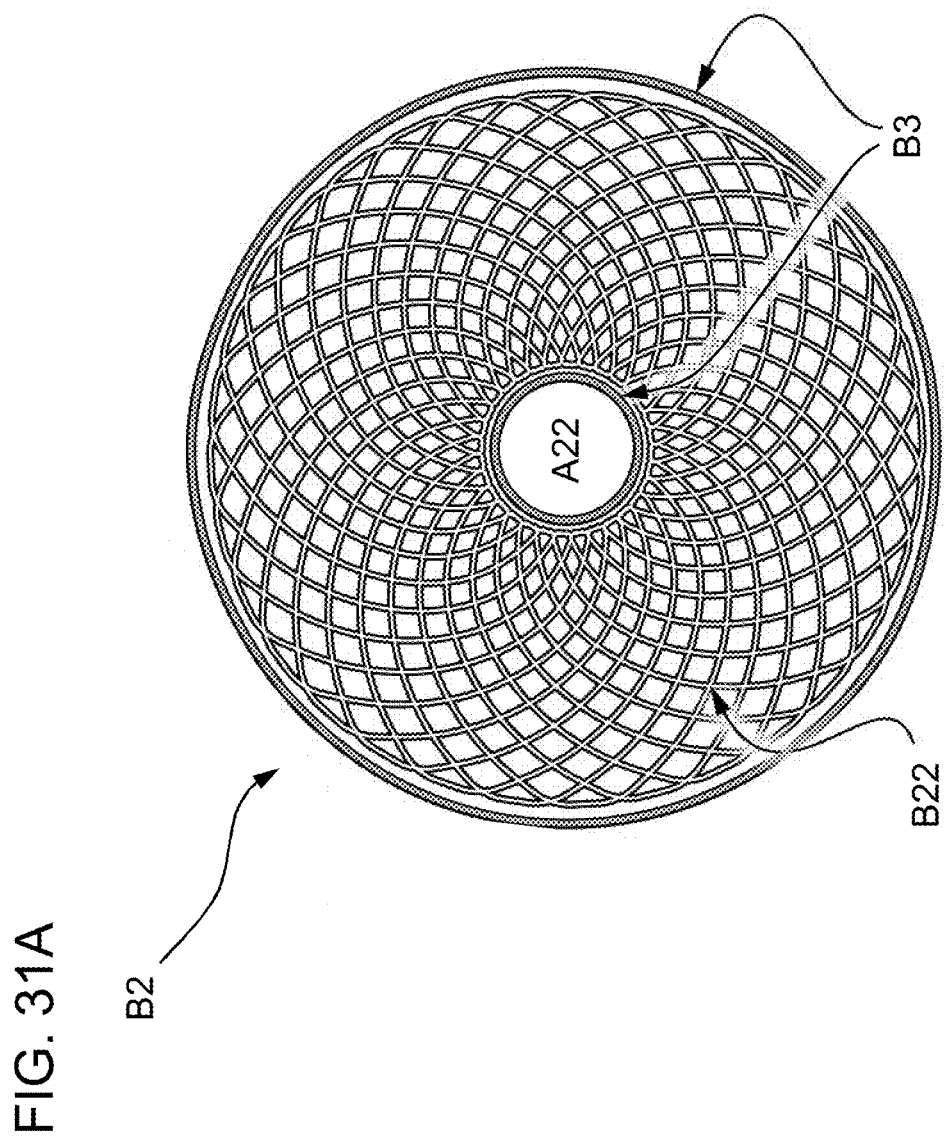
FIGS. 31A through 31C show top and cross-sectional views of exemplary drug-eluting pads having a malleable wire mesh inside the pad to permit shaping of the pad or having a mesh of interspersed fluid filled channels and malleable wires also to permit shaping of the pad.
Figure 31B:
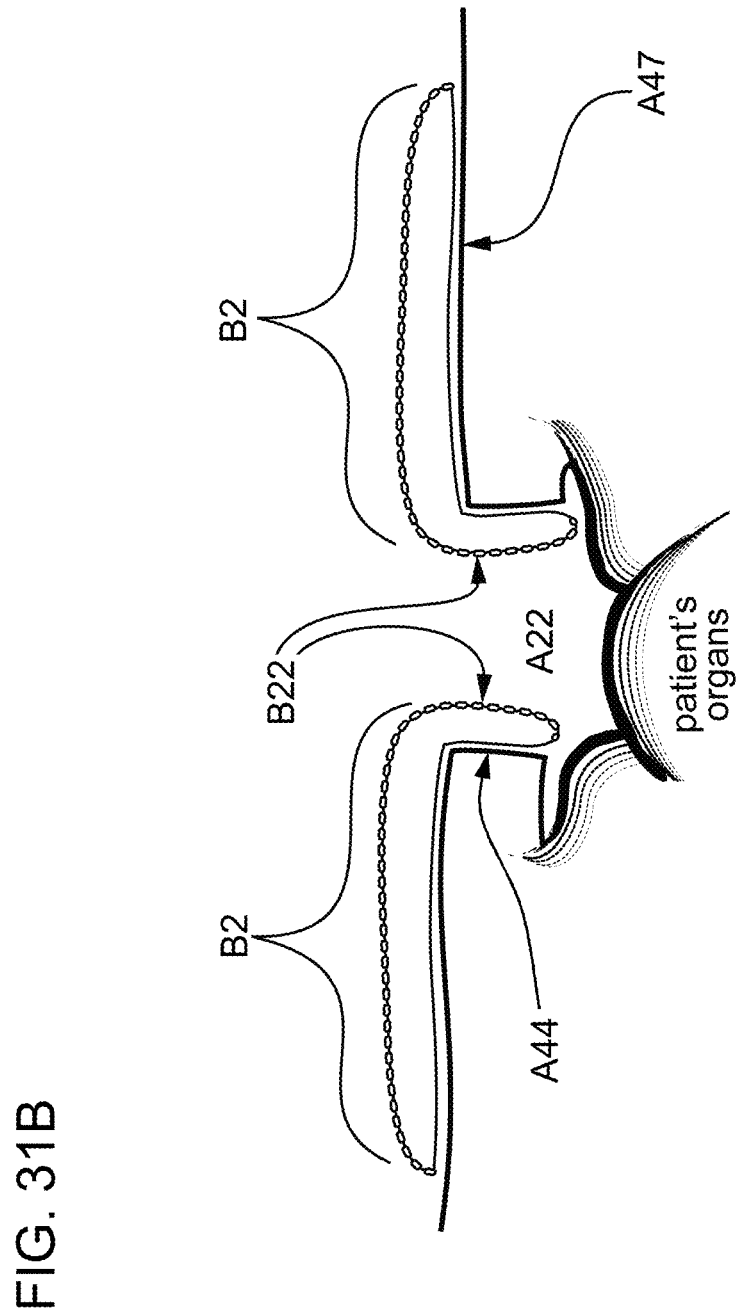
Figure 31C:
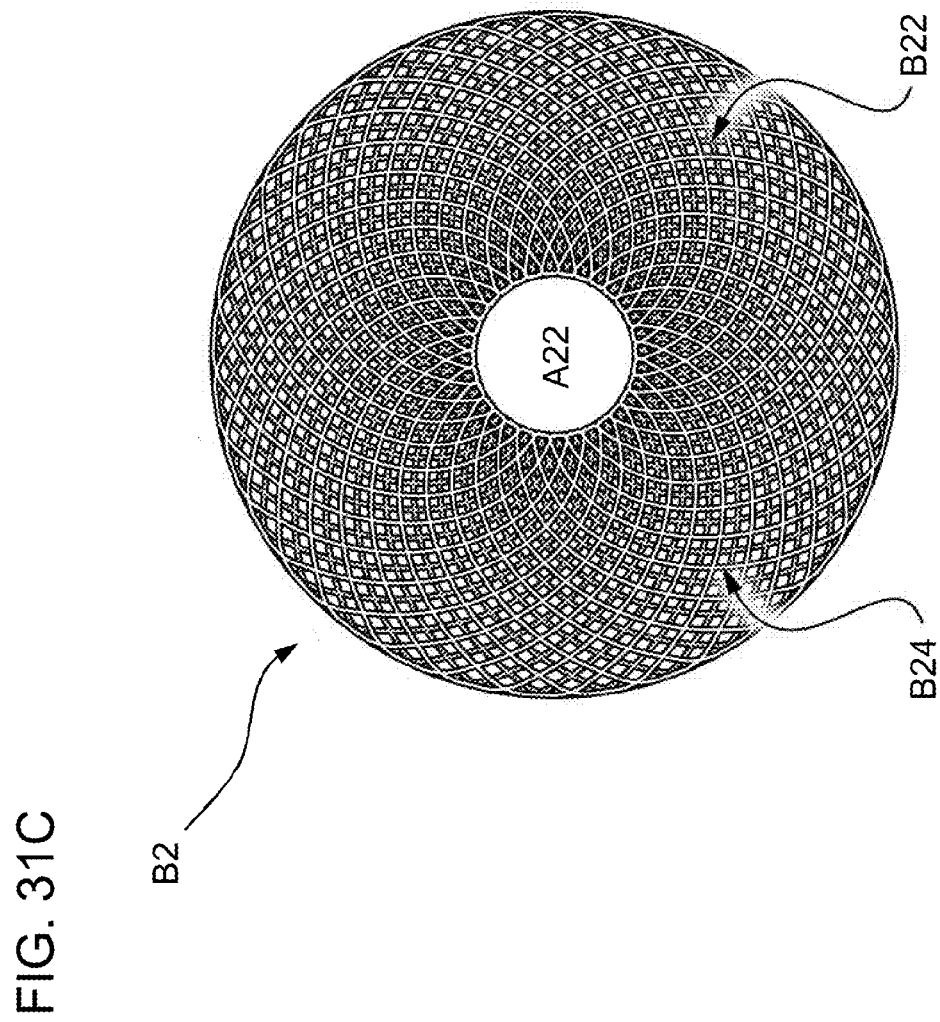

As shown in FIG. 30, DEP B2 can include malleable components B20 to facilitate conformation of the DEP B2 to the edge A44 of an incision A22 and to the skin A47, thereby facilitating delivery of drug to the exposed tissue and maintaining position on the skin. The malleable components B20 can be metal, or polymer, or any other material that holds a shape once it is deformed. The malleable components B20 can be formed into shape-holding structural elements permitting also complex curvature, such as wrinkled foils, wires, ribs, or stays. The malleable component B20 in FIG. 30 is shown as a folded metal foil (also numbered as B20) on the top surface of the DEP B2 (the surface not contacting the skin A47 nor the incision A22). The metal foil/malleable component B20 retains the shape of the DEP B2 when it is bent by the surgeon. FIGS. 31A and 31B show another embodiment having a malleable mesh B22 (e.g., a metal mesh) enclosed within a membrane B3. The membrane B3 contains a drug-eluting fluid B5, and the malleable mesh B22 permits the surgeon to deform the mesh B22 to shape the DEP B2 to the incision A22. The shape of the mesh B22 can be substantially two-dimensional, as shown in FIGS. 31A and 31B (FIG. 31A shows a top view and FIG. 31B shows a side view). Alternatively, as shown in FIG. 31C, the DEP B2 can be a woven mesh of tubes having porous walls ("porous tubes" B24), with no membrane surrounding the mesh of porous tubes B24, such that the drug-bearing fluid in the porous tubes B24 passes directly from inside of the porous tubes B24, across the wall of the porous tubes B24, to the tissues. This configuration (for example, if implemented in tubes of small radius) permits the use of high internal pressures in the fluid which would otherwise cause an elastomeric membrane DEP B3 to inflate like a balloon. DEP B2 can, optionally, include interwoven malleable mesh B22 to permit shaping of the DEP B2.

Figure 32:
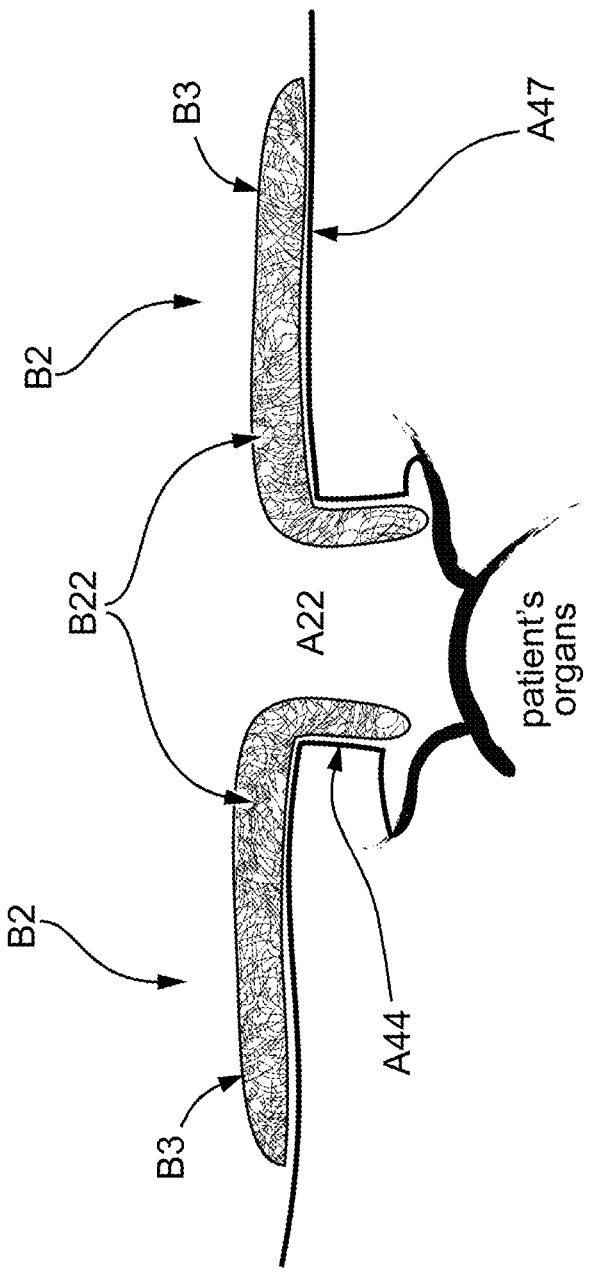
FIG. 32 shows an exemplary drug-eluting pad filled with both a drug-eluting fluid and a malleable mesh that permits shaping of the pad.

Alternatively, the shape of the mesh B22 inside DEP B2 can be substantially three-dimensional, or volume-spanning, as shown in FIG. 32, having a membrane B3 filled throughout with a malleable mesh B22 having a composition similar to a low density steel wool, with the steel wool filling the lumen of the DEP B2 such that DEP B2 can be pressed to shape but fluids can still circulate through the wool. For high pressures, the membrane B3 of the DEP B2 can be bonded to the surface of the mesh B22, which then resists inflation of the membrane B3 under pressure. Alternatively, the membrane B3 can incorporate within it tensily stiff fibers (not shown), the arrangement of which can create anisotropies in the membrane permitting any number of arbitrary shapes that resist or permit swelling in directions according to the distribution stresses and strains in the membrane. For example, membrane B3 stresses aligned with fibers in the membrane B3 would be resisted (no strain permitted), while stresses aligned perpendicular to the fibers in the membrane B3 permitted large strains. Such fiber-reinforced membranes can also be configured that when filled they actively deform three-dimensionally to conform to the contours of the patient and/or the incision A22.

Figure 33A:
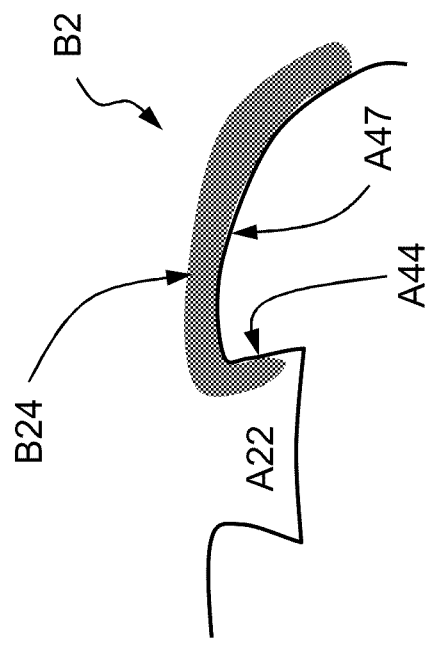
FIGS. 33A and 33B show exemplary drug-eluting pads formed of pliable materials.
Figure 33B:
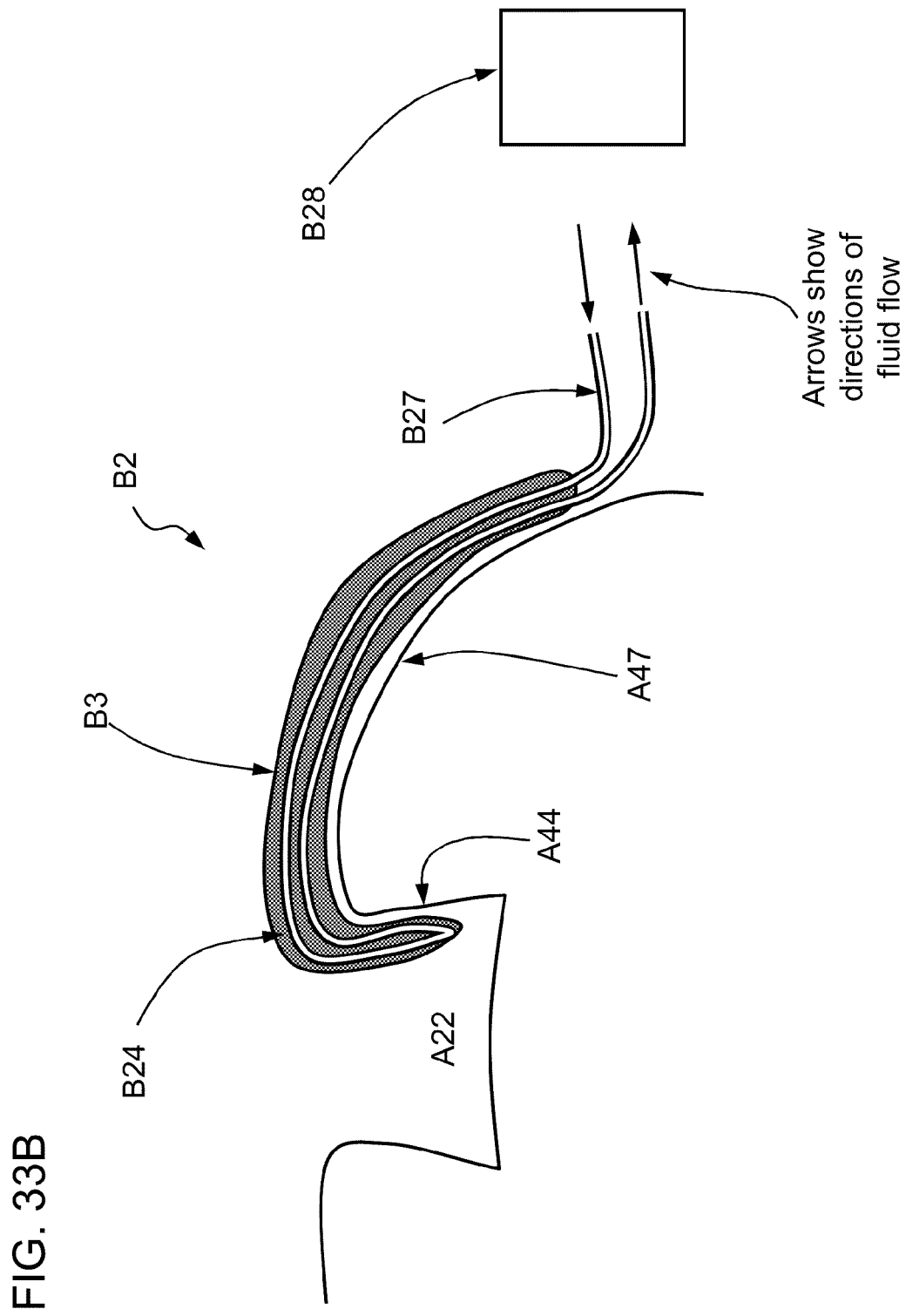

The DEP B2 can also be composed of a putty-like material B24 having sufficient pliability to permit manual shaping of the DEP B2. A drug (or drugs) is dissolved into the putty-like material B24, as shown in FIG. 33A. Alternatively, as shown in FIG. 33B, the DEP B2 can be filled with a putty-like material B24 having drug dissolved into the putty-like material B24, wrapped by an elastomeric membrane B3, such that the DEP B2 can be shaped by the surgeon. Such putty-like material B24 can include tubing B27 coursing through the putty to carry drug-bearing fluid from a fluid recirculating unit B28.

Figure 34:
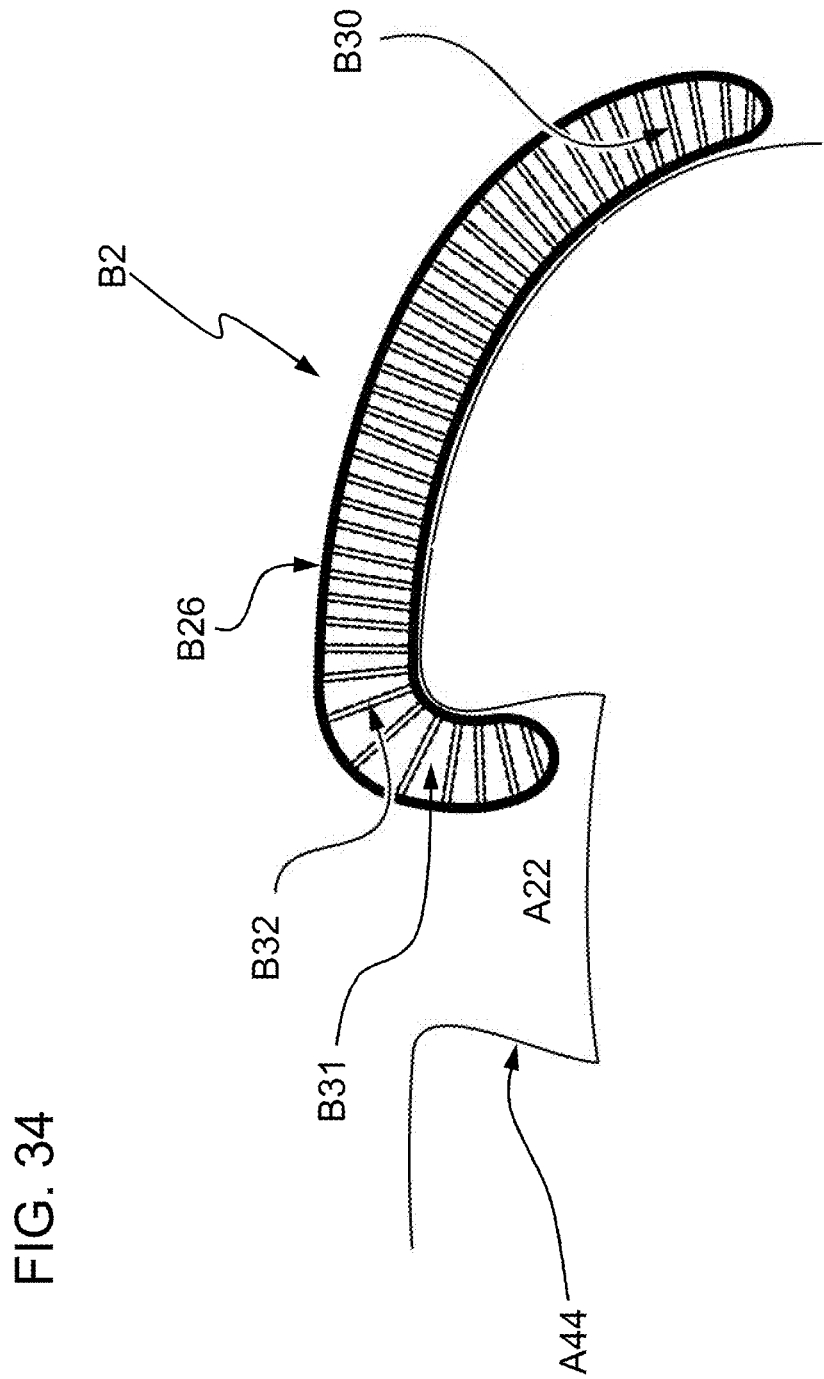
FIG. 34 shows an exemplary drug-eluting pad having internal struts to permit collapse of the bag due to motion of internal fluid to lower parts of the pad.

As shown in FIG. 34, when a DEP B2 is a membrane B3 filled with fluid B31 and placed such that one part is higher than the other, then fluid B31 can pool in the lower portions of the DEP B2, causing higher portions of the DEP B2 to empty. To resist such pooling, the DEP B2 can include internal struts, tensile stays, trebeculae or other reinforcements that act as internal tension-resisting elements B32 that resist swelling of the DEP B2 and could also act as internal compression-resisting elements B30 that resist emptying of the DEP B2. The direction and number of these internal spanning elements B30, B32 can be transverse, longitudinal, radial, oblique, helical, or in any combination.

A DEP B2 can be adjusted to match the circumference (or perimeter) of an incision A22 by overlapping itself to create an overlapped region B34, as shown in FIG. 35. Alternatively, as shown in FIGS. 36A and 36B, the DEP B2 can have a helically wound fiber surface B36, or alternatively the DEP B2 can possess a surface made of a bias-cut, warp and weft woven fabric, permitting adjustment of length, whereby pulling the DEP B2 to elongate it on one axis B40 causes the DEP B2 to shorten on the perpendicular axis B42. More complex geometries are possible.

Alternately, if the DEP B2 delivers drug from a solid or semi-solid (e.g., hydrogel) portion of the DEP B2, then the DEP B2 can be like a piece of tape or rope that is cut to length (not shown). If the DEP B2 delivers drug from a fluid-filled component, then, again, the DEP B2 can be like a piece of tape or rope that is cut to length with the cut end being closed by mechanical means, such as a clip or a fold.

The portion of the DEP B2 that wraps the edge A44 of the incision A22 can be configured for surgeries requiring incisions to different depths and penetrating through different tissues, as shown in FIGS. 37A and 37B. When the incision is through only skin A47 or other thin tissue, then the portion of the DEP B2 that wraps the edge A44 of the incision A22 extends only a short distance into the incision (FIG. 37A). When the incision is through the skin A47 and an underlying layer of tissue B46 (e.g., a muscle layer, fat layer, or other tissue), the portions of the DEP B2 wrapping the edge A44 of the incision A22 can extend down far enough to cover both the incisional margin of the skin and of the underlying layer of tissue B46 (FIG. 37B).

A DEP B2 can be transparent, or can have transparent windows, allowing the surgeon clear view of the tissues under the DEP B2.

A DEP B2 can include means for cooling the tissue to further suppress inflammation. Cooling can be via a fluid that is cooled by an external cooled recirculating fluid system, with the drug dissolved in the cooled fluid, or the drug can be dissolved in a second fluid separate from but cooled by the cooled fluid. Cooling can be by a thermoelectric device, such as a Peltier device or by ice that is held in a portion of the DEP B2. Similarly, all of the embodiments presented in Section A on cooling pads can be incorporated into a DEP B2.

B.2 Drug-Eluting Pad (DEP) Integral with a Retractor

Frequently, the edges A44 of an incision A22 are pulled apart with a surgical device called a retractor (also sometimes called a spreader). As discussed in Section A.3, retractors can be of several shapes and configurations, each having one or more tissue engaging elements. For example, as shown in FIG. 17, a Finochietto rib spreader A120 for thoracotomies has two opposing retractor blades A122 that serve as the tissue engaging elements. As shown in FIG. 18, a ring retractor A124 for abdominal surgeries has multiple retractor blades A126 (three (3) shown here) that serve as the tissue-engaging elements and these retractor blades A126 are mounted to a ring frame A127 to support them. As shown in FIG. 19, a Weitlander retractor A128 for retracting skin A47 has two opposing retractor forks A130 as the tissue engaging elements.

For all methods and instruments of retraction, it is desirable to treat the tissue before and during retraction, possibly including the entire duration of the procedure. In this Section B.2, new devices and means of integrating DEPs with retractors to treat tissues before and during retraction, optionally spanning the entire duration of the surgical procedure are described.

Figure 38:
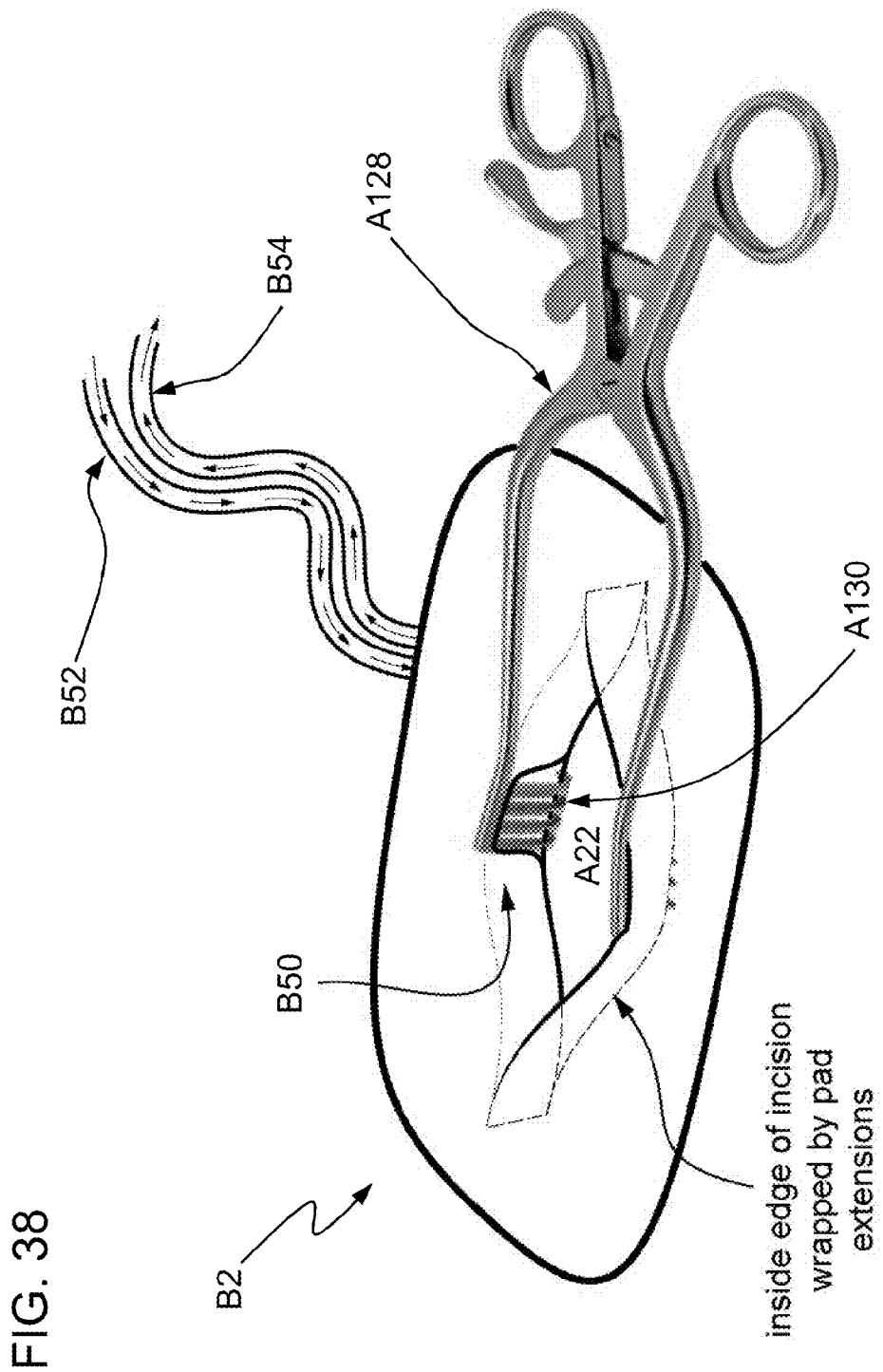
FIG. 38 shows an exemplary drug-eluting pad fitted to a Weitlander retractor.

DEPs B2 can be made to fit around the tissue engaging elements (e.g., retractor blades or forks) of such retractors. FIG. 38 shows a DEP B2 that wraps around the edge A44 of an incision A22 and fits around the forks A130 of a Weitlander retractor A128 by means of a cut-out B50 where the forks A130 engage the tissue. Such a DEP B2 can be placed after the incision is made and before retraction has commenced or, optionally, after retraction has advanced to the point that the DEP B2 can be easily positioned. The DEP B2 shown in FIG. 38 has a recirculating fluid (not shown) carrying drug into the DEP B2. A fluid inlet tube B52 and a fluid outlet tube B54 carry the fluid from a pump (not shown) to the DEP B2. Such a delivery system can be used if the drug must be kept chilled until the moment of use or if elution of drug by the DEP B2 depletes the fluid of drug.

Figure 39:
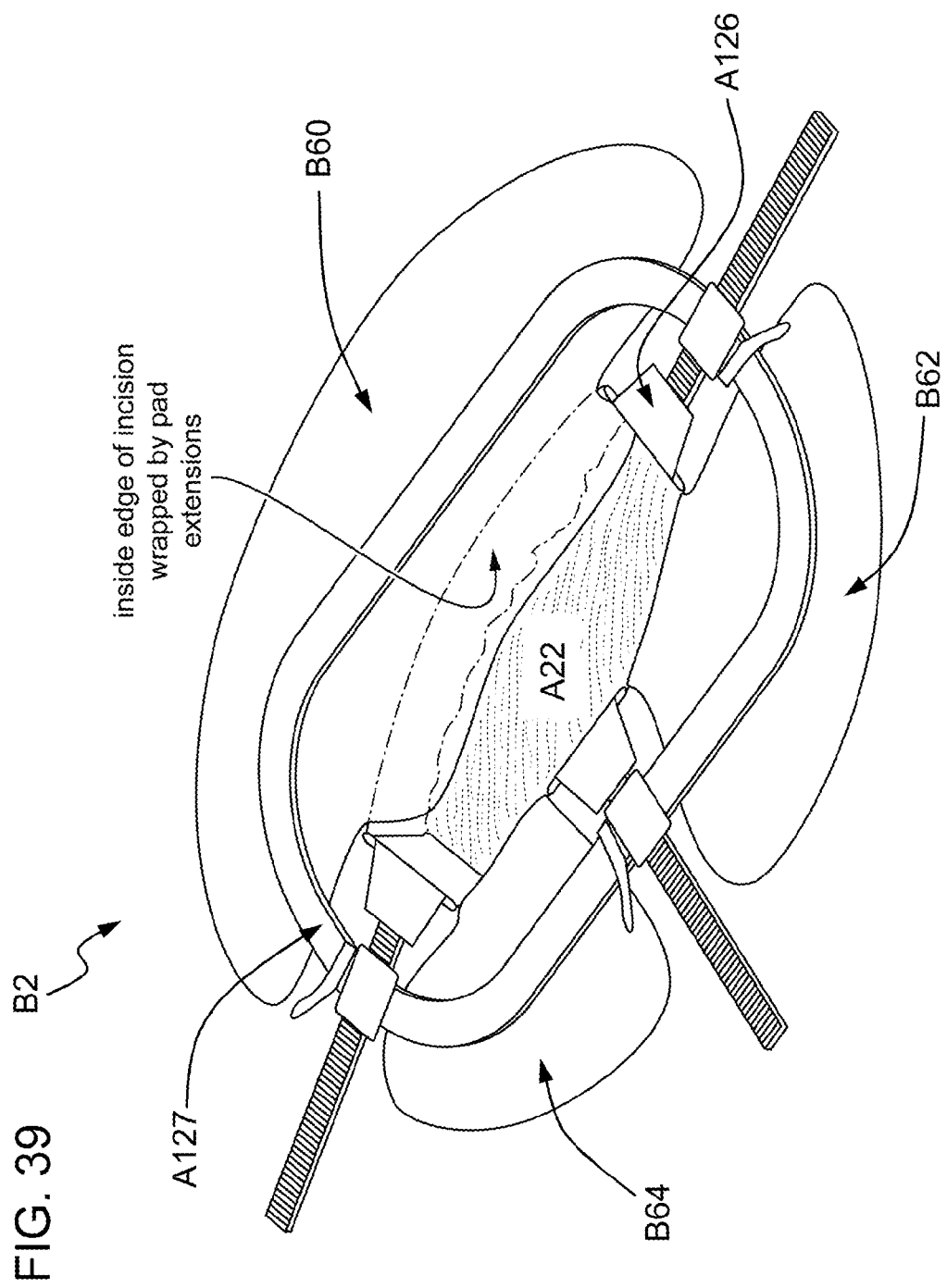
FIG. 39 shows an exemplary drug-eluting pad having multiple segments for variable placement around the margins of an incision.

FIG. 39 shows a multi-segment DEP B2 that permits adjustment to retractor blades that can be variably placed around the edge A44 of an incision A22. The segments (three (3) are shown here, B60, B62, B64, but more or less are possible) of the DEP B2 can, themselves, be independent DEPs. Conversely, the segments B60, B62, B64 of the DEP B2 can be connected, for example by tubing (directly, or through passages the ring frame) to permit flow of cooling fluid or of drug-bearing fluids between segments B60, B62, B64.

Figure 40:
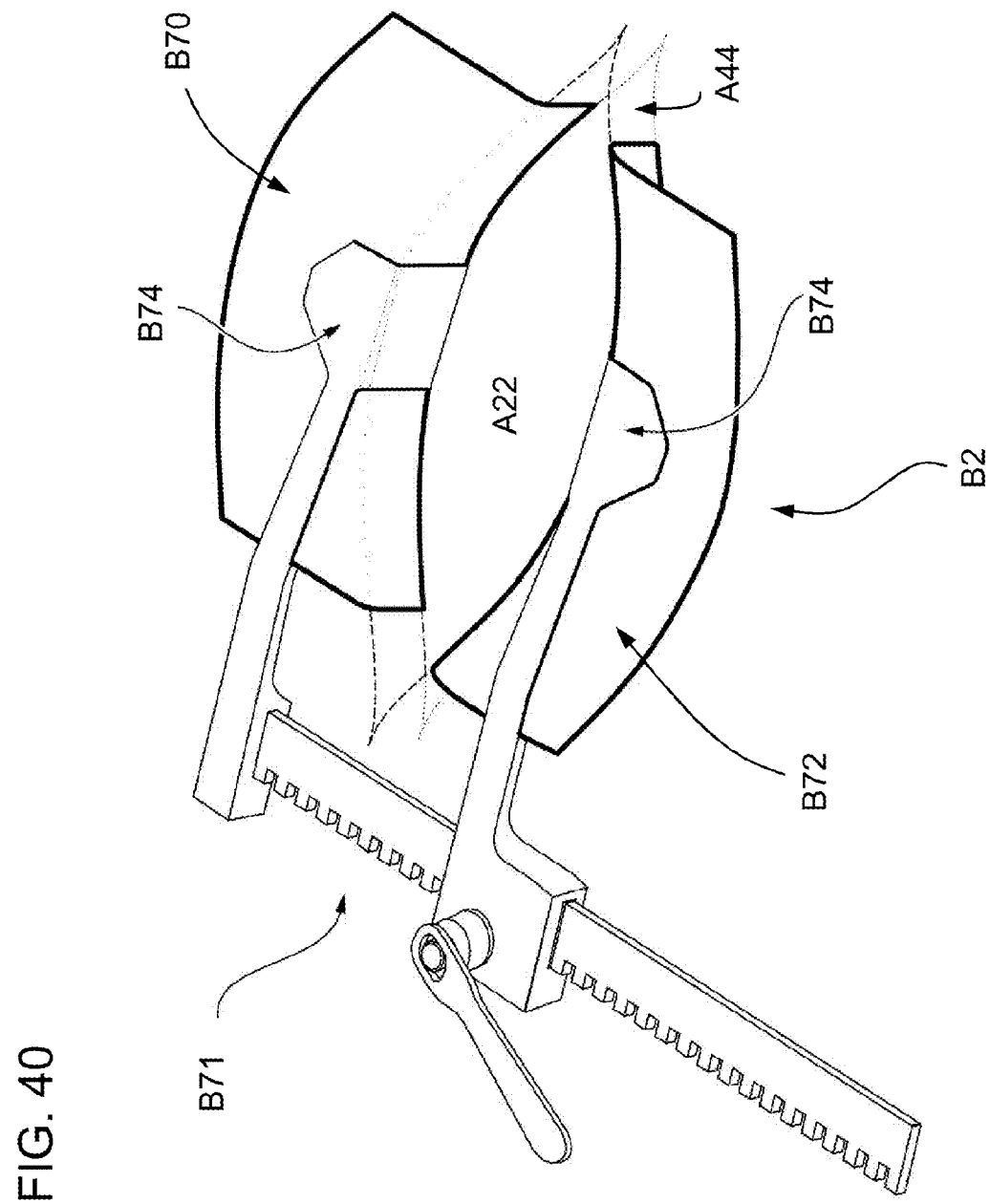
FIG. 40 shows a thoracic retractor with an exemplary drug-eluting pad attached.

DEPs can be integral to a retractor, permitting coordinated placement of the DEP with the retractor. FIG. 40 shows a thoracic retractor B71 with a DEP B2 attached to the retractor blades B74. The DEP B2 has two halves B70, B72, one attached to each of the two retractor blades B74. The halves B70, B72 are physically attached to the sides of the retractor blades B74, allowing each half B70, B72 to be inserted into the incision A22, during a thoracotomy for example, before retraction starts, allowing the edge A44 of the incision to be treated with drug immediately, before retraction, and throughout the duration of the surgical procedure.

Figure 41:
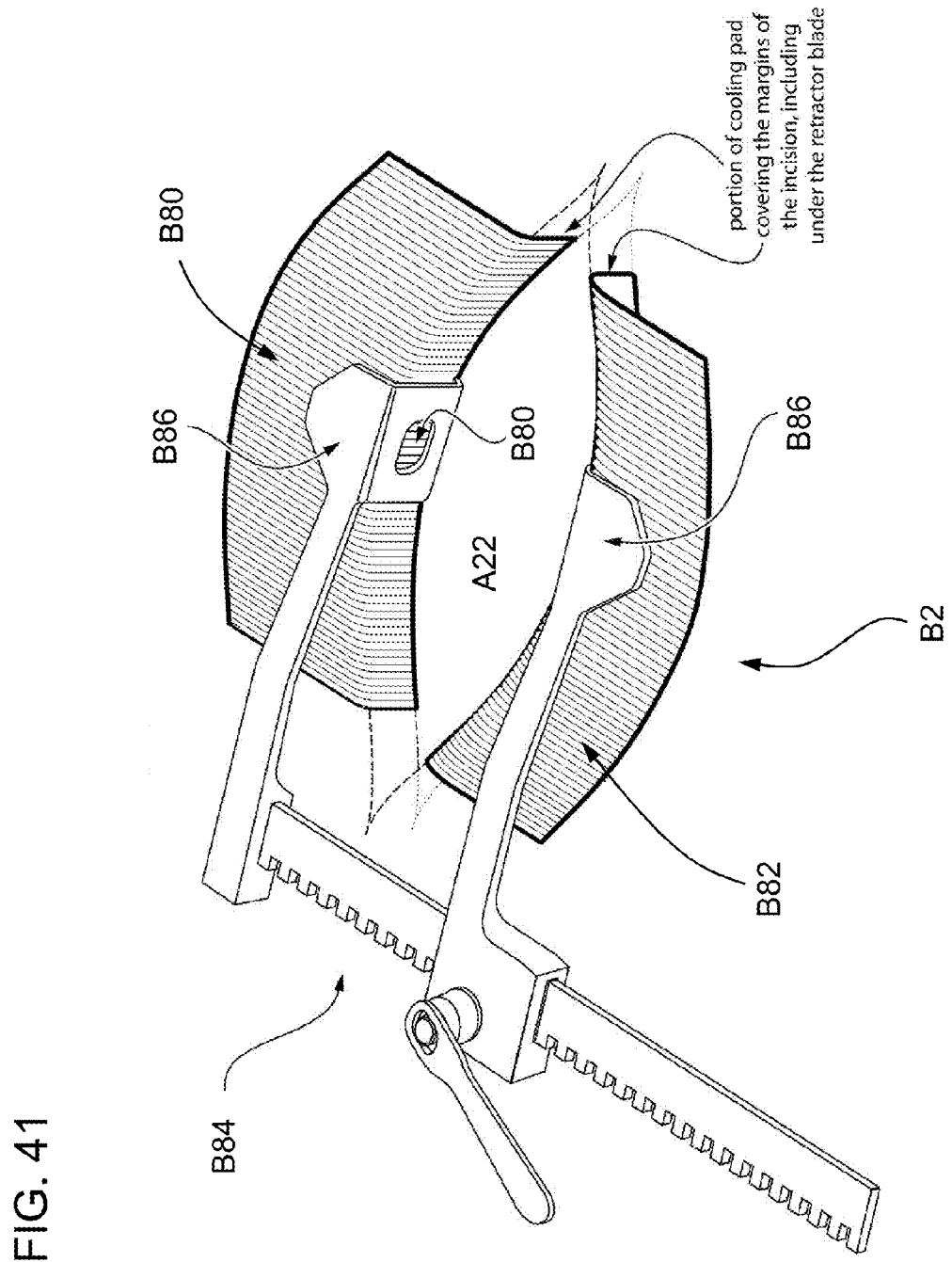
FIG. 41 shows an exemplary drug-eluting pad having two halves for use with a thoracic retractor.

DEPs can also be placed between the tissue and the tissue engaging element of a retractor. FIG. 41 shows a DEP B2 having two halves B80, B82 integrated into a thoracic retractor B84 such that the halves B80, B82 lie along the surface of the retractor blade B86, thereby being interposed between the tissue and the retractor blade B86. The material of the DEP B2 would need to be able to perform drug delivery while also withstanding the retraction pressure under the retractor blades B86 (alternatively, the retraction pressure under the retractor blades A122 can be tapped to drive drug delivery from inside the DEP B2). Thus, the halves B80, B82 can be composed of a stiff gel, or the halves B80, B82 can be fluid-filled and filled with a reticular material (like a stiff sponge or a series of tubes) that is able to withstand the retraction forces while still permitting fluid to flow through. Note that such a DEP B2 can also be separate from the retractor 84, with the DEP B2 placed after the incision is made and the retractor placed next, overlaying the DEP B2.

A DEP B2 can work with a sternal spreader in ways similar to those shown for the thoracic retractor B71, B84 in FIGS. 40 and 41. This permits delivery of drug to the margins of the bisected sternum throughout lengthy procedures, such as multiple coronary artery bypass grafting.

Figure 42:
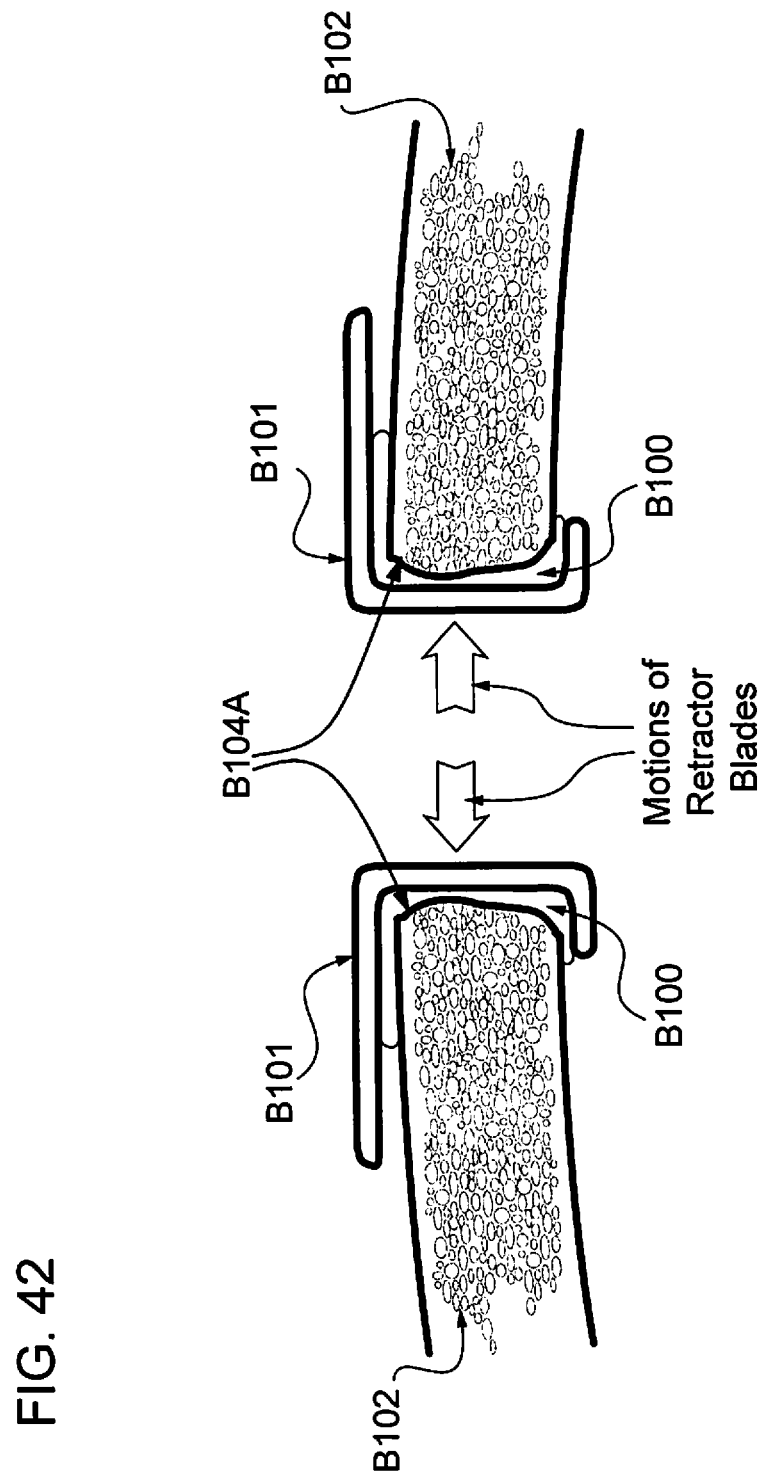
FIG. 42 shows an exemplary drug-eluting pad made from a hydrogel fitted into the retractor blades of a thoracic retractor.

Note that a DEP can also act as a pressure-distributing pad, reducing point loading (and thus stress concentration) in retracted tissues. As shown in FIG. 42, a hydrogel DEP (numbered here as B 100) deforms when loaded, but is stiff enough when contained within a retraction element, depicted as retractor blade B101, to withstand retraction pressures. DEP B 100 can distribute loads along the cut edges B104A of, for example, the bisected sternum during a sternotomy. Retraction is shown as being performed by a Finochietto rib spreader (B120 as shown in FIG. 41). As the retractor blades B101 push against the two halves B102 of the bisected sternum, the edges B104A of each half B102 of the bisected sternum push into DEP B100, deforming DEP B100 such that DEP B100 conforms to the surface of each half B102 of the bisected sternum. Drug dissolved into the hydrogel of DEP B100 diffuses into the tissue of the incised sternum. The DEP B100 can be reinforced with fibers to permit resisting shear as a part of a DEP B100; the fibers themselves can be hollow and form the drug storage portion of the DEP B100.

Figure 43:
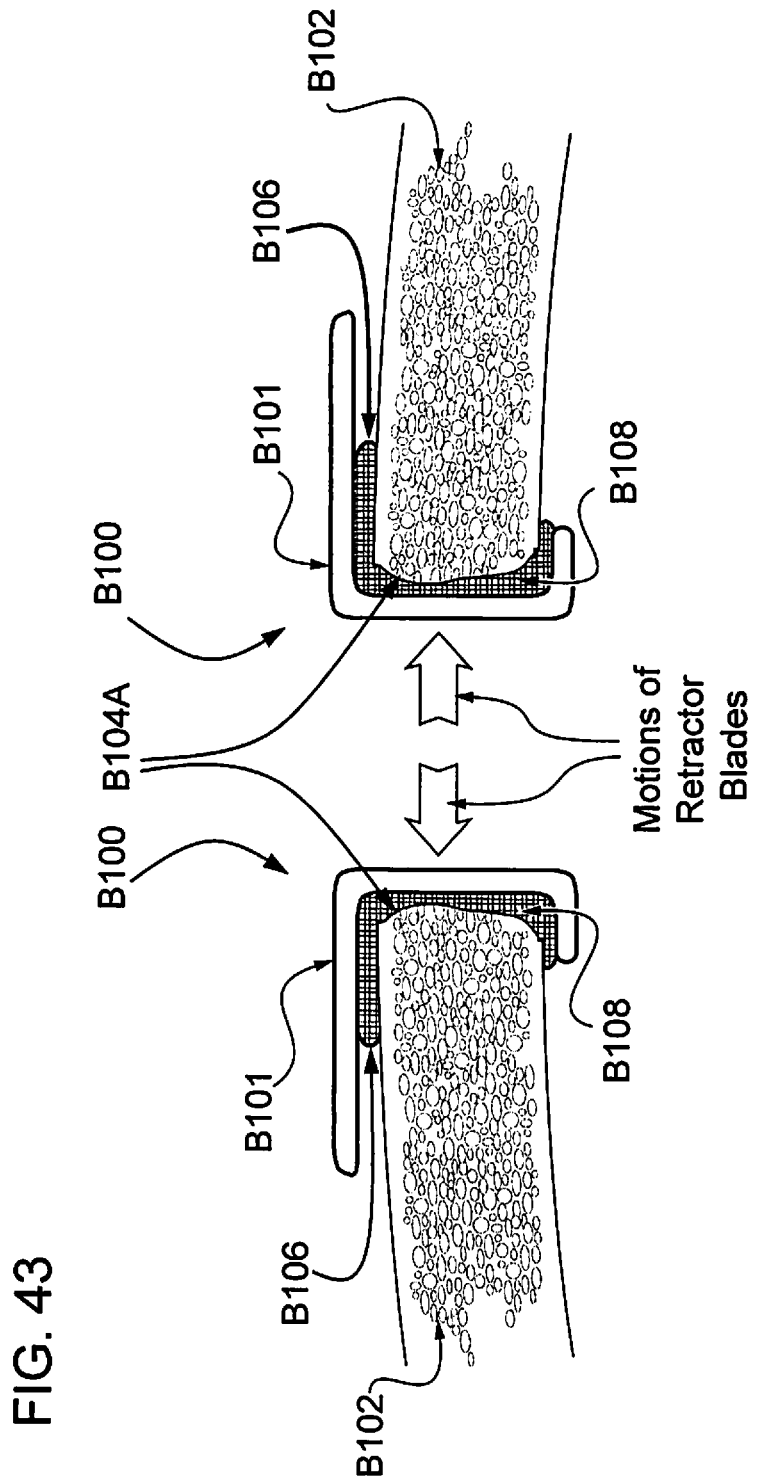
FIG. 43 shows an exemplary drug-eluting pad made from an elastomeric membrane filled with a drug-bearing fluid, where the pad is filled with a reticular material and is fitted into the retractor blades of a thoracic retractor.

Similarly, as shown in FIG. 43, a DEP B100 is formed by a fluid-filled porous membrane B106, optionally filled with a reticular material B108 (such as a flexible mesh or a stiff, open-cell foam), that cushions a tissue and also, by slow flow of drug-bearing fluid across the porous membrane B106, deliver drug to the tissue.

Figure 44:
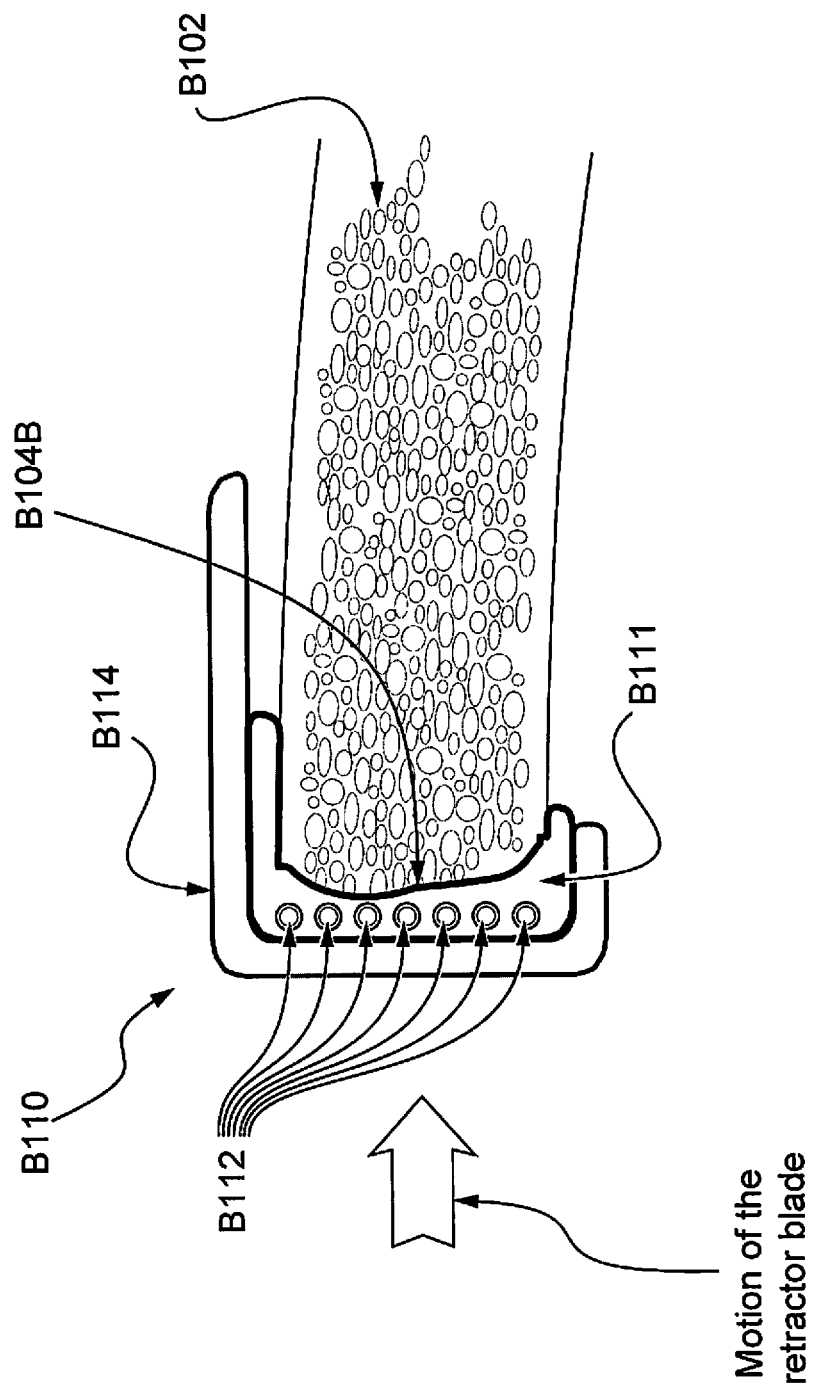
FIG. 44 shows an exemplary drug-eluting pad made from a hydrogel and having internal tubes through which a cooling fluid flows, where the pad is fitted into the retractor blades of a thoracic retractor.

FIG. 44 shows one embodiment of a sternal retractor, such as a Finochietto rib spreader, a DeBakey retractor, or an Ankeney retractor, fitted with a DEP (here numbered as B110) that cushions the freshly cut bone surfaces (for example, B104B), delivers drug to the cut surface B104B and cools the cut surface B104B. The DEP B110 is composed of a hydrogel B111 that covers the edge A44 of the incision A22, including the surface of the bone beneath the retractor blades B114 of the sternal retractor. The hydrogel DEP B110 thus cushions the cut bone surface B104B of the halves B102 of the bisected sternum from the retractor blades B114. Furthermore, drugs diffuse from the hydrogel DEP B110 into the cut surface B104B of the halves B102 of the bisected sternum. The drugs can include agents that block inflammation, stop bleeding, have antibiotic or anti-microbial action, encourage wound healing, or have other beneficial effects. Furthermore, there can be tubes B112 embedded in the hydrogel B111 that circulate cooling fluid from an external recirculating chiller (B28, not shown here), thereby cooling the hydrogel B111 and thus the cut surface B104 of the sternum. The tube B112 can be impermeable to the drug(s), to prevent loss of drug(s) in the cooling fluid, or the tubes B112 can be permeable to the drug(s) and the fluid used to deliver drug(s) to the DEP B110.

Figure 45:
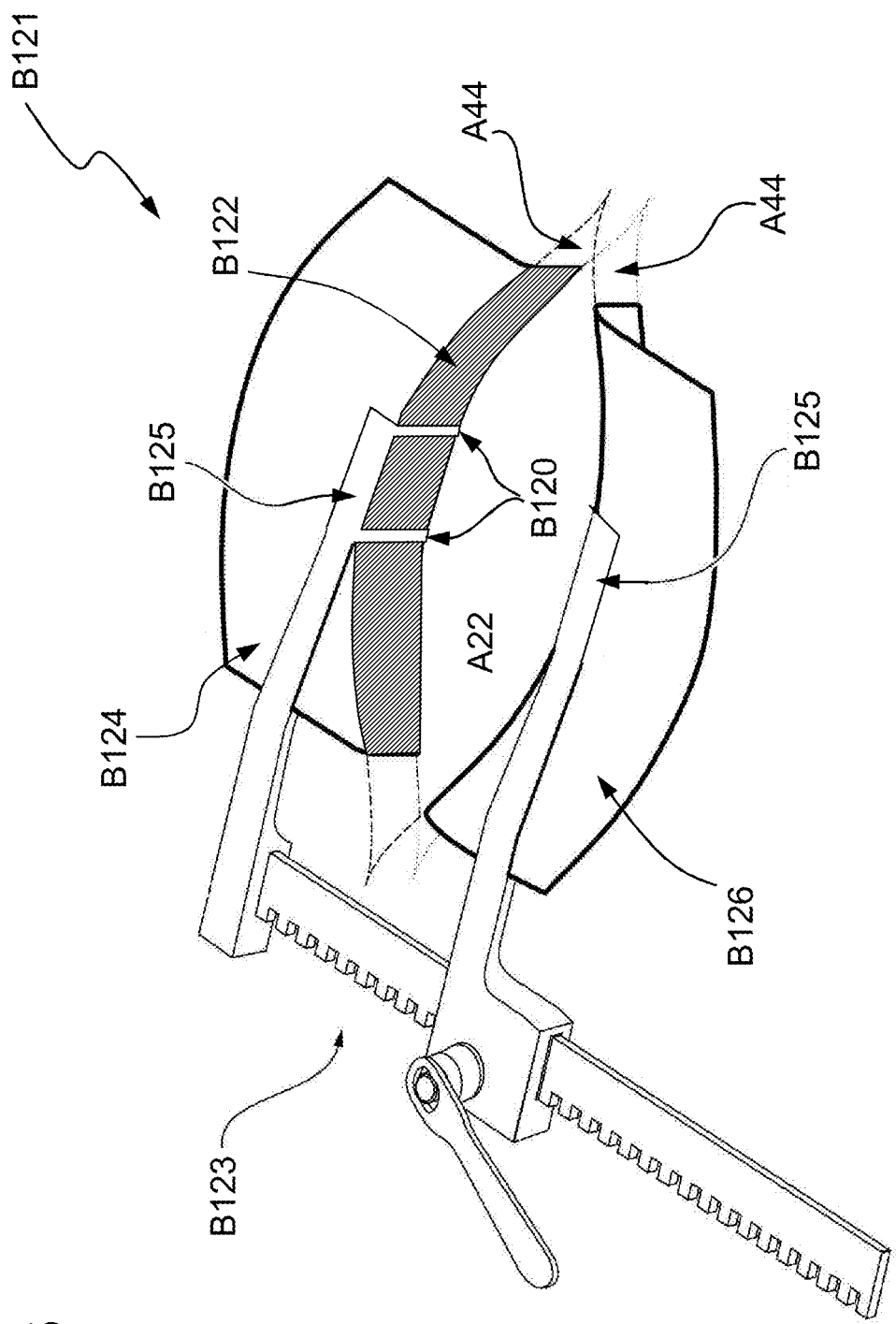
FIG. 45 shows exemplary drug-eluting pads fitted to the retractor blades of a thoracic retractor, where the drug-eluting pads have a rigid component to distribute force along the margin of the incision and for pressing the drug-eluting pads against the cut tissues at the margin of the incision.
Figure 46:
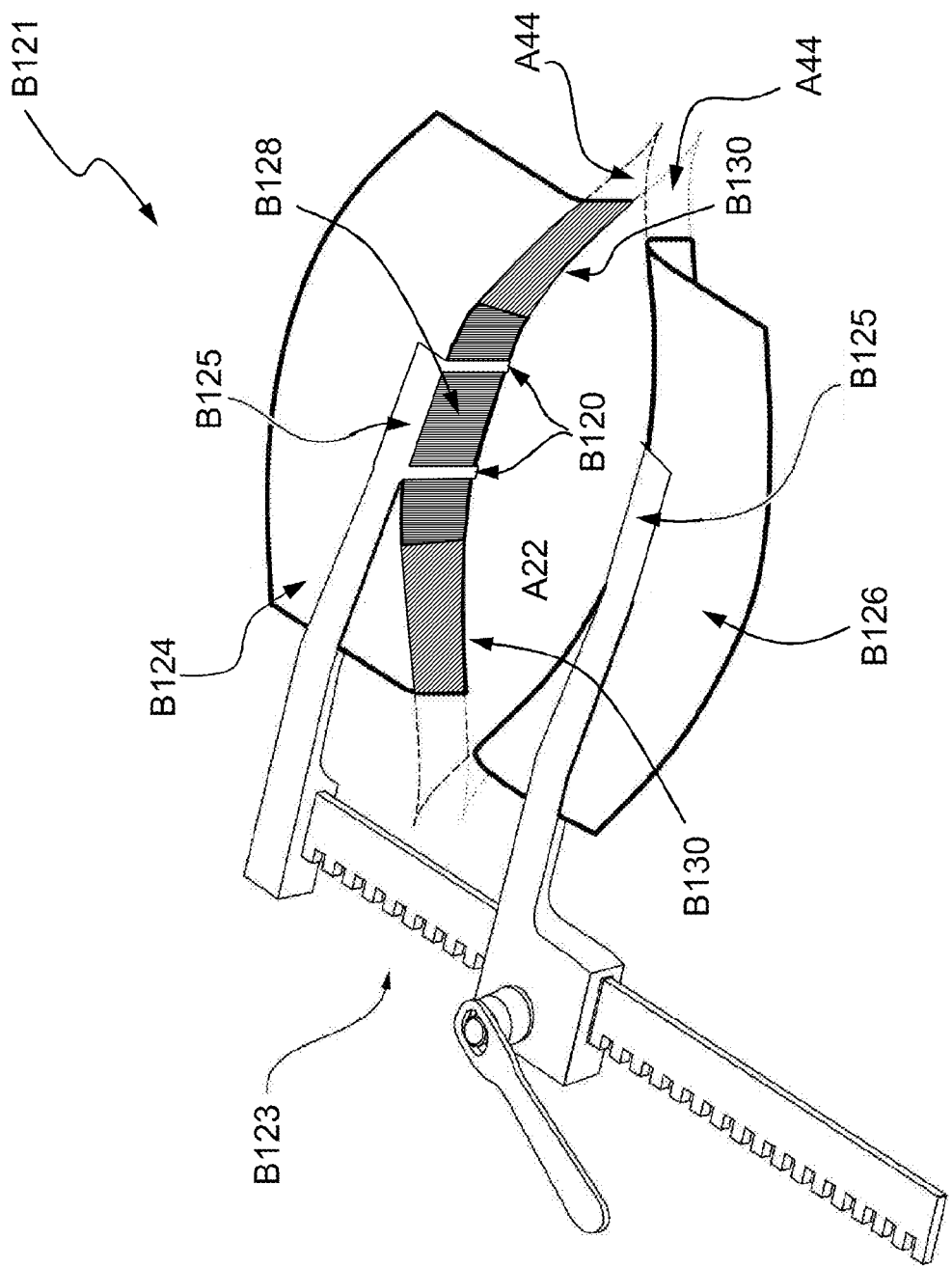
FIG. 46 shows exemplary drug-eluting pads fitted to the retractor blades of a thoracic retractor, where the drug-eluting pads have a rigid component divided into a more rigid central portion and a less rigid peripheral portion.

A DEP can include a mechanically rigid component, such as a metal plate that lines the side of the DEP opposite the tissue. This rigid component can then be engaged by a retractor such that the mechanically rigid component acts like a retractor blade that both distributes force along the edge of the incision and pushes the DEP under the plate against the edge of the incision. FIG. 45 shows an example of such an embodiment. Here a thoracic retractor B123 has modified retractor blades B125 that are formed by two descender posts B120 that engage and push against a rigid component B122, shown here as a flat plate apposing each edge A44 of the incision A22. There are two rigid components B122 (only one is visible in this perspective drawing) that line each edge A44 of the incision A22. The DEP B121 has two halves B124 and B126. Each rigid component B122 is integral with its respective half B124 or B126, optionally being fused together or fitting into a mechanical clasp or other fixture. The rigid component B122 can be highly rigid, or it can be flexible, or have flexible or sprung hinged portions, to allow differing distributions of retraction forces along edge A44 of the incision A22. For example, as shown in FIG. 46, the rigid component B122 can be more rigid at its center B128 where it pushes against the middle of the edge of the incision and more flexible at its ends B130 where it pushes against the ends of the incision. The rigid component B122 can also possess discreet regions of desired flexibility, for example narrowed sections or locally differing materials, or conversely, the rigid component can possess a smoothly, continuously varying gradient of flexibility. The gradient(s) above can be aligned to a straight axis, a curving axis, and/or multiple axes. The axes can cross each other.

Figure 47B:
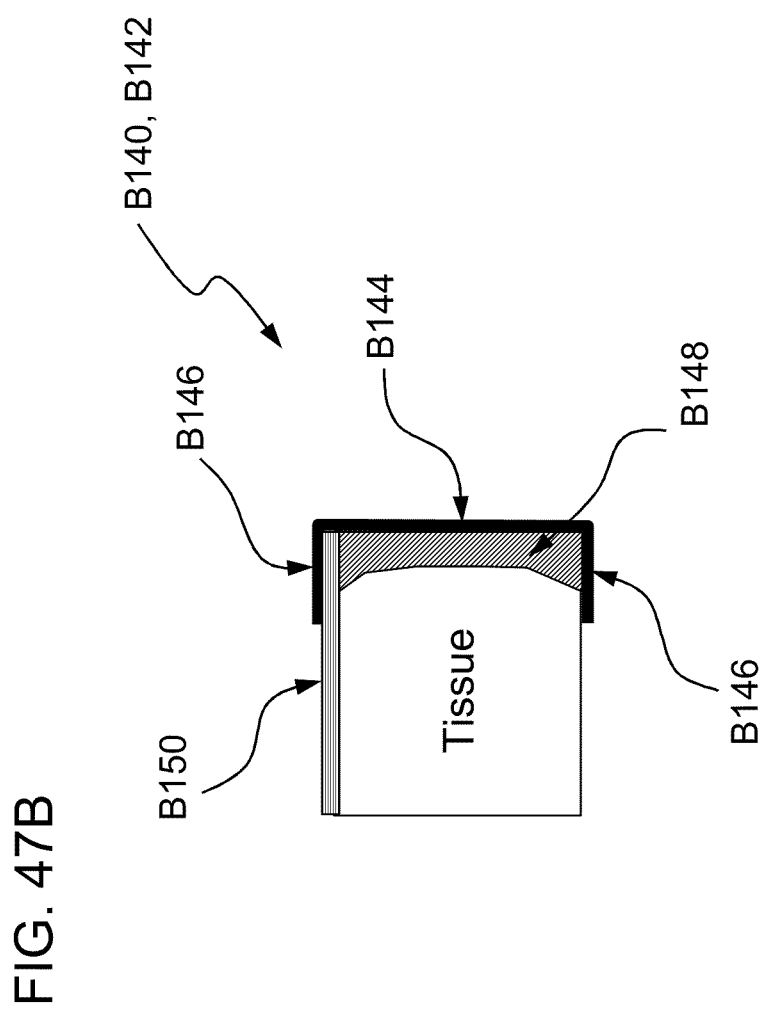

Such a DEP B121 with a rigid component B122 can include features or components that assist in engaging the tissue along the edge A44 of an incision A22. For example, if the rigid component B122 is a rigid plate, for example made of metal, rigid polymer or composite, that lines the side of the DEP B121 opposite the tissue, the plate can wrap around the DEP B123 such that it also wraps around the tissue at the edge A44 of the incision A22 (above and below, or exteriorly and interiorly, or along the edge A44 of the incision A22). Examples include wrapping around a rib at the edge A44 of an incision A22 during a thoracotomy or wrapping around the soft tissues of the abdominal wall during an abdominal surgery. Such wrapping around the tissue at the edge A44 of the incision A22 can reinforce mechanical engagement with the tissue; for example, the wrapping can help resist slipping of the DEP B121 against a cut sternum, or it can help resist torsion of the sternum during retraction. These portions of the rigid component B122 that wrap around the DEP B121 and tissue can be configured to facilitate bending, folding, or otherwise adaptive reconfiguring of the rigid component; for example, these portions can be divided into segments. The segments (i.e., the divisions forming them) may be oriented such that the segments automatically conform to the shape changes of the anatomy as retraction progresses. FIGS. 47A and 47B show such an embodiment.

FIG. 47A shows a perspective view, and FIG. 47B shows a cross-sectional view through one-half of the assembly. Similar to the embodiment shown in FIG. 46, a thoracic retractor B123 has modified retractor blades B125 comprising two descender posts B120. A DEP B121 has two halves, here numbered B140 and B142. Each half B140, B142 has a rigid component, here numbered B144, that has edges B146 that wrap abound the edge A44 of the incision A22. The drug-eluting portion is a hydrogel B148 apposed to rigid component B144 and wrapped by the edges B146, as shown in FIB. B26B. This example also shows cooling pads B150 (similar to the post-incision cooling pads disclosed in Section A) attached to the rigid component B144 such that cooling pads B150 cover and cool the tissues adjacent to the incision A22. The cooling pads B150 can be cooled by one of several means, such as a fluid circulating through cooling pads B150 from a recirculating chiller remote from the cooling pad B150 and attached by a set of tubes (not shown).

The rigid component of a DEP can include features to facilitate engagement with the arms of a retractor, such as fenestrations, flanges, holes, hinges, posts, pivots, hooks, pads, shocks, springs and features that specially match complimentary features on the retractor.

The rigid component of a DEP can also include features to facilitate engagement with the tissue. Such features can include blades, spikes, barbs, or roughened sections, including features that project through the drug-eluting portion of the DEP, to prevent slipping and to facilitate engagement with specific tissue components. FIGS. 48A and 48B show a DEP B155 used for a thoracotomy. Sharp-edged blades B160, oriented vertically with respect to the patient's skin and attached perpendicularly to the rigid component B122, are manufactured such that they project through the drug-eluting portion B148 to then slice or push through soft tissues B162 overlaying rib B164 (i.e., those tissues lying between the rib B164 and the exposed edge A44 of the incision A22) to directly engage the rigid edge of the rib B164 such that the intercostal nerve B166 of rib B164 is not touched (FIG. 48B).

Note that the rigid component of a DEP can include multiple features for engagement of the retractor or a portion thereof. These can be used to permit multiple placements of a retractor or repositioning of a retractor or a part of a retractor. Alternatively, the features of engagement can be used to engage each blade of a multi-bladed retractor, such as an Ankeney retractor, to assist in the distribution of forces along the sternum.

Figure 49A:
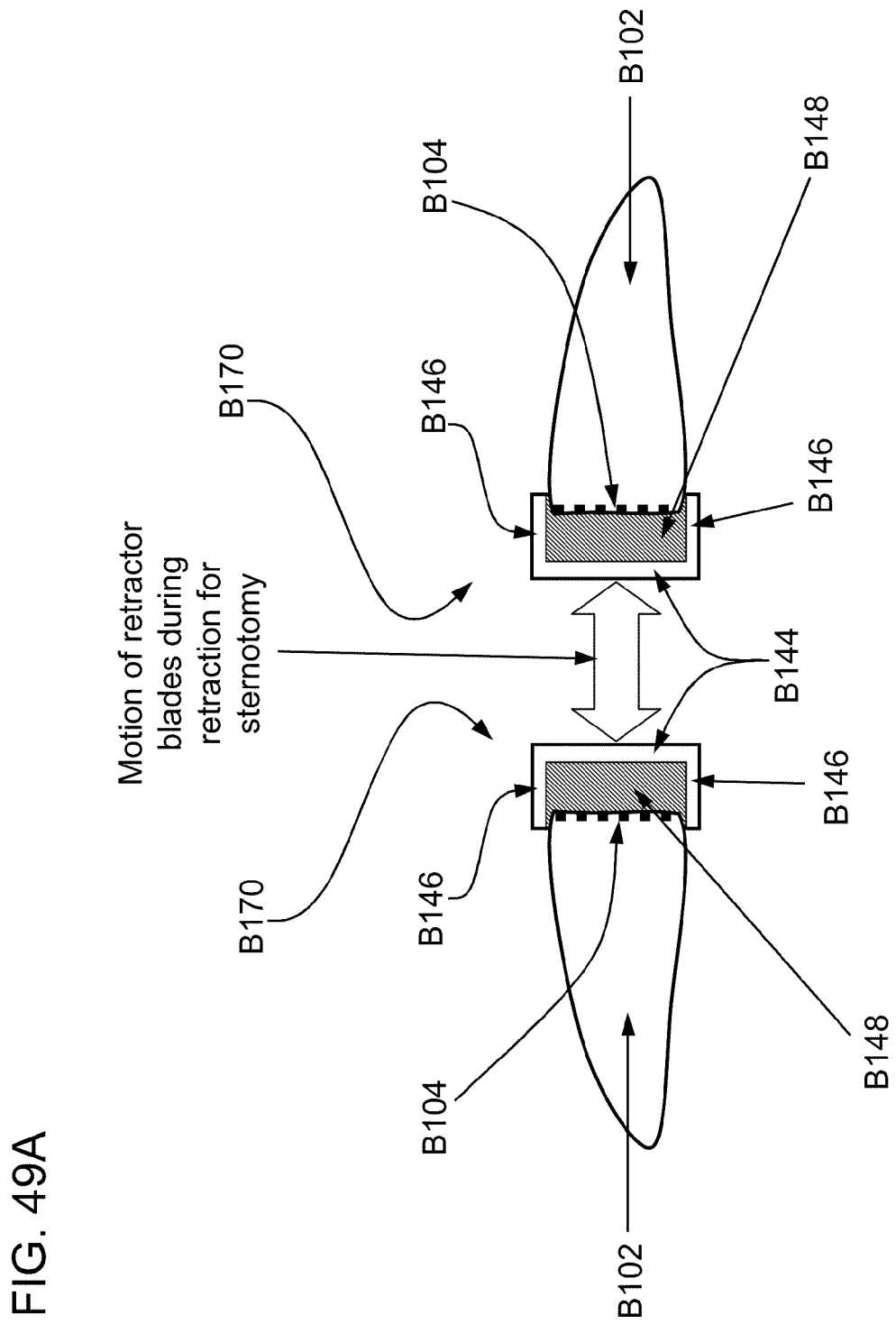
FIGS. 49A and 49B show cross-sectional and top views of exemplary drug-eluting pads fitted to the retractor blades of a thoracic retractor for sternotomy, where the drug-eluting pads have a rigid component to support the cut sternum and to press the drug-eluting pads against the cut sternal tissues during retraction.
Figure 49B:
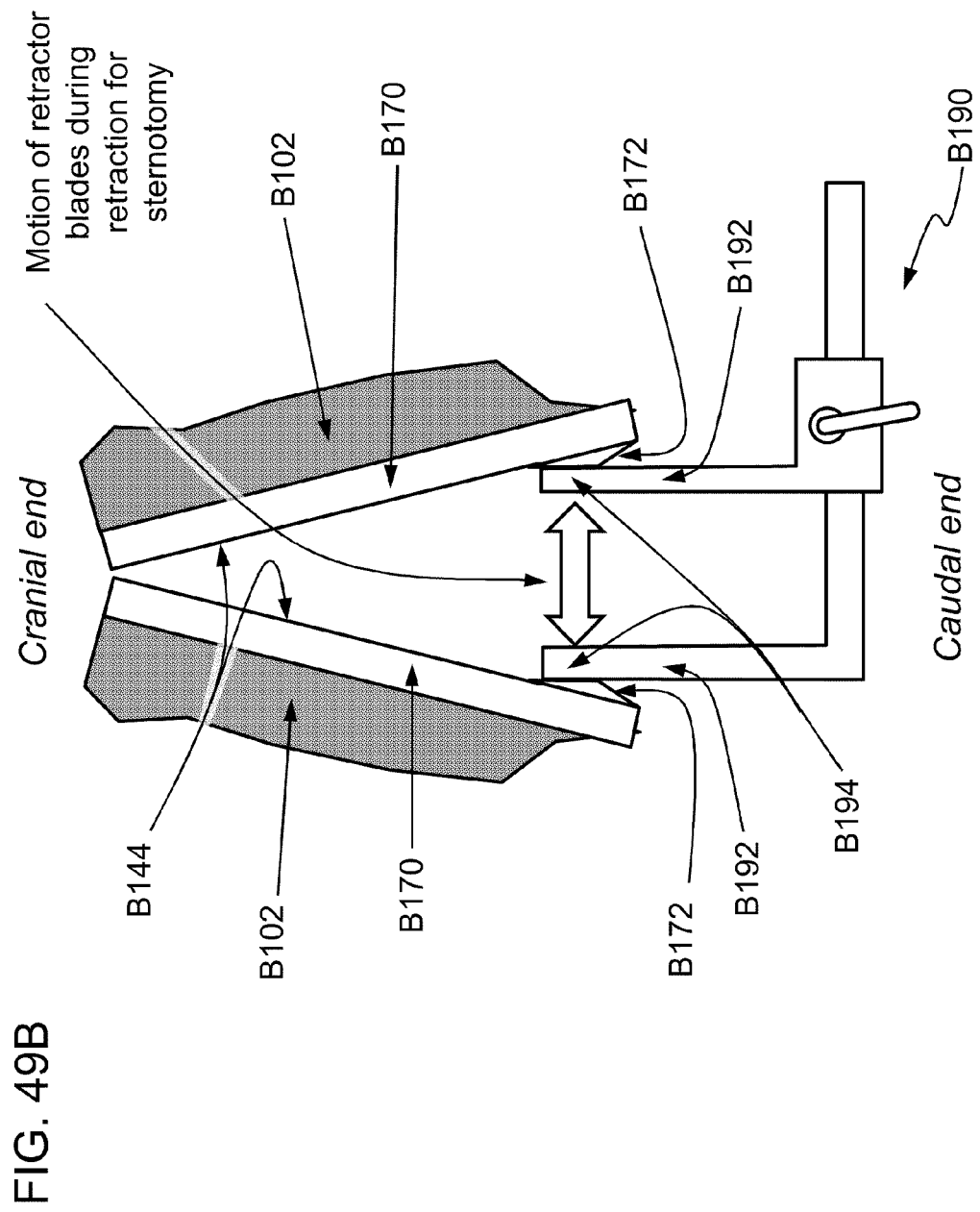

FIGS. 49A and 49B show a DEP B170 with a rigid component B122, B128, B144 (numbered here as B144) that is used to support the two halves B102 of the sternum during a medial sternotomy or other procedure requiring full or partial incision of the sternum. FIG. 49A shows a cross-sectional view of the sternum and DEP B170; FIG. 49B shows a top view (surgeon's view) of the sternum with the assembled DEP B170 and sternal retractor B190. (Note that this is similar to the DEP B100 shown in FIGS. 42 and 43, however, now a rigid component B144 is part of the assembly. Note also that the orientations and the mechanical properties of the segments in FIGS. 49A and 49B can be configured to create desirable deformations, such as an "A"-shaped aperture during a sternotomy with the cranial end of the incision being at the apex of the "A"). Two DEPs B170 are used, one supporting each of the two halves B102 of the bisected sternum. Each DEP B170 has a rigid component B144 that supports the edge B104 of each half B102 of the sternum along the entire incision and edges B146 that wrap the cut edge B104 of the sternum half B102. A drug-eluting hydrogel B148 delivers drug(s) to the cut edge B104 of the sternum half B102. Additionally, each rigid component B144 has a retractor blade engagement feature B172 to facilitate engagement with the arms B192 or retractor blades B194 of sternal retractor B190 so permitting a more caudal placement of the sternal retractor B190. This placement of rigid component B144 and retractor blade engagement feature B172 largely removes the thoracic retractor B190 from the surgical field, and provides maximum opening at the caudal end of the sternum (creating an "A"-shaped exposure), while also supporting the bisected sternum along the entire length of the cut face B104 of each half B102 of the sternum. (Other combinations of rigid components B144 and engagement features B172 can provide alternative placements of thoracic retractor B190 and/or DEP B170). The retractor blade engagement feature B172 is a reinforced section of the rigid component B144 possessing an angled face to provide a surface that is parallel to the blades B194 of sternal retractor B190; alternatively, this section could be a hole into which is placed a cylindrical post from the retractor arm B194 or any other combination of retractor component/DEP feature to provide a mechanically secure engagement between sternal retractor B190 and rigid component B144 of the DEP B170. This combination of a rigid component B144 along the entire length of the cut sternum half B102 plus a retractor blade engagement feature B172 to engage the sternal retractor B190 prevents slipping of the sternal retractor B190 against the angled sternum surface B104, provides mechanical support of each sternum half B102, and reduces point loads and other uneven distributions of force leading to stresses inside each sternum half B102 that could lead to the damage of tissues in the sternum or to fracture of the sternum half B102 during retraction. The drug-eluting hydrogel B148 cushions the cut face B104 of the sternum half B102, preventing further trauma of this tissue. The drug-eluting hydrogel B148 can release sterile physiological saline to keep the tissue hydrated, thrombin to reduce bleeding, a cocktail of antibiotics to reduce the chance of infection, and/or an opioid analgesic to reduce the local inflammation response and to prophylactically treat pain or any other pharmacologically advantageous compound or chemical. The drug-eluting hydrogel B148 can, optionally, be sufficiently soft that it easily deforms into the cut surface of the sternum and blocks off cut blood vessels, thereby acting as a physical dam to bleeding, in a fashion similar to bone wax, but without leaving a residue after surgery, like bone wax.

Figure 50B:
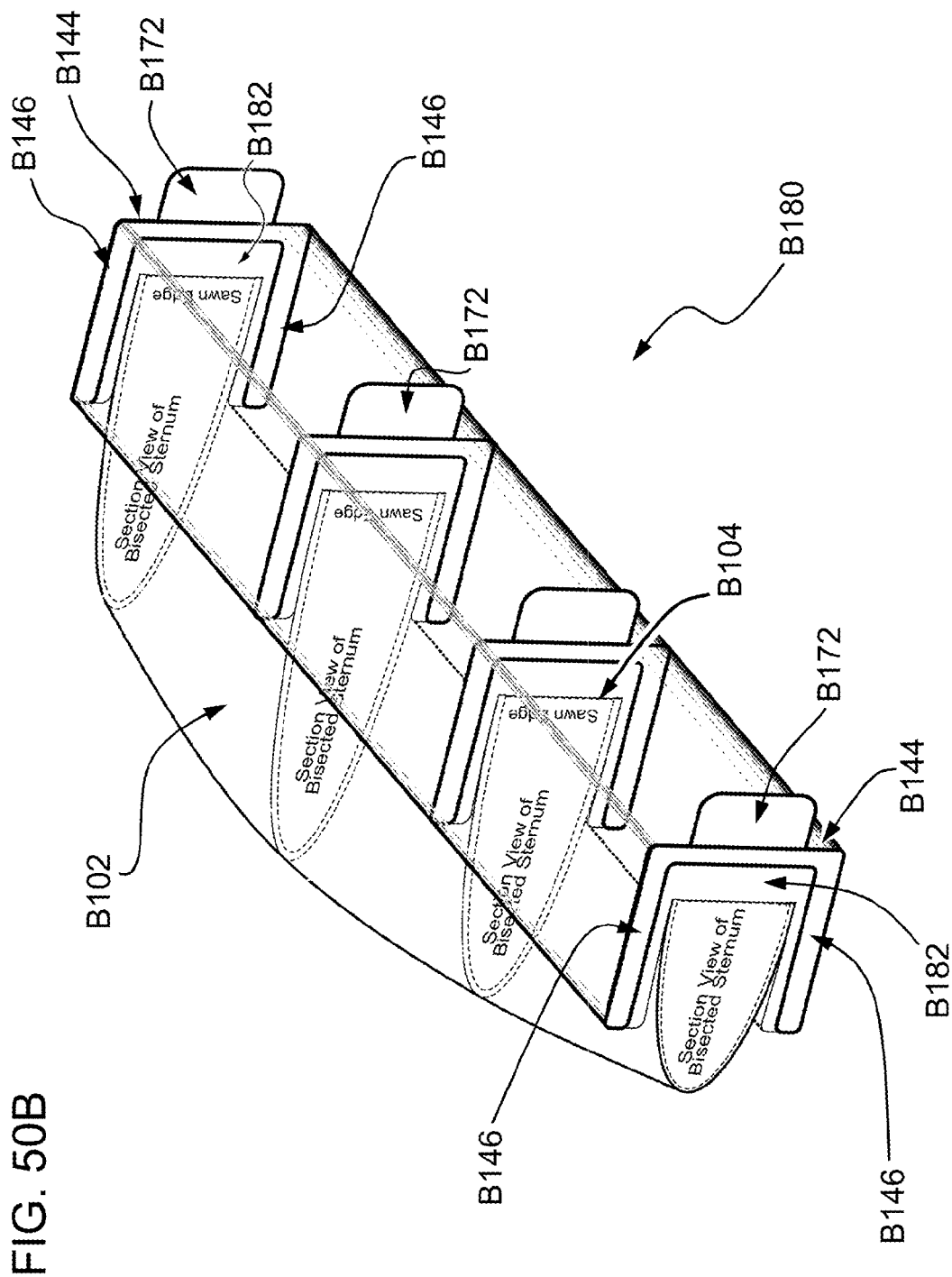

FIGS. 50A and 50B show an embodiment of a DEP B180 similar to that shown in FIGS. 49A and 49B, but in this embodiment, the drug-eluting portion B182 also wraps the tissues at the edge of the incision. The drug-eluting portion B182 is a hydrogel that cushions the cut edge B104 of the sternum half B102, and completely underlies the rigid component B144, including edges B146 that wrap the cut edge B104 of the sternum half B102. This arrangement provides a cushioned, but firm, engagement with the sternum half B102 that permits completely cradling the sternum half B102. FIG. 50B shows multiple cross-sections in an oblique view depicting how a DEP B180 can then be used to support the full edge B104 of the sternum half B102.

B.3 Drug-Eluting Pads (DEPs) and Devices Integral with Trocars and Other Inserted Devices Trocars A200 are surgical devices that are used to make openings through a body wall A94 for endoscopic procedures (e.g., laparoscopy) (see FIG. 24). Once inserted, trocars A200 provide a channel for the insertion of other surgical implements, such as a borescope, forceps, or scissors. As with retractors described above in Section B.2, this Section B.3 describes new devices and means for treating tissues commencing on insertion of the trocar A200 and, optionally, spanning the duration of the surgical procedure.

Figure 51A:
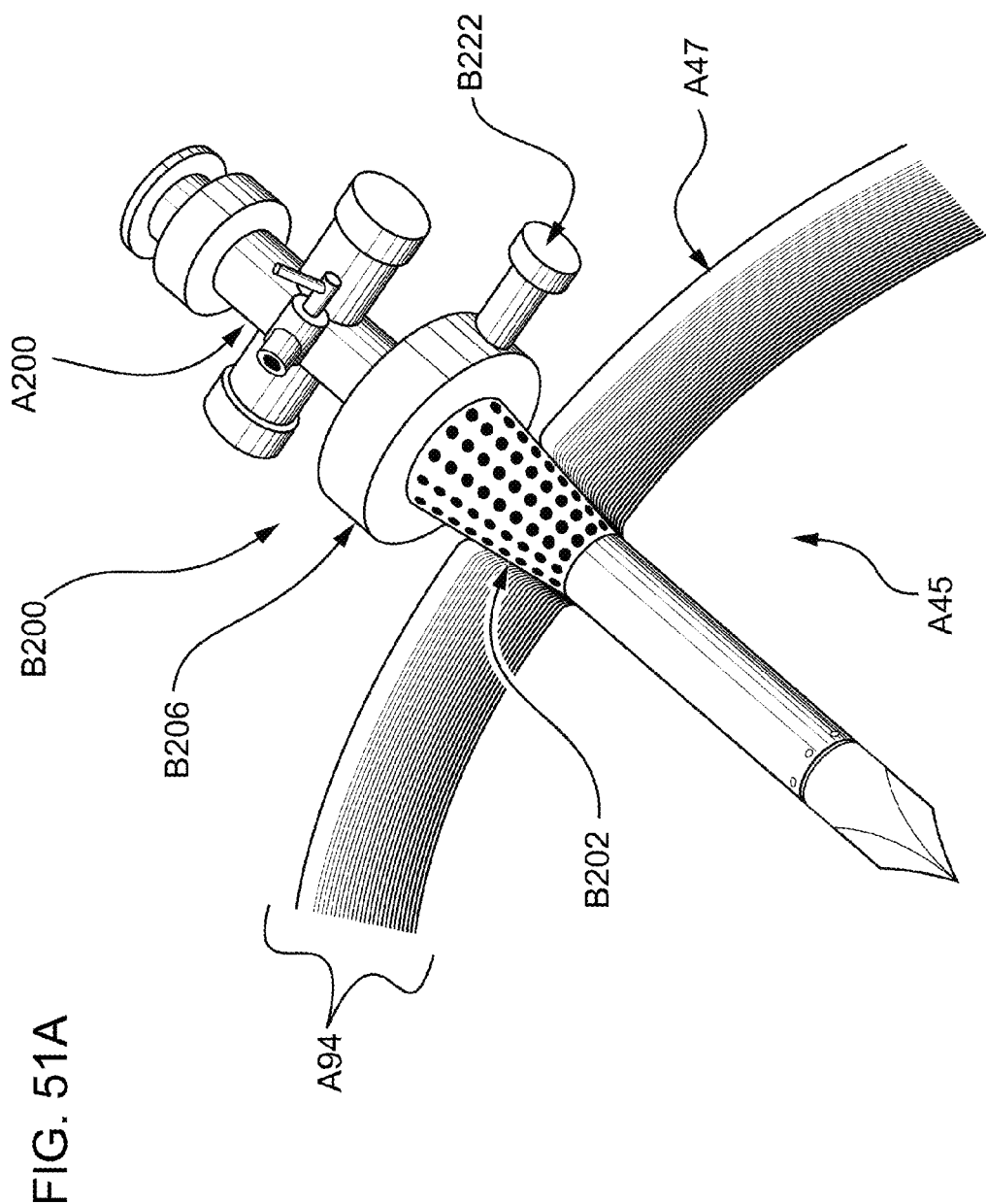
FIGS. 51A and 51B shows a trocar in side view fitted with an exemplary drug-eluting reservoir that pumps to a sleeve that delivers drug-bearing fluid to the cut tissues at the margin of the incision created with the trocar.
Figure 51B:
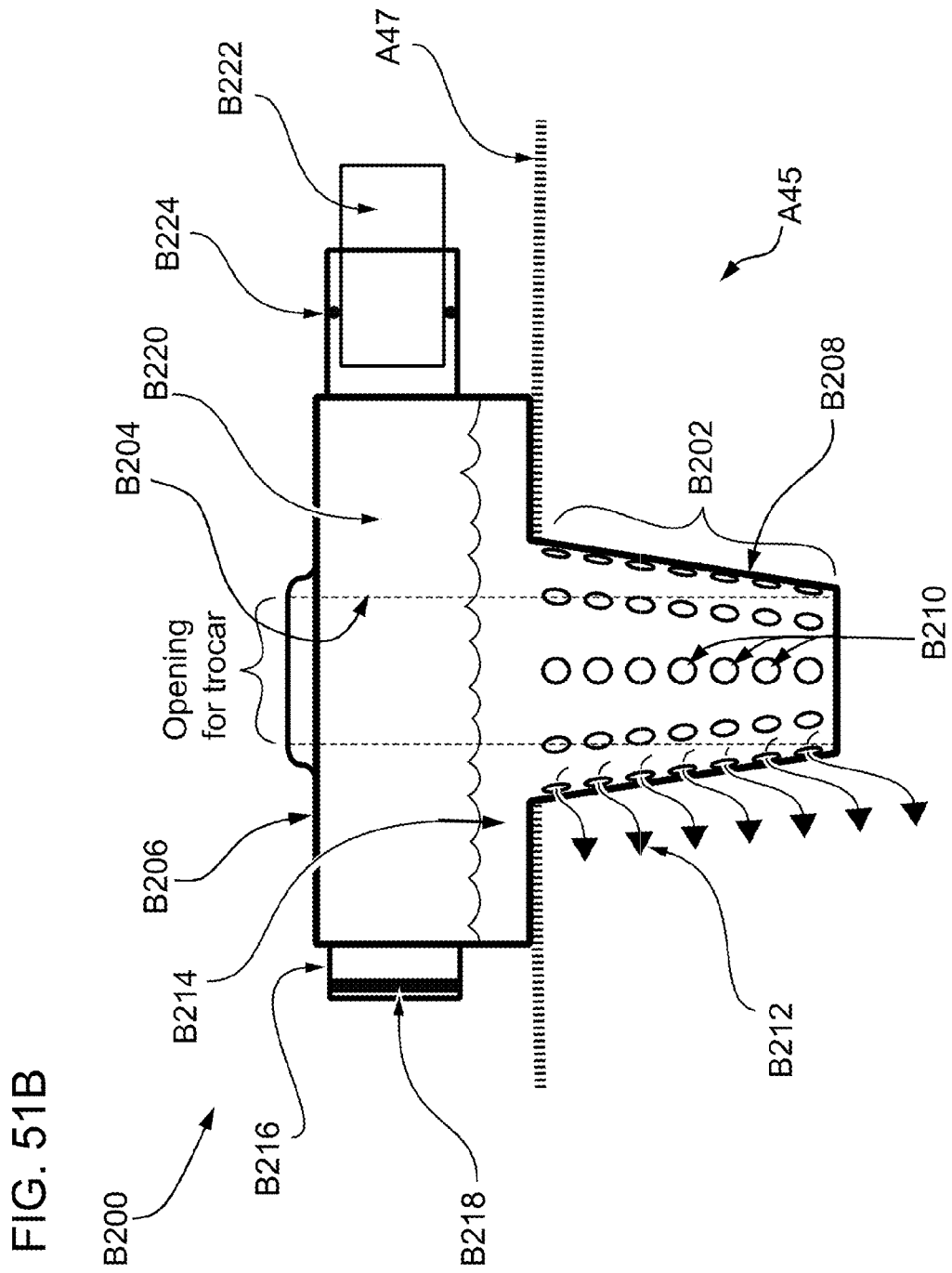

One example of a drug-eluting device B200 configured to treat the tissues cut by a trocar A200 is shown in FIG. 51A and FIG. 51B (FIG. 51B shows a cross-section of the device). Drug-eluting device B200 has a double-walled, hollow sleeve B202 whose inner wall B204 closely fits the shaft of the trocar A200. The double-walled sleeve B202 extends into the incision made by the trocar A200. A drug reservoir B206 is attached to the double-walled sleeve B202 such that the drug reservoir B206 sits just outside the patient's tissues A45, for example against the skin A47. The double-walled sleeve B202 has a hollow core permitting the flow of fluid from the drug reservoir B206 into the double-walled sleeve B202. On the tissue-facing side of the double-walled sleeve B202, a tissue-facing wall B208 of the double-walled sleeve B202 is perforated (perforations numbered as B210) such that drug-bearing fluids can directly flow (arrows marked B212) from the inside of the double-walled sleeve B202 out to the tissue A45. The perforations B210 can be any suitable means of permitting direct flow of fluid from inside double-walled sleeve B202 to the surrounding tissue A45, including holes that are open or that are covered with a frit to reduce fluid flow rates, or the perforations B210 can be covered with a permeable membrane to permit slow flow of fluid through the perforations B210. Alternatively, the perforations B210 can be so small as to prevent fluid flow but permit diffusion of drug from inside of the double-walled sleeve B202 out to the tissue A45. Drug-bearing fluid B214, such as a physiological saline, is placed into the drug reservoir B206 with a hypodermic syringe, through a fill port B216 that is closed by a self-sealing rubber membrane B218.

A drug can be placed into the drug reservoir B206 before the trocar A200 is inserted. After insertion, a gas-filled head B220 over the drug-bearing fluid B214 is pressurized by a small finger-actuated piston B222, thereby initiating the flow of the drug-bearing fluid B214 through the perforations B210 and onto the tissue A45. The piston B222 can be of the momentary action type (return spring from the internal gas pressure), a locking type which stays in once pushed, or an accumulating (valved) type that builds increasing internal pressure with multiple finger pushes. The seal between the drug reservoir B206 and the finger-actuated piston B222 can be formed by an o-ring B224 or other appropriate mechanism. The entire drug-eluting device B200 can be a single unit that slips onto the trocar A200 before use. Alternatively, the drug-eluting device B200 can be manufactured integrally with a trocar A200.

Figure 52:
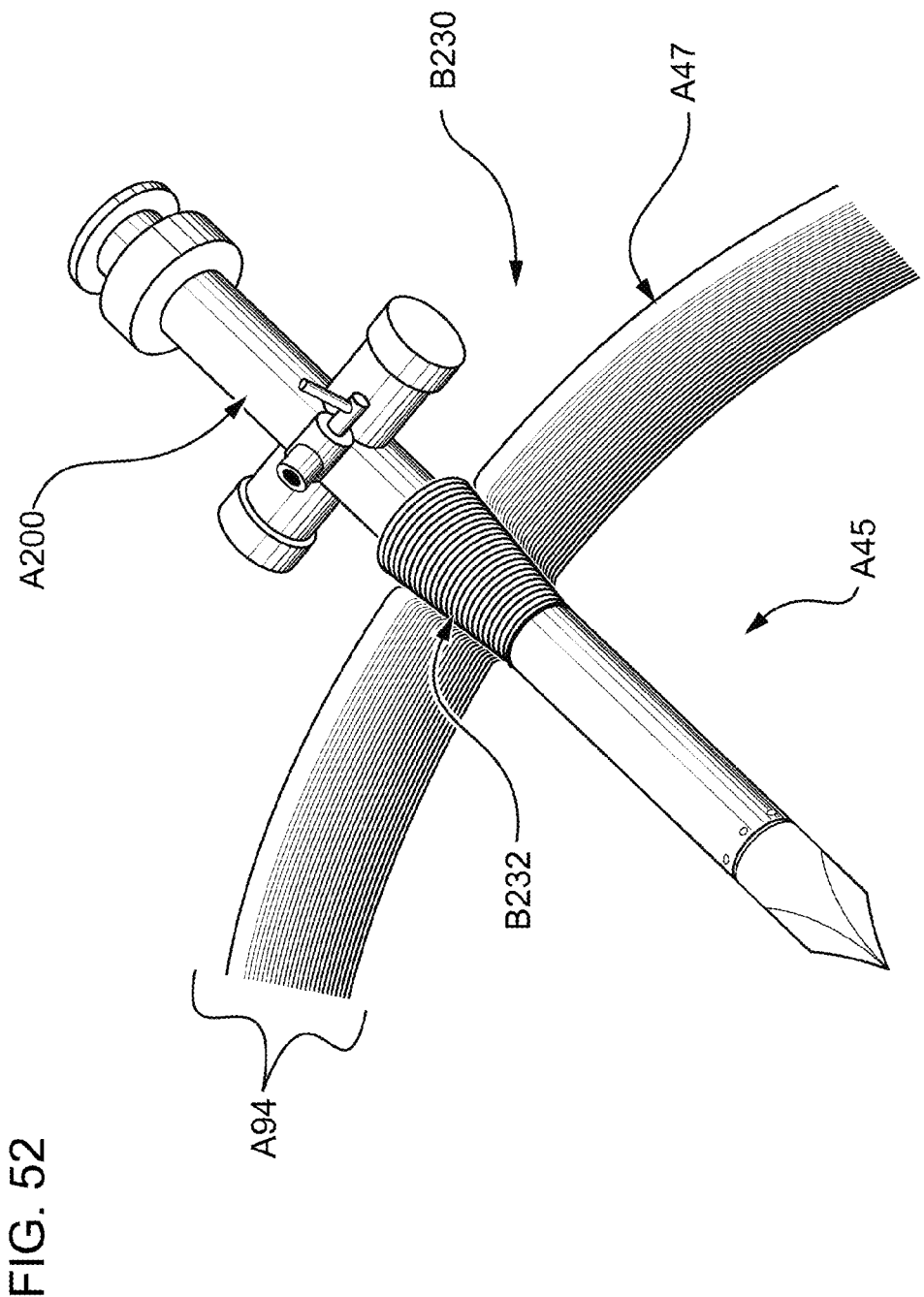
FIG. 52 shows a trocar in side view penetrating the body wall of a patient, where the trocar is fitted with an exemplary hydrogel coated sleeve for delivering drugs to the cut tissues at the margin of the incision created with the trocar.

FIG. 52 shows another drug-eluting device B230 in which a thin layer of hydrogel material B232, impregnated with drug, coats a thin-walled cylinder (not shown) that fits onto a trocar A200 as a sleeve. Delivery of drug is by diffusion from the hydrogel material B232 to the tissue A45 surrounding the trocar A200 incision. Again, this drug-eluting device B230 can slip onto a trocar A200 before use, or, trocars A200 might be manufactured with the drug-eluting device B230 in place.

Figure 53A:
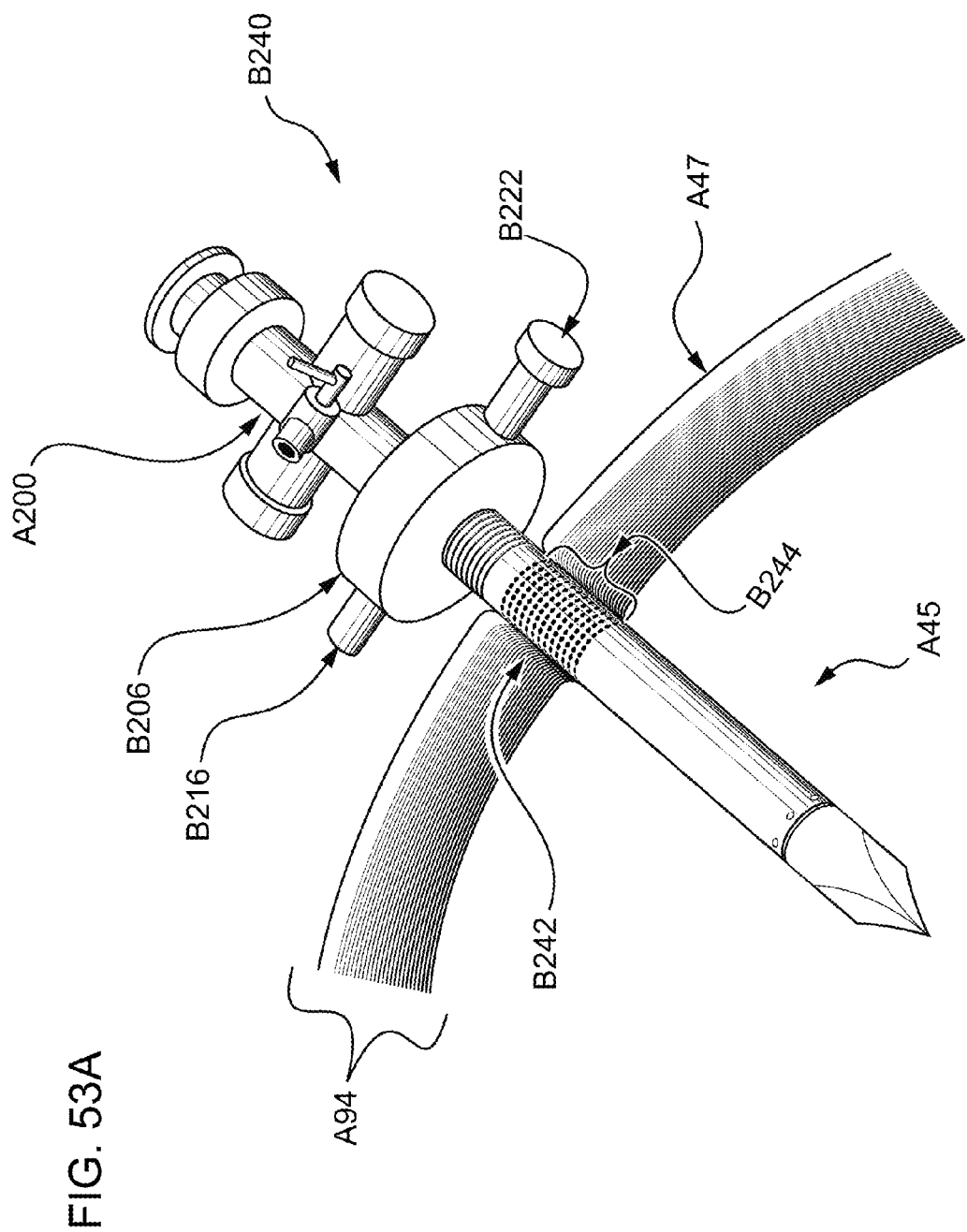
FIGS. 53A and 53B show a trocar in side view that has an exemplary, integral drug-eluting reservoir that pumps to perforations in the side wall of the trocar to deliver drug-bearing fluid to the cut tissues at the margin of the incision created with the trocar.
Figure 53B:
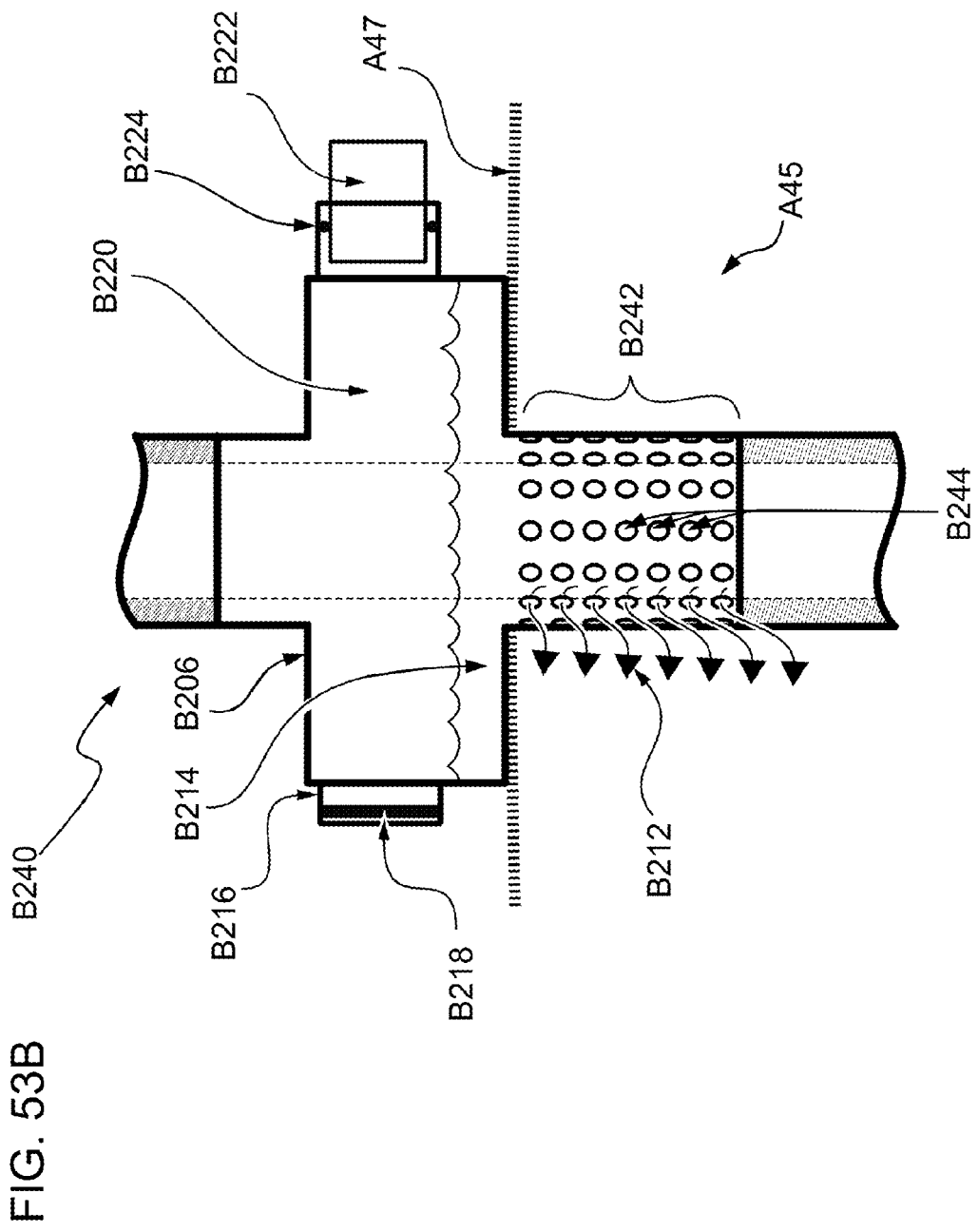

FIGS. 53A and 53B (FIG. 53B shows a cross-section of the device) show a drug-eluting device B240 that integrates the drug-eluting device B200 shown in FIGS. 51A and 51B with the trocar A200. In effect, the trocar A200 becomes a drug-eluting device B240. A wall B242 of the trocar A200 that apposes the patient's tissue A45 throughout the procedure possesses an array of perforations B244 that connects via a double-walled portion of the drug-eluting device B240 to a drug reservoir B206 filled with drug-bearing fluid B214. The wall B242 has perforations B244 such that drug-bearing fluid B214 can directly flow (arrows marked B212) from the inside of the wall B242 out to the tissue A45. The perforations B244 can be any suitable means of permitting direct flow of fluid from inside wall B242 to the surrounding tissue A45, including holes that are open or that are covered with a frit to reduce fluid flow rates, or the perforations B244 can be covered with a permeable membrane to permit slow flow of fluid through the perforations B244. Alternatively, the perforations B244 can be so small as to prevent fluid flow but permit diffusion of drug from inside of the wall B242 out to the tissue A45. A drug-bearing fluid B214, such as a physiological saline, is placed into the drug reservoir B206 with a hypodermic syringe, through a fill port B216 that is closed by a self-sealing rubber membrane B218. Drug can be placed into the drug reservoir B206 before drug-eluting device B240 is inserted. After insertion, a gas-filled head B220 in the drug reservoir B206 is pressurized by a small finger-actuated piston B222, thereby initiating the flow (arrows numbered B212) of the drug-bearing fluid B214 through the perforations B244 and onto the tissue A45.

It will be apparent to persons skilled in the art that many aspects, configurations, and functions of cooling pads and drug-eluting pads are complementary and can be combined. Functions such as drug-elution, cooling, cushioning, protection of the incision edge, and others can readily be combined into a single embodiment.

C. Pressure Pads

C.1 Damage to Tissues Caused by Current Retractors

Figure 54:
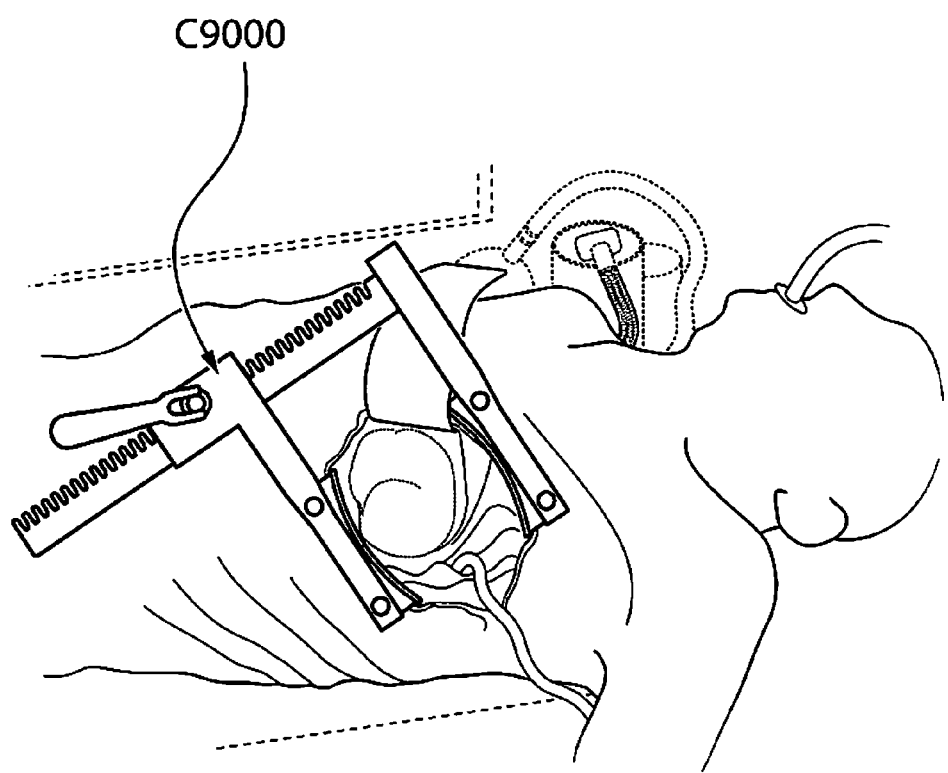
FIG. 54 shows an example a thoracic retractor used in a thoracotomy in the prior art.
Figure 55:
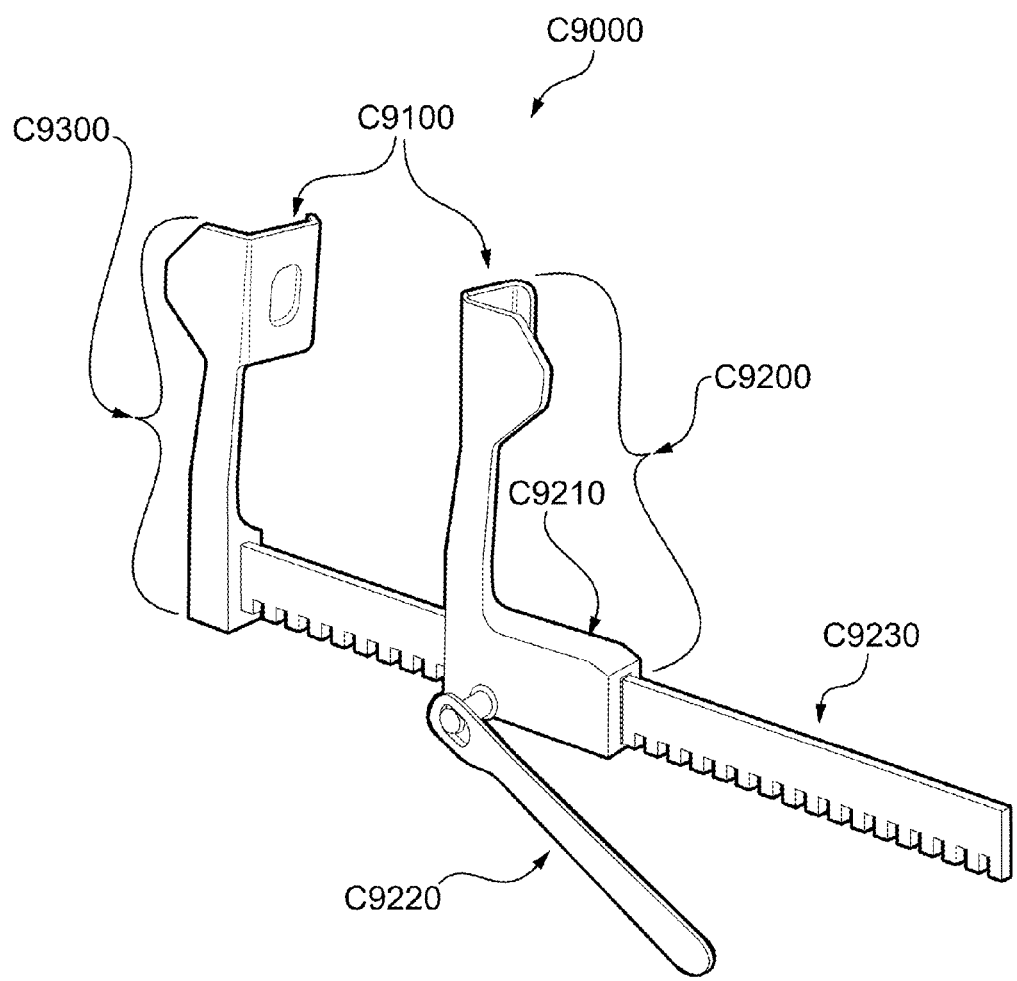
FIG. 55 shows another example a Finochietto thoracic retractor in the prior art.
Figure 56:
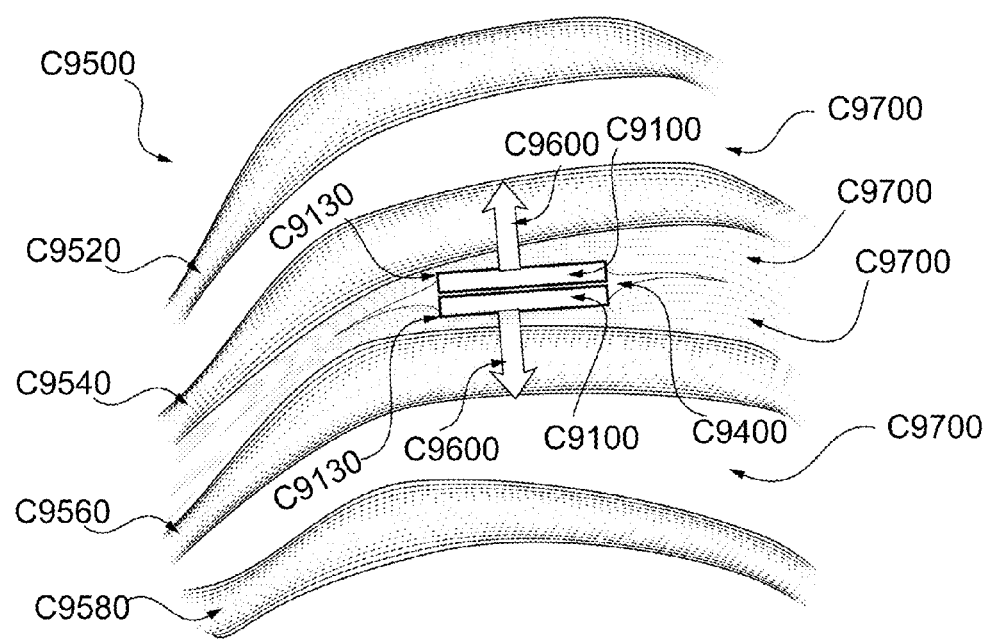
FIG. 56 shows the actions of the retractor blades of a retractor in the prior art when inserted between ribs for a thoracotomy.

Many medical procedures require a surgeon to deform a patient's bodily tissues. For example, to gain therapeutic access to a patient's heart or lungs (see FIG. 54 85, color photo of a Finochietto retractor in vivo), often a surgeon slices open the intercostal musculature between two ribs and inserts a thoracic retractor (i.e., a rib spreader, see FIG. 55). The blades C9100 of a retractor C9000 forcefully pry the rib cage apart. As shown in FIG. 55, the retractor C9000 is a steel jack usually sporting a rack-and-pinion drive C9210, a hand crank C9220, a fixed retraction element C9300, and a moveable retraction element C9200. Referring now to both FIG. 55, and to FIG. 56 (which shows a view of the surgical field and the position of the retractor blades C9100 therein), after insertion into an incision C9400 between ribs C9500, the surgeon turns the hand crank C9220 that operates the rack-and-pinion drive C9210 along a rack C9230 to separate retractor blades C9100 and thereby create an opening (or aperture) for surgical access. The steel retractor blades C9100 press directly onto, and into, the muscle, nerves and other soft tissue C9700 covering ribs C9500 on either side of, and, drive ribs C9540 and C9560 that border the incision C9400 into a next, adjacent set of ribs C9520 and C9580, crushing also the soft tissues C9700 situated between those bordering ribs (C9540 and C9560) and the adjacent ribs (C9520 and C9580). However, the force C9600 required to displace the patient's ribs C9500 is more than sufficient to damage the patient's intervening soft tissues and even large enough to fracture ribs and associated anatomy (2, 5, 9, 17, 25-27, 40, 47). In fact, referring now to FIG. 57, the design of some retractors C9000 and retractor blades C9100 is such that stresses on the soft tissues C9700 are concentrated into a tiny total contact area C9120 by virtue of large fenestrations C9110 in the retractor blade C9100. Other geometries of the retractor-tissue interface, such as the very sharp corners C9130 of the retractor blades C9100 create enormous stress concentrations there.

Thoracotomies and sternotomies require significant rib cage deformations (50-150 mm) that, with current retractor blade designs, generate local stresses and strains causing tissue trauma and so, subsequently, pain. Thoracotomies, especially, induce severe tissue trauma and are widely regarded as one of the most painful surgical procedures. Attempts to ameliorate this pain in the week or so following surgery have largely focused on analgesia for the thoracotomy patient population (~0.5 million people each year worldwide). However, for some of these patients, thoracotomy-associated pain and morbidity can be long-lasting (months to years), and sometimes the pain is permanent (1, 3, 4, 8, 11, 13-15, 18-24, 28-31, 33-39, 41-46, 48). Many patients may never recover full function. A primary cause of the pain is thought to be mechanically induced tissue trauma arising from rib spreading or sternal spreading with a retractor, warranting an improvement in the design of retractors and/or retractor blades.

The above examples are from thoracic surgery; however, post-surgical pain is common for other procedures, frequently being referred to as "port site pain" for laparoscopic procedures (or other procedures using trocars, such as video-assisted thoracoscopic surgery) or where retraction of soft tissue is used for surgical access, such as with full-access abdominal surgery. The inventions described here can be used whenever a biological tissue must be displaced during a surgical or other medical procedure.

Current retractors (e.g., Finochietto rib spreaders C9000, Ankeney sternal spreaders, single-blade hand-held retractors, ring retractors such as Bookwalter retractors, Mayo-Adson laminectomy retractors, Weitlander retractors, and others) apply hard, rigid materials (typically constructed of stainless steel) directly to the biological tissue to be retracted. The transition at the retractor-tissue interface is one of a material with a very high modulus of stiffness (e.g., steel with Young's modulus ~200 GPa or more) apposed against a material with a much lower modulus of stiffness (e.g., bone ~10 to 20 GPa; skin and muscle <0.5 MPa (for severed, relaxed muscle) to <500 MPa (for fully attached, fully active muscle). The materials on each side of this interface, therefore, can deform in very different fashion from each other, producing large interfacial stresses in the softer material, for example in the patient's tissues, easily exceeding the failure or yield stress.

Being in direct, firm contact with the patient's freshly exposed tissues, retractor blades are, therefore, ideally suited for measuring many aspects of the state of those tissues. However, the current state of the art is such that no commercially available retractor blades exploit this fact. The latest, most up-to-date retractors are made of drop-forged steel, with a ground, brushed, or polished surface, occasionally with a plastic overlay, and do not possess any capabilities for detecting tissue state beyond a simple, sudden mechanical report or pop when the patient's tendons or bones snap under load. Given that these tissue trauma events are already plainly audible to bystanders, current retractor blades provide no added sensing benefit. There exists a need for retractor blades capable of providing clinicians or automated mechanisms with obtainable data or information on the (constantly changing) state of the patient's tissues, that might not be obtainable any other way, that could quantify and possibly prevent tissue trauma, and thereby greatly improve patient outcomes.

Retractor blades merely pry open the patient's tissue to widen an access hole. Beyond this (and the tissue trauma caused by retractors, covered above), today's retractor blades do not modulate the patient's tissues. Given that there are phenomena where the physiological properties (say, the modulus) of living tissue change in response to some input, there clearly exists a need to exploit tissue modulation to improve patient outcomes.

C.1 Tissue Engaging Devices (TED) to Reduce Damage, Sense Tissue State and Modulate Tissue State In the first section below, forms of various components of the present embodiment, including shapes, materials and material arrangements, and some capabilities conferred by those are described. In the second section, some of the functional arrangements permitting tissue protection, sensing the state of the tissues, and tissue property modulation are described. In the third and final section, some embodiments that combine different elements of the present embodiment are described.

C.1.1 Forms of the Components

One might think that the simplest way to prevent an instrument from damaging a patient's tissues would be to just cover a steel retractor blade with an isotropic, homogeneous soft rubber pad. One surprising problem with this approach, though, is that in order for the rubber to remain attached to a rigid steel retractor blade, the pad should not distort at all along the interface where it meets the blade, because if it does, the stress concentrations between the steel blade and the soft rubber will be large, promoting dislodgement or delamination leading to failure of the instrument. Even the best adhesives cannot prevent delamination in the face of the large stress concentrations arising from large rubber strains against unyielding steel. To avoid detachment of a pad from a steel blade under load, the pad must be stiff, roughly within an order of magnitude or so of that of the steel's ~200 GPa, so the elastomer should possess a modulus of, at the very least, 10 GPa, the better to reduce any strain that might promote delamination. This value is still orders of magnitude greater than the modulus of a typical patient's soft tissues. Applying an object with a modulus of 10 GPa to the patient's tissues would impose nearly as much stress as the steel, and likely induce as much tissue trauma. It becomes clear that this problem warrants a novel approach.

Embodiments disclosed herein permit the delivery of adequate force from a surgical instrument's working surface (e.g., steel retractor blades) to the patient's tissues without inducing tissue trauma. These embodiments include some basic forms of a TED for surgical instruments. For commercially available rib retractors, a TED could take the form of a retrofit retractor blade pad (see for instance, FIG. 73A far below). The TED could alternatively be an entire retractor arm system that detachably mounts to a retractor base. Still another form can be a complete thoracic retractor, either a rib spreader or a one-hand abdominal retractor (e.g., a Balfour or a Deaver hand-held retractor) retrofitted with TEDs. The retractors might be manufactured at least partially from steel, titanium, fiber-reinforced composite, or other stiff material. Retractors could be designed from scratch to incorporate some of the embodiments herein.

Figure 58:
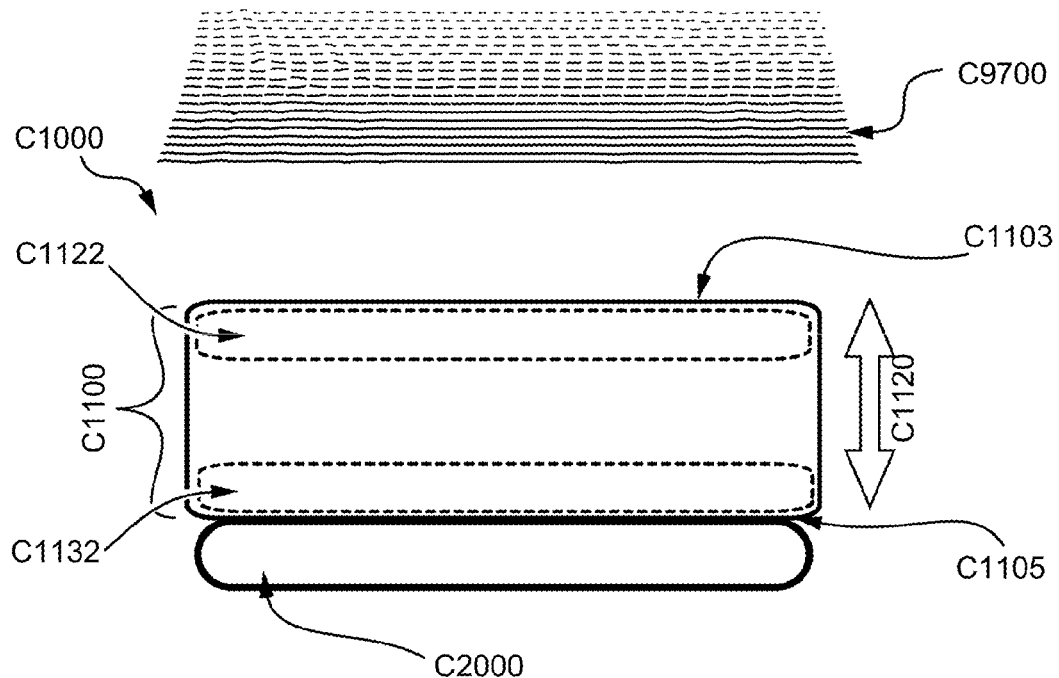
FIG. 58 shows an embodiment of an exemplary Tissue Engaging Device, TED comprising a pad having a gradient of stiffness placed between a retractor blade and a rib.

FIG. 58 shows an embodiment of a Tissue Engaging Device (TED), which can take the form of a gradient pad C1000 able to successfully incorporate or bond to rigid element C2000. The gradient pad C1000 possesses a tissue face C1103 for apposing a patient's soft tissues C9700 and an instrument face C1105 adapted to engage, mount, associate with, or bond to a rigid element C2000. The rigid element C2000 can be constructed out of medical grade, hardened 400 series stainless steel, titanium, fiber-reinforced polymer composite, or any other convenient material of high modulus or sufficient rigidity to be able to apply enough force to displace a patient's tissues during retraction. The gradient pad C1000 is comprised of a pad body C1100 which can be made out of a hydrogel or it can be made out of an elastomer, i.e., an elastomeric polymer or "rubber" which might be a latex, silicone, polyurethane, vinyl or any flexible, resilient material safe for medical use. The gradient pad C1000's pad body C1100 can include more than one modulus (hardness, stiffness) of elastomer in its makeup, and may include at least one portion made out of a soft elastomer C1122, and at least another portion made of a hard elastomer C1132. The soft elastomer C1122 can form (or otherwise be positioned near, or associated with) the tissue face C1103, while the hard elastomer C1132 can form (or otherwise be positioned near or associated with) the instrument face C1105. The modulus of the gradient pad C1000 thus can vary from portion to portion, in this example, there is a modulus gradient C1120 running from the softest material at the tissue face C1103 to the hardest material at the instrument face C1105. The soft elastomer C1122 and the hard elastomer C1132 may be separated from each other within the pad body C1100 by any distance, leaving intervening material between them. The intervening material may possess intermediate moduli.

The gradient pad C1000 can possess a modulus or stiffness gradient C1120 that smoothly and gradually changes from a very high value (for example by using a hard elastomer C1132) on the instrument face C1105 to a very low value (by using a soft elastomer C1122) on the tissue face C1103. The following variations could be made from medical grade polymers from a variety of commercially available sources, for one example, such as those available from Apple Rubber of Lancaster, N.Y.

Figure 59A:
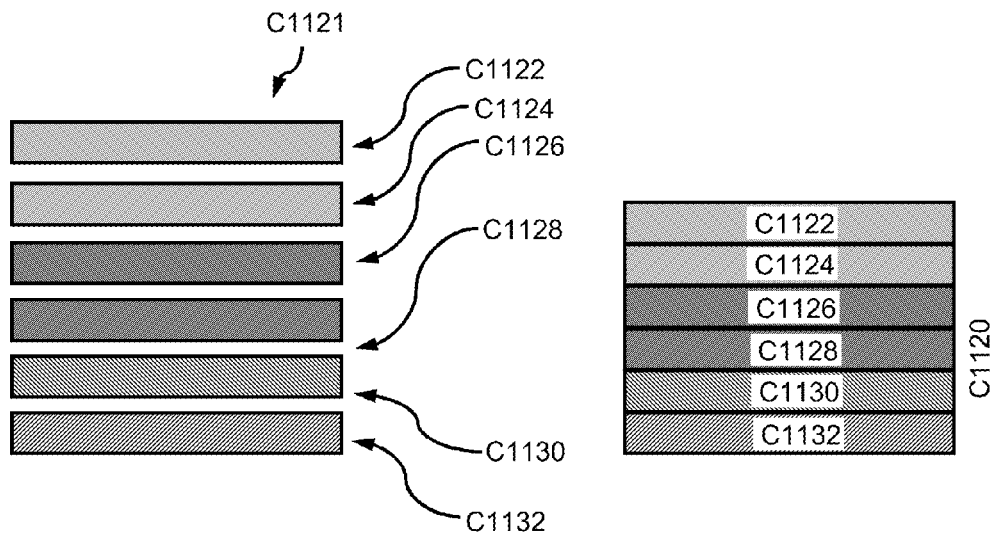
FIGS. 59A through 59H show different embodiments of exemplary TEDs having a gradient of stiffness and means for fabricating pads having a gradient of stiffness.

There are a number of ways to construct a gradient pad C1000 with a modulus gradient C1120. As shown in FIG. 59A, one could create a gradient C1120 in a gradient pad C1000 by producing of a series of bonded layers C1121 of increasingly softer or harder elastomer (from a very soft elastomer C1122 (e.g., modulus of 0.1 to 0.5 MPa), to a slightly less soft elastomer C1124, to a slightly harder elastomer C1126, to harder C1128, to even harder C1130, to the hardest elastomer C1132 (e.g., modulus of 10 to 100 GPa), as shown in the sequence where six layers produced separately on the left side of FIG. 59A are bonded into a single large pad shown on the right side of FIG. 59A).

Figure 59B:
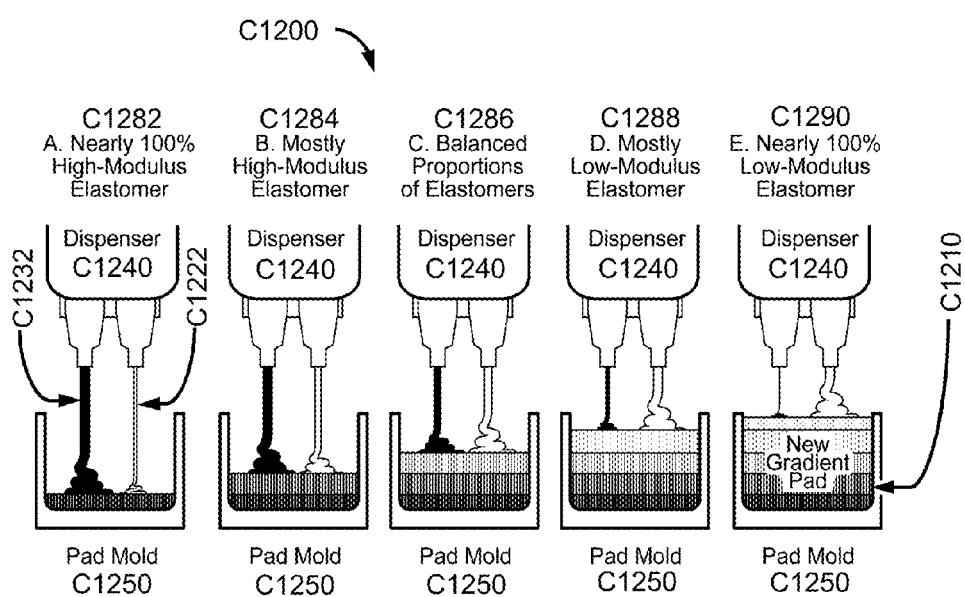

FIG. 59B discloses an alternate method C1200 of creating a pad C1210 possessing a stiffness gradient C1120, here by continuously casting a series, blend, or mix of increasingly soft elastomers on-the-fly during injection molding from a dispenser C1240 fitted with nozzled streams of two distinct elastomers C1222 (which can be soft) and C1232 (which can be hard) into a pad mold C1250. The process can begin (in FIG. 59B, left-hand side) by dispensing a highly disproportionate ratio of mostly hard elastomer C1232 and very little of soft elastomer C1222; this first portion of the cast pad C1210 would thus form a high modulus instrument face. The mix of the two (C1222 and C1232) can change over time (depicted with multiple views C1282, C1284, C1286, C1288, C1290 proceeding to the right-hand side of FIG. 59B), with less and less of hard rubber C1232 and more and more of the soft C1222 until the pad mold C1240 is topped off with a ratio of mostly soft elastomer C1222, appropriate for a tissue face.

Figure 59C:
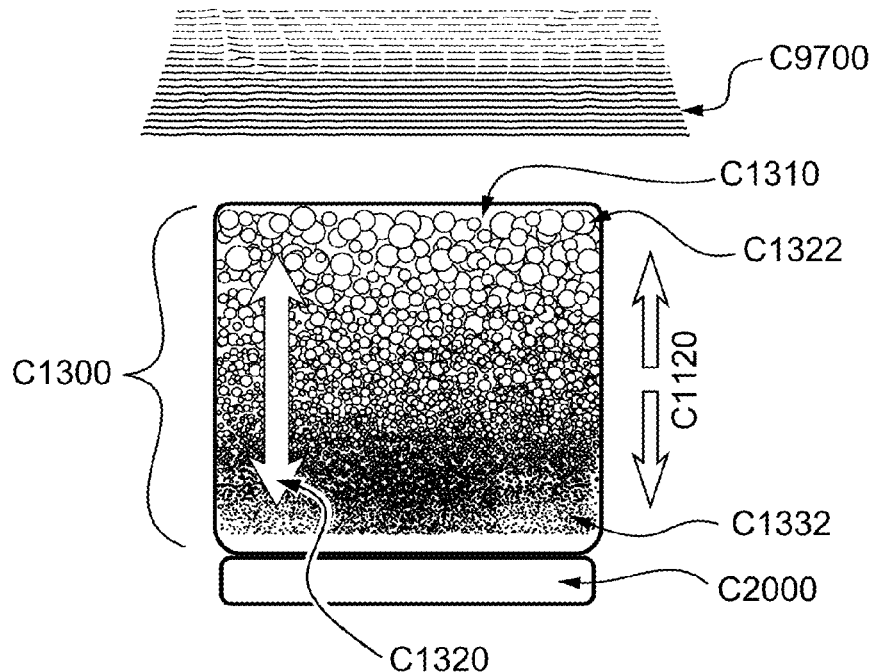

FIG. 59C shows a foam gradient pad C1300 formed by subjecting an elastomeric foam C1310 to a centrifuge during curing to enhance gravity in order to drive a bubble density gradient C1320 in the finished product. Larger bubbles C1322 float to the "top" of the uncured elastomer foam to create a softer (lower modulus) region appropriate for engaging the patient's soft tissues C9700, while at the "bottom" of the foam gradient pad C1300 the smallest (perhaps almost no) bubbles C1332 create a higher modulus region appropriate for the instrument face, for bonding with a rigid element C2000, which could be a steel retractor blade.

Figure 59D:
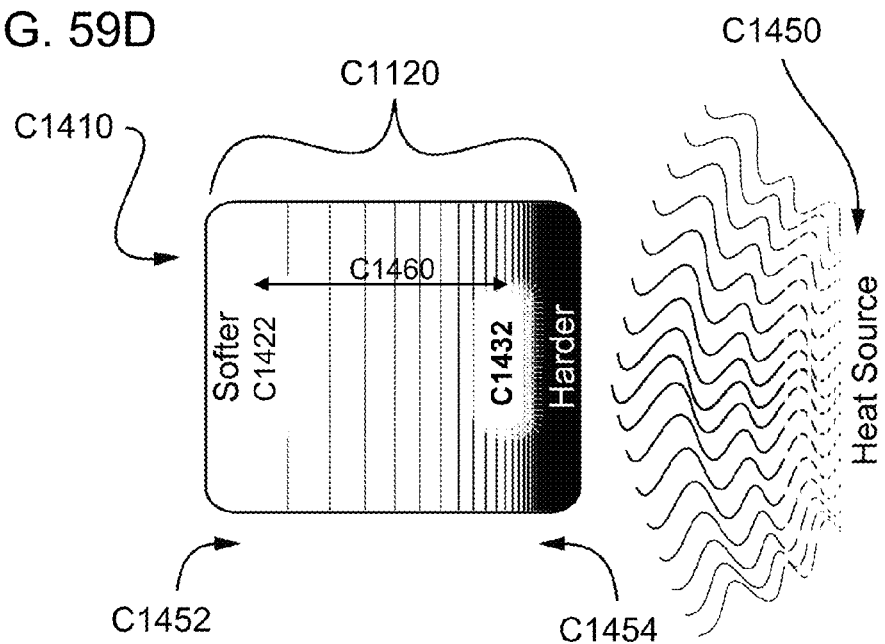

FIG. 59D shows yet another way of producing a gradient pad C1400 by curing an elastomer pad C1410 in the presence of a heat source C1450. By positioning heat source C1450 very close to a freshly curing elastomer pad C1410 in an otherwise cool room, this sets up a steep heat gradient. The stiffness of an elastomer is a function of the rate at which it cures (i.e., to produce an isotropic, homogenous rubber pad, it should be cured isothermally). An elastomer pad C1410 close to a heat source C1450 would result in a pad that is not isotropic: accelerated curing immediately adjacent to the heat source C1450 produces a harder region C1432, while slower curing more distant from the heat source C1450 produces a softer region C1422, forming a modulus gradient C1120 aligned with an axis C1460 oriented to the heat source C1450.

Figure 59E:
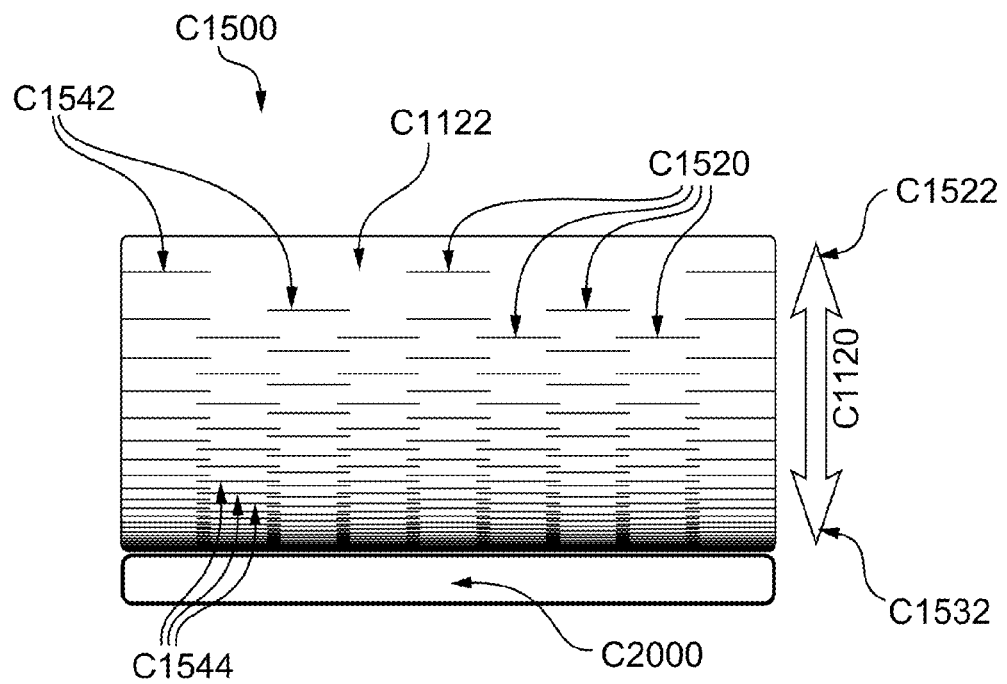

By manufacturing pads as shaped composites of elastomers, fibers, foams and controlling the distribution of same within, one can vary pad properties to suit. FIG. 59E shows a pad C1500 possessing a stiffness gradient C1120 formed by manufacturing a pad of a soft elastomer C1122 with a gradual spatial distribution of very short, transverse fibers C1520. The fibers C1520 are widely spaced C1542 near the low-modulus C1522 tissue face and densely packed, overlapping C1544 forming a higher modulus C1532 region near a rigid element C2000 and promoting bonding thereon.

Figure 59F:
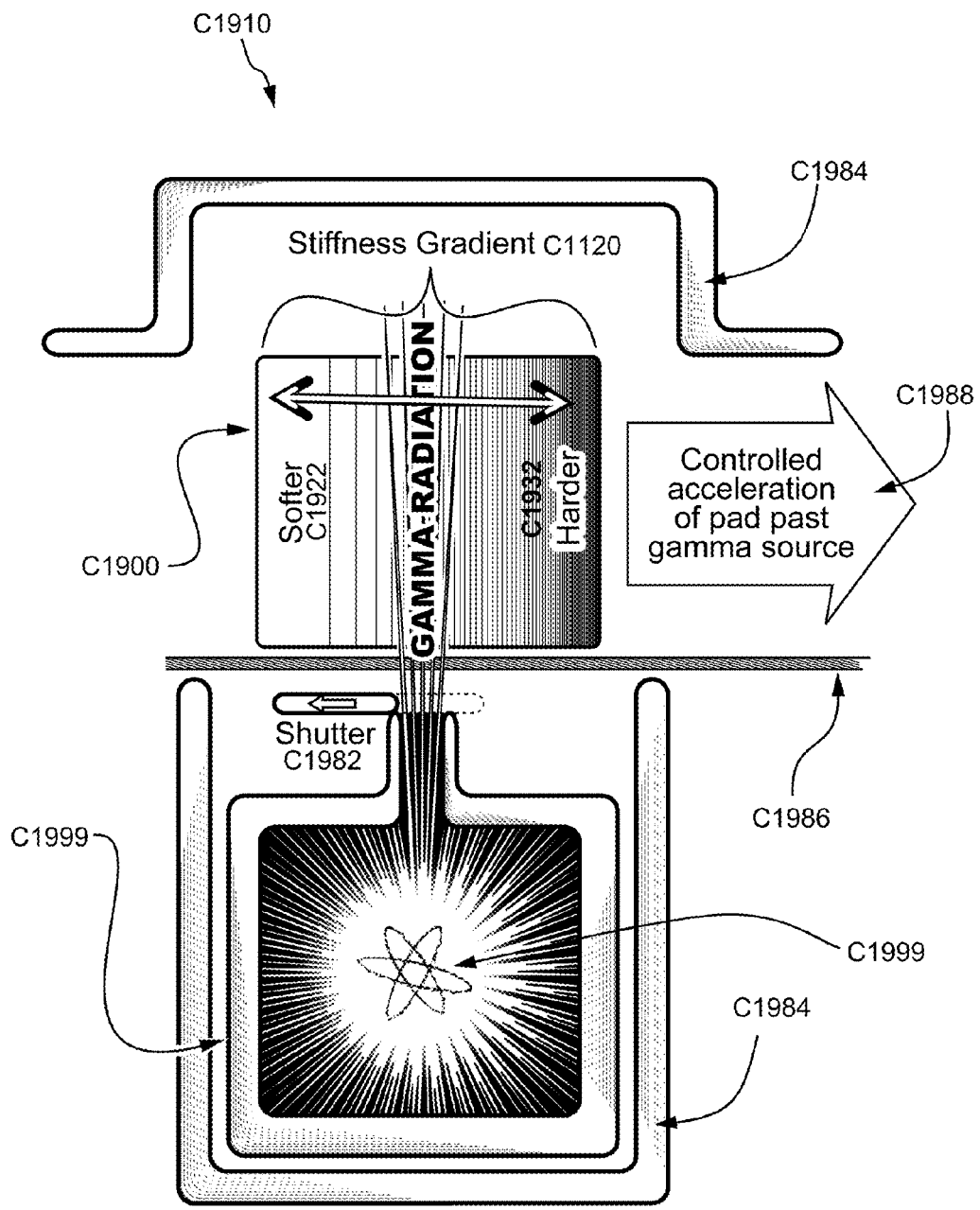

Gamma radiation is commonly used to induce changes in the modulus of polymers. FIG. 59F shows a method whereby subjecting a cured, bulk elastomer pad C1910 to a steep gamma radiation gradient, say, with a moving lead shutter C1982 controlling the emissions of a gamma ray source C1999 from a container C1980 can induce a stiffness gradient C1120 in the pad C1910. The pad C1910 can be moved in a controlled manner C1988 on a radiolucent conveyor belt C1986 past the source C1999 through a shielded box C1984.

Figure 59G:
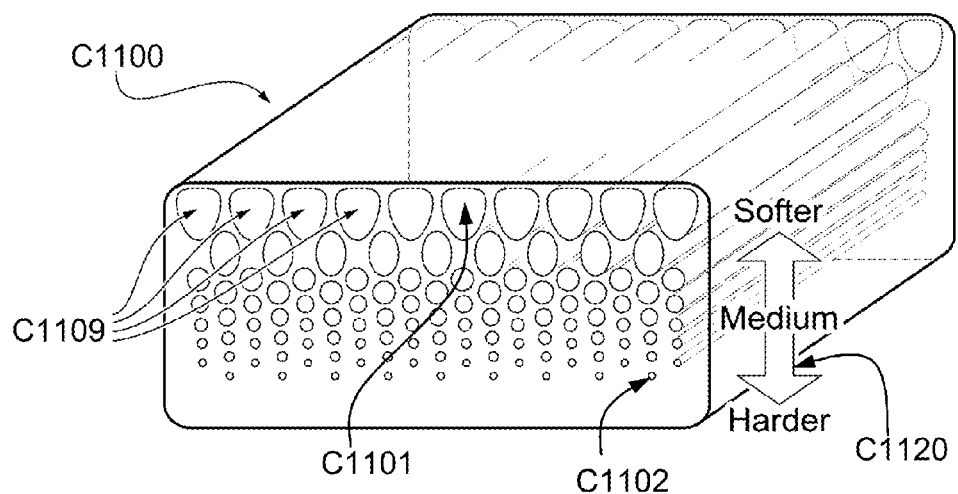

FIG. 59G discloses an embodiment whereby shaping the pad's cross-section using voids, columns, walls, or other structural features produces regions of greater or lesser stiffness. A stiffness gradient C1120 can be set up in an otherwise monolithic elastomer pad C1100 by a series C1109 of transverse holes or channels beginning with those of larger diameter C1101 near one face and progressing to some of smaller diameter C1102 at the other face. The larger holes on the soft tissue face act such that the soft tissue face collapses or gives way gradually, while the stiffer face can better bond with an instrument.

Figure 59H:
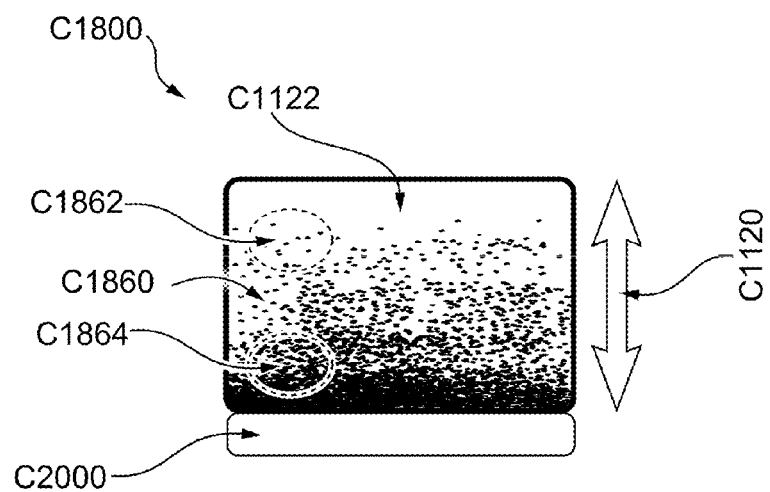

FIG. 59H shows another way of producing a particle gradient pad C1800, which is done by mixing small, hard particulate matter of a density different than the soft elastomer C1122 making up the particle gradient pad C1800, for example by introducing glass microballoons into an uncured elastomer resin, which is then cast into a mold; the buoyant microballoons rise during curing to form a smooth gradient of reinforcement, i.e., dense clouds of lightweight microballoons create stiffer regions of the elastomeric particle gradient pad C1800 near the top. This same method could be used with a dense filler C1860 as well, but in reverse, as the dense filler C1860 sinks, so in this case the stiffer region C1864 is near the bottom, where the particles collect, as opposed to the softer top region C1862, where there are fewest particles. The rigid element C2000 could be positioned so as to bond with the dense region.

Figure 60:
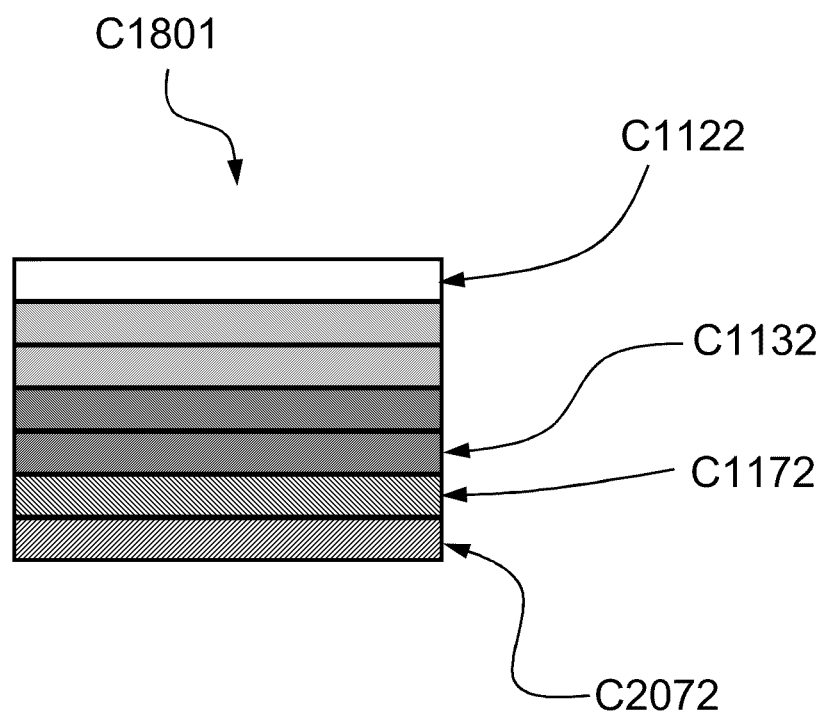
FIG. 60 shows an embodiment of an exemplary TED having a gradient of stiffness formed by layers of materials.

In FIG. 60, showing a gradient pad C1801, the stiffer region C1132 or instrument face can be designed to mount against, bond with, or otherwise couple with a steel retractor blade C2072; alternatively the stiffer portion C1132 or instrument face of the pad C1801 could bond with a rigid polymer plate C1172 itself possessing a modulus or modulus gradient between the steel and the stiffest rubber, and itself mounting to the steel, C2072. The softer tissue face C1103 of the gradient pad C1801 could be made of a soft elastomer C1122, possessing a modulus the same or substantially similar to the raw, soft tissue margins of an incision through the intercostal muscles, for example of a thoracotomy patient (e.g., possessing a modulus at least within 50% of the modulus of the incised intercostal muscle). Some versions of the TED pads incorporate non-steel elements of a retractor, such as arms, arm supports or base, a drive, and a handle, and these elements might not require any steel to be able to develop sufficient force for retraction. For example, a retractor (such as that shown in FIG. 55) incorporating many of the improvements herein might be constructed out of fiber-reinforced plastics, like fiberglass-reinforced epoxy resin or a carbon-carbon composite, including rigid polymer retractor blades to which the TEDs attach.

C.2.2 Pad Morphologies and Materials

Figure 61:
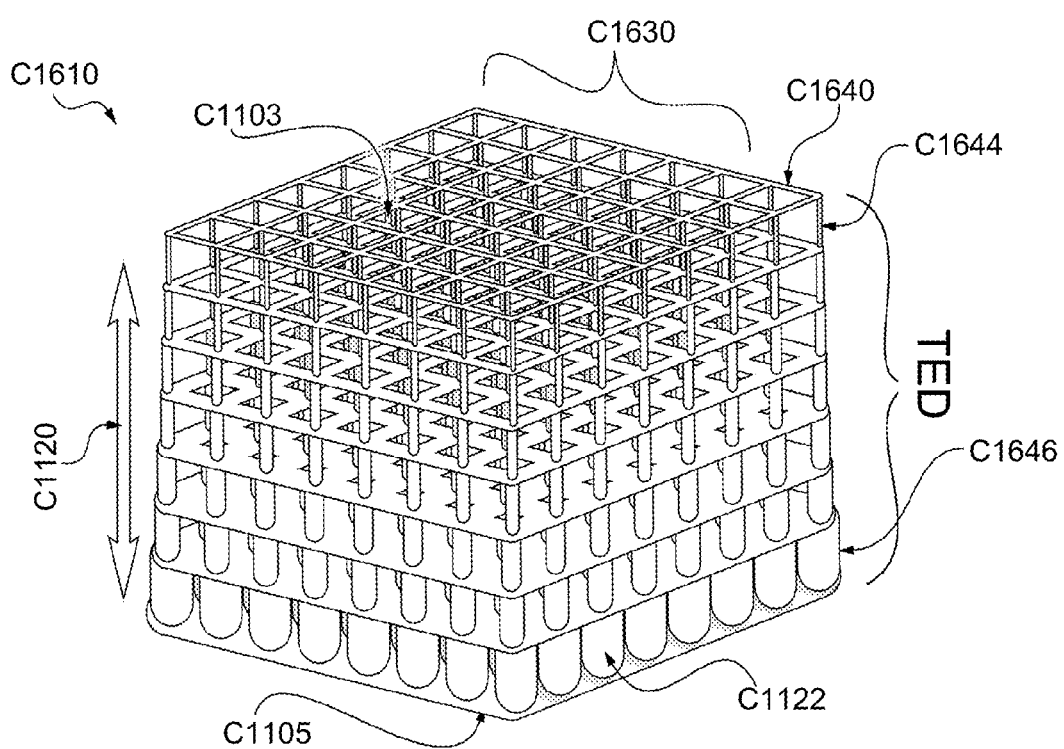
FIG. 61 shows another embodiment of an exemplary TED having a gradient of stiffness comprising a three-dimensional (3D) lattice with members of varying thickness.

FIG. 61 shows another way to arrange the geometry and distribution of the pad material (soft elastomer C1122) to achieve a gradient of modulus C1120. The modulus of the pad C1610, as mentioned above, is a problematic issue if one is to manage the transition from steel to flesh in just one step with a single material. However, the shape of the pad can be designed to accomplish modulus transition. For example, the softer tissue face C1103 can be an open mesh or network C1630 of fine sheets or elongate members (vertical posts C1644 and horizontal bars C1640) forming a highly flexible surface or region of the pad, applying orders of magnitude less force to the patient's tissues than would a solid mass of soft elastomer C1122. This open architecture then grades downwards to a more closed architecture (for example, the vertical posts at the bottom would be much thicker, C1646), possibly even transitioning to a solid block, to create a much stiffer region at the instrument face C1105.

While one pad might be sufficient for protecting a patient's soft tissues, providing more pads allows further advantages. For example, a line of pads arranged along the margin of a thoracotomy patient's incision can provide for several useful features: controllable application of pressure along the margins of a thoracotomy incision; regional measurements along the margin to detect regions of excessively high or low application of pressure; corrective control of applied pressure to even out irregularities via differential actuation; and active manipulation of patterns of pressure application. (See sections on sensing pads and active pads, below). Furthermore, multiple rows (or even multiple layers) of pads can be used to accomplish the intent of the present invention.

Figure 62A:
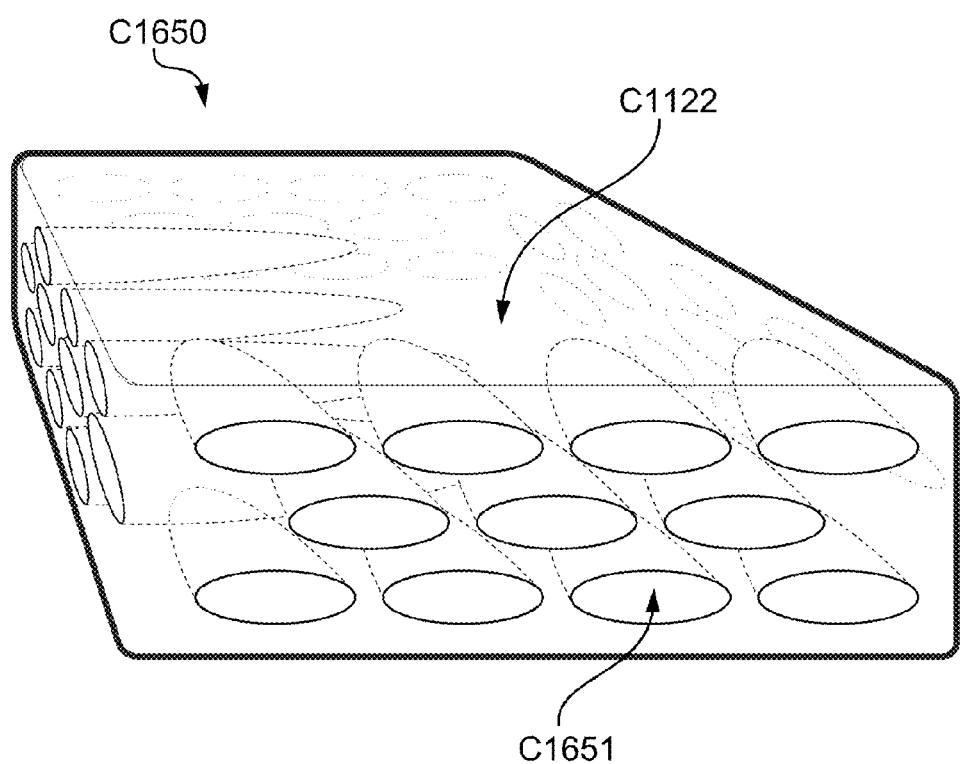
FIGS. 62A through 62C show different embodiments of exemplary TEDs having a gradient of stiffness.

When using a material having a single modulus, the simplest way for a retractor blade pad to develop chosen behaviors is to change the shape of the pad (for examples, see FIGS. 59G, 61, and C9A to 63C). Blocks of incompressible materials deform according to the interaction of their material properties, the three-dimensional distributions of those materials, and the contours of their three dimensional surfaces. By forming channels, holes, voids, corrugations, projections, deep textures, gaps, and other reticulate surface forms in otherwise solid pads, one may control how far an elastomeric pad deforms, and in which directions (and at which rates), when loaded. Consider for example FIG. 62A, indentations C1651 of greater or lesser depth and more or less numerous on the sides of a pad C1650 can control how firmly and what areas the pad C1650 loads the tissue it encounters. Providing transverse channels that pass entirely through from one side to another, placed close to the tissue-engaging surface, permit changes in the strength of the forces applied to the tissue (FIG. 59G).

Figure 62B:
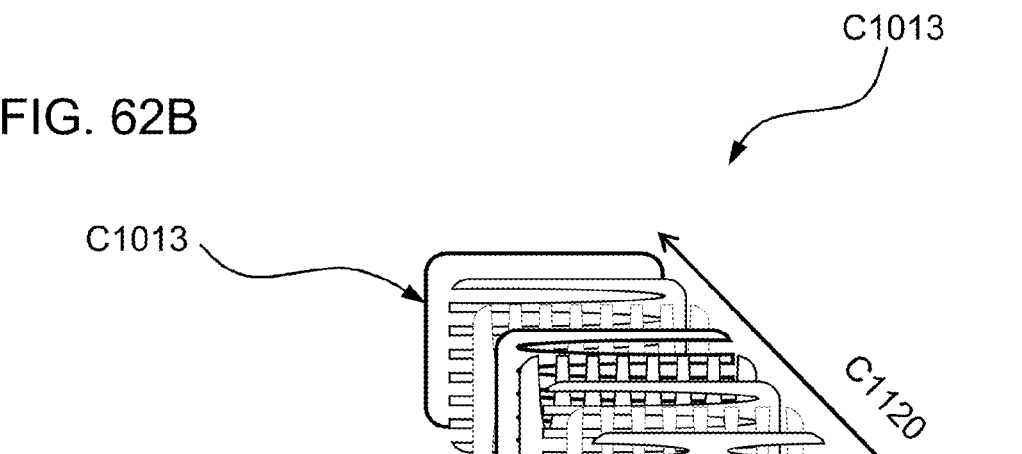
Figure 62C:
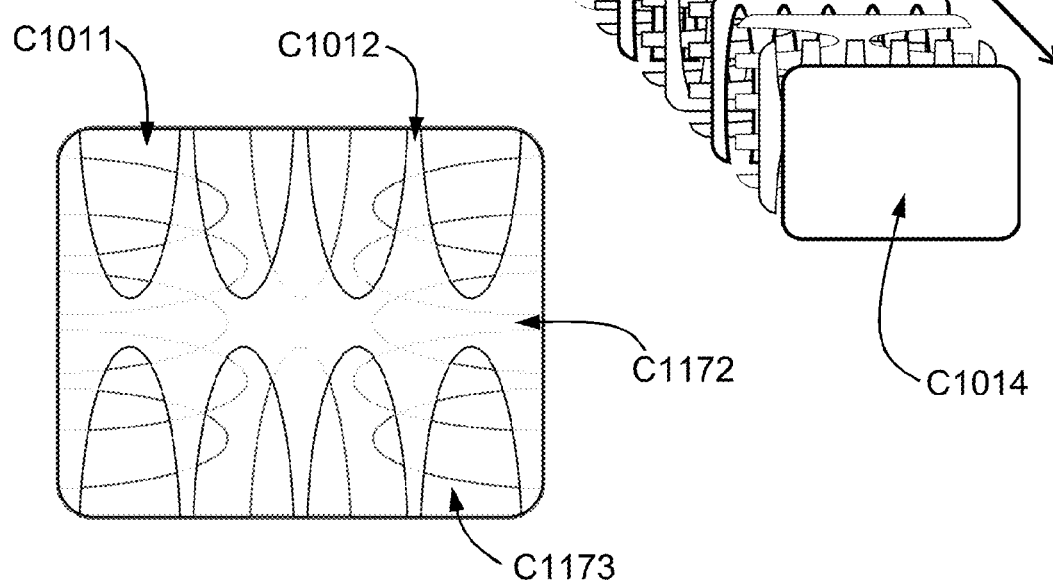

FIG. 62B and FIG. 62C show a pad C1010 possessing a stiffness gradient C1120. The pad C1010 is constructed of stacked and bonded layers (for example C1013 through C1014, not unlike FIG. 59A), some of which are solid and some of which have voids C1011 cut out leaving projections C1012. The resulting shape of one layer C1172 differs from that of another layer C1173, such that building up many layers of the same material but different shapes permits one to create arbitrary, three dimensional spatial distributions of stiffness, as desired.

Figure 63A:
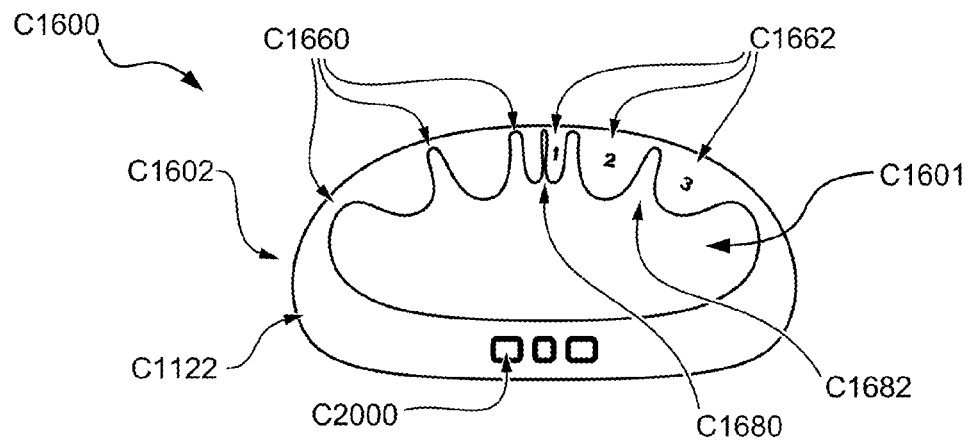
FIGS. 63A through 63C show an exemplary TED having a differential stiffness arising loading of the TED.
Figure 63B:
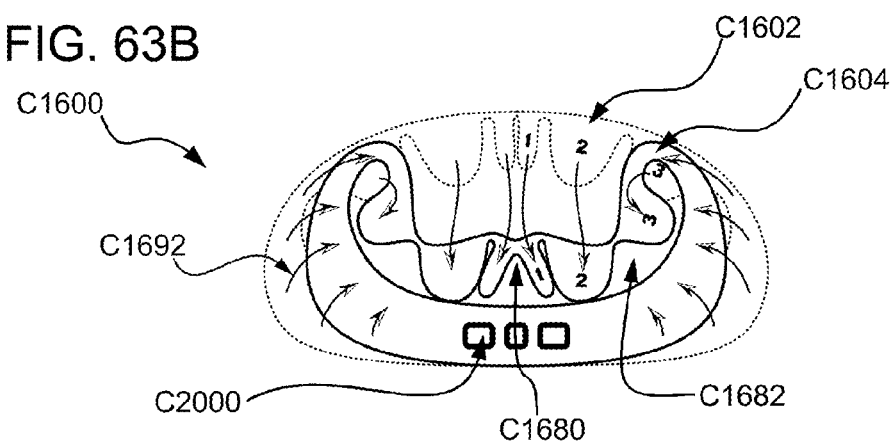
Figure 63C:
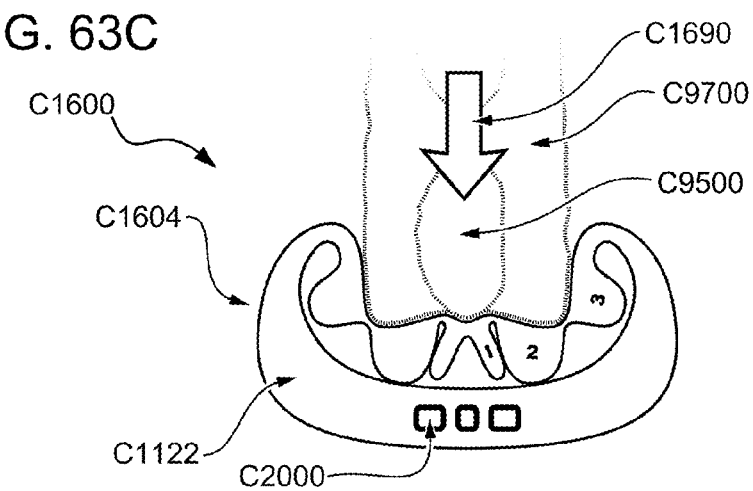

Alternatively, in FIGS. 63A through 63C, a monolithic pad C1600 can be formed of a single modulus of material (e.g., soft elastomer C1122) and includes one or more shaped voids C1601 in the pad, as well as incorporating the rigid element C2000. The void C1601 or voids can, for example, define internal projections C1662 (domes, cones, walls), linear trenches C1660, or other regions of extreme changes in thickness/thinness that can provide controlled, complex changes in either the force outputs or the shape and motions of the wall or other portions of the pad from an unloaded (C1602) to a loaded (C1604) state (see FIG. 63B); in other words, the pad can reconfigure its shape according to the tissue impinging upon that pad. The molded shape of the pad C1600 can be designed so that in an unloaded state C1602, certain inside regions (e.g., C1680) might exhibit contact between the extremities of internal projections, while other inside regions (C1682) might initially possess or exhibit wide spacing between the extremities of internal projections.

As shown in FIG. 63B, once loaded (C1604), the thick and thin regions of the wall of the pad C1600 move and reorient C1692 with respect to each other, according to the distribution of the thick and thin portions of the wall, where thick portions can act more-or-less as "stiff" segments and thin portions can act as hinges or relief joints, and where internal extremities once touched (C1680 in the unloaded state C1602), they now separate (C1680 in the loaded state C1604), becoming wide, while other regions where once internal extremities were not touching (C1682 in the unloaded state C1602) now collapse into contact (C1682 in the loaded state C1604). If there are no leaks, then internal pressure can be used to mediate the shape changes between the loaded (C1604) and unloaded (C1602) states. As shown in FIG. 63C, the loading imposed by impinging tissues can be used to drive the wall motions C1692 and pad shape changes that protect the patient's tissue. An alternative to the thin/thick portions of the pad shown in FIGS. 63A to 63C is to use fibers in the wall of the pad, with the fibers having controlled material properties and/or orientations in the wall of the pad to result in folding of the pad. These examples show a small range of the possible shapes capable of providing a stiff surface for bonding to steel or other stiff material and a soft surface for engaging a patient's tissue.

C.2.3 Composite Pads: Pad Material Plus Other Inclusions

Figure 64:
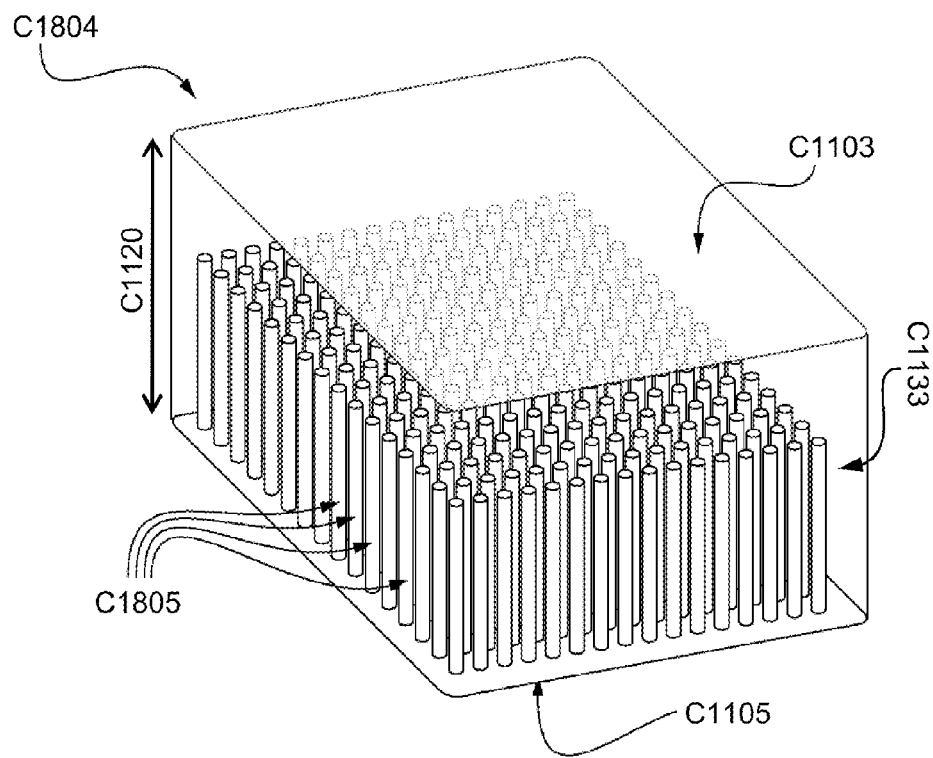
FIG. 64 shows another embodiment of an exemplary TED having a gradient of stiffness comprising a plurality of higher modulus rods interdigitated into a pad of lower modulus.
Figure 65A:
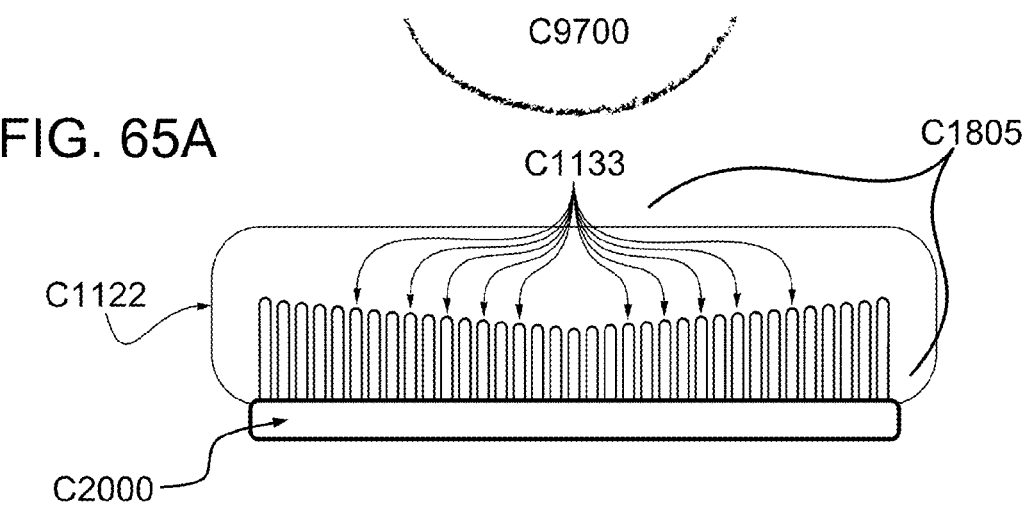
FIGS. 65A through 65C show how the exemplary TED depicted in FIG. 64 responds when loaded.
Figure 65B:
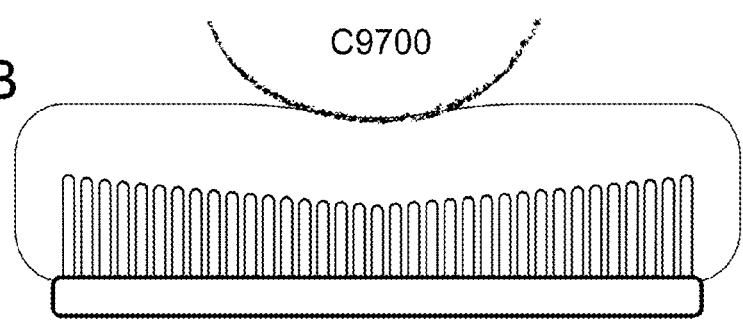
Figure 65C:
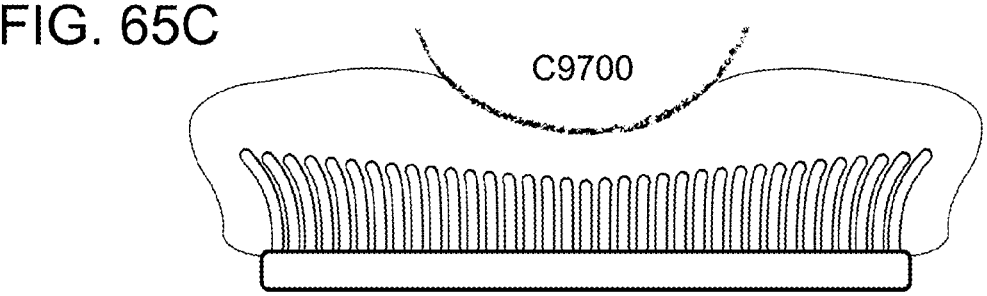

A number of variations on the theme of a solid (e.g., an elastomer) pad enable features useful for a TED. One may create composites using different types of elastomers, or similar elastomers of differing modulus. For example, pre-cured elastomer components (such as spheres, ellipsoids, rods, rings, etc.) mixed and cast into a different, uncured, elastomer create properties neither elastomer possessed before. As one example shown in FIG. 64, a sparsely spaced forest C1805 of small, short parallel rods of a somewhat hard elastomer C1132 are cast against, projecting from, or near the rigid element C2000 (or instrument face, C1105) of an otherwise very soft pad C1804 of elastomer C1122, with the rod's axes aligned perpendicular to the instrument face C1103. Such a pad C1804 will at first react to an impinging object (e.g., tissue C9700) similarly to a simple soft pad, as shown in FIGS. 65A to 65C, but as the impingement (or force) increases, the rods C1805 come into play, providing more support later in the process than would a simple soft pad. As the impingement by the tissue C9700 proceeds further, as shown in FIG. 65C, at some point the rods C1805 begin to spread apart or otherwise deform at their tops, changing the response of the pad C1804. The response of such a TED to deformation can be changed by changing the rods: their spacing, their orientation across the array, their taper, distribution of rods of differing modulus, etc.

Figure 66:
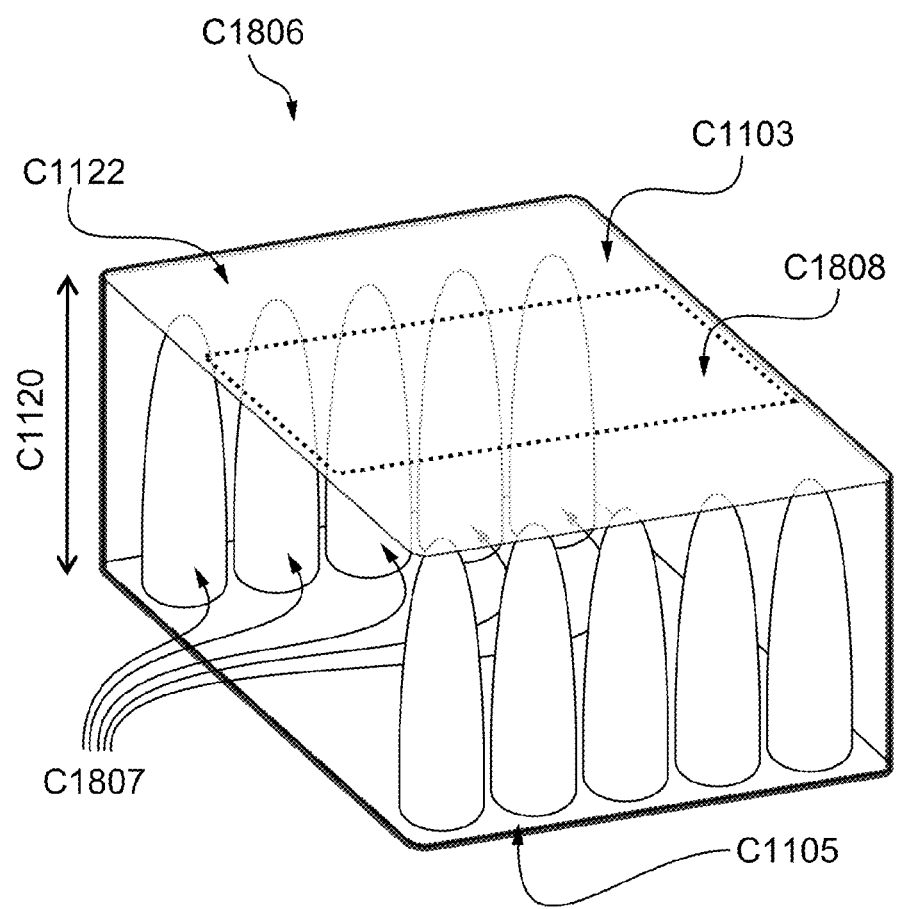
FIG. 66 shows another embodiment of an exemplary TED comprising blocks of higher modulus elastomer at the periphery of a pad having lower modulus.

Another way to produce a solid, composite elastomer pad is shown in FIG. 66. Pad C1806 is formed by casting blocks of an elastomer of higher modulus C1807 into the volume of a pad of otherwise very low modulus material (e.g., soft elastomer C1122). The arrangement of the blocks C1807 will control the development of shape as the pad impinges on the soft tissue of the patient. As one example, suspending large blocks C1807 near the periphery of the pad C1806 while leaving the middle of the pad C1806 filled with the low modulus material (soft elastomer C1122) ensures that the sides remain proud (raised) as the soft tissue of the patient impinges on the region C1808 in the center of the pad's C1806 tissue face C1103. Any number of mutually compatible elastomers are applicable to this embodiment. Hydrogels, too, are suitable as pad materials, and offer other advantages (for example, hydrogels containing drugs can deliver these compounds directly to the wound site when in contact with the margin of the incision).

C.2.4 Other Inclusions

Figure 67A:
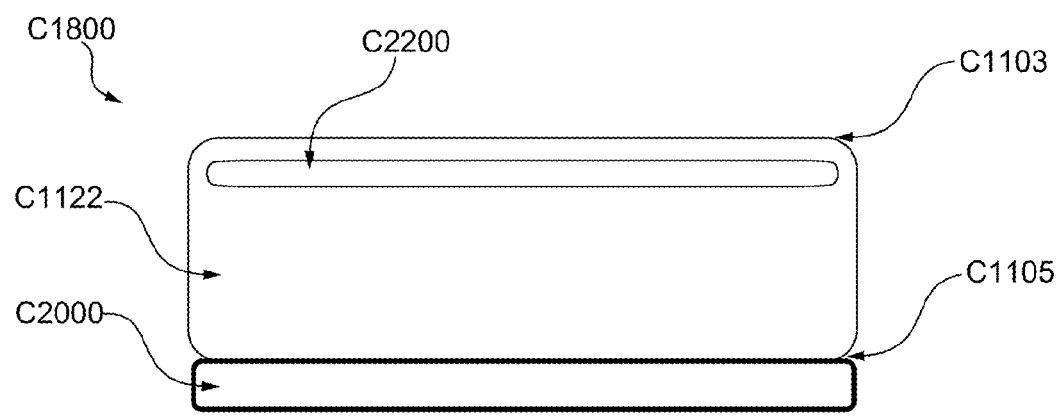
FIGS. 67A and 67B show another embodiment of an exemplary TED comprising a low modulus pad having a higher modulus plate near the tissue face of the TED.
Figure 67B:
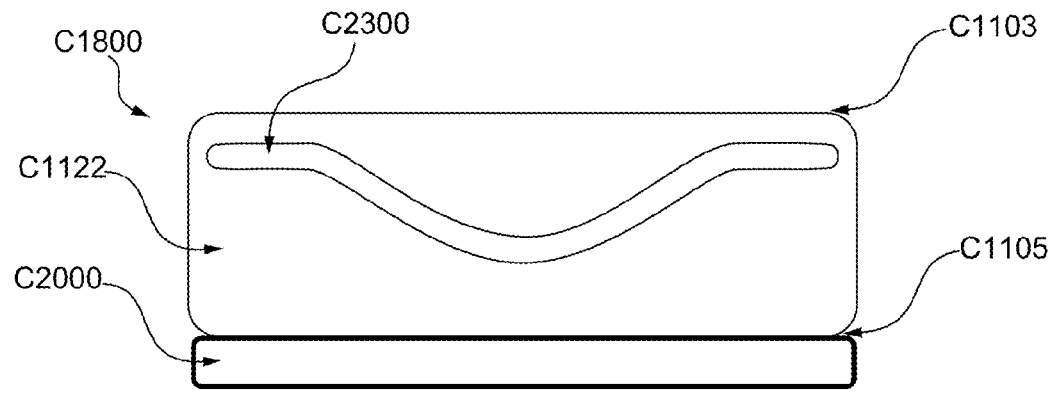

As mentioned above, the modulus of solid inclusions affects the behavior of the pad. Further, the low-force response of a very soft retractor blade pad and the shape the pad takes upon loading the patient's tissue can be relatively decoupled. For example, as shown in FIG. 67A, if a stiff inclusion like a flat sheet or a plate C2200 is included parallel to and close to the tissue surface C1103 of a very soft pad C1809 (and a rigid element C2000, perhaps a retractor blade, is attached to the instrument face C1105) then the pad C1809 will at first give way under load while the surface C1103 remains flat. On the other hand, as shown in FIG. 67B, if the steel insert sheet C2300 is carefully pre-contoured, then this might be useful, for example, where the tissue face C1803 of a very soft pad C1810 must first conformally mate with the surface of an impinging rib while still avoiding any loading of the intercostal neurovascular bundle.

FIGS. 68A and 68B depict another useful form of a pad C1800 with solid inclusions (FIG. 68A shows a side view, and FIG. 68B shows a front view). Soft pad C1800 possessing a series C2010 of rods C2020 (made of steel or composed of another stiff material), "floating" within the pad, here parallel to a rigid element C2000. These rods C2020 could be designed at their ends C2240 to couple well with (and so distribute the loads to) the soft elastomer C1122 there, while the middles C2220 of their length remain uncoupled to the elastomer pad, their ends C2240 separated by spaces C2266 permitting the rods C2020 some leeway for moving and shifting within the pad C1800. The coupling means might be expanded rod ends C2242, fenestrations C2244, or fibrous anchors projecting from a fiber-reinforced rod. These rods C2020 might have their middles C2220 exposed to the oncoming margin of the incision. When a properly prepared margin of the incision impinges on these pads C1800, the soft elastomer C1122 meets (and matches the modulus of) the muscle while the middles C2220 of the steel rods C2020 meet the edges of the ribs, and so avoiding crushing the soft tissues.

Figure 69:
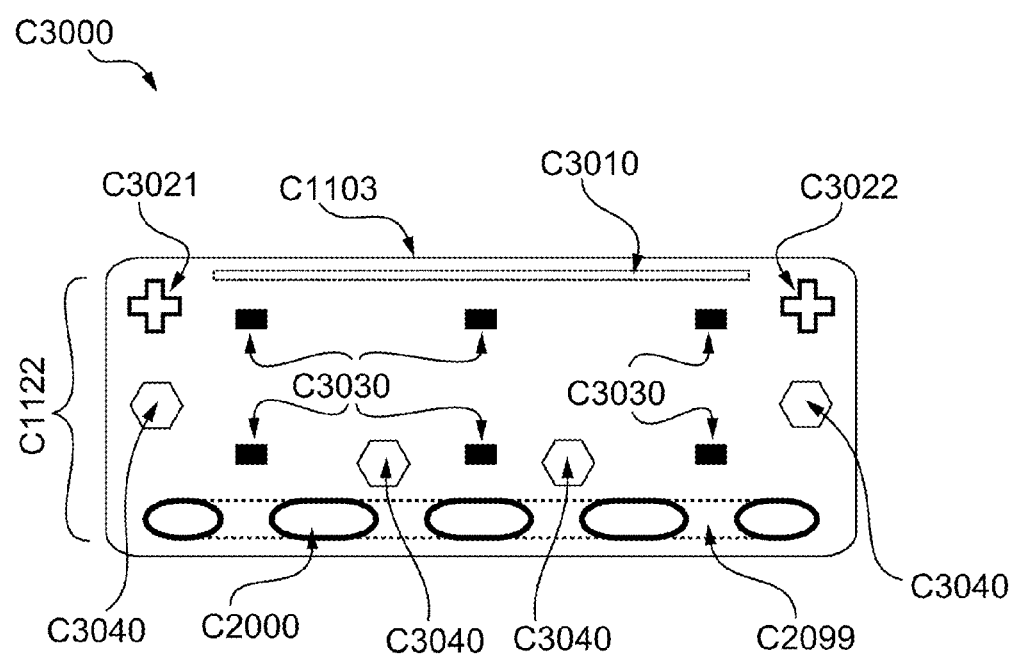
FIG. 69 shows another embodiment of an exemplary TED comprising a pad with multiple sensors embedded into the pad.
Figure 70A:
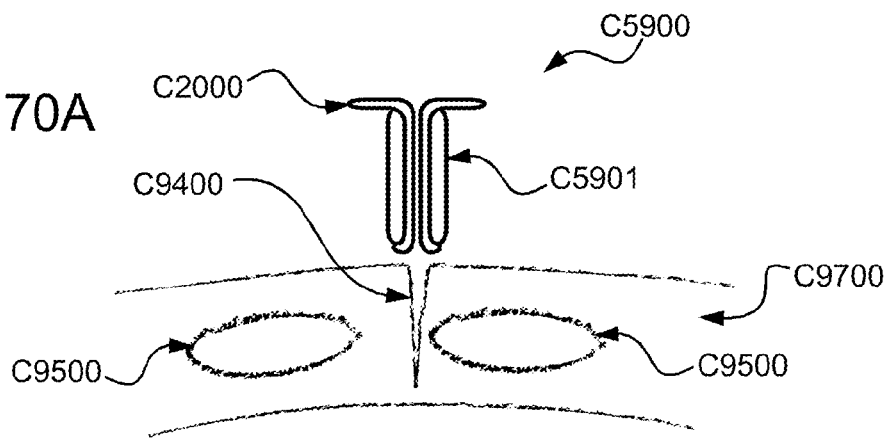
FIGS. 70A through 70D show another embodiment of an exemplary TED comprising a pad filled with a foam that expands on being placed into the incision.
Figure 70B:
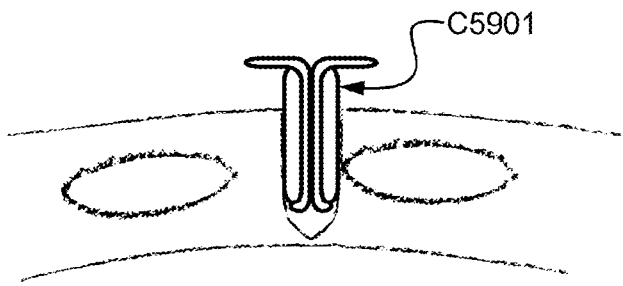
Figure 70C:
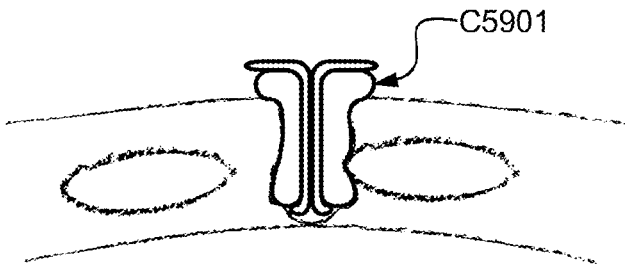
Figure 70D:
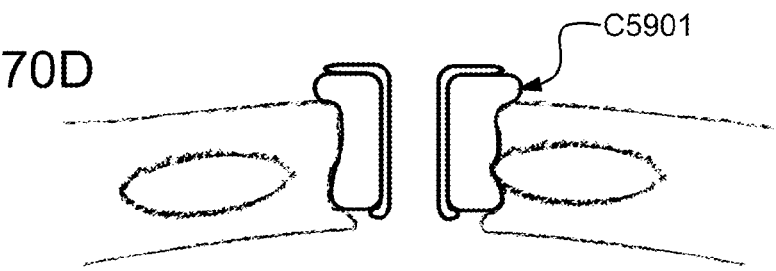

FIG. 69 shows a sensor pad C3000. The sensor pad C3000 contains active inclusions that may be mechanical and or electrical; objects permitting other functions can be included (as inclusions cast within the elastomer, say). For instance, sensors and actuators may be suspended within the soft body of a sensor pad C3000 to allow, for example, tissue property modulation. Electronic sensors for pressure C3040, acceleration C3021 and C3022, acoustic-positional C3030, force C3010, and light (e.g., IR) may also be suspended so as to be able to detect tissue state parameters. Actuators might also be cast within a soft pad. Note that one can include the rigid element C2000 itself as an inclusion or insert, with fenestrations C2099 therein being one means for facilitating bonding the rigid element C2000 (e.g., a retractor blade) inside the sensor pad C3000.

Fluids can be incorporated into a TED. Fluids can provide a medium for sensing (e.g. pressure sensing), a structural material for resisting compression, a hydraulic medium for distributing a load or transmitting forces or pressures to remote locations, and/or a means for cooling or warming the tissue under or near retractor blades. For example, a fluid that circulates from a water-filled pad to a chiller and back can be used to cool a tissue next to the pad. Conversely, including gas within an elastomer makes the pad lighter, cheaper, and can provide thermal insulation. Similarly, the acoustic properties of pads can be designed by controlling the proportions and types of gas and/or fluid filled bubbles. Elastomers can be obtained as foam, which is one way of achieving gas inclusions (admixing gases and elastomers), but one may also arrange large bubbles, or single chambers (as with a balloon), or a gradient of air inclusions (see for instance FIGS. 59C, 59G, and 63C). Gases are compressible, whereas liquids are incompressible, each affecting pad construction differently.

Referring to FIGS. 70A through 70D, an expandable TED C5900 can be constructed by mounting a hollow bladder C5901 on a rigid element C2000 and filling the inside with a mixture (not shown) of gases or liquids or both appropriate for creating wet foams, expanding foams, or emulsified foams. Prior to use (FIG. 70A), the TEDs C5900 may be constructed as thin, low-profile, and easy to insert into the incision. The components of an expanding foam can first be separated inside the bladder C5901 by walling them off from one another, by emulsifying one component, or by arranging the internal structure of the bladder C9501 into separate compartments, that connect to drive internal mixing when the bladder C5901 is squeezed or sheared. The foam components can be reacted to expand when desired, for example once the bladders C5901 are sheared or distorted upon insertion (FIG. 70B) of the retractor blades into the incision C9400. The advantage of an expanding TED is that it allows the pads C5901 to start out thin and small (i.e., easy to insert into the incision C9400) and then react the foam components and grow (FIG. 70C, expand to fit the shape of the margins of the incision) when the rigid element C2000, here represented as retractor blades, are fully inserted, and to the extent needed (FIG. 70D) to adapt to and cushion the patient's soft tissues C9700 and or hard tissues C9500.

The fluid component of a TED pad can also convey other benefits, for instance the fluid can facilitate cooling (if the fluid is pre-chilled, or if it contains an endothermic reaction, or if it is pumped through the pads, or from pad to pad, and/or through a chiller), or the fluid can serve as the carrier for (or it could itself be) a therapeutic pharmaceutical agent or bathe a tissue to prevent tissue dehydration, should provisions be made for the fluid's emergence into or onto the tissues.

Note also that fluids can circulate within the boundaries of a single pad; the pad may contain internal volumes (e.g., channels, conduits, chambers, membranous walls, valves and other forms of fluid-accommodating passages). These passages can possess sections that are straight, sinuous, branching, converging, dendritic and otherwise tortuous. The passages can be arranged in layers, arrays, and complex three dimensional patterns. Such features can permit useful loading-rate-sensitive pad behaviors: for instance (A) where multiple thin-walled, soft, interconnecting fluid-filled chambers forming the soft tissue face soften initial impact with a tissue but then give way over time to conform to the irregular surface of the tissue as fluid flows and redistributes in the pad; or (B) If cyclic loading is applied through the pads via an outside actuator, the fluid channels may be fitted with narrowed sections (perhaps with vessel-like valves) so that the fluid flows slowly and the pad gives way easily for slow, low-frequency motions, but becomes stiffer to higher frequency flows owing to the resistance to rapid flows in the narrowed channels, permitting faithful delivery of high-frequency vibrations for modulating tissue properties (effectively this is an hydraulic low band-pass filter, or a high-band-pass filter, depending on whether you want accommodation or vibration transmittance); or (C) If an elastomer retractor blade pad is properly designed it can possess a first set of fluid-filled chambers in the middle of the soft tissue face, held full by the tension in a second, thicker-walled set of chambers around the sides of the pad that communicate with the first set, so that when the surgeon initially presses the pad into and against the patient's tissues at the margin of an incision, the centers of the pads apply sufficient pressure to force their way into place, but then as the pads remain in place over time and retraction increases, the fluid is driven out of the first set of pads, inflating the second set, which wrap around the upper and lower edges of the margin of the incision to secure the pads in place. As retraction eases off at the end of the operation, the second set of chambers finally overcome their loading and disengage the tissue, refilling the first set of chambers, which push off to help with the removal of the retractor blades.

Figure 71A:
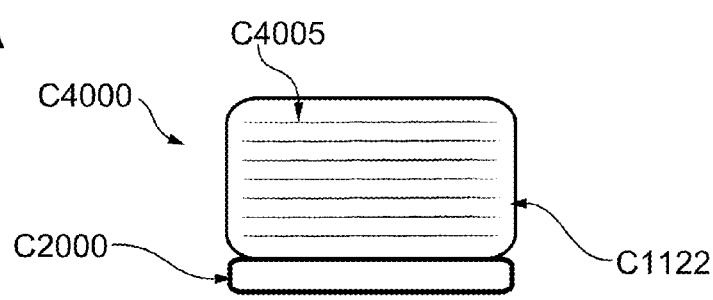
FIGS. 71A through 71D show more embodiments of exemplary TEDs comprising an elastomeric pad having fibers embedded within.
Figure 71B:
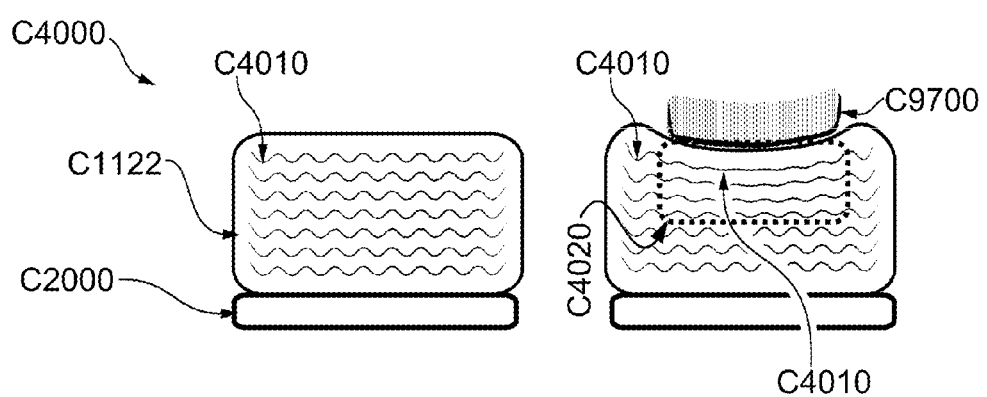

Including fibers within an elastomeric TED effectively creates a compliant, elastomeric composite that can enhance the TED's function (e.g., by more effectively surrounding and supporting a patient's tissues), as the mechanical properties of included fibers modify and so control the behaviors of the TED, the better to match the mechanical properties of the patient's tissues. FIGS. 71A, 71B, 71C and 71D show embodiments of compliant elastomeric TEDs. For example, as shown in FIG. 71A (and as depicted in FIG. 59E), incorporating straight, high tensile strength (stiff, elastic) fibers C4005 oriented transversely within the structure of a pad C4000 backed by a rigid element C2000 will prevent stretching in the direction(s) parallel to those fibers provided the fibers are well-bonded to the matrix (which can be a soft elastomer C1122). If fibers C4010 are instead kinked when in place (FIG. 71B) the pad C4000 can stretch under load. An elastomeric pad C4000 will stretch out under load in the strained portion C4020 of the pad C4000 until those stiff fibers C4010 become more nearly straight, halting the soft elastomer's C1122 stretching. As loading progresses, the effective stiffness of the pad C4000 rises as a function of the decreasing curvature of the fibers C4010. Beginning with more sinuous (i.e., longer) fibers C4010 permits greater elastomer pad strains before the fibers C4010 straighten fully and stop the pad's C4000 deforming. Provided that the fibers C4010 bond well with the matrix (for example, soft elastomer C1122), elastic recoil of the entire structure (pad C4000) is assured. Adding lower tensile strength (extensible, elastic)

fibers C4010 permits larger strains; changing the angles of these fibers C4010 changes the distribution of (and axes for) the elastic deformation.

Figure 71C:
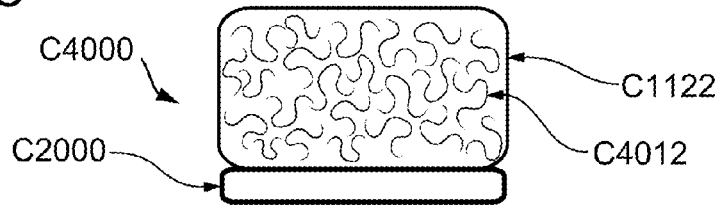
Figure 71D:
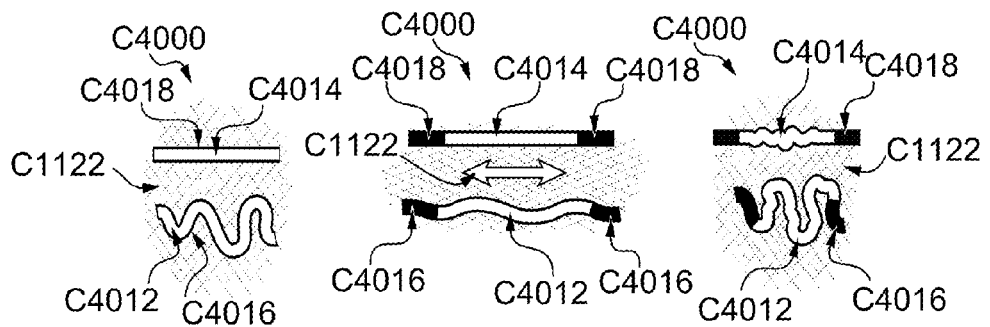

Referring now to FIGS. 71C and 71D, one may add fibers C4012 to the pad C4000 that absorb energy by deforming in some way—either by themselves plastically deforming, or as illustrated by non-reversibly dislocating within the matrix itself. FIG. 71C depicts an elastomeric composite pad C4000, filled with tiny sinuous fibers C4012 throughout its volume and mounted on a rigid element C2000. Upon retraction, this pad slowly loads the patient's tissues, deforms permanently to accommodate the greatest strains therein, dissipates the energy of doing so and on-the-fly customizes the shape of pad C4000 to that portion of that patient's tissues. Referring now to the sequence of images in FIG. 71D, we see in the first of three images relatively inextensible fibers that are sinuous (C4012) or straight (C4014) suspended within a soft elastomer C1122 (depicted as a cross-hatched, gridlike region). The fibers C4012, and C4014 may possess a poor bond with respect to the soft elastomer C1122, and so those fibers each create around themselves a close-fitting cavity (for example, cavity C4018 around the straight fiber C4014, and cavity C4016 around the sinuous fiber C4012) of the same shape as the fiber. Since the inextensible fibers C4012 and C4014 resist length changes, should the elastomeric composite pad C4000 be strained sufficiently (as seen in the second image of FIG. 71D), the fiber cavities stretch along with the matrix (observe the stretched grid), but the fibers C4012, C4014 do not: the cavities C4016 and C4018 become longer than the fibers C4012, C4014 that created them, i.e., the fibers C4012, C4014 dislocate within their respective cavities, especially the fibers retreat from the ends of the cavities. Gaps appear between each end of the strained cavities C4016 and C4018 and each end of the particular fiber (here, either C4012 or C4014) that created that cavity. Straight fibers C4014 resist strains immediately, creating a steep rise in the forces applied to the patient's tissues, and they begin to slip and dislocate immediately, redirecting and dissipating some of that energy. Conversely, upon loading the elastic pad C4000, sinuous fibers C4012 will first straighten, then take up the load, then slip (dissipating energy); these sinuous fibers C4012 create a slower rise in the stiffness under increased loading than will the straight fibers C4014. Given the friction between the surface of the fibers C4012 and C4014 and the interior edge of the cavities formed in the soft elastomer C1122, and given that fibers C4012, C4014 in general possess almost zero stiffness in compression or bending, the chances are vanishingly small that the fibers C4012, C4014 would reinsert themselves back into the gaps formed in the ends of the cavities C4016, C4018 when the load is removed from the pad C4000. The third image of FIG. 71D shows that the fibers C4012, C4014 instead collapse and buckle (remaining trapped in the middle of the length of the cavity) as the soft elastomer C1122 recoils with decreasing load on the pad C4000. This means that, for those sections of the pad C4000 that both experienced strain and contained the short fibers C4012, C4014, the pad C4000 does not fully recoil there, so the pad C4000 as a whole retains a memory of its strain (as depicted in the third image of FIG. 71D as a distorted, unloaded grid of the soft elastomer C1122). Given this, then, short fibers C4012, C4014 cast into elastomer pad C4000 permit pad C4000 to cushion the patient's tissues, adaptively conform to the patient's tissues and the loads during retraction, and to dissipate the energy and stresses of retraction, thereby reducing tissue trauma. The length of included fibers C4012, C4014 will also affect the behavior of the pad C4000, and the fiber trajectory will control the direction of force transmission within the material of the TED pad C4000. As stated above, fluids may also be present; a lubricating fluid that permits the short fibers C4012, C4014 to slowly reinsert themselves within their respective cavities would add to the previous embodiment the ability to permit repeated adapting to changes in the tissue loading pattern arising from substantial repositioning of the retractor. This would permit using such pads C4000 on patients possessing wide variations in size, shape, required procedures and tissue properties.

Of course, mixing multiple types of fibers within a pad is possible. This is specifically disclosed by us as desirable, as the patient's own tissues are composed this way. One embodiment would be, for example, arranging in a pad: (A) some low modulus, highly resilient, elastic fibers that are largely pre-aligned with expected retractor blade pad strains, (B) some high tensile strength fibers that are substantially kinked, bent, coiled, folded, or otherwise arranged to be not initially aligned with the expected retractor blade pad strains, and (C) a very low modulus elastomer. The foregoing design could be expected to behave statically, quasi-statically and potentially dynamically much like the tissue of the patient, thereby reducing or eliminating stress concentrations between the pad and the patient's tissue.

Figure 72:
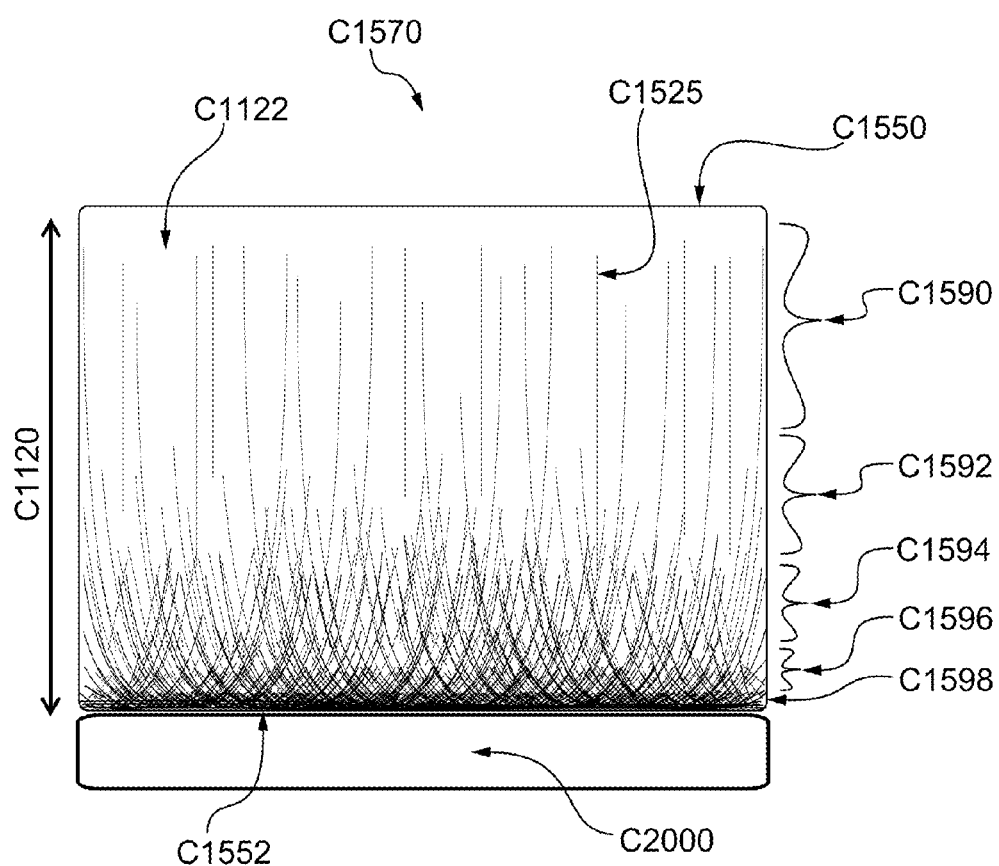
FIG. 72 shows another embodiment of an exemplary TED comprising an elastomeric pad having fibers with varying angles of orientation embedded within.

Referring now to FIG. 72, another pad C1570, this time with a gradient C1120, can be created using a single, very low-modulus, jellylike material (for example, soft elastomer C1122), and a single type of stiff fiber C1525, all associated with a rigid element C2000 of a surgical instrument. For example, consider the spatial arrangement of such fibers C1525. The soft tissue face C1550 of such a pad C1570 possesses mostly the jellylike soft elastomer C1122 and beneath that a very sparse population of long fibers C1590 oriented substantially perpendicular (90°) to tissue face C1550 (i.e., parallel to an axis of initial loading when the tissue face C1550 of the pad C1570 is compressed between a rigid element C2000 and the patient's tissues C9700). On the other hand, the instrument face C1552 of such a pad C1570 possesses a dense population of transverse fibers C1598 oriented substantially parallel to that face (i.e., perpendicular to the axis C1580 of initial loading); the transverse fibers C1598 at or near that instrument face C1552 could be arranged in plan view like a sheet of woven cloth, a felt, or a mat pressed against the surface of a rigid element C2000. In the region in between the two faces C1550, C1552, the fiber angle (and fiber density) of the fibers C1525 can change rapidly from fibers C1598 at nearly 0° (and very densely fiber-packed) at the instrument face C1552 to fibers C1596 aligned at 5-10° (and less well packed) a little farther in (i.e., farther from the instrument face C1552), to fibers C1594 aligned at 10-30° (with decreasing fiber density) still farther in, to fibers C1592 aligned at ~45° (even fewer fibers) more-or-less one-third through the thickness of the pad, gradually to 50-80° (fibers thinning out) from that region to the soft tissue face where the fibers C1590 possess an angle substantially near 90°. (These fiber angles are provided only for this example; other distributions and orientations of fibers would produce different pad mechanics. The fiber angles provided here are expected to produce a stiffness gradient C1120 and so pad behavior generally useful for preventing tissue trauma). When a plain elastomer pad (an isotropic, homogenous mass), being of constant volume, is loaded in compression between two faces, the pad tends to get thinner (along the axis of initial loading) and wider (perpendicular to the axis of initial loading). The fibrous pad C1570 in FIG. 72, however, behaves differently. The soft tissue face, being mostly low-modulus elastomer, gives way easily, applies only gentle direct pressure to the patient's tissues, and gets wider, as permitted by the lack of any transverse fibers in that region (containing fibers C1590 to C1592) of the pad C1570. The region near the instrument face C1552, though, being highly reinforced by many stiff, more-or-less transverse fibers C1596 and C1598, cannot get wider because the transverse fibers C1596, C1598 prevent it. Thus that region containing transverse fibers C1596, C1598 near the instrument face C1550 is nearly as stiff in the transverse direction as the rigid element C2000, and so reduces strain there, thus reducing stress concentrations that otherwise would dislodge the pad C1570 from rigid element C2000. The fiber angle changes, from very high angled fibers C1590 near the tissue face C1550, to high-angled fibers C1592, to moderately angled fibers C1594, to low-angled fibers C1596, to very low angled (transverse) fibers C1598, as distributed between the two pad faces C1550, C1552, provide a stiffness gradient appropriate to both matching the properties of flesh on one face (the tissue face C1550) and steel, for example, on the other (the instrument face C1552) thus both protecting the patient's tissues while delivering the force from the rigid element C2000 in a stable manner.

One might also combine the device shown in FIG. 72 with more than one elastomer or fiber type permitting fine tailoring of pad properties, for example for matching distinct tissue types, for accommodating different procedures, or for creating pads C1570 with properties that vary across the tissue face C1550 to permit engaging multiple tissue types presented simultaneously. Note also that the fibers C1525 need not be straight; curved fibers can provide fiber angle spatial distributions roughly equivalent to those described above.

C.3 Pad Functions—Protection, Sensing, and Modulation

Outlined above are ways in which a TED in pad form might protect the patient's tissues. Consider other functionality that can be delivered using the TEDs described above, such as sensing, actuating, and modulating the tissue's mechanical properties. The TED can sense a number of clinically relevant parameters during the course of a surgery. The TED can provide, for example, measurements of the force applied by each pad to the tissue. If the pads are fluid-filled, then pressure (force per unit area) is easily obtained for each pad. If the pads are designed for heat conduction through their surfaces, then temperature of the tissue can be measured. Many measurements may be combined simultaneously.

The parameter of interest (for example, force) might be sensed by a load cell constructed within the TED. In this case, the load cell outputs a signal readable by electronics. Similarly, the TED might contain a piezo-active polymer that sends an electrical signal corresponding to the rate of deformation of the piezo-active polymer (or acceleration, or the rate of change of acceleration, or the rate of change of force).

Figure 73A:
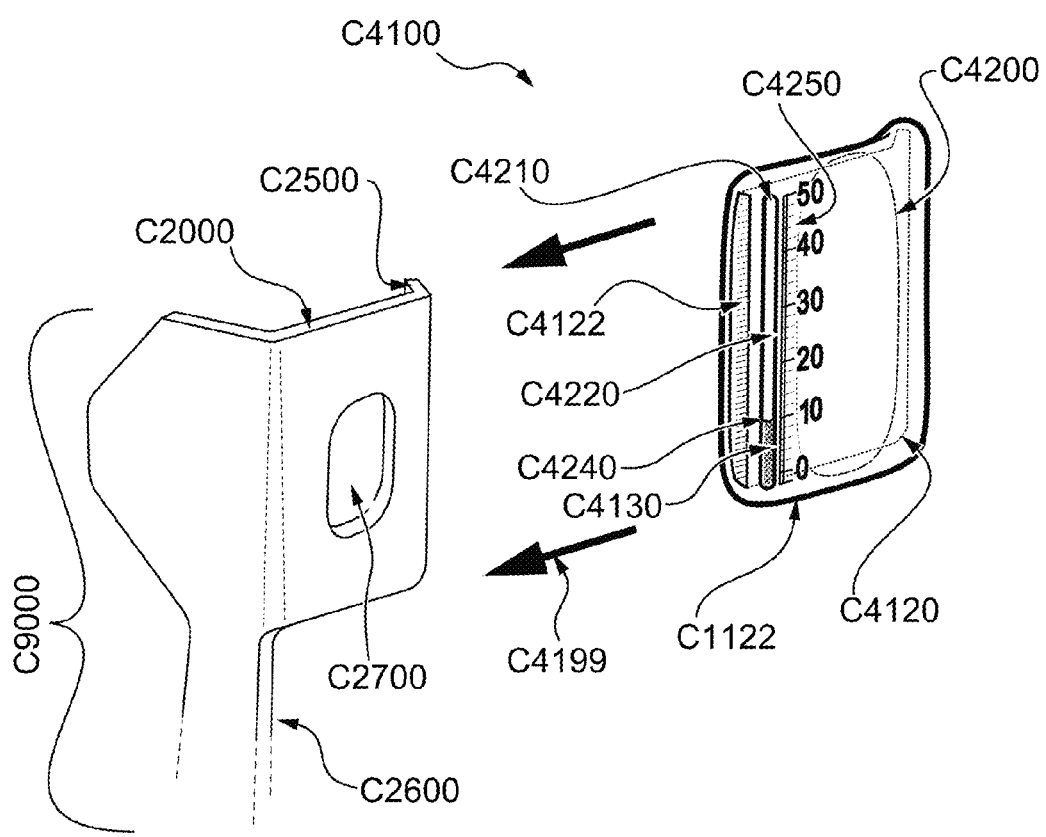
FIGS. 73A and 73B show another embodiment of an exemplary TED comprising a pad attached to the blade of a retractor and includes a fluid-filled internal compartment in communication with a pressure signal display.

One embodiment of a TED can be constructed comprising a substantially elastomeric, liquid-filled pad equipped with a display. Referring to FIG. 73A, in the case of measuring pressure (for example the pressure generated when a retractor displaces a patient's tissues during a thoracotomy), one might construct a retrofit retractor blade pad C4100 that fits on a rigid element C2000 (for example, a steel retractor blade) of existing retractors C9000. The retrofit retractor blade pad C4100 can be constructed out of a compliant, resilient material such as a soft elastomer C1122, and can possess a blade-accepting cavity C4120 molded to fit a rigid element C2000 (like a retractor blade) including a retractor blade tip C2500, a blade-accepting opening C4122 that allows the rigid element C2000 access to the blade-accepting cavity C4120 so that the rigid element C2000 can be inserted (motion arrows C4199) into the retrofit retractor blade pad C4100.

The retrofit retractor blade pad C4100 may also be provided with a closed, sealed internal volume C4200 (distinct from, and not communicating with, blade-accepting cavity C4120). The sealed internal volume C4200 communicates hydraulically with an externally visible (but still sealed) conduit, or transparent pressure signal display window C4210. The pressure signal display window C4210 can possess a dead end (trapping a gas bubble there), the internal chamber passing from the interior volume of the pad to the surface (or near the surface) of the pad, and running parallel to the surface of the pad. The form of this pressure signal display window C4210 may be a long, thin cylinder, a portion of which is forms the exterior surface of the retrofit retractor blade pad C4100. The retrofit retractor blade pad C4100 may also be equipped with a graduated (vernier) pressure scale C4250 that is spatially associated with the pressure signal display window C4210 (for example, positioned alongside). The graduated markings (vernier) of the pressure scale C4250 can be located on the outside of the retrofit retractor blade pad C4100, or they can be positioned on the inside of the pressure signal display window C4210, or in any visually accessible location. The pressure scale C4250 can be printed onto or molded into any convenient surface of the retrofit retractor blade pad C4100. The sealed internal volume C4200 can further be provided with a liquid C4230 (for example, colored water or some other contrast agent) partially filling the sealed internal volume C4200, a gas C4230 (for example, nitrogen) filling the remainder of the sealed internal volume C4200, and a meniscus C4240 between the gas C4220 and the liquid C4230.

Candidates for the liquid C4230 are practically incompressible near ambient pressure, while candidates for the gas C4220 are easily compressed. The position of the meniscus C4240 along the pressure scale C4250 is therefore a function of the pressure inside the sealed internal volume C4200 that is inside of the retrofit retractor blade pad C4100, so the meniscus C4240 serves as the demarcation (indicium) of the internal pressure of the sealed internal volume C4200 of retrofit retractor blade pad C4100 to the operator (for example, a surgeon). As a the retrofit retractor blade pad C4100 forcefully impinges upon the patient's tissues during retraction, the position of the meniscus C4240 moves along (for example, up) the pressure scale C4250 to provide the operator a quantitative indication of the forces being applied to the patient's tissues by the retractor. The pressure scale C4250 may be calibrated to indicate pressure (for example in Pascals), but it may also be calibrated to indicate force (in units of Newtons, kilogram-force, or dynes), or displacement (in millimeters). The markings forming the pressure scale C4250 may be letters, numbers, tick marks, shapes, colors or a combination of these, and they may be equally spaced, logarithmically spaced, or placed in some other convenient pattern alongside the pressure signal display window C4210.

The retrofit retractor blade pad C4100 can also be designed to avoid impingement on the retractor arm C2600, and may include a provision for anchoring itself more securely to the rigid element C2000 by the blade-accepting cavity C4120 being molded to fit a hole pattern C2700 (for example, resembling the hole pattern on a retractor blade) in the rigid element C2000. This embodiment provides an inexpensive upgrade of immediate benefit to hospitals worldwide that use conventional retractors. Measurement of pressure can also be by one of many commercially available pressure sensors that is placed in communication with the fluid C4230 in the retrofit retractor blade pad C4100. Such commercially available pressure sensors produce an electrical signal as a function of applied pressure. The features above may be combined in a number of convenient arrangements. For example, a plurality of such pads can be arranged so that the clinician gains a sense of how the forces are changing as the retraction proceeds, just by watching the indicator tubes. The disclosed retrofit retractor blade pad C4100 thus permits surgeons to reduce tissue trauma by retrofitting retractors currently in hospital inventories.

Figure 73B:
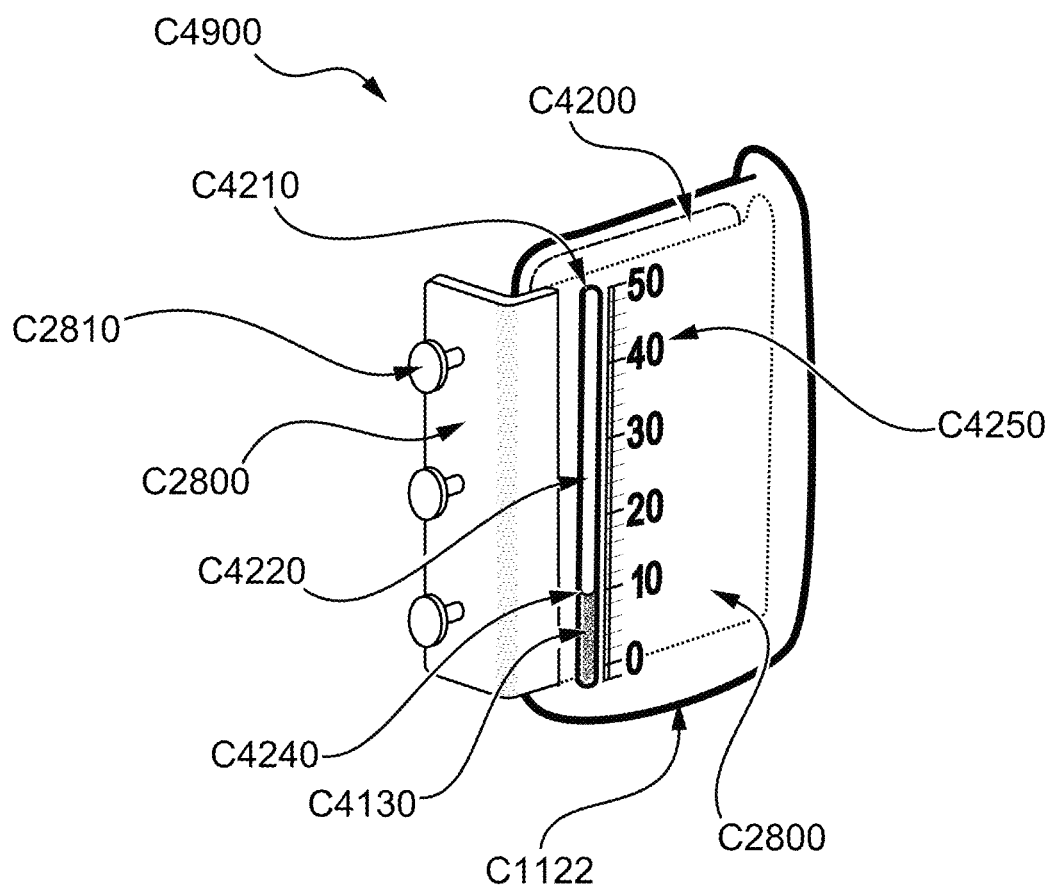

Some thoracic retractors employ removable retractor blades, for example by providing locking pins on removable the retractor blade and locking slots (holes) in the retractor's arms. In FIG. 73B shows an embodiment to take advantage of this opportunity, a removable retractor blade with integral display pad C4900 designed especially for those instruments. The removable retractor blade with integral display pad C4900 can be molded from a compliant, resilient, soft elastomer C1122, and can be provided with a retractor blade insert C2800 (which can be made of steel, fiber-reinforced polymer, or another convenient stiff material) that is bonded with soft elastomer C1122. The removable retractor blade with integral display pad C4900 is also provided with retractor blade mounting pins C2810. The retractor blade mounting pins C2810 can be designed to fit the locking slots in the arms of commercially available thoracic retractors, thus enabling hospitals to increase the functionality of their current instrument inventories. As with the retrofit retractor blade pad C4100 (above, FIG. 73A), the removable retractor blade with integral display pad C4900 can also be provided with a sealed internal volume C4200 that communicates with a pressure signal display window C4210, a pressure scale C4250 associated with the pressure signal display window C4210, a liquid C4230 and a gas C4220 to fill the sealed internal volume C4200, a meniscus C4240 (forming the boundary between the liquid C4230 and the gas C4220) visible within the pressure signal display window C4210 and readable along the pressure scale C4250, thus indicating to a surgeon retracting the patients tissues the magnitude of the force being applied to those tissues along the margin of the incision, thus enabling amelioration of the retraction force, and so reducing tissue trauma.

The signals noted above might be presented to the clinician (e.g., a surgeon or an anesthesiologist) as visual or audio output for consideration as part of the available information on the state of the patient. The signals could also be routed to the input of a control program directing the behaviors of actuators, for example pressure actuated pads, that thus react to the signals in advantageous fashion, for example to take corrective actions to prevent application of too much force.

Figure 74A:
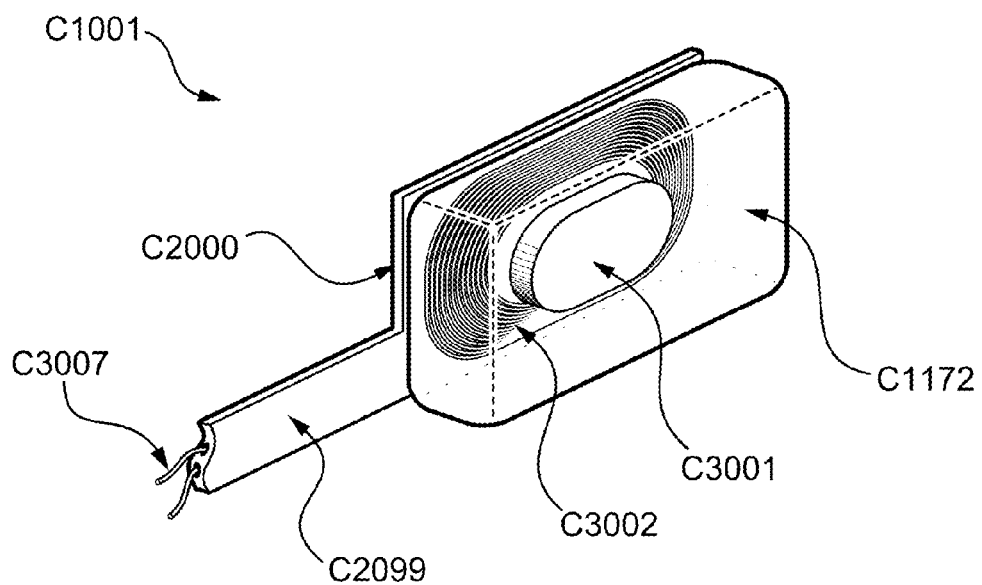
FIGS. 74A and 74B show another embodiment of an exemplary TED comprising a soft elastomer pad having a magnetic mass suspended inside and an electromagnetic coil that drives the magnet in an oscillating motion.
Figure 74B:
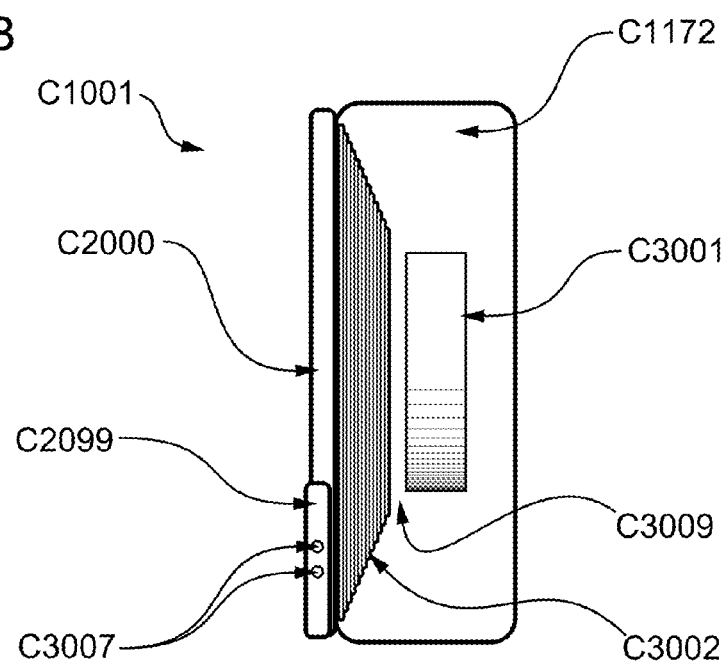

To reduce tissue trauma, patterns of activation of the TED can provide useful effects. For example, the pads in a TED can actively deform, as an actuator, for example to apply cyclic loading to modulate tissue properties. Cyclically changing the internal pressure of a fluid-filled pad can cause the pad to swell repeatedly and thus push more strongly (or weakly) against the tissue. Alternatively, as shown in FIGS. 74A and C22B (FIG. 74A shows an oblique view and FIG. 74B shows a cross-section view), electromagnetic excitation (via power supplied via wires C3007 to electric coils C3002 embedded near the instrument face C1105 of the pad C1001) of magnetic mass C3001 suspended within a pad C1001 made of a soft, highly resilient (i.e., low loss modulus) elastomer C1172 can cyclically load the tissues C9500 and C9700 of the patient for work softening to reduce the force required to displace those tissues. To be free to move, the magnetic mass C3001 can be suspended within the pad C1001, surrounded by the low loss modulus elastomer C1172, leaving a gap C3009 between the magnetic mass C3001 and the electric coils C3002. The elastomer C1172 can be resilient (i.e., possess a low damping coefficient, say of 20% to 5% or less) so that the magnetic mass C3001 supported by the pad C1001 can resonate, transferring some of the energy to the tissues of the patient. The material of the retractor, retractor arm C2099, or the rigid element C2000, can be a fiber-reinforced polymer composite, thus also rendering the retractor nonmagnetic (magnetically transparent). Cyclic loading by the pad can also be performed by cycling the pressure within a fluid-filled pad.

Figure 75:
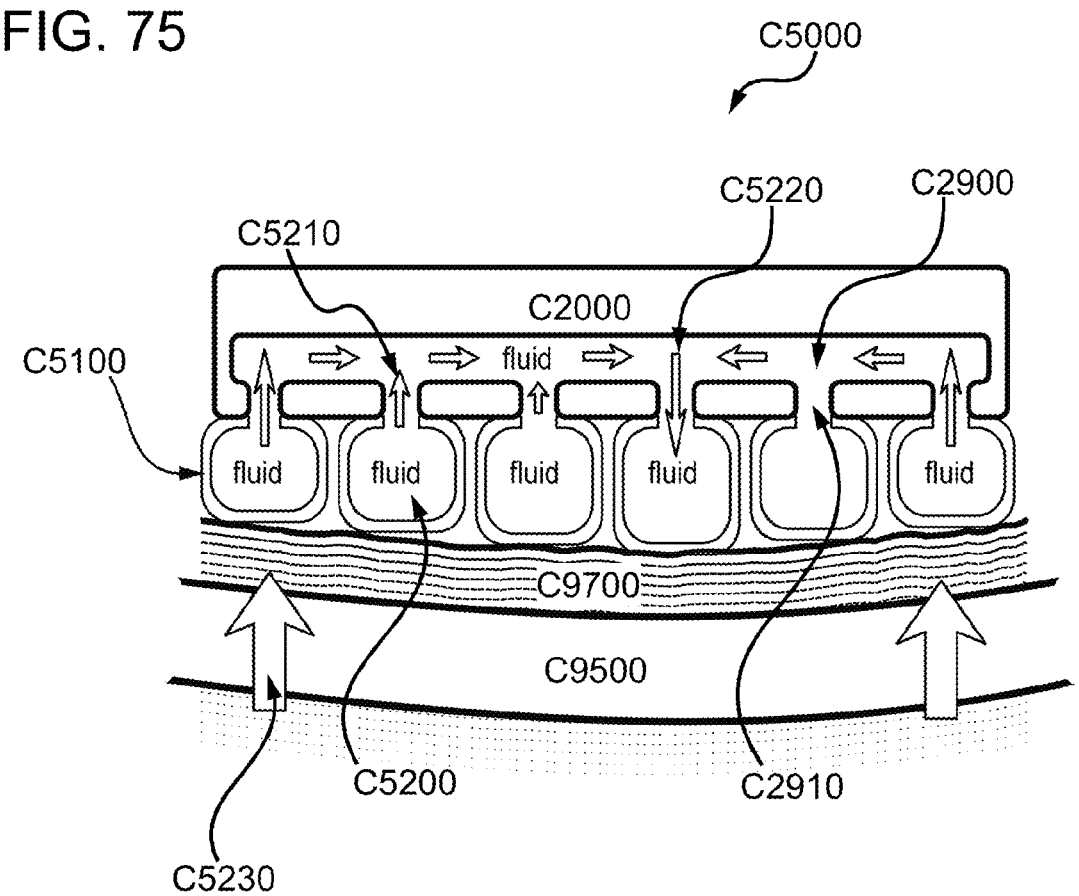
FIG. 75 shows another embodiment of an exemplary TED comprising multiple fluid-filled elastomer bladders all in communication with a common plenum.

In another example of active actuation of a TED, multiple, active pressure pads enable controllable, addressable application of pressure. This could be used, for example, to detect regions of excessively high or low application of pressure and then to perform corrective control of applied pressures to even out irregularities through differential actuation; and active manipulation of pressure actuation patterns. FIG. 75 shows a TED C5000 where hollow compliant pads C5100 filled with fluid C5200 communicate between each other for adjusting load via openings C2910 a plenum C2900 formed by a hollow steel element of the retractor or retractor blade (rigid element C2000). If the TED is made of at least two of these hollow compliant pads C5100 filled with an internal fluid C5200, then communication between hollow compliant pads C5100 confers benefits. If in one example, the pads are fluid-filled and communicate via this manifold system (including the plenum C2900 and openings C2910 permitting flow C5210 into the plenum from the pads C5100 and flow C5220 from the plenum back into the pads C5100), then an excessive loading on one pad C5100 during retraction C5230 will automatically be transmitted hydraulically to the other pads C5100, resulting in an even application of pressure to the patient's tissues C9700 and C9500 by all of the pads C5100 in concert, thus reducing stress concentrations and so reducing patient tissue trauma.

Figure 76:
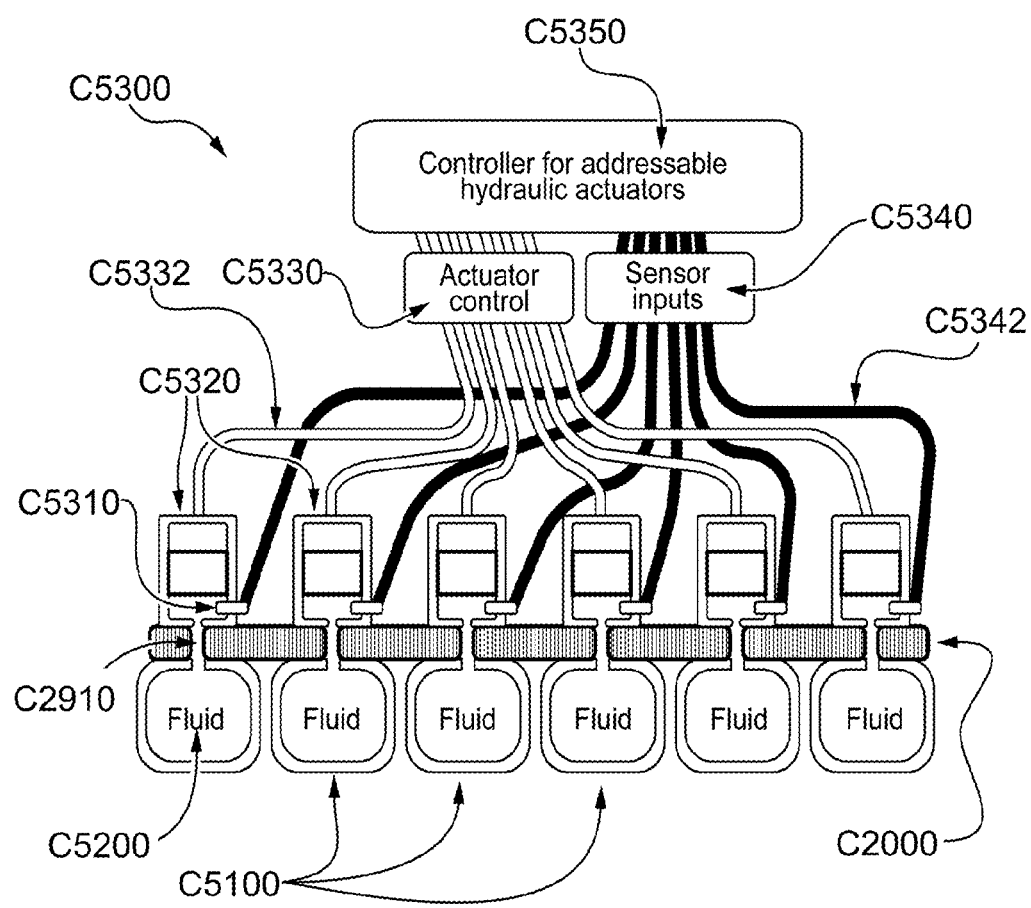
FIG. 76 shows another embodiment of an exemplary TED comprising multiple fluid-filled elastomer bladders attached to a rigid retractor blade and individually in communication with hydraulic cylinders that are controlled by external sensors and controllers.

FIG. 76 shows another embodiment, a TED C5300 composed of variable pressure pads C5100 (filled with fluid C5200) that do not interconnect directly by pressure tubes, but are each connected by an orifice C5210 in a rigid element C2000 to individually addressable hydraulic actuators C5320 (that are themselves each connected by wires C5332 to an actuator control C5330) and each pad C5100 is further fitted with a pressure sensor C5310 electronically connected by wires C5342 to a sensor input C5340; the actuator control C5330 and sensor input C5340 are connected to each other by a control circuit C5350. The control circuitry C5350 and associated software can provide for the comparisons of pressures between individual pads C5100, and so enables modulation of the applied pressure per pad, for the whole array, and for creating whatever spatial, temporal, or spatiotemporal patterns of applied pressure are desired.

One activation pattern of a series of fluid-filled pads (such as TED C5300 shown in FIG. 76) can be sequential (or "metachronal") waves of applied pressure, where peaks of pressure follow troughs of pressure across a linear array of variable pressure pads C5100). This pattern, properly applied, can develop traction against the margin of the incision and in the direction of travel of the waves. This action can provide for active control of the position of the array (and so retraction forces), including corrective travel to restore the original position of the variable pressure pads C5100 in the case of slippage. Combined with sensing the pattern of pressure distribution across the array, this feature allows for the continuous maintenance of the most clinically appropriate application of forces throughout a surgery despite changes in loading, posture, etc.

Figure 77:
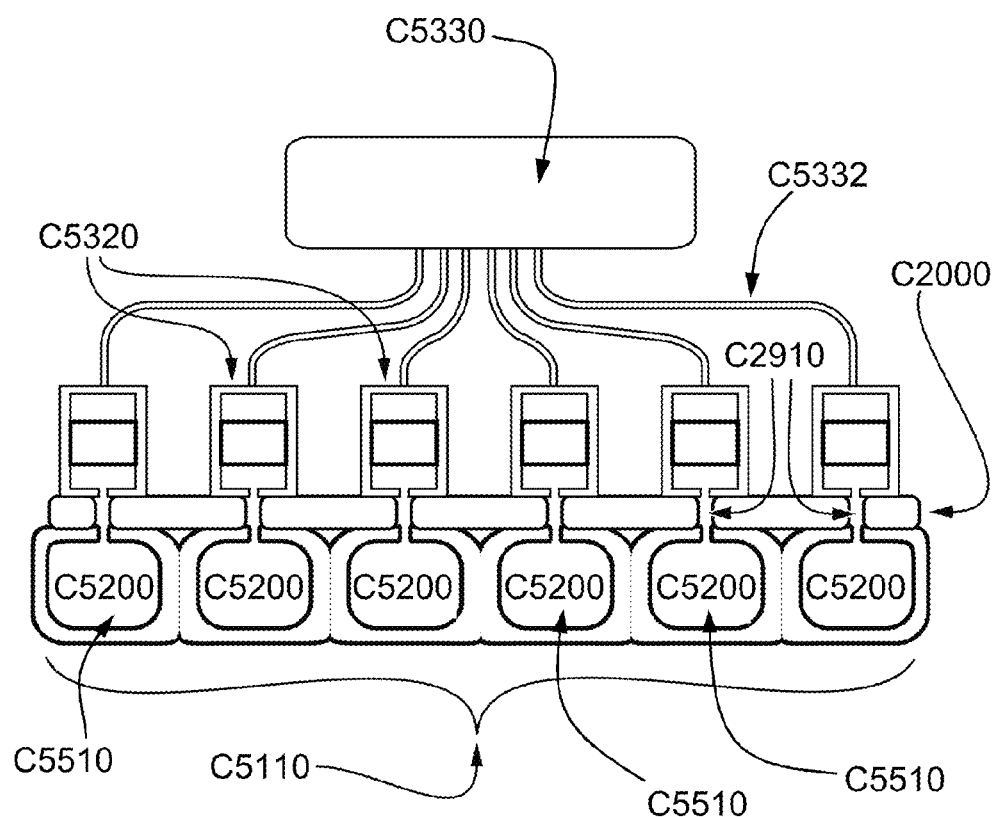
FIG. 77 shows another embodiment of an exemplary TED comprising an elastomer pad having multiple fluid-filled compartments attached to a rigid retractor blade and individually in communication with hydraulic cylinders that are controlled by an external controller.
Figure 78A:
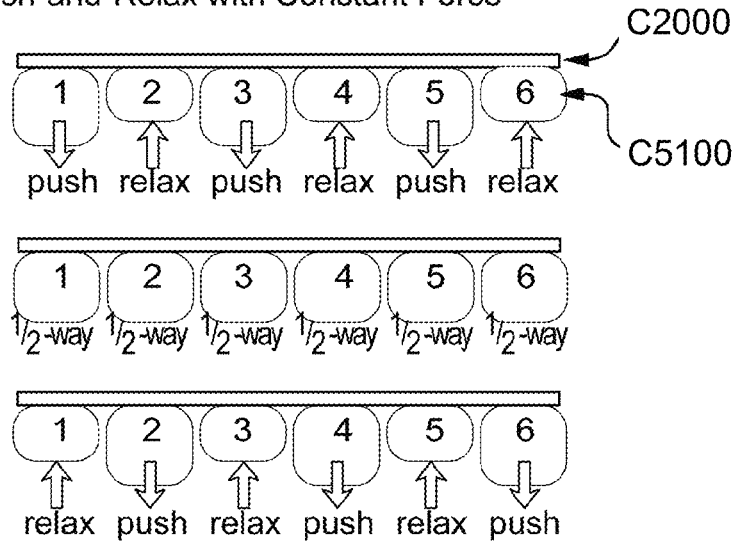
FIGS. 78A and 78B show exemplary sequences of activation of the bladders or compartments in a TED, such as shown in FIG. 77.
Figure 78B:
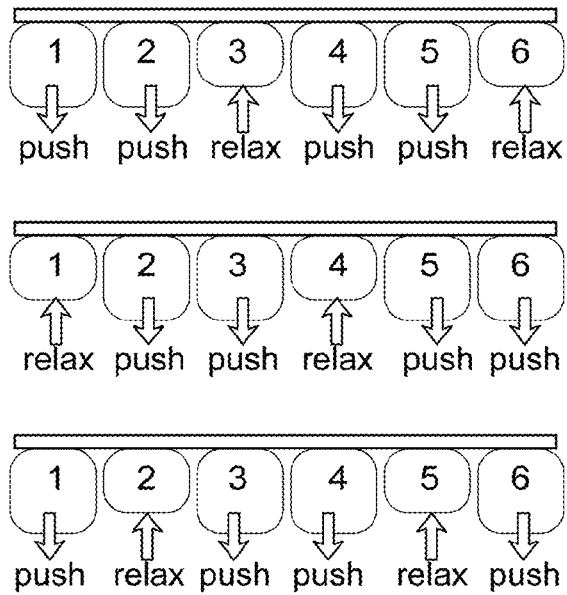

TED component arrays also provide the basis for maintaining perfusion of the tissues retracted by, say, a rib spreader. When current rib spreaders (e.g. C9000 in FIG. 54) retract ribs C9500, the soft tissue C9700 between the ribs and the steel retractor blades C9100 is compressed, so much so that perfusion (e.g., blood flow supplying oxygen, nutrients, waste removal) is blocked. An operation like a thoracotomy can last 2-8 hours, or more, so that the cells in the retracted soft tissues die (either from lack of perfusion, or from reperfusion injury, or the tissues are simply crushed). Given the need for continuous surgical access, relieving retraction to allow periodic perfusion is often not possible. Our invention can avoid loss of perfusion, perhaps entirely, thereby eliminating soft tissue trauma from this cause. For example, a TED that takes the form of a hydraulically actuated array of individual pads C5100 (as shown in FIG. 76) or as an array of elastically linked pads C5110 (as shown in FIG. 77). Such an array C5110 can be designed with more total contact area than that required to apply sufficient force to hold the tissues during retraction. Given this, one may use fewer than the full number of pads, or less than the complete area of contact of large multi-compartment pad C5110 to support retraction. Provided with this contact area surplus, proper cycling of the volumes of fluid C5200 (and so the internal pressures of compartments C5510) individual control of pad actuation can provide a substantially continuous and sufficient force for retraction while simultaneously relieving pressure on selected areas of tissue, thus permitting regular perfusion of tissues under the retraction elements. FIGS. 78A and 78B show two of many possible pad C5100, C5110 actuation sequences that deliver full retraction force while simultaneously frequent perfusion providing (i.e., by relieving pressure) to those same retracted tissues. The sequence C5334 shown in FIG. 78A alternately pushes-and-relaxes on every other hydraulically actuated pad C5100 (numbered here 1, 2, 3, 4, 5 and 6) while delivering a constant force to the patient's tissues. The individual hydraulic pad actuation control pattern simply alternates from fully inflated to fully deflated each pad C5100. This sequence pushes most of the time with half the total area of the array of pads C5100. In the first phase, shown in the top row, every odd-numbered pad C5100 is inflating and so pushes against the tissue while every even-numbered pad C5100 deflates, relieving pressure on the retracted (or retracting) tissues underlying those even numbered pads C5100. In the second row showing the second phase, we can observe that all of the pads C5100 are in mid-travel, hydraulically inflated to about the same (intermediate) dimensions, albeit at a pressure less than that required to fully extend the pads C5100, and more than that lower pressure permitting elastic recoil of the pad C5100 to return them each to their original, deflated, smaller size (as they would be before inserting the array of pads C5100 into the thoracotomy incision for retraction). The third row shows the third phase, a similar situation to the first row, save that the sequence has progressed further so that all of the odd-numbered pads C5100 are now deflated while the even-numbered pads C5100 are inflated. The fourth phase of the sequence visually matches the second phase (shown in the second row), with all pads C5100 inflated to roughly the same extent, save that the direction of inflation is reversed from the second phase. FIG. 78B shows an alternate sequence C5336, briefly described as allowing every third hydraulic pad C5100 to deflate whilst maintaining the hydraulically inflated state of the two pads C5100 between, and cycling the pattern ahead by one pad C5100 at a time. The individual hydraulic pad C5100 actuation control pattern in this instance can be written as "inflate for ⅔ of a cycle, then deflate for ⅓ of the cycle." One difference here is that this sequence pushes with an area of ⅔ the total area of the array of pads C5100 at once, and so for example permits the surgical instrument designer to reduce the total number of pads C5100 (and so the total area of the array). Note that one advantage of providing an array of individually addressable hydraulic retraction pads C5100 is that any desired arbitrary pattern of actuation can be created via software modifications to suit any conceivable procedure in which the device C5300 or other array of pads C5100 might be used. Every section of soft tissue under the influence of the retractor can thus be perfused often enough to maintain a healthy tissue.

C.4 Examples of TEDS for Specific Applications

Figure 79A:
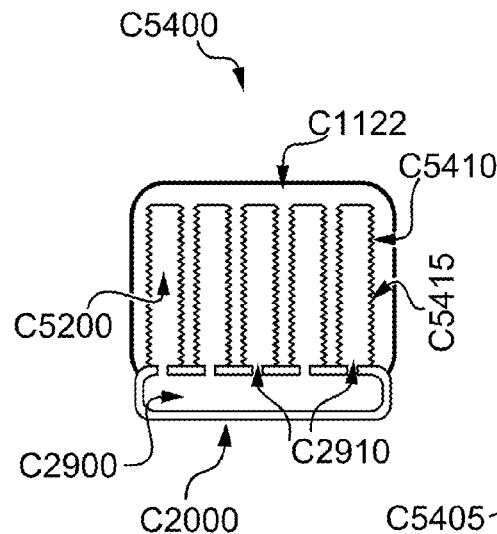
FIGS. 79A and 79B show a side and oblique view of an exemplary TED comprising a pad with internal fluid-filled columns.
Figure 79B:
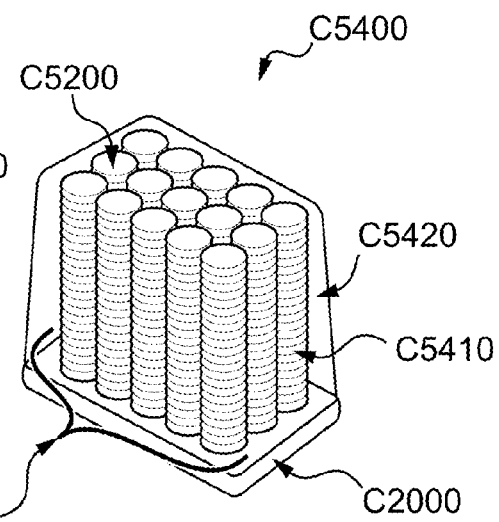

Referring now to FIGS. 79A to 83, FIG. 79A shows a side view and FIG. 79B shows an oblique view of a TED, here a counter-conforming anisotropic pad C5400 that can be applied to the margins of a thoracotomy incision. The counter-conforming anisotropic pad C5400 is capable of displacing the ribs C9500 of a patient while preserving the neurovascular bundle (part of the soft tissues C9700) by using the compression of one part of the counter-conforming anisotropic pad C5400 to drive expansion of another part of counter-conforming anisotropic pad C5400. Disclosed here is a counter-conforming anisotropic pad C5400 that can be in the form of a single retractor blade pad that adaptively reconfigures its shape to evenly distribute the required loads applied to the hard and soft tissues at the margin of the incision. Counter-conforming anisotropic pad 5400 can comprise a multi-columnar (i.e., array of columns, C5405) structure making up a portion of the interior of counter-conforming anisotropic pad C5400 (which may be formed of a soft elastomer C1122) where each column C5410 possesses access to a hydraulic plenum C2900, a fluid volume C5200, a plenum communication component, such as an orifice C5210, and a column cohesion means C5420. FIGS. 80A, 80B and 80C show three instances of a counter-conforming anisotropic pad C5400 in action. FIG. 80A shows the counter-conforming anisotropic pad C5400 just before tissue impinges upon the embodiment. FIG. 80B shows what happens when tissue impinges on a portion of the counter-conforming anisotropic pad C5400, showing that compressed columns C5411 drive fluid into other columns C5412 which rise to meet the tissue that has not yet impinged on the counter-conforming anisotropic pad C5400, thus evening out the load before full force develops, thus reducing stress concentrations in the patient's tissue, thus reducing tissue trauma. FIG. 80C shows that this process works across the whole of the counter-conforming anisotropic pad C5400 to accommodate tissues impinging at angles, again evening out the loads.

Figure 80A:
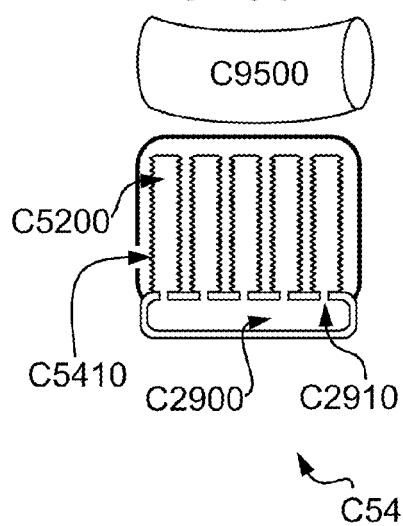
FIGS. 80A through 80C show multiple views of the TED depicted in FIGS. 79A and 79B when loaded.
Figure 80B:
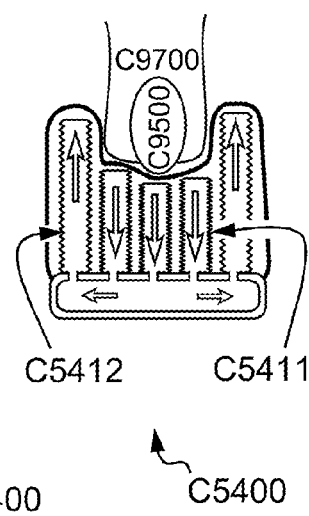
Figure 80C:
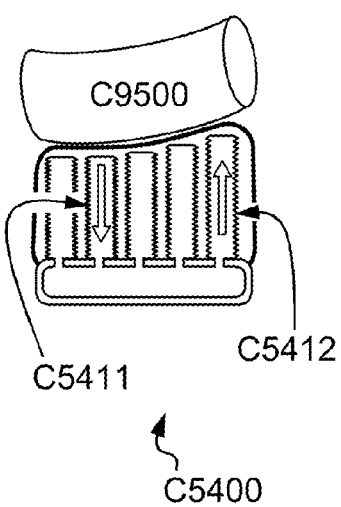
Figure 81:
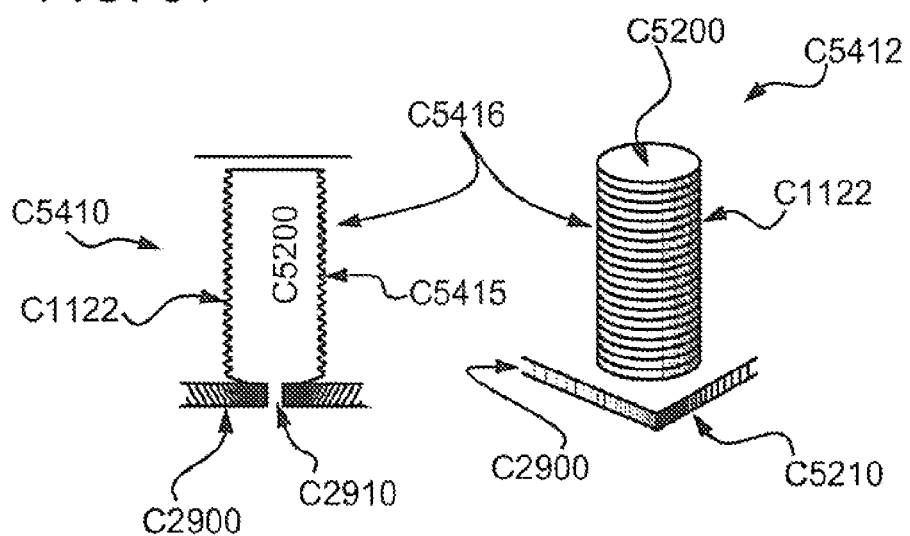
FIG. 81 shows an embodiment of an exemplary fluid-filled column, such as those shown in FIGS. 79A and 79B, comprising a fluid-filled bellow with a fluid port for communicating with a plenum.
Figure 82:
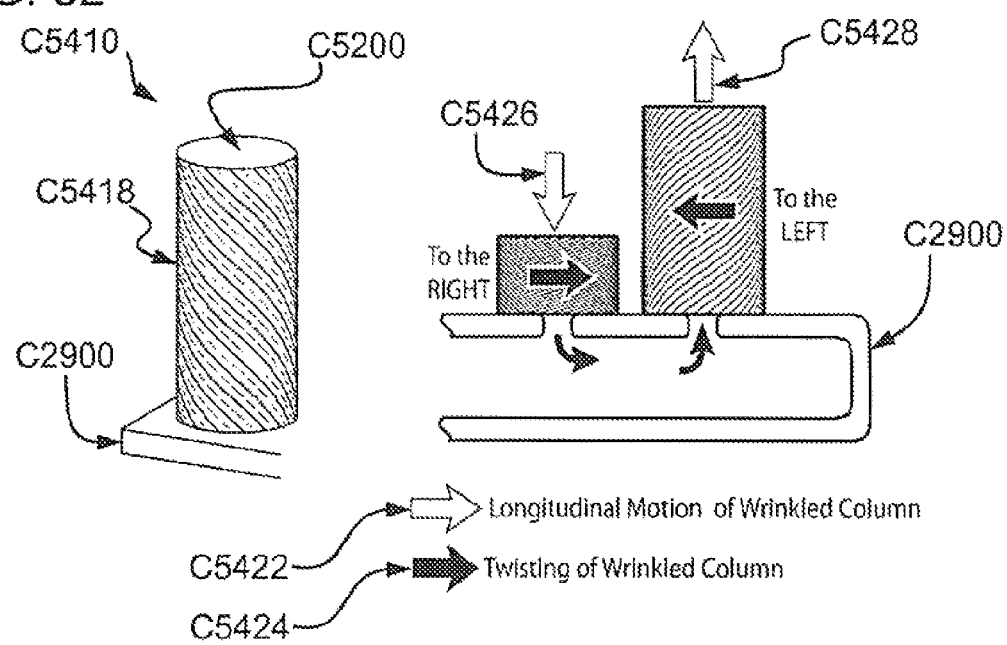
FIG. 82 shows another embodiment of an exemplary fluid-filled column including a fluid-filled bellow with a fluid port for communicating with a plenum.
Figure 83:
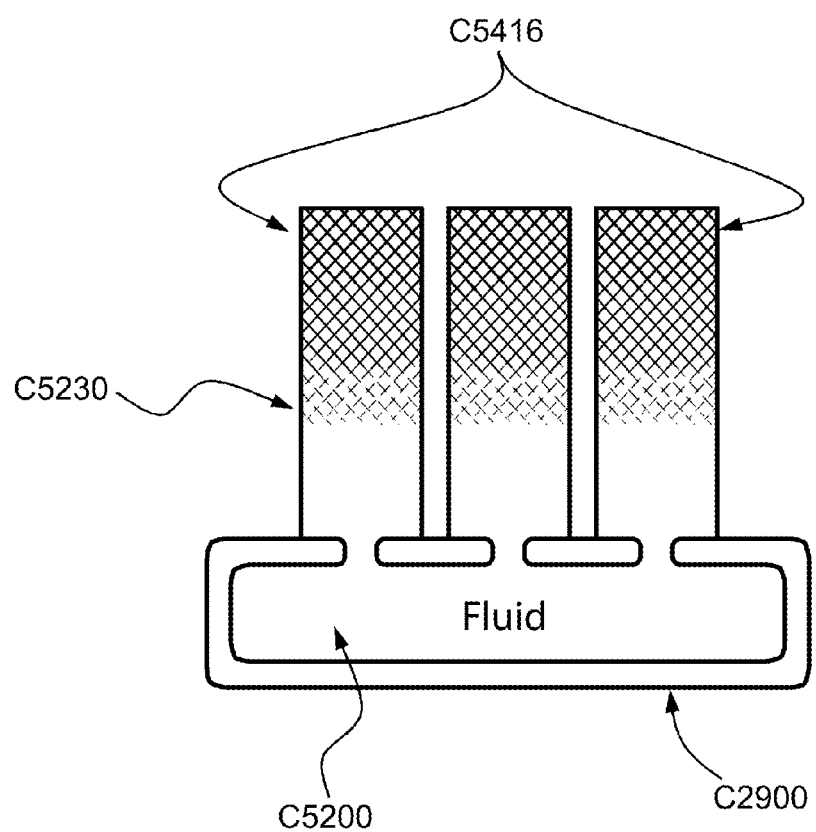
FIG. 83 shows another embodiment of an exemplary fluid-filled column that is helically wrapped by fibers.

FIGS. 81 through 83 show alternate embodiments of single components and elements that fit inside of larger monolithic elastomeric bladders. These FIGS. 81 through 83 show the walls C5415 of columns C5405, with walls C5415 of the column C5405 having corrugated, bellows-like walls C5416 (FIG. 81), twisted ribs or wrinkles C5418 (FIG. 82), or walls C5415 helically wrapped by fibers C5416 (FIG. 83). Such wall constructions permit column length changes in response to loads. The wall C5415 may be integral to the bulk material (soft elastomer C1122) of the pad C5400, or the wall C5415 might be a separate membrane from that of the exterior wall C5499 of the larger monolithic elastomeric bladder, alternatively, the wall C5415 may be comprised of distinct materials (for example, it may be reinforced with fibers, such as the helical fibers C5416 depicted as forming the wall C5415 of the column in FIG. 83). The multiple columns C5410 within each single pad C5400 are fluid-filled (as with a gas or a liquid C5200) and communicate via ports C5210 to a single plenum C2900 to which other columns also connect. As shown in FIG. 80A through 80C, for example, when some of the columns C5411 in a single pad compress under the load of retraction against tissues, those impacted columns drive their internal fluid C5200 out of their individual ports C5210 into the plenum C2900 and in through the ports C5210 of other columns C5412 which are not compressed. This influx of fluid pressurizes columns C5412, which then extend forwards (or upwards, as appropriate for the drawing) to meet the oncoming tissue. To extend like this, the walls C5415 of the columns C5410 might be constructed as bellows C5416 (FIG. 81), or the walls C5415 could be built to permit length changes C5422 (FIG. 82) by employing helical creases or wrinkles C5418, so as to be able to wrinkle and un-wrinkle by twisting C5424 one way as they rise C5428 (lengthen) and twisting C5424 the other way as they fall C5426 (shorten) in response to changes in internal volume (or pressure). So, if a column's wrinkling and twisting counterclockwise was associated with its getting shorter and a decrease in internal volume, then increasing the internal pressure (or volume) drives un-wrinkling, un-twisting, and so lengthening. If a wrinkled column was compressed by tissue, then its internal volume would decrease under the load, the twisting and wrinkling would increase, and the rise in pressure (given the imposed decrease in volume) would drive the fluid out of that column and into other, less loaded columns.

Alternatively, the columns C5410 embedded in the elastomer matrix (soft elastomer C1122) could be helically fiber-wound with high tensile strength cordage or fibers C5416 in the walls C5415 (FIG. 83), which arrangement permits length changes in response to changes in internal volume (or pressure). If the helical fiber angle C5230 (pitch angle with respect to the long axis of the column) was larger than 54.7 degrees (e.g., from 60 to 70 degrees) when the column was unstrained, then increasing the internal pressure or volume of such a column would drive the fiber angle C5230 down to ~54.7 degrees, which drives active self-lengthening of the column (and the column diameter decreases). If the fiber angle C5230 were instead smaller than 54.7 degrees (e.g., 20 to 30 degrees), then increasing the internal pressure or volume of the column drives the fiber angle C5230 up to ~54.7 degrees and the column actively, forcefully shortens (and the column diameter increases). Motions like these can be individually tuned per column according to the needs of the region of the pad C5400. Also, the columns C5410 can be omitted from the region where the TED C5400 contacts the neurovascular bundle (or other softer tissue) to reduce pressure applied to this sensitive tissue; alternatively, this region of the TED C5400 can have columns C5410 that are modified such that they extend to a lesser degree when responding to plenum C2900 pressure (by changing the shape of the bellows C5416 there, by reducing the initial pitch angle C5230 of the twisted wrinkling C5418, or by beginning with a lower pitch helical fiber angle C5230). Other configurations of TEDs disclosed above can be used in thoracotomy or in other procedures, such as in a sternotomy in which stiffer portions of the TEDS C5400 push against the harder compact bone on the outside of the sternum and push only lightly, or not at all, on the fragile trabecular bone exposed at the surface of the incision of the bisected sternum.

Figure 84:
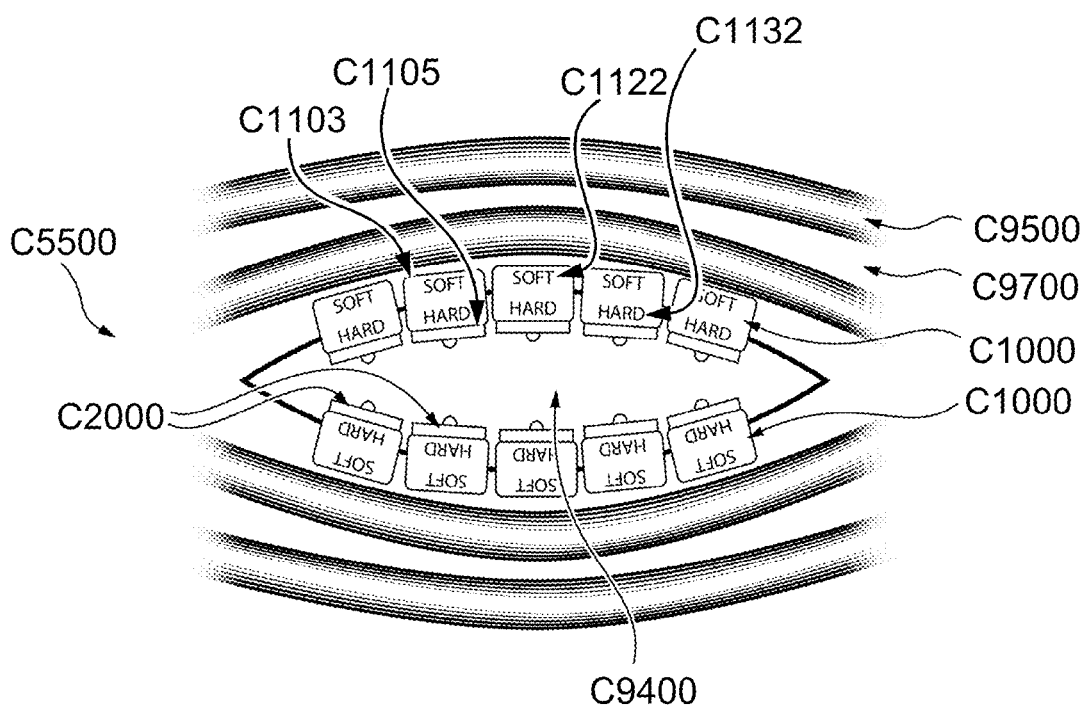
FIG. 84 shows another embodiment of an exemplary retractor comprising multiple steel blades each fitted with a TED having a modulus gradient.

Given the above useful design space for the TED and given the fact that the rigid steel blades C9100 of current retractors C9000 crush the soft tissues against the ribs and block perfusion during thoracotomy, there is a need for a retractor blade pad that reduces or eliminates stress concentrations in soft tissue. This can be accomplished as shown in FIG. 84 whereby multiple gradient pads C1000 are attached to the rigid elements C2000 of a surgical instrument, say, a new retractor or a retrofit set of retractor blades C9100 for a prior art retractor C9000. This embodiment, if rendered in a retractor blade TED C5500, could take the form of smoothly varying elastomeric (rubber) gradient pads C1000 that start with a very high modulus hard elastomer C1132 on one side (the instrument face C1105) and transition to a very low modulus, soft elastomer C1122 on another (soft tissue face C1103) (FIG. 84).

Figure 57:
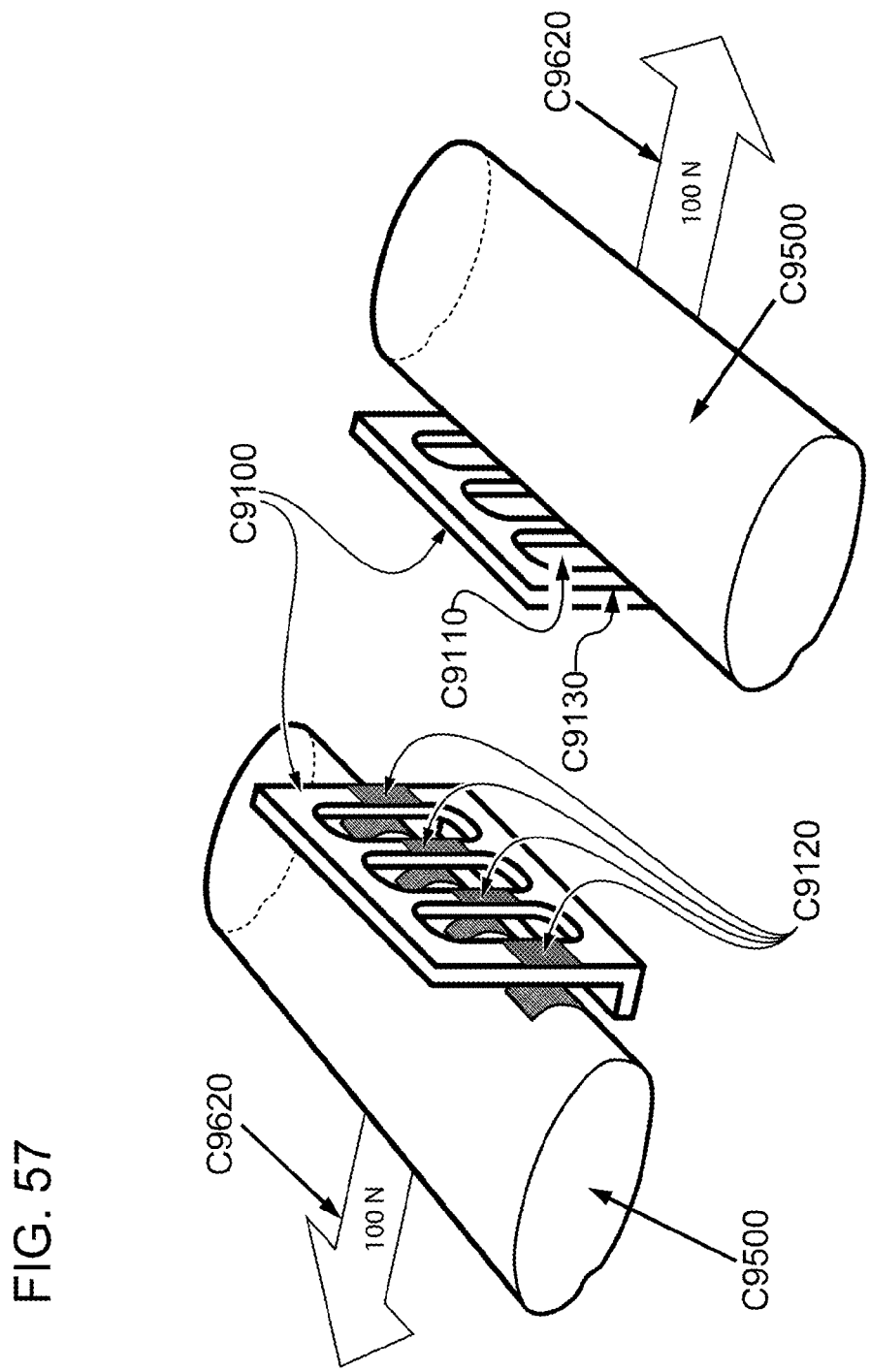
FIG. 57 shows another example of the prior art in which fenestrations in blades decrease contact area with the rib.

FIGS. 85A through 85F disclose another TED C7000 that is a variation on the devices depicted in FIGS. 75 and 77. TED C7000 has both pressure sensing and traction control. TED C7000 addresses another shortcoming of currently available retractors C9000: in order to prevent the retractor blades' C9100 slipping or sliding along the raw, exposed margin of an incision C9400, some prior art blades C9100 sport spikes that project into the flesh, as an anchor, or prior art blades C9100 possess fenestrations C9110 to (A) actually reduce the area of the steel pressed into the muscle, increasing the stress there, and (B) increase the edge length, to increase the bite of the blade C9100 (as shown in FIG. 57). These fenestrations C9110 (and the outside perimeter of the blades C9100, as well) are made with unrelieved, sharp edges that bite into the tissue to help anchor the retractor blades C9100; thus the designers expect tissue to bulge (i.e., herniate) through the fenestrations C9110 to ensure that the retractor C9000 does not slip when the surgeon bears down to pry open the patient's rib cage. The "spikes" and "fenestrations" solution is an unsatisfactory answer to the problems inherent in using steel retractor blades C9100, given that the body wall damage is believed by many clinicians to be the greatest source of patients' pain. Given that some embodiments of our invention includes the use of low modulus elastomers (e.g., soft elastomer C1122 in FIGS. 59A and 59B) and multiple actuators (e.g., C5110 in FIG. 77), one can better secure the purchase of the retractor on tissues by cycling the actuation of the several pads C5100, C5100', C5100", C5100'" to develop laterally stabilizing forces while simultaneously protecting the raw margin of the incision. TED C7000, shown in FIGS. 85A-85F, possesses a row of elastomeric pads C5100 each connected to its own individually addressable hydraulic actuator C5320 (not shown). The hydraulic actuators C5320 are controlled by a central controller C5350 (not shown) that cycles the hydraulic actuators C5320 in patterns (which may take the form of metachronal waves) that creates a rolling motion C7010 of the combined surface of the row of pads C5100. A single, continuous layer of fabric C1104 is attached to the tissue surface C1103 of the pads C5100 to convey lateral forces to the neighboring pads C5100 and to the tissue C9700. As shown in the sequence in FIGS. 85A through 85F, there is a sequential inflation of pads such that pads C5100 are un-inflated, pad C5100' is inflating, pad C5100" is maximally inflated, and pad C5100'" is deflating. The point of greatest projection into the tissue (marked "X") is formed by fully inflated pad C5100", with the pads on either side of pad C5100' inflating on the forward traveling side (pad C5100') and deflating on the rearward traveling side (pad C5100'"). The fabric C1104 makes contact at point X, rolls rearward, and releases, under the sequential inflation/deflation of pads C5100', C5100", C5100'" and so acts there like the limb of a rotating wheel, developing traction in a direction parallel to the long axis of the row of pads C5100 and opposite the direction of travel C7020, as depicted in views at successive times presented in FIGS. 85A through 85F. Thus, activation of the hydraulic actuators C5320 of pads C5100 generates traction along the surface of the tissue C9700 that can be used to prevent slipping of the TED C7000 or even to move TED C7000 along the surface of the tissue, for example to adjust the position in a incision of TED C7000.

Figure 86A:
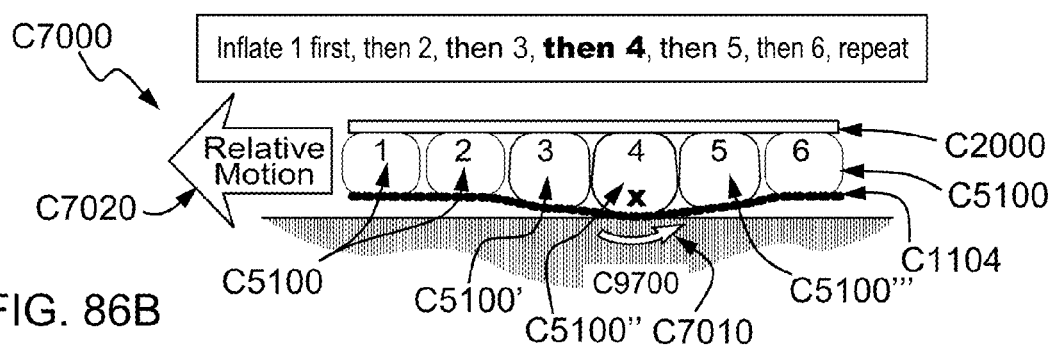
FIGS. 86A through 86D show another exemplary means by which a retractor blade can be made to move sideways in either of two directions, or multiple points of traction can be generated, or two opposing forces can be generated.
Figure 86B:
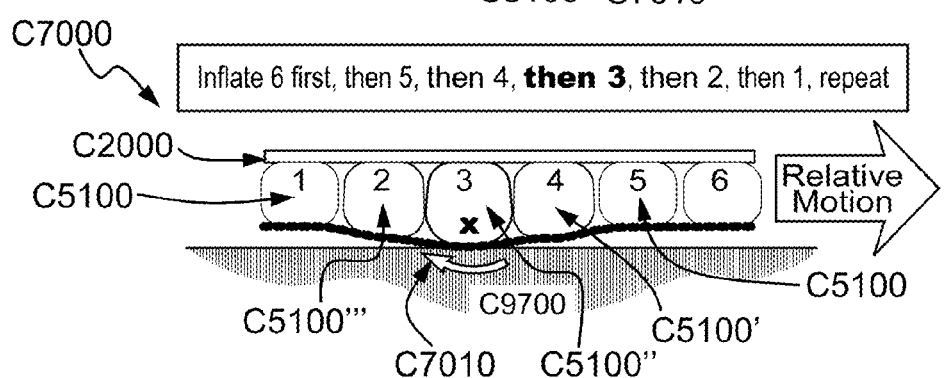
Figure 86C:
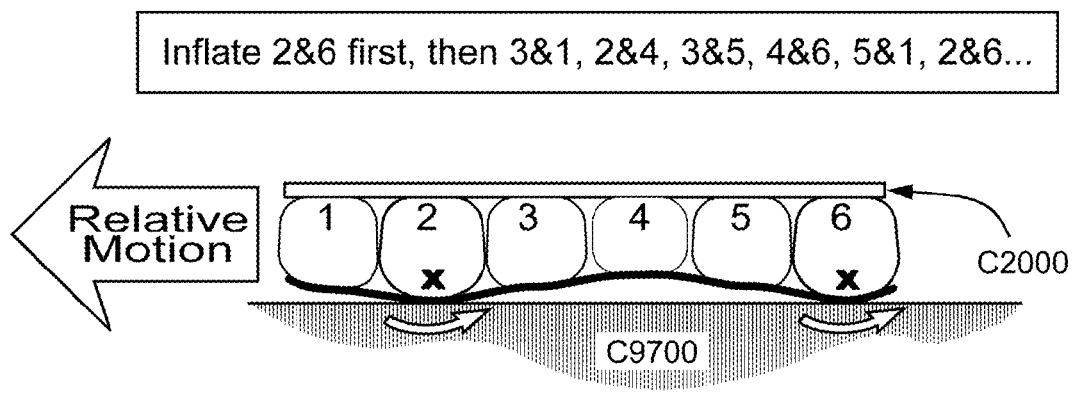
Figure 86D:
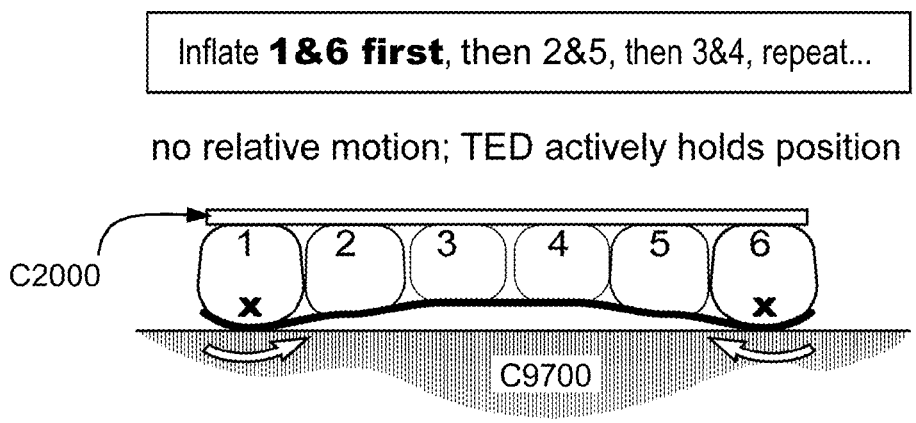

One may change the pressure actuation pattern of TED C7000 to generate forces in either direction (FIG. 86A and FIG. 86B), or to create multiple points of traction (FIG. 86C), or to develop forces in two directions at once (FIG. 86D). These patterns can be generated by the appropriate control software. The software might further parse the outputs of sensors to create traction and active transport of the retractor blades across the landscape of an incision to correct for slippage, swelling, movement, changes in the conformation of the patient, or strategic redeployments of the surgical instrumentation by the surgeons.

Figure 87:
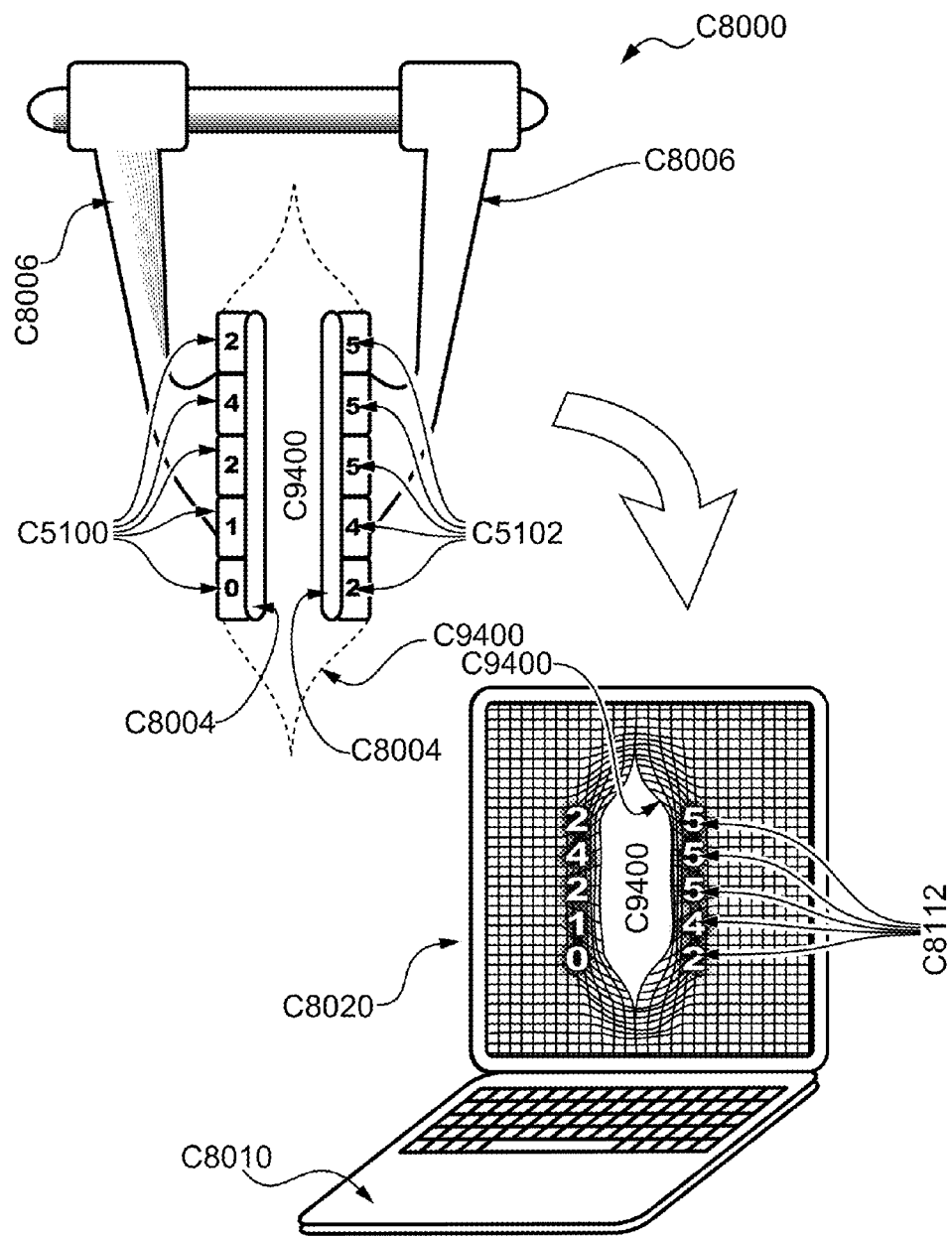
FIG. 87 shows a bottom view of an exemplary retractor comprising pressure sensors to generate a map of the forces applied to the margin of an incision.

Given the design space for TEDs, and given the fact that commercially available retractors are mute when it comes to sensing tissue state, and given that clinicians welcome timely information that improves their situational awareness and so improves patient outcome, there is a need for a retractor that can rapidly and simply provide the surgeon with a clear sense of the condition of the tissues in the region of the incision throughout the surgery. FIG. 87 discloses a parameter mapping device C8000 that provides information about at least one relevant parameter of tissue condition—for example, pressure inside the pads, indicating the tissue pressure underlying the pads (i.e., the force applied by the pads, divided by their area), is used as an example here, but other parameters can be measured, such as tissue oxygenation. Parameter mapping device C8000 possesses a TED comprised of at least two rows of sensor pads C5100, at least one of which is associated with each of two retractor blades C8004 attached to two retractor arms C8006, where each of the sensor pads C5100 senses at least one parameter of interest and produces at least one signal, for example a magnitude C5102 (as indicated by the value on each pad). The parameter mapping device C8000 further comprises a plurality of signal pathways (not shown), at least one signal coordinator or comparator (not shown), at least one pad controller (not shown), hydraulic actuators (not shown), (all of which might be accomplished by a laptop computer C8010), and, for each sensor pad C5100, actuator control software, imaging software, and at least one display C8010 (which may be the screen of the laptop computer C8010). As shown in FIG. 87, the parameter mapping device C8000 (here depicted as a form of thoracic retractor) is operated by inserting the retractor blades C8004 into the fresh incision C9400. Upon widening the incision C9400 with the parameter mapping device C8000, the TEDs measure at least one parameter of interest with sensors inside the sensor pads C5100 and then transmit the resulting signal(s) to the signal coordinator (which may be a software program operating on the laptop computer C8010). The signal coordinator then processes the signals for the imaging software (the signal coordinator might also be a part of the imaging software, which may be on the laptop computer C8010) and sends information to at least one display C8020. The display shown in FIG. 87 reports pressure both as a numeric value along the margin of the incision (numbers C8112 on the display C8020 correspond to magnitudes C5102 reported by the sensor pads C5100) and as a visual map of signal intensity, with regions of higher pressure being indicated by color, brightness, or distortions in a grid (as shown in FIG. 87). The display C8010 may be in the form of an LCD screen, or it may take the form of color-coded LEDs directly associated with each sensor pad C5100, or it may take the form of an audio output, or at least one vernier scale. Alternatively, a color-coded array can be used, with each retractor element indicating the magnitude of say, the pressure (or stress in the tissue) applied to that portion of the margin of the incision. In this case, green might indicate that the stress is an "appropriate applied stress," that is, sufficient or adequate to displace the tissues without damage; yellow could caution that the applied stress is going too high; and red could indicate that damage is imminent or extremely likely. Any number of indicia could be arranged that conveyed the state of the various regions of the margin of the incision. Also, the determination of "appropriate applied stress" can be made, for example, with reference to known values for maximum sustainable stress for the tissue types normally encountered along the margins of the incision, or, it might be assessed directly, by sensing some relevant parameter about the state of the tissue. Another way to determine appropriate applied stress is by measuring the change in the magnitude of the applied stress from the initial, "zero" position (or start time, or both) of that retraction for that patient to the value(s) observed later on for the same patient as retraction proceeds. Still another way to determine the appropriate applied stress might be to compare the magnitude of the pressure observed under one retractor element to those for adjacent ones. One can, for instance, decide that a high enough stress differential between two adjacent retractor elements is problematic as that might indicate large stress gradients in the tissue. The resolution of the display need not be high. The display C8020 allows the surgeon to see at a glance a map of the tissue conditions during retraction and so can modify actions accordingly.

Figure 88:
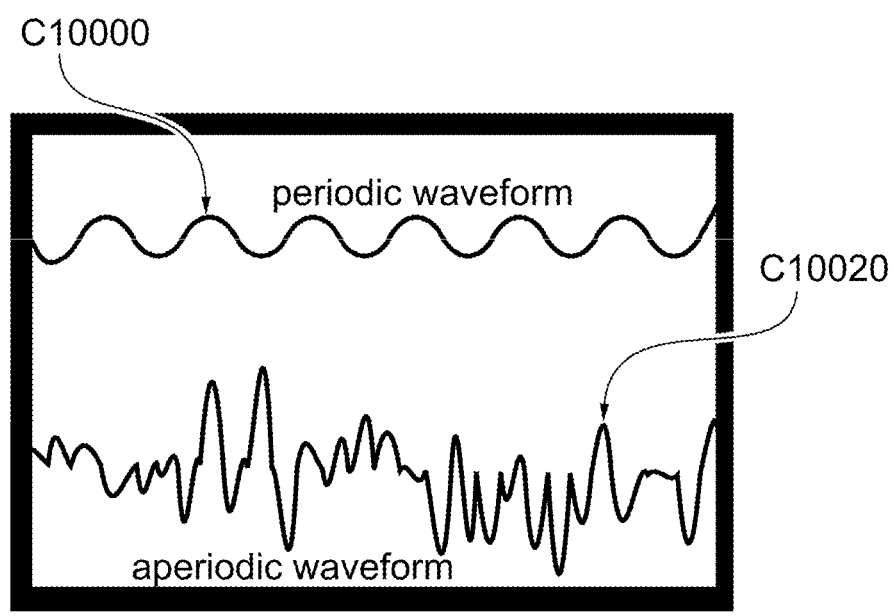
FIG. 88 shows exemplary means for cyclically loading a tissue with a TED using a periodic waveform or an aperiodic waveform.

Given the design space for a TED, and given the fact that current retractors cause damage due to forcefully breaking bones, ligaments, tendons, and tearing muscle, surgical practice can be improved by active modulation of the patient's tissues during the course of retraction in order to reduce the force required for retraction. We disclose an embodiment for a rib spreader that cyclically loads the patient's tissues as retraction proceeds. The cyclic loading may be applied to the tissue by oscillating internal pressures within hollow, fluid-filled TEDs. The cyclic loading may take many forms. The cyclic loading might be a large amplitude motion (on the order of, or up to the value of, the width of the surgical aperture, say, 100 millimeters), a small amplitude motion (on the order of 1-5 mm), a low frequency motion (on the order of, or equal to, that of the overall retraction action itself, say a period of 2-6 minutes), and/or a higher frequency motion matching physiological rates of deformation (0.1 Hz to 20 Hz), and/or a very high frequency motion matching the resonant frequencies of microstructures and microcomponents of the tissue (20 Hz to 20 KHz). The cycle, or oscillation, may possess a roughly periodic waveform C10010, that is, a motion profile that is roughly the same from cycle to cycle (FIG. 88), or, as may be useful for actuator feedback control with very high update rates, or with waveforms combining several frequencies, the oscillation may take a more complex form C10020, with aperiodic behavior (FIG. 88). A very high update rate servo system could serve the requests emerging out of a signal processor that rapidly monitors, detects, characterizes, and responds to, as one example, the second time derivative of the measured force acting on at least one retractor blade pad.

Figure 89:
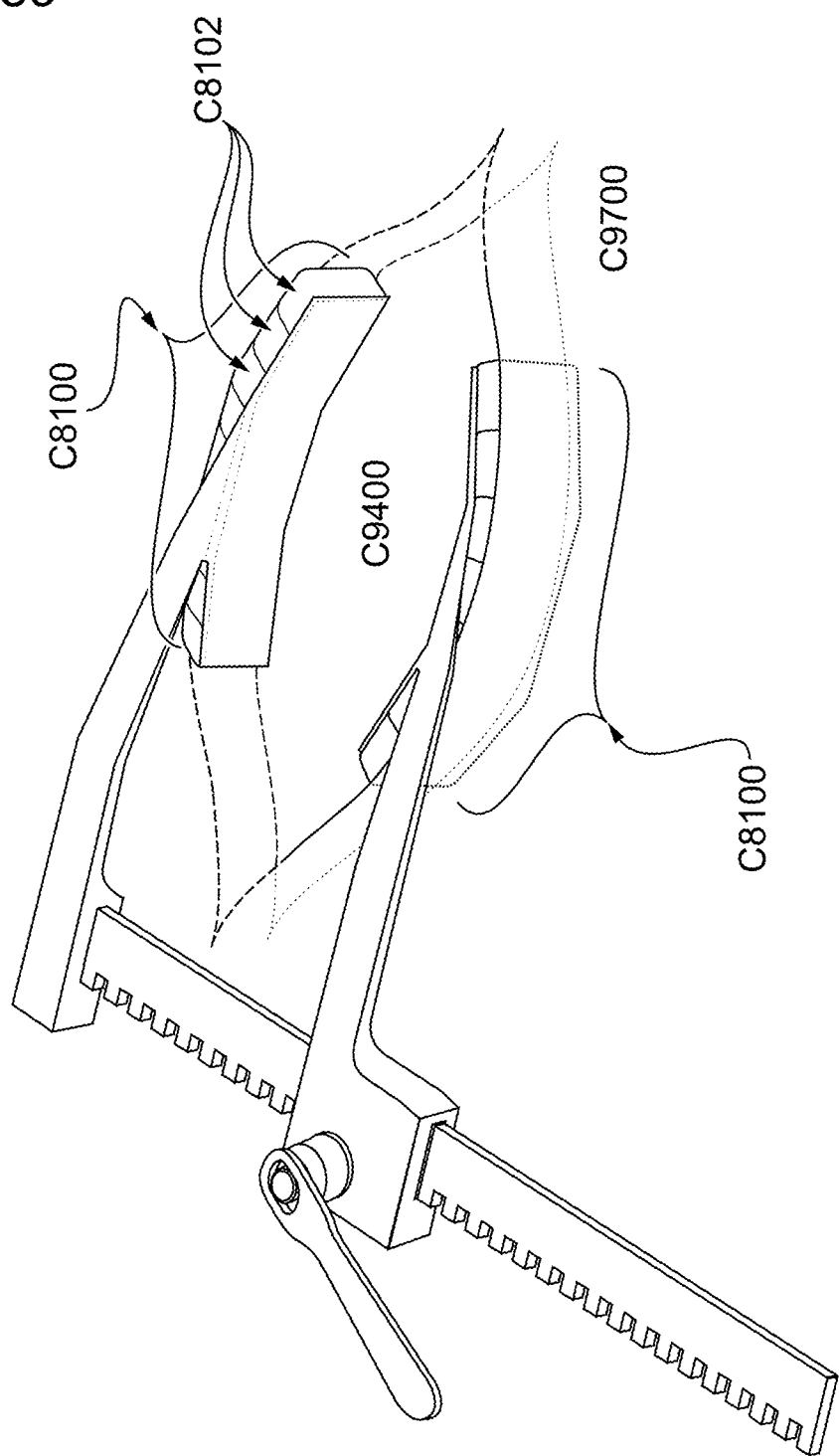
FIG. 89 shows another embodiment of a exemplary retractor comprising two opposed retractor blades each fitted with a TED, where the TED comprises a row of individually addressable fluid- and foam-filled pads that can be individually actuated and possess multiple sensors.

Given the previous examples, it is reasonable to combine the benefits of the earlier embodiments into one surgical instrument (FIG. 89). A rib spreader C19000, similar to that in FIG. 55, is fitted with a TED C8100 that is an array of individually addressable fluid- and foam-filled retractor blade pads C8102 themselves comprised of fiber-reinforced, anisotropic, elastomer bladders. Each blade pad C8102 within the array of pads can be of the type shown in FIG. 83 in which fibers C5416 helically wrap fluid filled columns C5410 connected by a plenum on the instrument face of the pad C8102. The helically wrapped columns C5410 are then encased in a block of low-stiffness gas-bubble filled elastomer that possesses a density gradient C1320 as shown in FIG. 59C. This pad C8102 is designed to provide a soft tissue face C1103 to the tissue such that pad C8102 cups the tissue as the pad C8102 is pressed against the tissue (e.g. a rib during a thoracotomy).

FIG. 90 shows a different TED C8500 illustrating how each pad (C5100 in this example) forming a similar array of pads C111 can also each be equipped with a pressure sensor C2222, a temperature sensor C3333, and an IR-based oxygen sensor, comprised of IR emitter C8560 and IR detector C8570 for measuring tissue oxygen saturation (FIG. 90). Each pad is mounted onto a rigid element C2000, with each rigid element C2000 operably attached by blade mount C8530 to a motor C8540, mounted on retractor arm C8520, that positions the rigid element C2000, and thus the pad C5100. Thus, each pad C5100 can be independently positioned to increase or decrease the pressure in the pad C5100 and thus the force that the rigid element C2000 exerts on the edge of the incision. Optionally, pads C5100 can include columns C5410 wrapped by helical fibers C5416, and, further, each column C5410 can be modulated via its own individually controllable hydraulic actuator (either one actuator per helically wrapped cylinder or one actuator per pad in the array of pads such that all cylinders in one pad have the same pressure). The pad array C1111, supplied with a controller, becomes a hydraulic servo array (with the pressure sensors as the feedback). The controller can further contain sensor monitoring software that receives the inputs from all the sensors in the array, compares all their values, checks for impending tissue trauma events, and actively, automatically modulates the behavior of the array to prevent damage from occurring as the surgeon retracts the patient's ribs to obtain surgical access. The controller might further possess the capability to control the influx of a temperature-modulating fluid from a temperature-controlled supply into individual pads within the pad array, for example to cool the tissue and thereby slow the metabolic rate of the tissue, or optionally to cool just those regions that appear to be most at risk. This device also allows the surgeon to heat the tissue for other reasons, as desired, and the temperature-controlled fluid can serve this purpose, too. If the pads are built with permeable surfaces or volumes, then the circulating fluid might also be titrated (for example, at the source, or at the temperature-modulating unit) to release a desired amount of pharmacological agent from the surface of the pads and into the tissue. In these ways, the pressure, temperature, and pharmacological state of the patient's tissues can all be controlled before and throughout retraction, the better to ameliorate or prevent any tissue trauma, and so improve patient outcomes.

It will be apparent to those readers who are skilled in the art that there are many other combinations and variations on the themes above; all of those fall within the scope of the present series of embodiments and are not relieved from protection herein.

REFERENCES

1. Benedetti F, Amanzio M, Casadio C, Filosso P L, Molinatti M, Oliaro A, et al. Postoperative pain and superficial abdominal reflexes after posterolateral thoracotomy. Ann Thorac Surg 1997 July; 64 (1):207-10.
2. Bolotin G, Buckner G D, Jardine N J, Kiefer A J, Campbell N B, Kocherginsky M, et al. A novel instrumented retractor to monitor tissue-disruptive forces during lateral thoracotomy. J Thorac Cardiovasc Surg 2007 April; 133 (4):949-54.
3. Bromage P R. The control of post-thoracotomy pain. Anaesthesia 1989 May; 44 (5):445-6.
4. Candaele S, Herijgers P, Demeyere R, Flameng W, Evers G. Chest pain after partial upper versus complete sternotomy for aortic valve surgery. Acta Cardiol 2003 February; 58 (1):17-21.
5. Cerfolio R J, Bryant A S, Patel B, Bartolucci A A. Intercostal muscle flap reduces the pain of thoracotomy: A prospective randomized trial. J Thorac Cardiovasc Surg 2005 October; 130 (4):987-93.
6. Clark J D, Qiao Y, Li X, Shi X, Angst M S, Yeomans D C. Blockade of the complement c5a receptor reduces incisional allodynia, edema, and cytokine expression. Anesthesiology 2006 June; 104 (6):1274-82.
7. Clark J D, Shi X, Li X, Qiao Y, Liang D, Angst M S, et al. Morphine reduces local cytokine expression and neutrophil infiltration after incision. Mol Pain 2007; 3:28.
8. Dajczman E, Gordon A, Kreisman H, Wolkove N. Long-term postthoracotomy pain. Chest 1991 February; 99 (2):270-4.
9. Datta G, Gnanalingham K K, Peterson D, Mendoza N, O'Neill K, Van Dellen J, et al. Back pain and disability after lumbar laminectomy: Is there a relationship to muscle retraction? Neurosurgery 2004 June; 54 (6):1413-20; discussion 20.
10. De Silva R J, Vuylsteke A, Fritchley S J, Trull A K, Dunning J J, Wallwork J. Apt070 inhibits complement activation during in vitro cardiopulmonary bypass. Eur J Cardiothorac Surg 2006 July; 30 (1):72-6.
11. Defalque R J, Boyd G L. Long-term postthoracotomy pain. Chest 1992 March; 101 (3):884.
12. Dowling R, Thielneier K, Ghaly A, Barber D, Boice T, Dine A. Improved pain control after cardiac surgery: Results of a randomized, double-blind, clinical trial. J Thorac Cardiovasc Surg 2003 November; 126 (5):1271-8.
13. Eisenberg E, Pultorak Y, Pud D, Bar-El Y. Prevalence and characteristics of post coronary artery bypass graft surgery pain (pcp). Pain 2001 May; 92 (1-2):11-7.
14. Eng J, Sabanathan S. Post-thoracotomy analgesia. J R Coll Surg Edinb 1993 April; 38 (2):62-8.
15. Erdek M A, Staats P S. Chronic pain and thoracic surgery. Thorac Surg Clin 2005 February; 15 (1):123-30.
16. Fanning N F, Porter J, Shorten G D, Kirwan W O, Bouchier-Hayes D, Cotter T G, et al. Inhibition of neutrophil apoptosis after elective surgery. Surgery 1999 September; 126 (3):527-34.
17. Flatters S J. Characterization of a model of persistent postoperative pain evoked by skin/muscle incision and retraction (smir). Pain 2007 Jun. 20.
18. Fonseca P. Postthoracotomy pain. J Thorac Cardiovasc Surg 1998 December; 116 (6):1081-2.
19. Hazelrigg S R, Cetindag I B, Fullerton J. Acute and chronic pain syndromes after thoracic surgery. Surg Clin North Am 2002 August; 82 (4):849-65.
20. Ho S C, Royse C F, Royse A G, Penberthy A, McRae R. Persistent pain after cardiac surgery: An audit of high thoracic epidural and primary opioid analgesia therapies. Anesth Analg 2002 October; 95 (4):820-3, table of contents.
21. Kalso E, Mennander S, Tasmuth T, Nilsson E. Chronic post-sternotomy pain. Acta Anaesthesiol Scand 2001 September; 45 (8):935-9.
22. Karmakar M K, Ho A M. Postthoracotomy pain syndrome. Thorac Surg Clin 2004 August; 14 (3):345-52.
23. Katz J, Jackson M, Kavanagh B P, Sandler A N. Acute pain after thoracic surgery predicts long-term post-thoracotomy pain. Clin J Pain 1996 March; 12 (1):50-5.

24. Kavanagh B P, Katz J, Sandler A N. Pain control after thoracic surgery. A review of current techniques. Anesthesiology 1994 September; 81 (3):737-59.
25. Kawaguchi Y, Matsui H, Tsuji H. Back muscle injury after posterior lumbar spine surgery. Part 1: Histologic and histochemical analyses in rats. Spine 1994 Nov. 15; 19 (22): 2590-7.
26. Kawaguchi Y, Matsui H, Tsuji H. Back muscle injury after posterior lumbar spine surgery. A histologic and enzymatic analysis. Spine 1996 Apr. 15; 21 (8):941-4.
27. Kawaguchi Y, Matsui H, Gejo R, Tsuji H. Preventive measures of back muscle injury after posterior lumbar spine surgery in rats. Spine 1998 Nov. 1; 23 (21):2282-7; discussion 8.
28. Koehler R P, Keenan R J. Management of postthoracotomy pain: Acute and chronic. Thorac Surg Clin 2006 August; 16 (3):287-97.
29. Kruger M, McRae K. Pain management in cardiothoracic practice. Surg Clin North Am 1999 April; 79 (2):387-400.
30. Magnano D, Montalbano R, Lamarra M, Ferri F, Lorini L, Clarizia S, et al. Ineffectiveness of local wound anesthesia to reduce postoperative pain after median sternotomy. J Card Surg 2005 July-August; 20 (4):314-8.
31. Minor A A. Alternative management for post-thoracotomy pain syndrome. Can J Surg 1996 October; 39 (5): 430-1.
32. Murphy G S, Szokol J W, Marymont J H, Avram M J, Vender J S. The effects of morphine and fentanyl on the inflammatory response to cardiopulmonary bypass in patients undergoing elective coronary artery bypass graft surgery. Anesth Analg 2007 June; 104 (6):1334-42, table of contents.
33. Ochroch E A, Gottschalk A. Impact of acute pain and its management for thoracic surgical patients. Thorac Surg Clin 2005 February; 15 (1):105-21.
34. Ochroch E A, Gottschalk A, Troxel A B, Farrar J T. Women suffer more short and long-term pain than men after major thoracotomy. Clin J Pain 2006 June; 22 (5): 491-8.
35. Peeters-Asdourian C, Gupta S. Choices in pain management following thoracotomy. Chest 1999 May; 115(5 Suppl):122S-4S.
36. Perkins F M, Kehlet H. Chronic pain as an outcome of surgery. A review of predictive factors. Anesthesiology 2000 October; 93 (4):1123-33.
37. Perttunen K, Tasmuth T, Kalso E. Chronic pain after thoracic surgery: A follow-up study. Acta Anaesthesiol Scand 1999 May; 43 (5):563-7.
38. Pluijms W A, Steegers M A, Verhagen A F, Scheffer G J, Wilder-Smith O H. Chronic post-thoracotomy pain: A retrospective study. Acta Anaesthesiol Scand 2006 August; 50 (7):804-8.
39. Richardson J, Smith T, Tsiamis A, Shah R D. Postthoracotomy pain. Ann Thorac Surg 1998 January; 65 (1):300-2.
40. Rogers M L, Henderson L, Mahajan R P, Duffy J P. Preliminary findings in the neurophysiological assessment of intercostal nerve injury during thoracotomy. Eur J Cardiothorac Surg 2002 Feb. 1, 2002; 21 (2):298-301.
41. Sabanathan S, Richardson J, Mearns A J. Management of pain in thoracic surgery. Br J Hosp Med 1993 Jul. 14-Aug. 17; 50 (2-3):114-20.
42. Sandler A N. Post-thoracotomy analgesia and perioperative outcome. Minerva Anestesiol 1999 May; 65 (5):267-74.
43. Savage C, McQuitty C, Wang D, Zwischenberger J B. Postthoracotomy pain management. Chest Surg Clin N Am 2002 May; 12 (2):251-63.
44. Sihoe A D, Lee T W, Wan I Y, Thung K H, Yim A P. The use of gabapentin for post-operative and post-traumatic pain in thoracic surgery patients. Eur J Cardiothorac Surg 2006 May; 29 (5):795-9.
45. Strebel B M, Ross S. Chronic post-thoracotomy pain syndrome. CMAJ 2007; 177 (9):1029.
46. Takamori S, Yoshida S, Hayashi A, Matsuo T, Mitsuoka M, Shirouzu K. Intraoperative intercostal nerve blockade for postthoracotomy pain. Ann Thorac Surg 2002 August; 74 (2):338-41.
47. Taylor H, McGregor A H, Medhi-Zadeh S, Richards S, Kahn N, Zadeh J A, et al. The impact of self-retaining retractors on the paraspinal muscles during posterior spinal surgery. Spine 2002 Dec. 15; 27 (24):2758-62.
48. Tiippana E, Nilsson E, Kalso E. Post-thoracotomy pain after thoracic epidural analgesia: A prospective follow-up study. Acta Anaesthesiol Scand 2003 April; 47 (4):433-8.
49. White P F, Rawal S, Latham P, Markowitz S, Issioui T, Chi L, et al. Use of a continuous local anesthetic infusion for pain management after median sternotomy. Anesthesiology 2003 October; 99 (4):918-23.

What is claimed is:

1. A device for preventing tissue trauma when applying force to a patient's tissue comprising:
   a rigid element configured to apply force to a tissue;
   a gradient pad connected to the rigid element, the gradient pad comprising:
   a tissue face configured to be apposed to the tissue;
   an instrument face configured to engage the rigid element; and
   a pad body having a continuously varying gradient of Young's modulus;
   wherein a modulus of the gradient pad at the tissue face is a lower Young's modulus than a modulus of the gradient pad at the instrument face;
   wherein the gradient of Young's modulus of the pad body is substantially perpendicular to the tissue face of the gradient pad; and
   wherein the gradient pad is configured to apply a pushing compressive force toward a surface of the tissue.

2. The device of claim 1, wherein the gradient of Young's modulus of the gradient pad is formed by a series of bonded layers, with at least one of the series of bonded layers having a different modulus than another of the series of bonded layers.

3. A device for preventing tissue trauma when applying force to a patient's tissue comprising:
   a rigid element configured to apply force to a tissue;
   a gradient pad connected to the rigid element, the gradient pad comprising:
   a tissue face configured to be apposed to the tissue;
   an instrument face configured to engage the rigid element; and
   a pad body having a continuously varying gradient of Young's modulus;
   wherein a modulus of the gradient pad at the tissue face is a lower Young's modulus than a modulus of the gradient pad at the instrument face;
   wherein the gradient of Young's modulus of the pad body is substantially perpendicular to the tissue face of the gradient pad;
   wherein the gradient pad is configured to apply a pushing compressive force toward a surface of the tissue; and
   wherein the gradient of Young's modulus of the gradient pad is formed by a changing ratio of a plurality of elastomeric components along the modulus gradient, each of the plurality of elastomeric components having a different modulus.

4. The device of claim 1, wherein the gradient of Young's modulus of the gradient pad is created by internal fibers.

5. The device of claim 1, wherein the gradient of Young's modulus of the gradient pad is formed by a bubble density gradient.

6. The device of claim 1, wherein the gradient of Young's modulus of the gradient pad is formed by at least one of voids, columns, walls, and other structural features to produce regions of greater or lesser stiffness.

7. A device for decreasing trauma to sternal tissues when separating cut surfaces of a sternum with a sternal retractor having opposing retractor blades configured to force apart the cut surfaces of the sternum, comprising:
a first gradient pad configured to be applied to one cut surface of a sternum,
a second gradient pad configured to be applied to an opposing cut surface of the sternum, opposite to the one cut surface of the sternum,
wherein the first gradient pad comprises:
a first tissue face configured to be apposed to the one cut surface of the sternum,
a first instrument face configured to engage a first retractor blade of the sternal retractor, and
a first pad body having a continuously varying gradient of young's modulus;
wherein the gradient of Young's modulus of the first pad body is substantially perpendicular to the first tissue face of the first gradient pad; and
wherein the second gradient pad comprises:
a second tissue face configured to be apposed to the opposing cut surface of the sternum,
a second instrument face configured to engage a second retractor blade of the sternal retractor, and
a second pad body having a continuously varying gradient of young's modulus;
wherein the gradient of Young's modulus of the second pad body is substantially perpendicular to the second tissue face of the second gradient pad; and
wherein at least one of the first gradient pad and the second gradient pad is configured to apply a pushing compressive force toward its respective cut surface of the sternum.

8. The device of claim 7, wherein the gradient pad further comprises the tissue face having a sufficiently low modulus configured to conform to and deform into the cut surface of the sternum and thereby distribute loads along the cut surface of the sternum, and also block cut blood vessels to stop bleeding on the cut surface of the sternum.

9. The device of claim 7, wherein the gradient pad further comprises a means for delivering at least one physiologically or pharmacologically active agent to the cut surface of the sternum.

10. A device for decreasing trauma to sternal tissues when separating cut edges of a sternum with a sternal retractor, comprising:
a plurality of drug eluting gradient pads, wherein each of the plurality of drug eluting gradient pads contains at least one physiologically or pharmacologically active agent and is configured to transmit force from the sternal retractor to each of the cut edges of the sternum;
wherein at least one of the plurality of drug eluting gradient pads comprises:
a means for transmitting force from the sternal retractor to a drug eluting material, the drug eluting material configured to be apposed to one or more of the cut edges of the sternum,
a tissue face configured to be apposed to the cut edges of the sternum;
a pad body having a continuously varying gradient of Young's modulus;
wherein the gradient of Young's modulus of the pad body is substantially perpendicular to the tissue face of the drug eluting gradient pad; and
the drug eluting material comprising:
a means for delivering the at least one physiologically or pharmacologically active agent to one or more of the cut edges of the sternum; and
a deformable material that is sufficiently soft such that force from the sternal retractor causes the drug eluting material to conform to and deform into one or more of the cut edges of the sternum and thereby distribute loads along one or more of the cut edges of the sternum, and also block cut blood vessels to stop bleeding on one or more of the cut edges of the sternum, and
wherein at least one of the plurality of drug eluting gradient pads is configured to apply a pushing compressive force toward one or more of the cut edges of the sternum.

11. The device of claim 10, wherein the deformable material is a hydrogel.

12. The device of claim 10, wherein the deformable material is an elastomer.

13. The device of claim 10, wherein the means for transmitting force comprises:
a rigid component configured to mechanically support one or more of the cut edges of the sternum along an entire sternal incision; and
a retractor blade attachment feature configured to attach the rigid component to a blade or arm of the sternal retractor.

14. The device of claim 10, wherein the means for delivering the at least one physiologically or pharmacologically active agent is diffusion from the drug eluting material.

15. The device of claim 10, wherein the at least one physiologically or pharmacologically active agent includes one or more of the following: agents that block inflammation, agents that stop bleeding, agents that have antibiotic or anti-microbial action, agents that encourage wound healing, and agents that reduce pain.

16. The device of claim 10, wherein the drug eluting gradient pad is configured to reduce drying of tissue at the cut edges of the sternum.

17. The device of claim 16, wherein the drug eluting gradient pad is configured to reduce drying of tissue at the cut edges of the sternum via a fluid delivery system that is configured to directly perfuse the tissue at the cut edges of the sternum with a fluid.

18. The device of claim 16, wherein the drug eluting gradient pad is configured to reduce drying of tissue at the cut edges of the sternum by acting as a barrier to evaporation or absorption.

19. The device of claim 1, wherein the gradient of Young's modulus of the gradient pad is formed by a changing ratio of a plurality of elastomeric components along the modulus gradient, each of the plurality of elastomeric components having a different modulus.

* * * * *